US 9,200,044 B2

(12) United States Patent
Blais et al.

(10) Patent No.: US 9,200,044 B2
(45) Date of Patent: Dec. 1, 2015

(54) MODIFIED ANTIGENS

(71) Applicants: GlaxoSmithKline Biologicals S.A., Rixensart (BE); Glaxo Group Limited, Greenford, Middlesex (GB)

(72) Inventors: Normand Blais, Laval (CA); Anne-Marie Gelinas, Laval (CA); James Brown, Collegeville, PA (US); Dennis Murphy, Collegeville, PA (US); Pascal Mettens, Rixensart (BE)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 0 days.

(21) Appl. No.: 14/557,929

(22) Filed: Dec. 2, 2014

(65) Prior Publication Data
US 2015/0093414 A1    Apr. 2, 2015

Related U.S. Application Data

(62) Division of application No. 13/574,816, filed as application No. PCT/EP2011/051158 on Jan. 27, 2011, now Pat. No. 8,932,600.

(60) Provisional application No. 61/298,710, filed on Jan. 27, 2010.

(51) Int. Cl.
*A61K 39/04* (2006.01)
*C07K 14/35* (2006.01)

(52) U.S. Cl.
CPC .............. *C07K 14/35* (2013.01); *A61K 39/04* (2013.01); *C07K 2319/00* (2013.01)

(58) Field of Classification Search
CPC ................................ A61K 39/04; C07K 14/35
USPC ......................................... 536/23.7; 514/44 R
See application file for complete search history.

(56) References Cited

U.S. PATENT DOCUMENTS

| | | | |
|---|---|---|---|
| 1,786,412 A * | 12/1930 | Crisson | 333/24 R |
| 6,290,969 B1 | 9/2001 | Reed et al. | |
| 6,338,852 B1 | 1/2002 | Reed et al. | |
| 6,350,456 B1 | 2/2002 | Reed et al. | |
| 6,458,366 B1 | 10/2002 | Reed et al. | |
| 6,544,522 B1 | 4/2003 | Skeiky et al. | |
| 6,555,653 B2 | 4/2003 | Alderson et al. | |
| 6,592,877 B1 | 7/2003 | Reed et al. | |
| 5,627,198 A1 | 9/2003 | Reed et al. | |
| 6,613,881 B1 | 9/2003 | Alderson et al. | |
| 6,627,198 B2 | 9/2003 | Reed et al. | |
| 7,186,412 B1 | 3/2007 | Skeiky et al. | |

(Continued)

FOREIGN PATENT DOCUMENTS

| | | |
|---|---|---|
| WO | 9118926 | 8/1991 |
| WO | 9304175 | 3/1993 |

(Continued)

OTHER PUBLICATIONS

U.S. Appl. No. 08/523,436, filed Sep. 1, 1995, Dillon, et al.

(Continued)

*Primary Examiner* — Albert Navarro
*Assistant Examiner* — Ginny Portner
(74) *Attorney, Agent, or Firm* — Eric J. Kron

(57) ABSTRACT

Modified Rv3616c proteins and their use as medicaments, particularly for the prevention of reactivation of tuberculosis.

25 Claims, 26 Drawing Sheets

(56) References Cited

U.S. PATENT DOCUMENTS

| | | | |
|---|---|---|---|
| 7,311,922 B1* | 12/2007 | Skeiky et al. | 424/248.1 |
| 7,357,936 B1 | 4/2008 | Gardon et al. | |
| 7,670,609 B2 | 3/2010 | Shafferman et al. | |
| 7,927,818 B2* | 4/2011 | Felgner et al. | 435/7.1 |
| 7,982,025 B2* | 7/2011 | Skeiky et al. | 536/23.7 |
| 8,067,016 B2* | 11/2011 | Skeiky et al. | 424/248.1 |
| 8,110,200 B2 | 2/2012 | Skeiky et al. | |
| 8,110,201 B2 | 2/2012 | Skeiky et al. | |
| 8,475,803 B2 | 7/2013 | Olwill et al. | |
| 8,932,600 B2* | 1/2015 | Blais et al. | 424/190.1 |
| 2003/0175294 A1* | 9/2003 | Skeiky et al. | 424/190.1 |
| 2004/0086523 A1* | 5/2004 | Skeiky et al. | 424/190.1 |
| 2004/0197896 A1 | 10/2004 | Cole | |
| 2006/0147477 A1* | 7/2006 | Cabezon Siliva et al. | 424/277.1 |
| 2007/0212329 A1* | 9/2007 | Bruck et al. | 424/85.2 |
| 2008/0226672 A1 | 9/2008 | Garcon et al. | |
| 2008/0269151 A1* | 10/2008 | Skeiky et al. | 514/44 |
| 2008/0279926 A1 | 11/2008 | Vandepapeliere | |
| 2009/0285847 A1 | 11/2009 | Felgner et al. | |
| 2009/0306195 A1 | 12/2009 | Skeky et al. | |
| 2010/0055166 A1* | 3/2010 | Voss | 424/450 |
| 2011/0117119 A1 | 5/2011 | Mettens et al. | |
| 2013/0052229 A1 | 2/2013 | Campos-Neto et al. | |
| 2014/0178428 A1 | 6/2014 | Klein | |

FOREIGN PATENT DOCUMENTS

| | | |
|---|---|---|
| WO | 9709428 | 3/1997 |
| WO | 9709429 | 3/1997 |
| WO | 9816645 | 4/1998 |
| WO | 9816646 | 4/1998 |
| WO | 9853075 | 11/1998 |
| WO | 9853076 | 11/1998 |
| WO | 9112325 | 8/1999 |
| WO | 9940188 | 8/1999 |
| WO | 9942076 | 8/1999 |
| WO | 9942118 | 8/1999 |
| WO | 9951748 | 10/1999 |
| WO | 0124820 | 4/2001 |
| WO | 0198460 | 12/2001 |
| WO | 03070187 | 8/2003 |
| WO | 2006117250 | 11/2006 |
| WO | 2007068907 | 6/2007 |
| WO | 2008007942 | 1/2008 |
| WO | 2008043774 | 4/2008 |
| WO | 2009024822 | 2/2009 |
| WO | 2010001077 | 1/2010 |
| WO | 2010010177 | 1/2010 |
| WO | 2010121618 | 10/2010 |

OTHER PUBLICATIONS

U.S. Appl. No. 08/658,800, filed Jun. 6, 1996, Reed, et al.
U.S. Appl. No. 08/659,683, filed Jun. 6, 1996, Reed, et al.
U.S. Appl. No. 08/858,998, filed May 20, 1997, Alderson, et al.
U.S. Appl. No. 08/859,381, filed May 20, 1997, Alderson, et al.
U.S. Appl. No. 08/942,341, filed Oct. 1, 1997, Reed, et al.
U.S. Appl. No. 08/942,578, filed Oct. 1, 1997, Reed, et al.
Motiwala, Alifiya S et ai, Tuberculosis Evolution, Journal of Infectious Diseases, Mar. 15, 2010, pp. 881-888, Mutations in Extensively Drug-Resistant Myobacterium tuberculosis That do not code for Known Drug Resistance Mechanisms.
Sassetti, Christopher M. et ai, PNAS, Oct. 28, 2003, vol. 100(22), pp. 12989-12994, Genetic Requirements for mycobacterial survival during infection.
Atmakuri et al., "Regulation of Protein Secretion by . . . Protein Secretion?", Cell Host & Microbe, Sep. 11, 2008, vol. 4, pp. 190-191.
Derrick, et al., "Vaccine Induced Anti-Tuberculosis Protective Immunity in Mice Correlates with the Magnitude and Quality of Multifunctional CD4 T Cells", Vaccine, 2011, vol. 27, pp. 2902-2909.
Coler, et al., "Identification of Mycobacterium Tuberculosis Vaccine Candidates Using Human CD+4 T-Cells Expression Cloning", Vaccine, 2009, vol. 27, pp. 223-233.

Boslego, John W et al, Vaccines and Immunotherapy, 1991, pp. 211-223, Chapter 17.
Ellis, Ronald W, Ph.D, Chapater 29, New Technologies for Making Vaccines, 1988, pp. 568-575, Plotkin and Mortimer Vaccines.
Alderson et al., "Expression cloning of an immunodominant family of Mycobacterium Tuberculosis antigens using human CD4+ T Cells", J. Exp. Med., 2000 The Rockefeller University Press, 191(3):551-559.
Al-Attiyah, et al., "In vitro cellular immune responses to complex and newy defined receombinant antigens of Mycobacterium tuberculosis", Clin Exp Immunol, 2004 Blackwell Publishing Ltd., 138:139-144.
Beibarth, et al., "A systematic approach h for comprehensive T-cell epitope discovery using peptide libraries", Bioinformatics, 2005 Oxford University Press, 2I(SI)i29-i37.
Betts, et al.,"Evaluation of a nutrient starvation model of Mycobaterium tuberculosis persistence by gene and protein expression profiling", Molecular Microbiology, 43(3):717-731, 2002 Blackwell Science Ltd.
Bhasin, et ai., "A hybrid approach for prediction promiscuous MHC class I restricted T cell epitopes", 1. Biosci., 2007 Indian Academy of Sciences, 32(1 ):31-42.
Bian, et ai., "Discovery of promiscuous HLA-II restricted T cell epitopes with TEPITOPE", Methods, 2004 Elsevier Inc., 34:468-475.
Camus, et al., "Re-annotation of the genome sequence of Mycobacterium tuberculosis H37Rv", Microbiology, 2002 SGM, 148:2967-2973.
Chalker, et al., "Systematic identification of selective essential genes in Helicobacter pylori by genome prioritization and allelic replacement mutagenesis", Journal of Bacteriology, 2001 American Society for Microbiology, 183(4):1259-1268.
Claros, et al., "TopPredll: an improved software from membrane protein structure predictions", Cabios Applications Notes, 1994 Oxford University Press, 10(6):686-686.
Cole, et al., "Deciphering the biology ofMycobacterium Tuberculosis from the complete genome sequence", Nature, 1998 Macmillan Publishers Ltd, 396:190-197.
Coler, et al., "Identification of Mycobacterium tuberculosis vaccine candidates using human CD4+ Tcells expression cloning", Vaccine, 2008 Elsevier Ltd., 27:223-233.
Coler, et al., "Molecular cloning and immunologic reactivity of a novel low molecular mass antigen ofMycobacterium tuberculosis", The Journal ofImmunology, 1998 The American Association ofImmunologists, 161 :2356-2364.
Content, et al., "The genes coding for the Antigen 85 complexes of Mycobacterium tuberculosis and Mycobaterium bovis BCG are members of a gene family: cloning, sequence determination, and genomic organization of the gene coding for Antigen 85-C of the M tuberculosis", Infection and Immunity, 1991 American Soci8ety for Microbiology, 59(9):3205-3212.
Dietrich, et al., "Exchanging ESAT6 with TB10,4 in an Ag85B Fusion molecule-based tuberculosis subunit vaccine: efficient protection and ESAT6-based sensitive monitoring of vaccine efficacy", The Journal ofImmunology, 2005 The American Association ofImmunologists, Inc., 174:6332-6339.
Dillon, et al., Molecular characterization and human T-Cell responses to a member of a novel Mycobacterium tuberculosis mtb39 Gene Family, Infection and Immunity, 1999, American Society for Microbiology, 67(6):2941-2950.
Doherty, et al., Comparative analysis of different vaccine constructs expressing defined antigens from Mycobacterium Tuberculosis, JID, 2004 Infectious Diseases Society of America, 190:2146-.
Donnes, et al., "Prediction ofMHC class I binding peptides, using SVMHC", BMC Bioinformatics, 2002 BMC Bioinformatics 3:25.
Doytchinova, et al., "EpiJen: a server for multistep T cell epitope prediction", BMC Bioinformatics, 2006 BMC Bioinformatics, 7: 131.
Engleman, et al., "Identifying nonpolar transbilayer helices in amino acid sequences of membrane proteins", Ann. Rev. Biophys. Biophys. Chern., 1986 Annual Reviews Inc., 15:321-353.

(56) References Cited

OTHER PUBLICATIONS

Friscia, et al., "Human T cell responses to peptide epitopes of the I6kD antigen in tuberculosis", Clin Exp *Immunol, 1995 Blackwell Science, 102:53-57.
Garcia, et al., "nucleotide sequence and expression of the pneumococcal autolysin gene from its own promoter in *Escherichia coli*", Gene, 1986 Elsevier Science Publishers B.V., 43:265-272.
Hampshire, et al., "Stationary phase gene expression of Mycobaterium tuberculosis following a progressive nutrient depletion: a model for persistent organisms?" Tuberculosis, 84:228-238,2004 Elsevier Ltd.
Hardy, "B Lymphocyte Development and Biology", Fundamental Immunology, 6th ed., 2008 Lippincott Williams, a Wolters Kluwer business, pp. 237-247.
Huygen, et al., "Immunogenicity and protective efficacy of a tuberculosis DNA vaccine", Nature Medicine, 1996 Nature Publishing Group, 3(8):893.
Karakousis, et al., "Dormancy phenotype displayed by extracellular Mycobacterium tuberculosis within artificial granulomas in mice", The Journal of Experimental Medicine, 2004 The Rockefeller University Press, 200(5):647.
Kuttler, et al., "An algorithm for the prediction of proteasomal cleavages", 1. Mol. Biol., 2000 Academic Press, 298:417-429.
Larsen, et al., "An integrative approach to CTL epitope prediction: A combined algorithm integrating MHC class I binding, TAP transport efficiency, and proteasomal cleavage predictions", Eur. J. Immunol., 2005 Wiley-VCH Verlag GmbH & Co. KGaA, Weinheim, 35 :2295-2303.
Mustafa, et al., "Immunogenicity of Mycobacterium Tuberculosis antigens in Mycobacterium Bovis BCG-Vaccinated and M. bovis-infected cattle", Infection and Immunity, 2006 American Society for Microbiology, 74(8):4566-4572.
Muttucumaru, et al., "Gene expression profile in Mycobacterium tuberculosis in a non-replicating state", Tuberculosis, 2004 Elsevier Ltd, 84:239-246.
Nussbaum, et al., PAProC: a prediction algorithm for the proteasomal cleavages available on the WWW, Immunogenetics, 2001 Springer-Verlag, 53:87-94.
Rammensee, et al., "SYFPEITHI: database for MHC ligands and peptide motifs", Immunogenetics, 1999 Springer-Verlag, 50:213-219.
Rengarajan, et al., "Genome-wide requirements for Mycobacterium tuberculosis adaptation and survival in macrophages", PNAS 2005 The National Academy of Sciences of the USA, 102(23):8327-8332.
Roche, et al., "Human T-cell epitopes on the Mycobacterium tuberculosis secreted protein MPT64", Scand. J. Immunol., 1996 Blackwell Science Ltd., 43:662-670.
Sassetti, et al., "Genetic requirements for mycobacterial survival during infection", PNAS, 2003 The National Academy of the Sciences of the USA, 100(22):1289-1294.
Sassetti, et al.,"Genes required for mycrobacterial grown defined by high density mutagenesis", Molecular Microbiology, 48(1 ):77-84, 203 Blackwell Publishing Ltd.
Schnappinger, et al., "Transcriptional adaption of Mycobacterium tuberculosis within Macrophages: Insights into the phagosomal environment", The Journal of Experimental Medicine, 2003 The Rockefeller University Press, 198(5) 693.
Schuck, et al. "Identification of T-Cell antigens specific for latent Mycobacterium Tuberculosis infection", PLoS ONE, www.plosone.org, 2009 4(5):e5590. Doi: 10. 1371/iournal.pone.0005590.
Singh, et al., "ProPred: prediction of HLA-DR binding sites", Bioinformatics, 2001 Oxford University Press, 17(12):1236-1237.
Skeiky, et al., "Differential immune responses and protective efficacy induced by components of a tuberculosis polyprotein vaccine, Mtb72F, delivered as naked DNA or recombinant protein", The Journal of Immunology, 2004 The American Association of Immunologists, Inc., 172:7618-7628.
Skeiky, et al., "T cell expression cloning of a mycobacterium tuberculosis gene encoding a protective antigen associated with the early control of infection", The Journal of Immunology, 2000 The American Association of Immunologists, 165:7140-7149.
Sorensen, et al., Purification and characterization of a low-molecular-mass T-cell antigen secreted by Mycobacterium tuberculosis, Infection and Immunity, 1995 American Society for Microbiology, 63(5):1710-1717.
Talaat, et al., "The temporal expression profile of Mycobacterium tuberculosis infection in mice", PNAS, 2004 The National Academy of Sciences of the USA, 101(13):4602-4607.
Verbon, et al., The I4,000-Molecular-Weight antigen of mycobacterium tuberculosis is related to the Alpha-crystallin family of low-molecular-weight heat shock proteins, Journal of Bacteriology, 1992 American Society for Microbiology, 174(4): 1352-1359.
Von Heijine, et al., "Membrane protein structure prediction hydrophobicity analysis and the positive-inside rule", 1. Mol. Biol., 1992 Academic Press Limited, 225:487-494.
Voskuil , et al., "Mycobacterium tuberculosis gene expression during adaptation to stationary phase and low oxygen dormancy", Tuberculosis, 2004 Elsevier Ltd, 84:218-227.
Woodworth, et al., "Bacterial protein secretion is required for priming of CD8+ T Cells specific for the Mycobacterium Tuberculosis antigen CFP10", Infection and Immunity, 2008 American Society for Microbiology, 76(9):4199-4205.
Zhang, et al., "Multipred: a computational system for prediction of promiscuous HLA binding peptides", Nucleic Acids Research, 2005 Oxford University Press, 33:W172-W179.
Zhang, et al., PREDTAP: a system for prediction of peptide binding to the human transporter associated with antigen processing, Immunome Research, 2006 Immunome Research, 2:3.
Reece, Stephen T. et ai, Clinical and Vaccine Immunology, Mar. 2006, vol. 13(3), pp. 333-340, ML0405 and ML2331 are antigens of Mycobacterium leprae with Potential for Diagnosis of Leprosy.
Duthie, Malcom S et ai, Clinical and Vaccine Immunology, Nov. 2007, vol. 14(11) pp. 1400-1408, Use of Protein Antigens for Early Serological Diagnosis of Leprosy.

* cited by examiner

Figure 3
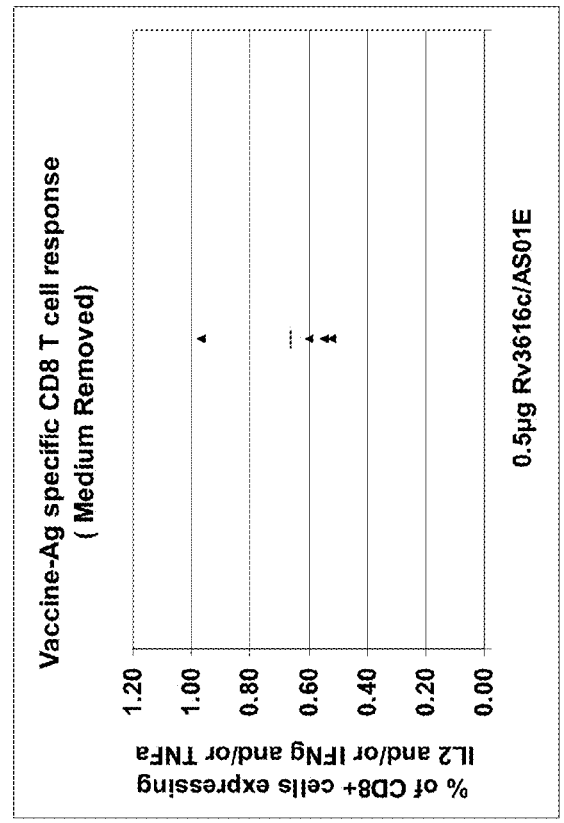
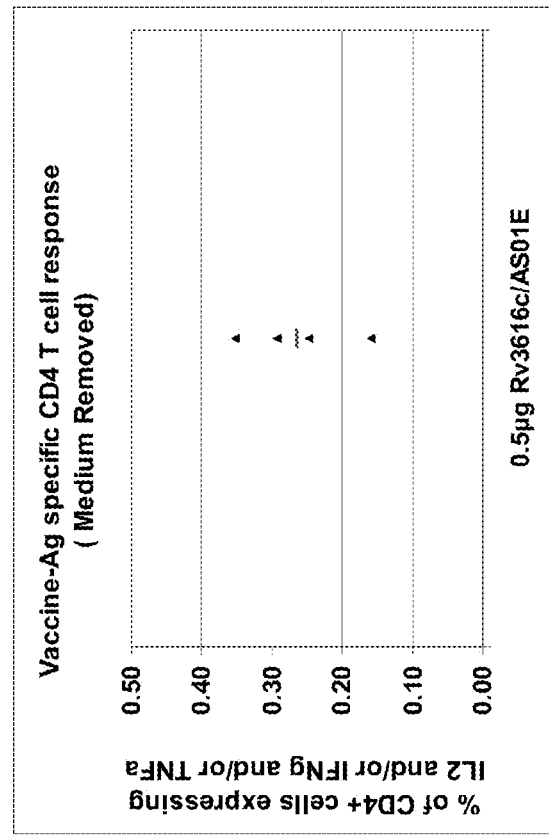

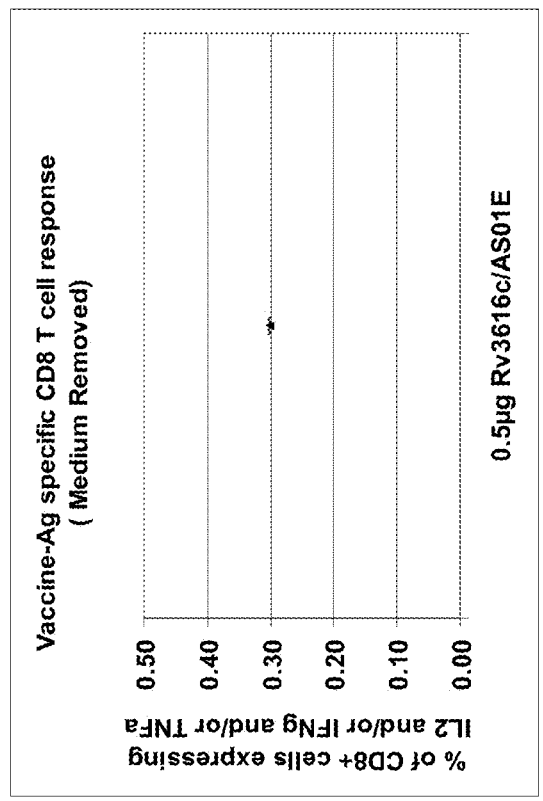
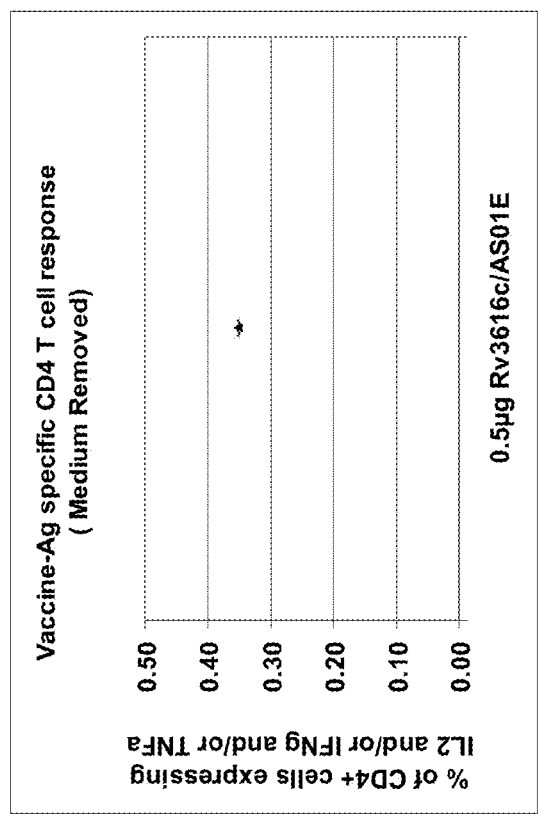
Figure 6

Figure 9
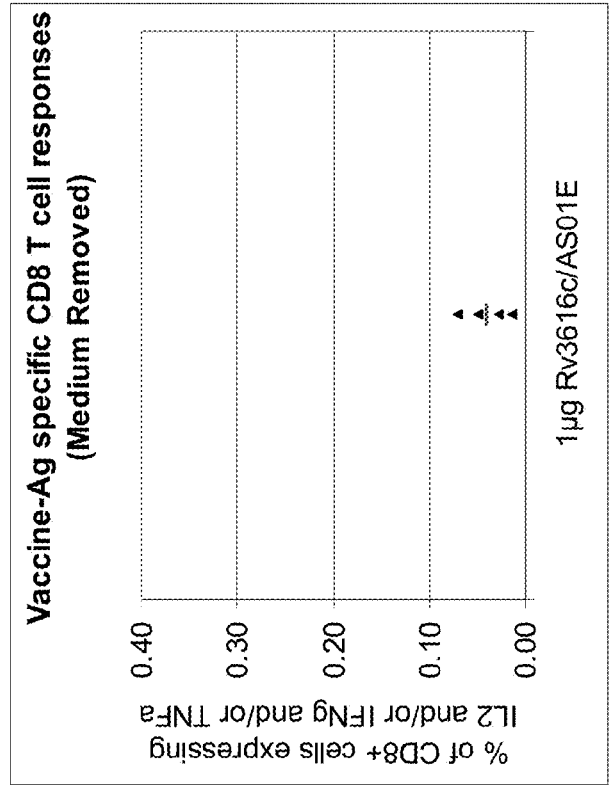
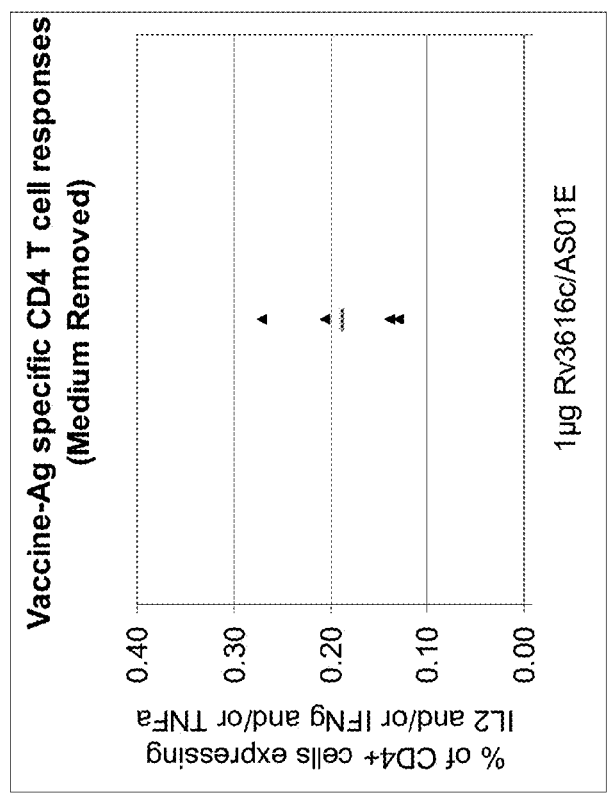

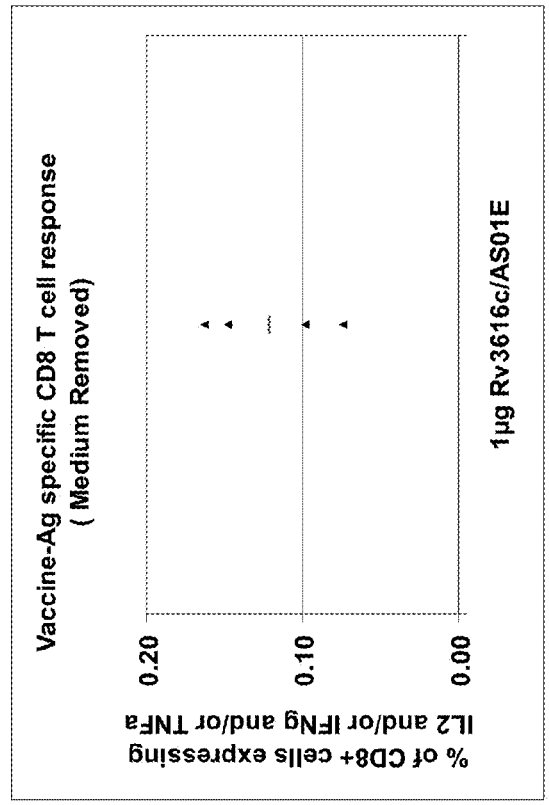
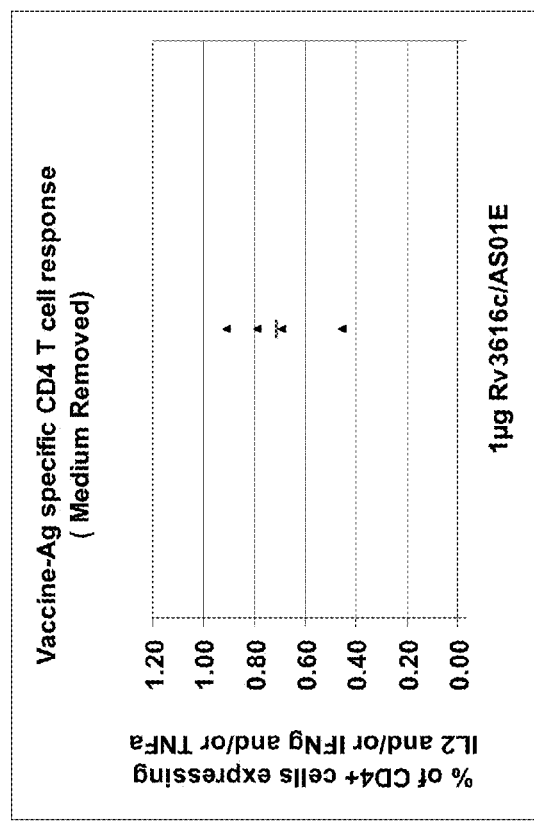
Figure 11

Figure 15

```
H37Rv     1   MSRAFIIDPTISAIDGLYDLLGIGIPNQGGILYSSLEYFEKALEELAAAFPGDGWLGSAA
CDC1551   1   MSRAFIIDPTISAIDGLYDLLGIGIPNQGGILYSSLEYFEKALEELAAAFPGDGWLGSAA
F11       1   MSRAFIIDPTISAIDGLYDLLGIGIPNQGGILYSSLEYFEKALEELAAAFPGDGWLGSAA
Haarlem   1   MSRAFIIDPTISAIDGLYDLLGIGIPNQGGILYSSLEYFEKALEELAAAFPGDGWLGSAA
StrainC   1   MSRAFIIDPTISAIDGLYDLLGIGIPNQGGILYSSLEYFEKALEELAAAFPGDGWLGSAA
BCG       1   MSRVFIIDPTISAIDGLYDLLGIGIPNQGGILYSSLEYFEKALEELAAAFPGDGWLGSAA H37Rv     61  DKYAGKNRNHVNFFQELADLDRQLISLIHDQANAVQTTRDILEGAKKGLEFVRPVAVDLT
CDC1551   61  DKYAGKNRNHVNFFQELADLDRQLISLIHDQANAVQTTRDILEGAKKGLEFVRPVAVDLT
F11       61  DKYAGKNRNHVNFFQELADLDRQLISLIHDQANAVQTTRDILEGAKKGLEFVRPVAVDLT
Haarlem   61  DKYAGKNRNHVNFFQELADLDRQLISLIHDQANAVQTTRDILEGAKKGLEFVRPVAVDLT
StrainC   61  DKYAGKNRNHVNFFQELADLDRQLISLIHDQANAVQTTRDILEGAKKGLEFVRPVAVDLT
BCG       61  DKYAGKNRNHVNFFQELADLDRQLISLIHDQANAVQTTRDILEGAKKGLEFVRPVAVDLT H37Rv     121 YIPVVGHALSAAFQAPFCAGAMAVVGGALAYLVVKTLINATQLLKLLAKLAELVAAAIAD
CDC1551   121 YIPVVGHALSAAFQAPFCAGAMAVVGGALAYLVVKTLINATQLLKLLAKLAELVAAAIAD
F11       121 YIPVVGHALSAAFQAPFCAGAMAVVGGALAYLVVKTLINATQLLKLLAKLAELVAAAIAD
Haarlem   121 YIPVVGHALSAAFQAPFCAGAMAVVGGALAYLVVKTLINATQLLKLLAKLAELVAAAIAD
StrainC   121 YIPVVGHALSAAFQAPFCAGAMAVVGGALAYLVVKTLINATQLLKLLAKLAELVAAAIAD
BCG       121 YIPVVGHALSAAFQAPFCAGAMAVVGGALAYLVVKTLINATQLLKLLAKLAELVAAAIAD H37Rv     181 IISDVADIIKGTLGEVWEFITNALNGLKELWDKLTGWVTGLFSRGWSNLESFFAGVPGLT
CDC1551   181 IISDVADIIKGILGEVWEFITNALNGLKELWDKLTGWVTGLFSRGWSNLESFFAGVPGLT
F11       181 IISDVADIIKGILGEVWEFITNALNGLKELWDKLTGWVTGLFSRGWSNLESFFAGVPGLT
Haarlem   181 IISDVADIIKGILGEVWEFITNALNGLKELWDKLTGWVTGLFSRGWSNLESFFAGVPGLT
StrainC   181 IISDVADIIKGILGEVWEFITNALNGLKELWDKLTGWVTGLFSRGWSNLESFFAGVPGLT
BCG       181 IISDVADIIKGILGEVWEFITNALNGLKELWDKLTGWVTGLFSRGWSNLESFFAGVPGLT H37Rv     241 GATSGLSQVTGLFGAAGLSASSGLAHADSLASSASLPALAGIGGGSGFGGLPSLAQVHAA
CDC1551   241 GATSGLSQVTGLFGAAGLSASSGLAHADSLASSASLPALAGIGGGSGFGGLPSLAQVHAA
F11       241 GATSGLSQVTGLFGAAGLSASSGLAHADSLASSASLPALAGIGGGSGFGGLPSLAQVHAA
Haarlem   241 GATSGLSQVTGLFGAAGLSASSGLAHADSLASSASLPALAGIGGGSGFGGLPSLAQVHAA
StrainC   241 GATSGLSQVTGLFGAAGLSASSGLAHADSLASSASLPALAGIGGGSGFGGLPSLAQVHAA
BCG       241 GATSGLSQVTGLFGAAGLSASSGLAHADSLASSASLPALAGIGGGSGFGGLPSLAQVHAA H37Rv     301 STRQALRPRADGPVGAAAEQVGGQSQLVSAQGSQGMGGPVGMGGMHPSSGASKGTTTKKY
CDC1551   301 STRQALRPRADGPVGAAAEQVGGQSQLVSAQGSQGMGGPVGMGGMHPSSGASKGTTTKKY
F11       301 STRQALRPRADGPVGAAAEQVGGQSQLVSAQGSQGMGGPVGMGGMHPSSGASKGTTTKKY
Haarlem   301 STRQALRPRADGPVGAAAEQVGGQSQLVSAQGSQGMGGPVGMGGMHPSSGASKGTTTKKY
StrainC   301 STRQALRPRADGPVGAAAEQVGGQSQLVSAQGSQGMGGPVGMGGMHPSSGASKGTTTKKY
BCG       301 STRQALRPRADGPVGAAAEQVGGQSQLVSAQGSQGMGGPVGMGGMHPSSGASKGTTTKKY H37Rv     361 SEGAAAGTEDAERAPVEADAGGGQKVLVRNVV
CDC1551   361 SEGAAAGTEDAERAPVEADAGGGQKVLVRNVV
F11       361 SEGAAAGTEDAERAPVEADAGGGQKVLVRNVV
Haarlem   361 SEGAAAGTEDAERAPVEADAGGGQKVLVRNVV
StrainC   361 SEGAAAGTEDAERAPVEADAGGGQKVLVRNVV
BCG       361 SEGAAAGTEDAERAPVEADAGGGQKVLVRNVV
```

Figure 16A

```
Rv3616_wt    1  MSRAFIIDPTISAIDGLYDLLGIGIPNQGGILYSSLEYFEKALEELAAAFPGDGWLGSAA
d136-183     1  MSRAFIIDPTISAIDGLYDLLGIGIPNQGGILYSSLEYFEKALEELAAAFPGDGWLGSAA
d150-160     1  MSRAFIIDPTISAIDGLYDLLGIGIPNQGGILYSSLEYFEKALEELAAAFPGDGWLGSAA
d136-154     1  MSRAFIIDPTISAIDGLYDLLGIGIPNQGGILYSSLEYFEKALEELAAAFPGDGWLGSAA
d166-182     1  MSRAFIIDPTISAIDGLYDLLGIGIPNQGGILYSSLEYFEKALEELAAAFPGDGWLGSAA
d135-139     1  MSRAFIIDPTISAIDGLYDLLGIGIPNQGGILYSSLEYFEKALEELAAAFPGDGWLGSAA
d142-145     1  MSRAFIIDPTISAIDGLYDLLGIGIPNQGGILYSSLEYFEKALEELAAAFPGDGWLGSAA
d138-145     1  MSRAFIIDPTISAIDGLYDLLGIGIPNQGGILYSSLEYFEKALEELAAAFPGDGWLGSAA
d145-152     1  MSRAFIIDPTISAIDGLYDLLGIGIPNQGGILYSSLEYFEKALEELAAAFPGDGWLGSAA
d149-154     1  MSRAFIIDPTISAIDGLYDLLGIGIPNQGGILYSSLEYFEKALEELAAAFPGDGWLGSAA

Rv3616_wt   61  DKYAGKNRNHVNFFQELADLDRQLISLIHDQANAVQTTRDILEGAKKGLEFVRPVAVDLT
d136-183    61  DKYAGKNRNHVNFFQELADLDRQLISLIHDQANAVQTTRDILEGAKKGLEFVRPVAVDLT
d150-160    61  DKYAGKNRNHVNFFQELADLDRQLISLIHDQANAVQTTRDILEGAKKGLEFVRPVAVDLT
d136-154    61  DKYAGKNRNHVNFFQELADLDRQLISLIHDQANAVQTTRDILEGAKKGLEFVRPVAVDLT
d166-182    61  DKYAGKNRNHVNFFQELADLDRQLISLIHDQANAVQTTRDILEGAKKGLEFVRPVAVDLT
d135-139    61  DKYAGKNRNHVNFFQELADLDRQLISLIHDQANAVQTTRDILEGAKKGLEFVRPVAVDLT
d142-145    61  DKYAGKNRNHVNFFQELADLDRQLISLIHDQANAVQTTRDILEGAKKGLEFVRPVAVDLT
d138-145    61  DKYAGKNRNHVNFFQELADLDRQLISLIHDQANAVQTTRDILEGAKKGLEFVRPVAVDLT
d145-152    61  DKYAGKNRNHVNFFQELADLDRQLISLIHDQANAVQTTRDILEGAKKGLEFVRPVAVDLT
d149-154    61  DKYAGKNRNHVNFFQELADLDRQLISLIHDQANAVQTTRDILEGAKKGLEFVRPVAVDLT

Rv3616_wt  121  YIPVVGHALSAAFQAPFCAGAMAVVGGALAYLVVKTLINATQLLKLLAKLAELVAAAIAD
d136-183   121  YIPVVGHALSAAFQA---------------------------------------------
d150-160   121  YIPVVGHALSAAFQAPFCAGAMAVVGGAL----------TQLLKLLAKLAELVAAAIAD
d136-154   121  YIPVVGHALSAAFQA------------------KTLINATQLLKLLAKLAELVAAAIAD
d166-182   121  YIPVVGHALSAAFQAPFCAGAMAVVGGALAYLVVKTLINATQLLK---------------
d135-139   121  YIPVVGHALSAAFQ-----GAMAVVGGALAYLVVKTLINATQLLKLLAKLAELVAAAIAD
d142-145   121  YIPVVGHALSAAFQAPFCAGA----GGALAYLVVKTLINATQLLKLLAKLAELVAAAIAD
d138-145   121  YIPVVGHALSAAFQAPF--------GGALAYLVVKTLINATQLLKLLAKLAELVAAAIAD
d145-152   121  YIPVVGHALSAAFQAPFCAGAMAV--------VVKTLINATQLLKLLAKLAELVAAAIAD
d149-154   121  YIPVVGHALSAAFQAPFCAGAMAVVGGA------KTLINATQLLKLLAKLAELVAAAIAD

Rv3616_wt  181  IISDVADIIKGTLGEVWEFITNALNGLKELWDKLTGWVTGLFSRGWSNLESFFAGVPGLT
d136-183   136  ---DVADIIKGTLGEVWEFITNALNGLKELWDKLTGWVTGLFSRGWSNLESFFAGVPGLT
d150-160   170  IISDVADIIKGTLGEVWEFITNALNGLKELWDKLTGWVTGLFSRGWSNLESFFAGVPGLT
d136-154   162  IISDVADIIKGTLGEVWEFITNALNGLKELWDKLTGWVTGLFSRGWSNLESFFAGVPGLT
d166-182   166  --SDVADIIKGTLGEVWEFITNALNGLKELWDKLTGWVTGLFSRGWSNLESFFAGVPGLT
d135-139   176  IISDVADIIKGTLGEVWEFITNALNGLKELWDKLTGWVTGLFSRGWSNLESFFAGVPGLT
d142-145   177  IISDVADIIKGTLGEVWEFITNALNGLKELWDKLTGWVTGLFSRGWSNLESFFAGVPGLT
d138-145   173  IISDVADIIKGTLGEVWEFITNALNGLKELWDKLTGWVTGLFSRGWSNLESFFAGVPGLT
d145-152   173  IISDVADIIKGTLGEVWEFITNALNGLKELWDKLTGWVTGLFSRGWSNLESFFAGVPGLT
d149-154   175  IISDVADIIKGTLGEVWEFITNALNGLKELWDKLTGWVTGLFSRGWSNLESFFAGVPGLT
```

Figure 16B

```
Rv3616_wt  241 GATSGLSQVTGLFGAAGLSASSGLAHADSLASSASLPALAGIGGGSGFGGLPSLAQVHAA
d136-183   193 GATSGLSQVTGLFGAAGLSASSGLAHADSLASSASLPALAGIGGGSGFGGLPSLAQVHAA
d150-160   230 GATSGLSQVTGLFGAAGLSASSGLAHADSLASSASLPALAGIGGGSGFGGLPSLAQVHAA
d136-154   222 GATSGLSQVTGLFGAAGLSASSGLAHADSLASSASLPALAGIGGGSGFGGLPSLAQVHAA
d166-182   224 GATSGLSQVTGLFGAAGLSASSGLAHADSLASSASLPALAGIGGGSGFGGLPSLAQVHAA
d135-139   236 GATSGLSQVTGLFGAAGLSASSGLAHADSLASSASLPALAGIGGGSGFGGLPSLAQVHAA
d142-145   237 GATSGLSQVTGLFGAAGLSASSGLAHADSLASSASLPALAGIGGGSGFGGLPSLAQVHAA
d138-145   233 GATSGLSQVTGLFGAAGLSASSGLAHADSLASSASLPALAGIGGGSGFGGLPSLAQVHAA
d145-152   233 GATSGLSQVTGLFGAAGLSASSGLAHADSLASSASLPALAGIGGGSGFGGLPSLAQVHAA
d149-154   235 GATSGLSQVTGLFGAAGLSASSGLAHADSLASSASLPALAGIGGGSGFGGLPSLAQVHAA

Rv3616_wt  301 STRQALRPRADGPVGAAAEQVGGQSQLVSAQGSQGMGGPVGMGGMHPSSGASKGTTTKKY
d136-183   253 STRQALRPRADGPVGAAAEQVGGQSQLVSAQGSQGMGGPVGMGGMHPSSGASKGTTTKKY
d150-160   290 STRQALRPRADGPVGAAAEQVGGQSQLVSAQGSQGMGGPVGMGGMHPSSGASKGTTTKKY
d136-154   282 STRQALRPRADGPVGAAAEQVGGQSQLVSAQGSQGMGGPVGMGGMHPSSGASKGTTTKKY
d166-182   284 STRQALRPRADGPVGAAAEQVGGQSQLVSAQGSQGMGGPVGMGGMHPSSGASKGTTTKKY
d135-139   296 STRQALRPRADGPVGAAAEQVGGQSQLVSAQGSQGMGGPVGMGGMHPSSGASKGTTTKKY
d142-145   297 STRQALRPRADGPVGAAAEQVGGQSQLVSAQGSQGMGGPVGMGGMHPSSGASKGTTTKKY
d138-145   293 STRQALRPRADGPVGAAAEQVGGQSQLVSAQGSQGMGGPVGMGGMHPSSGASKGTTTKKY
d145-152   293 STRQALRPRADGPVGAAAEQVGGQSQLVSAQGSQGMGGPVGMGGMHPSSGASKGTTTKKY
d149-154   295 STRQALRPRADGPVGAAAEQVGGQSQLVSAQGSQGMGGPVGMGGMHPSSGASKGTTTKKY
```

1- Novex protein standard
2- Rv3616Δ136-183 Before induction (BI)
3- Rv3616Δ136-183 After induction (AI) 37°C
4- Rv3616Δ136-183 After induction (AI) 16°C
5- Rv3616Δ150-160 BI
6- Rv3616Δ150-160 AI 37°C
7- Rv3616Δ150-160 AI 16°C
8- Rv3616Δ136-154 BI
9- Rv3616Δ136-154 AI 37°C
10- Rv3616Δ136-154 AI 16°C
11- Rv3616Δ166-182 BI
12- Rv3616Δ166-182 AI 37°C
13- Rv3616Δ166-182 AI 16°C 1- Novex protein standard
2- Rv3616 Before induction (BI)
3- Rv3616Δ135-139 After induction (AI) 37°C
4- Rv3616Δ142-145 AI 37°C
5- Rv3616Δ145-152 AI 37°C
6- Rv3616Δ138-145 AI 37°C
7- Rv3616Δ149-154 AI 37°C
8- Rv3616 AI 37°C 1- Novex protein standard
2- Rv3616 Before induction (BI)
3- Rv3616 After induction (AI)
4- Rv3616Δ150-160 AI
5- Rv3616Δ136-154 AI
6- Rv3616Δ166-182 AI
7- Rv3616Δ135-139 AI
8- Rv3616Δ142-145 AI
9- Rv3616Δ145-152 AI
10- Rv3616Δ138-145 AI
11- Rv3616Δ149-154 AI

Figure 21

Cytokine profile of the Rv3616c -specific CD4 T cell response (medium removed-7dPII)

MODIFIED ANTIGENS

This application is a divisional application of U.S. Ser. No. 13/574,816 filed 24 Jul. 2012, which is the US National Stage of International Application No. PCT/EP2011/051158, filed 27 Jan. 2011, which claims benefit of the filing date of U.S. Provisional Application No. 61/298,710, filed 27 Jan. 2010, which is incorporated herein by reference in its entirety.

FIELD OF THE INVENTION

The present invention relates to modified *Mycobacterium tuberculosis* Rv3616c proteins, associated polynucleotides and the use of such proteins and polynucleotides in the treatment or prevention of tuberculosis, in particular use in the treatment or prevention of latent tuberculosis and in the prevention or delay of reactivation of tuberculosis.

BACKGROUND OF THE INVENTION

Tuberculosis (TB) is a chronic infectious disease caused by infection with *Mycobacterium tuberculosis* and other *Mycobacterium* species. It is a major disease in developing countries, as well as an increasing problem in developed areas of the world. More than 2 billion people are believed to be infected with TB bacilli, with about 9.2 million new cases of TB and 1.7 million deaths each year. 10% of those infected with TB bacilli will develop active TB, each person with active TB infecting an average of 10 to 15 others per year. While annual incidence rates have peaked globally, the number of deaths and cases is still rising due to population growth (World Health Organisation *Tuberculosis Facts* 2008).

*Mycobacterium tuberculosis* infects individuals through the respiratory route. Alveolar macrophages engulf the bacterium, but it is able to survive and proliferate by inhibiting phagosome fusion with acidic lysosomes. A complex immune response involving CD4+ and CD8+ T cells ensues, ultimately resulting in the formation of a granuloma. Central to the success of *Mycobacterium tuberculosis* as a pathogen is the fact that the isolated, but not eradicated, bacterium may persist for long periods, leaving an individual vulnerable to the later development of active TB.

Fewer than 5% of infected individuals develop active TB in the first years after infection. The granuloma can persist for decades and is believed to contain live *Mycobacterium tuberculosis* in a state of dormancy, deprived of oxygen and nutrients. However, recently it has been suggested that the majority of the bacteria in the dormancy state are located in non-macrophage cell types spread throughout the body (Locht et al, *Expert Opin. Biol. Ther.* 2007 7(11):1665-1677). The development of active TB occurs when the balance between the host's natural immunity and the pathogen changes, for example as a result of an immunosuppressive event (Anderson P *Trends in Microbiology* 2007 15(1):7-13; Ehlers S *Infection* 2009 37(2):87-95).

A dynamic hypothesis describing the balance between latent TB and active TB has also been proposed (Cardana P-J *Inflammation & Allergy—Drug Targets* 2006 6:27-39; Cardana P-J *Infection* 2009 37(2):80-86).

Although an infection may be asymptomatic for a considerable period of time, the active disease is most commonly manifested as an acute inflammation of the lungs, resulting in tiredness, weight loss, fever and a persistent cough. If untreated, serious complications and death typically result.

Tuberculosis can generally be controlled using extended antibiotic therapy, although such treatment is not sufficient to prevent the spread of the disease. Actively infected individuals may be largely asymptomatic, but contagious, for some time. In addition, although compliance with the treatment regimen is critical, patient behaviour is difficult to monitor. Some patients do not complete the course of treatment, which can lead to ineffective treatment and the development of drug resistance.

Multidrug-resistant TB (MDR-TB) is a form which fails to respond to first line medications. 5% of all TB cases are MDR-TB, with an estimated 490,000 new MDR-TB cases occurring each year. Extensively drug-resistant TB (XDR-TB) occurs when resistance to second line medications develops on top of MDR-TB. It is estimated that 40,000 new cases of the virtually untreatable XDR-TB arise annually (World Health Organisation *Tuberculosis Facts* 2008).

Even if a full course of antibiotic treatment is completed, infection with *M. tuberculosis* may not be eradicated from the infected individual and may remain as a latent infection that can be reactivated.

In order to control the spread of tuberculosis, an effective vaccination programme and accurate early diagnosis of the disease are of utmost importance.

Currently, vaccination with live bacteria is the most widely used method for inducing protective immunity. The most common *Mycobacterium* employed for this purpose is *Bacillus* Calmette-Guerin (BCG), an avirulent strain of *M. bovis* which was first developed over 60 years ago. However, the safety and efficacy of BCG is a source of controversy—while protecting against severe disease manifestation in children, BCG does not prevent the establishment of latent TB or the reactivation of pulmonary disease in adult life. Additionally, some countries, such as the United States, do not vaccinate the general public with this agent.

Almost all new generation TB vaccines which are currently in clinical development have been designed as pre-exposure vaccines. These include subunit vaccines, which have been particularly effective in boosting immunity induced by prior BCG vaccination, and advanced live mycobacterial vaccines which aim to replace BCG with more efficient and/or safer strains. Although these vaccines aim to improve resistance to infection, they are likely to be less effective as post-exposure or therapeutic vaccines in latent TB cases (Lin M Y et al *Endocrine, Metabolic & Immune Disorders—Drug Targets* 2008 8:15-29).

Example 2 of US20080269151 discloses the cloning, construction and expression of certain modified Rv3616c proteins, including: ΔTM-1, an Rv3616c polypeptide wherein residues 150 to 160 have been deleted (SEQ ID No: 22 of US20080269151); ΔTM-2, an Rv3616c polypeptide wherein residues 101 to 203 have been deleted (SEQ ID No: 24 of US20080269151); and a sequence wherein residues 150 to 160 of Rv3616c have been replaced by the antigen TbH9 (SEQ ID No: 60 of US20080269151).

BRIEF SUMMARY OF THE INVENTION

The present invention relates generally to the use of modified Rv3616c polypeptides, or polynucleotides encoding them, in the field of latent Mycobacterial infections. Additionally, the present invention relates to particular modified Rv3616c proteins. The inventors have surprisingly discovered that disrupting the hydrophobicity of a particular region of a Rv3616c sequence can lead to improved expression without detrimental impact to immunogenic properties. The modified Rv3616c proteins are of use as TB antigens, in particular as latent TB antigens.

In its broadest aspect the present invention provides a modified Rv3616c protein in which the hydrophobicity of the amino acid residues corresponding to residues 134-183 of the H37Rv sequence has been disrupted, suitably a modified Rv3616c protein in which the hydrophobicity of the amino acid residues corresponding to residues 135-154 of the H37Rv sequence is disrupted.

In one aspect of the invention there is provided a modified Rv3616c protein, said modified Rv3616c protein comprising a first polypeptide and a second polypeptide, the first polypeptide being located towards the C-terminus of the modified Rv3616c protein relative to the second polypeptide, and wherein:
 (i) the first polypeptide is a sequence having at least 90% identity to residues 1-133 of SEQ ID No: 1; and
 (ii) the second polypeptide is a sequence having at least 90% identity to residues 184-392 of SEQ ID No: 1;
wherein the first and second polypeptides are directly or indirectly linked.

In a second aspect of the invention there is provided a modified Rv3616c protein, said modified Rv3616c protein comprising a first polypeptide and a second polypeptide, the first polypeptide being located towards the C-terminus of the modified Rv3616c protein relative to the second polypeptide, and wherein:
 (i) the first polypeptide is a contiguous sequence of at least 100 amino acids within residues 1-133 of SEQ ID No: 1; and
 (ii) the second polypeptide is a contiguous sequence of at least 155 amino acids within residues 184-392 of SEQ ID No: 1;
wherein the first and second polypeptides are directly or indirectly linked.

In a third aspect of the invention there is provided a modified Rv3616c protein, said protein comprising or, alternatively, consisting essentially or consisting of, a Rv3616c sequence in which at least one amino acid (e.g. at least 2) has been deleted from the region corresponding to residues 134-183 in SEQ ID No:1.

A fourth aspect of the invention provides a modified Rv3616c protein, said protein comprising a first polypeptide and a second polypeptide, the first polypeptide being located towards the N-terminus relative to the second polypeptide, and wherein:
 (i) the first polypeptide is a contiguous sequence of at least 100 amino acids within residues 1-133 of SEQ ID No: 1; and
 (ii) the second polypeptide is a contiguous sequence of at least 155 amino acids within residues 184-392 of SEQ ID No: 1;
wherein the first and second polypeptides are directly or indirectly linked via a third polypeptide, said third polypeptide corresponding to residues 134-183 in SEQ ID No:1 in which at least 1 amino acid (e.g. at least 2) has been deleted.

A fifth aspect of the invention provides modified Rv3616c proteins comprising a first polypeptide and a second polypeptide, the first polypeptide being located towards the N-terminus relative to the second polypeptide, and wherein:
 (i) the first polypeptide is a contiguous sequence of at least 100 amino acids within residues 1-134 of SEQ ID No: 1; and
 (ii) the second polypeptide is a contiguous sequence of at least 175 amino acids within residues 155-392 of SEQ ID No: 1;
wherein the first and second polypeptides are either directly linked or indirectly linked via a third polypeptide, wherein said third polypeptide corresponds to residues 135-154 in SEQ ID No:1 in which at least 1 amino acid (e.g. at least 2) has been deleted.

A sixth aspect of the invention provides a modified Rv3616c protein, said protein comprising a first polypeptide and a second polypeptide, the first polypeptide being located towards the N-terminus relative to the second polypeptide, and wherein:
 (i) the first polypeptide is a sequence having at least 90% identity to residues 1-133 of SEQ ID No: 1; and
 (ii) the second polypeptide is a sequence having at least 90% identity to residues 184-392 of SEQ ID No: 1;
wherein the first and second polypeptides are directly linked or indirectly linked via a third polypeptide, said third polypeptide having at least 90% identity to a sequence corresponding to residues 134-183 in SEQ ID No:1 in which a contiguous portion of at least 3 amino acids (e.g. at least 4) has been deleted.

A seventh aspect of the invention provides modified Rv3616c proteins comprising a first polypeptide and a second polypeptide, the first polypeptide being located towards the N-terminus relative to the second polypeptide, and wherein:
 (i) the first polypeptide is a sequence having at least 90% identity to residues 1-134 of SEQ ID No: 1; and
 (ii) the second polypeptide is a sequence having at least 90% identity to residues 155-392 of SEQ ID No: 1;
wherein the first and second polypeptides are either directly linked or indirectly linked via a third polypeptide, said third polypeptide having at least 80% identity to a sequence corresponding to residues 135-154 in SEQ ID No:1 in which a contiguous portion of at least 3 amino acids (e.g. at least 4) has been deleted.

In an eighth aspect of the invention there is provided a modified Rv3616c protein, said protein comprising a Rv3616c sequence in which a contiguous portion of at least 3 amino acids (e.g. at least 4) from the region corresponding to residues 134-183 in SEQ ID No: 1 has been substituted with hydrophilic residues.

Modified Rv3616c proteins may be based on a wild-type Rv3616c protein sequence from any strain of *M. tuberculosis*. For example, any one of SEQ ID Nos: 3-7, in particular any one of SEQ ID Nos: 3-6, may be substituted for SEQ ID No:1 in the foregoing embodiments.

Exemplary modified Rv3616c proteins according to the present invention are those comprising the amino acid sequences provided in SEQ ID Nos: 161-169, 179 and 180 (such as those consisting of the amino acid sequences provided in SEQ ID Nos: 161-169, 179 and 180). Of particular interest are those comprising the amino acid sequences provided in SEQ ID Nos: 161, 163-169, 179 and 180 (such as those consisting of the amino acid sequences provided in SEQ ID Nos: 161, 163-169, 179 and 180).

Also provided are such modified Rv3616c proteins for use as medicaments.

A further aspect of the invention relates to a method for inducing an immune response in a subject, comprising the administration of a modified Rv3616c protein.

A further aspect of the invention relates to a method for the treatment, amelioration or prevention of TB comprising the administration of an effective amount of a modified Rv3616c protein to a subject in need thereof, wherein said polypeptide induces an immune response. In a further aspect, the method further comprises inducing an immune response against *Mycobacterium tuberculosis*.

The use of a modified Rv3616c protein in the manufacture of a medicament for the treatment, amelioration or prevention of TB, represents another aspect of the invention.

The present invention provides a polynucleotide comprising a nucleic acid sequence encoding a modified Rv3616c protein. Exemplary polynucleotides comprising a nucleic acid sequence encoding modified Rv3616c proteins are those comprising the nucleotide sequences provided in SEQ ID Nos: 170-178, such as those consisting of the nucleotide sequences provided in SEQ ID Nos: 170-178. Other exemplary polynucleotides comprising a nucleic acid sequence encoding modified Rv3616c proteins are those comprising (e.g. consisting of) a nucleotide sequence encoding an amino acid sequences provided in SEQ ID Nos: 161-169, 179 or 180, such as SEQ ID Nos: 161, 163-169, 179 or 180.

Also provided is a polynucleotide comprising a nucleic acid sequence encoding a modified Rv3616c protein for use as a medicament.

A further aspect of the invention relates to a method for inducing an immune response in a subject, comprising the administration of a polynucleotide comprising a nucleic acid sequence encoding a modified Rv3616c protein.

A further aspect of the invention relates to a method for the treatment, amelioration, delaying or prevention of tuberculosis reactivation comprising the administration of an effective amount of a polynucleotide comprising a nucleic acid sequence encoding a modified Rv3616c protein to a subject in need thereof, wherein said polypeptide induces and immune response. In a further aspect, the method further comprises inducing an immune response against *Mycobacterium tuberculosis*.

Use of a polynucleotide comprising a nucleic acid sequence encoding a polypeptide comprising a modified Rv3616c protein in the manufacture of a medicament for the treatment, amelioration or prevention of TB, represents another aspect of the invention.

Additionally, there is provided a pharmaceutical composition comprising:
(a) a modified Rv3616c protein; or
(b) a polynucleotide comprising a nucleic acid sequence encoding a modified Rv3616c protein;
and
(c) a pharmaceutically acceptable carrier or excipient.

Further, there is provided an immunogenic composition comprising:
(a) a modified Rv3616c protein; or
(b) a polynucleotide comprising a nucleic acid sequence encoding a modified Rv3616c protein;
and
(c) a non-specific immune response enhancer.

Also provided is an expression vector comprising a nucleic acid sequence encoding a modified Rv3616c protein.

Host cells, transformed with said expression vector, form a further aspect of the invention. Additionally provided is a host cell which recombinantly expresses a modified Rv3616c protein.

Further, there is provided a method for the production of a modified Rv3616c protein; said method comprising the step of recombinantly expressing said polypeptide within a host cell.

Also provided are diagnostic kits comprising:
(a) a modified Rv3616c protein;
(b) apparatus sufficient to contact said modified Rv3616c protein with a sample (e.g. whole blood or more suitably PBMC) from an individual; and
(c) means to quantify the T cell response of the sample.

Another aspect of the invention relates to a diagnostic kit comprising:
(a) a modified Rv3616c protein; and
(b) apparatus sufficient to contact said modified Rv3616c protein with the dermal cells of a patient.

A further aspect of the invention relates to a method for detecting *Mycobacterium tuberculosis* infection in a subject comprising:
(a) contacting a sample from said subject with a modified Rv3616c protein; and
(b) detecting in the biological sample the presence of antibodies that bind to the modified Rv3616c protein.

The invention also provides a diagnostic kit comprising:
(a) a modified Rv3616c protein, which protein is optionally immobilised on a solid support; and
(b) a detection reagent.

In one embodiment the subject receiving a modified Rv3616c protein, polynucleotide or composition according the invention may have active tuberculosis (e.g. active infection by *M. tuberculosis*). In a second embodiment the subject may have latent tuberculosis (e.g. dormant infection by *M. tuberculosis*). In a third embodiment the subject may be free from tuberculosis (e.g. free from infection by *M. tuberculosis*).

A subject receiving a modified Rv3616c protein, polynucleotide or composition according to the invention may have previously been vaccinated for tuberculosis (e.g. vaccinated against infection by *M. tuberculosis*), such as having been vaccinated with a *Bacillus* Calmette-Guerin (BCG). Alternatively, a subject receiving a polypeptide, polynucleotide or composition of the invention may not have previously been vaccinated for tuberculosis (e.g. not vaccinated against infection by *M. tuberculosis*), such as not having been vaccinated with a *Bacillus* Calmette-Guerin (BCG).

A modified Rv3616c protein, polynucleotide or composition according the invention may be provided for the purpose of:
treating active tuberculosis;
preventing active tuberculosis (such as by administering to a subject who is uninfected, or alternatively a subject who has a latent infection);
treating latent tuberculosis;
preventing latent tuberculosis; or
preventing or delaying reactivation of tuberculosis (especially the delay of TB reactivation, for example by a period of months, years or even indefinitely).

There is also provided a method for the treatment of latent TB comprising the steps:
(i) identifying a subject as having a latent TB infection (e.g. by PPD or T cell based assays); and
(ii) administering to said subject a safe and effective amount of a modified Rv3616c protein or polynucleotide encoding a modified Rv3616c protein (such as in the form of a pharmaceutical composition or immunogenic composition).

Also provided is the use of a polypeptide of the present invention in the manufacture of a diagnostic kit for the identification of TB (e.g. latent TB) in a test subject.

DESCRIPTION OF THE FIGURES

FIG. 3: Percentage of CD4 and CD8 cells from immunised CB6F1 mice expressing IFN-gamma and/or IL-2 and/or TNF-alpha cytokines at day 21 (i.e. 7 days post second immunisation).

FIG. 6: Percentage of CD4 and CD8 cells from immunised CB6F1 mice expressing IFN-gamma and/or IL-2 and/or TNF-alpha cytokines at day 35 (i.e. 7 days post third immunisation).

FIG. 9: Percentage of CD4 and CD8 cells from immunised C57BL/6 mice expressing IFN-gamma and/or IL-2 and/or TNF-alpha cytokines at day 21 (i.e. 7 days post second immunisation).

FIG. 11: Percentage of CD4 and CD8 cells from immunised C57BL/6 mice expressing IFN-gamma and/or IL-2 and/or TNF-alpha cytokines at day 35 (i.e. 7 days post third immunisation).

FIG. 15: Alignment of wild-type Rv3616c protein sequences from *Mycobacterium tuberculosis* H37Rv (SEQ ID No: 1), CDC1551 (SEQ ID No: 3), F11 (SEQ ID No: 4), Haarlem (SEQ ID No: 5), Strain C (SEQ ID No: 6) and *Mycobacterium bovis* BCG (SEQ ID No: 7).

FIGS. 16A and 16B: Alignment of exemplary modified Rv3616c protein sequences Rv3616 wt (SEQ ID No: 1), d136-183 (SEQ ID No: 161), d150-160 (SEQ ID No: 162), d136-154 (SEQ ID No: 163), d166-182 (SEQ ID No: 164), d135-139 (SEQ ID No: 165), d142-145 (SEQ ID No: 166), d138-145 (SEQ ID No: 167), d145-152 (SEQ ID No: 168) and d149-154 (SEQ ID No: 168).

FIG. 21: Cytokine profile of the Rv3616 specific CD4 T cell response at 7 days post second immunisation with Rv3616Δ138-145.

DESCRIPTION OF THE LISTED SEQUENCES

Figure 1:
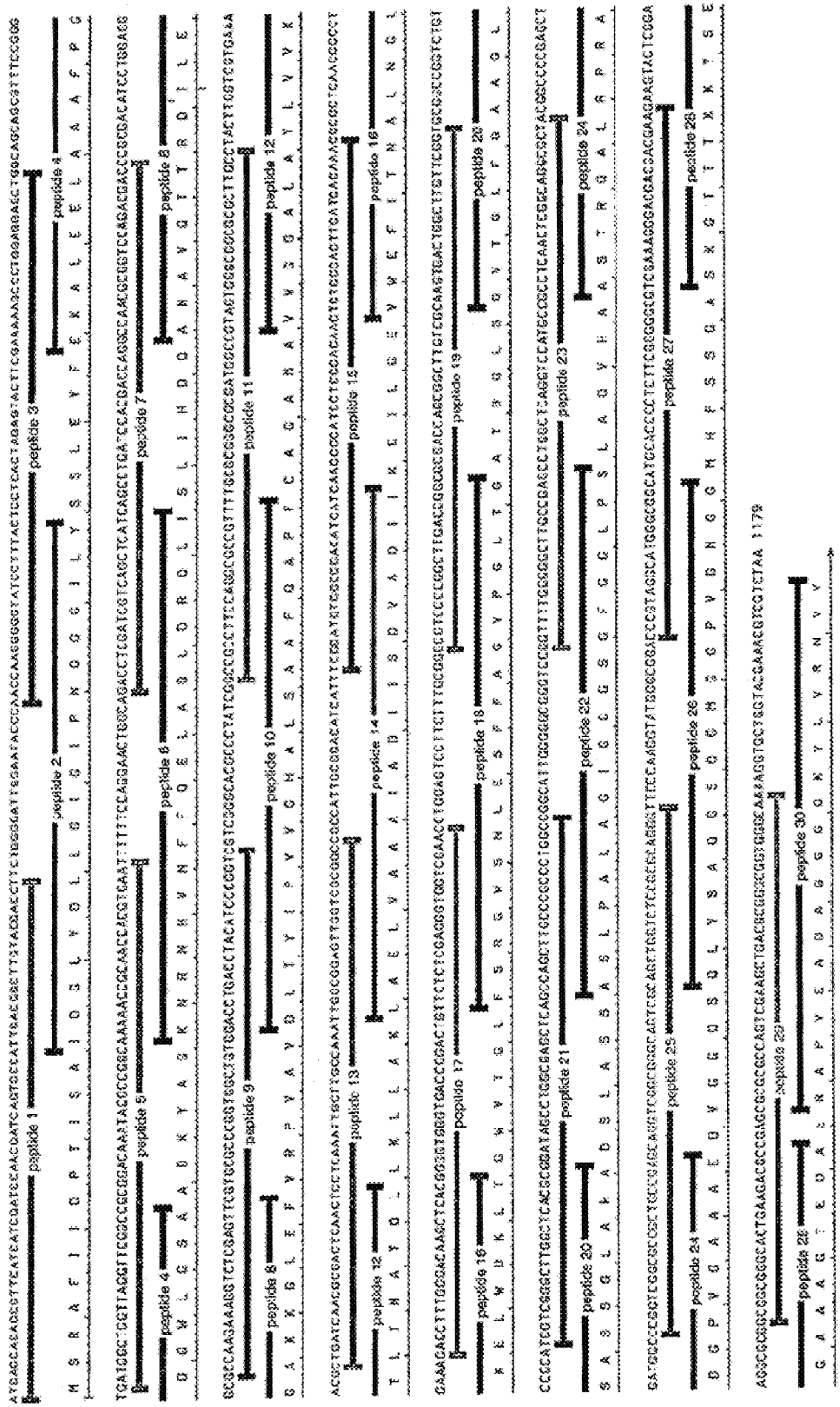
FIG. 1: Rv3616c peptide alignment with full length polypeptide sequence (SEQ ID NO: 1 and polynucleotide sequence (SEQ ID NO:2).

SEQ ID No: 1: polypeptide sequence of Rv3616c from *M. tuberculosis* H37Rv strain.
SEQ ID No: 2: polynucleotide sequence of Rv3616c from *M. tuberculosis* H37Rv strain.
SEQ ID No: 3: polypeptide sequence of Rv3616c from *M. tuberculosis* CDC1551 strain.
SEQ ID No: 4: polypeptide sequence of Rv3616c from *M. tuberculosis* F11 strain.
SEQ ID No: 5: polypeptide sequence of Rv3616c from *M. tuberculosis* Haarlem A strain.
SEQ ID No: 6: polypeptide sequence of Rv3616c from *M. tuberculosis* C strain.
SEQ ID No: 7: polypeptide sequence of Rv3616c from BCG.
SEQ ID No: 8: polypeptide sequence of Mtb8.4.
SEQ ID No: 9: polypeptide sequence of Mtb9.8.
SEQ ID No: 10: polypeptide sequence of Mtb9.9.
SEQ ID No: 11: polypeptide sequence of Ra12.
SEQ ID No: 12: polypeptide sequence of Ra35.
SEQ ID No: 13: polypeptide sequence of TbH9.
SEQ ID No: 14: polypeptide sequence of Mtb41.
SEQ ID No: 15: polypeptide sequence of ESAT-6.
SEQ ID No: 16: polypeptide sequence of Ag85A.
SEQ ID No: 17: polypeptide sequence of Ag85B.
SEQ ID No: 18: polypeptide sequence of alpha-crystallin.
SEQ ID No: 19: polypeptide sequence of MPT64.
SEQ ID No: 20: polypeptide sequence of Mtb32A.
SEQ ID No: 21: polypeptide sequence of Ser/Ala mutated mature Mtb32A.
SEQ ID No: 22: polypeptide sequence of TB10.4.
SEQ ID No: 23: polypeptide sequence of Mtb72f.
SEQ ID No: 24: polypeptide sequence of M72.
SEQ ID No: 25: polypeptide sequence of Mtb71f.
SEQ ID No: 26: polypeptide sequence of M92 fusion.
SEQ ID No: 27: polypeptide sequence of M103 fusion.
SEQ ID No: 28: polypeptide sequence of M114 fusion.
SEQ ID No: 29: putative human CD4 cell epitope 1.
SEQ ID No: 30: putative human CD4 cell epitope 2.
SEQ ID No: 31: putative human CD4 cell epitope 3.
SEQ ID No: 32: putative human CD4 cell epitope 4.
SEQ ID No: 33: putative human CD4 cell epitope 5.
SEQ ID No: 34: putative human CD4 cell epitope 6.
SEQ ID No: 35: putative human CD4 cell epitope 7.
SEQ ID No: 36: putative human CD4 cell epitope 8.
SEQ ID No: 37: putative human CD4 cell epitope 9.
SEQ ID No: 38: putative human CD4 cell epitope 10.
SEQ ID No: 39: putative human CD4 cell epitope 11.
SEQ ID No: 40: putative human CD4 cell epitope 12.
SEQ ID No: 41: putative human CD4 cell epitope 13.
SEQ ID No: 42: putative human CD4 cell epitope 14.
SEQ ID No: 43: putative human CD4 cell epitope 15.
SEQ ID No: 44: putative human CD4 cell epitope 16.
SEQ ID No: 45: putative human CD4 cell epitope 17.
SEQ ID No: 46: putative human CD4 cell epitope 18.
SEQ ID No: 47: putative human CD4 cell epitope 19.
SEQ ID No: 48: putative human CD8 cell epitope 1.
SEQ ID No: 49: putative human CD8 cell epitope 2.
SEQ ID No: 50: putative human CD8 cell epitope 3.
SEQ ID No: 51: putative human CD8 cell epitope 4.
SEQ ID No: 52: putative human CD8 cell epitope 5.
SEQ ID No: 53: putative human CD8 cell epitope 6.
SEQ ID No: 54: putative human CD8 cell epitope 7.

SEQ ID No: 55: putative human CD8 cell epitope 8.
SEQ ID No: 57: putative human CD8 cell epitope 10.
SEQ ID No: 58: putative human CD8 cell epitope 11.
SEQ ID No: 59: putative human CD8 cell epitope 12.
SEQ ID No: 60: putative human CD8 cell epitope 13.
SEQ ID No: 61: putative human CD8 cell epitope 14.
SEQ ID No: 62: putative human CD8 cell epitope 15.
SEQ ID No: 63: putative human CD8 cell epitope 16.
SEQ ID No: 64: putative human CD8 cell epitope 17.
SEQ ID No: 65: putative human CD8 cell epitope 18.
SEQ ID No: 66: putative human CD8 cell epitope 19.
SEQ ID No: 67: putative human CD8 cell epitope 20.
SEQ ID No: 68: putative human CD8 cell epitope 21.
SEQ ID No: 69: putative human CD8 cell epitope 22.
SEQ ID No: 70: putative human CD8 cell epitope 23.
SEQ ID No: 71: putative human CD8 cell epitope 24.
SEQ ID No: 72: putative human CD8 cell epitope 25.
SEQ ID No: 73: putative human CD8 cell epitope 26.
SEQ ID No: 74: putative human CD8 cell epitope 27.
SEQ ID No: 75: putative human CD8 cell epitope 28.
SEQ ID No: 76: putative human CD8 cell epitope 29.
SEQ ID No: 77: putative human CD8 cell epitope 30.
SEQ ID No: 78: putative human CD8 cell epitope 31.
SEQ ID No: 79: putative human CD8 cell epitope 32.
SEQ ID No: 80: putative human CD8 cell epitope 33.
SEQ ID No: 81: putative human CD8 cell epitope 34.
SEQ ID No: 82: putative human CD8 cell epitope 35.
SEQ ID No: 83: putative human CD8 cell epitope 36.
SEQ ID No: 84: putative human CD8 cell epitope 37.
SEQ ID No: 85: putative human CD8 cell epitope 38.
SEQ ID No: 86: putative human CD8 cell epitope 39.
SEQ ID No: 87: putative human CD8 cell epitope 40.
SEQ ID No: 88: putative human CD8 cell epitope 41.
SEQ ID No: 89: putative human CD8 cell epitope 42.
SEQ ID No: 90: putative human CD8 cell epitope 43.
SEQ ID No: 91: putative human CD8 cell epitope 44.
SEQ ID No: 93: putative human CD8 cell epitope 46.
SEQ ID No: 94: putative human CD8 cell epitope 47.
SEQ ID No: 95: putative human CD8 cell epitope 48.
SEQ ID No: 96: putative human CD8 cell epitope 49.
SEQ ID No: 97: putative human CD8 cell epitope 50.
SEQ ID No: 98: putative human CD8 cell epitope 51.
SEQ ID No: 99: putative human CD8 cell epitope 52.
SEQ ID No: 100: putative human CD8 cell epitope 53.
SEQ ID No: 101: putative human CD8 cell epitope 54.
SEQ ID No: 102: putative human CD8 cell epitope 55.
SEQ ID No: 103: putative human CD8 cell epitope 56.
SEQ ID No: 104: putative human CD8 cell epitope 57.
SEQ ID No: 105: putative human CD8 cell epitope 58.
SEQ ID No: 106: putative human CD8 cell epitope 59.
SEQ ID No: 107: putative human CD8 cell epitope 60.
SEQ ID No: 108: putative human CD8 cell epitope 61.
SEQ ID No: 109: putative human CD8 cell epitope 62.
SEQ ID No: 110: putative human CD8 cell epitope 63.
SEQ ID No: 111: putative human CD8 cell epitope 64.
SEQ ID No: 112: putative human CD8 cell epitope 65.
SEQ ID No: 113: putative human CD8 cell epitope 66.
SEQ ID No: 114: putative human CD8 cell epitope 67.
SEQ ID No: 115: putative human CD8 cell epitope 68.
SEQ ID No: 116: putative human CD8 cell epitope 69.
SEQ ID No: 117: putative human CD8 cell epitope 70.
SEQ ID No: 118: putative human CD8 cell epitope 71.
SEQ ID No: 119: putative human CD8 cell epitope 72.
SEQ ID No: 120: putative human CD8 cell epitope 73.
SEQ ID No: 121: putative human CD8 cell epitope 74.
SEQ ID No: 122: putative human CD8 cell epitope 75.
SEQ ID No: 123: putative human CD8 cell epitope 76.
SEQ ID No: 124: putative human CD8 cell epitope 77.
SEQ ID No: 125: putative human CD8 cell epitope 78.
SEQ ID No: 126: putative human CD8 cell epitope 79.
SEQ ID No: 127: peptide 1.
SEQ ID No: 129: peptide 3.
SEQ ID No: 130: peptide 4.
SEQ ID No: 131: peptide 5.
SEQ ID No: 132: peptide 6.
SEQ ID No: 133: peptide 7.
SEQ ID No: 134: peptide 8.
SEQ ID No: 135: peptide 9.
SEQ ID No: 136: peptide 10.
SEQ ID No: 137: peptide 11.
SEQ ID No: 138: peptide 12.
SEQ ID No: 139: peptide 13.
SEQ ID No: 140: peptide 14.
SEQ ID No: 141: peptide 15.
SEQ ID No: 142: peptide 16.
SEQ ID No: 143: peptide 17.
SEQ ID No: 144: peptide 18.
SEQ ID No: 145: peptide 19.
SEQ ID No: 146: peptide 20.
SEQ ID No: 147: peptide 21.
SEQ ID No: 148: peptide 22.
SEQ ID No: 149: peptide 23.
SEQ ID No: 150: peptide 24.
SEQ ID No: 151: peptide 25.
SEQ ID No: 152: peptide 26.
SEQ ID No: 153: peptide 27.
SEQ ID No: 154: peptide 28.
SEQ ID No: 155: peptide 29.
SEQ ID No: 156: peptide 30.
SEQ ID No: 157: polypeptide sequence of Rv1753c from *M. tuberculosis* H37Rv strain.
SEQ ID No: 158: polypeptide sequence of Rv2386c from *M. tuberculosis* H37Rv strain.
SEQ ID No: 159: polypeptide sequence of Rv2707c from *M. tuberculosis* H37Rv strain.
SEQ ID No: 160: *E. coli* codon optimised polynucleotide sequence for Rv3616c from *M. tuberculosis* H37Rv strain.
SEQ ID No: 161: polypeptide sequence of Rv3616cΔ136-183 derived from *M. tuberculosis* H37Rv strain.
SEQ ID No: 162: polypeptide sequence of Rv3616cΔ150-160 derived from *M. tuberculosis* H37Rv strain.
SEQ ID No: 163: polypeptide sequence of Rv3616cΔ136-154 derived from *M. tuberculosis* H37Rv strain.
SEQ ID No: 164: polypeptide sequence of Rv3616cΔ166-182 derived from *M. tuberculosis* H37Rv strain.
SEQ ID No: 165: polypeptide sequence of Rv3616cΔ135-139 derived from *M. tuberculosis* H37Rv strain.
SEQ ID No: 166: polypeptide sequence of Rv3616cΔ142-145 derived from *M. tuberculosis* H37Rv strain.
SEQ ID No: 167: polypeptide sequence of Rv3616cΔ138-145 derived from *M. tuberculosis* H37Rv strain.
SEQ ID No: 168: polypeptide sequence of Rv3616cΔ145-152 derived from *M. tuberculosis* H37Rv strain.
SEQ ID No: 169: polypeptide sequence of Rv3616cΔ149-154 derived from *M. tuberculosis* H37Rv strain.
SEQ ID No: 170: *E. coli* codon optimised polynucleotide sequence encoding Rv3616cΔ136-183 derived from *M. tuberculosis* H37Rv strain.
SEQ ID No: 171: *E. coli* codon optimised polynucleotide sequence encoding Rv3616cΔ150-160 derived from *M. tuberculosis* H37Rv strain.
SEQ ID No: 172: *E. coli* codon optimised polynucleotide sequence encoding Rv3616cΔ136-154 derived from *M. tuberculosis* H37Rv strain.

SEQ ID No: 173: E. coli codon optimised polynucleotide sequence encoding Rv3616cΔ166-182 derived from M. tuberculosis H37Rv strain.

SEQ ID No: 174: *E. coli* codon optimised polynucleotide sequence encoding Rv3616cΔ135-139 derived from *M. tuberculosis* H37Rv strain.

SEQ ID No: 175: *E. coli* codon optimised polynucleotide sequence encoding Rv3616cΔ142-145 derived from *M. tuberculosis* H37Rv strain.

SEQ ID No: 176: *E. coli* codon optimised polynucleotide sequence encoding Rv3616cΔ138-145 derived from *M. tuberculosis* H37Rv strain.

SEQ ID No: 177: *E. coli* codon optimised polynucleotide sequence encoding Rv3616cΔ145-152 derived from *M. tuberculosis* H37Rv strain.

SEQ ID No: 178: *E. coli* codon optimised polynucleotide sequence encoding Rv3616cΔ149-154 derived from *M. tuberculosis* H37Rv strain.

SEQ ID No: 179: polypeptide sequence of modified Rv3616c protein based on separating and rearrangement around the residues 137-139 from *M. tuberculosis* H37Rv strain, including deletion of Cys138.

SEQ ID No: 180: polypeptide sequence of modified Rv3616c protein based on separating and rearrangement around the residues 152-153 from *M. tuberculosis* H37Rv strain.

DETAILED DESCRIPTION

The present invention relates generally to the use of modified Rv3616c polypeptides, or polynucleotides encoding them, in the field of latent Mycobacterial infections. Additionally, the present invention relates to particular modified Rv3616c proteins. The inventors have surprisingly discovered that disrupting the hydrophobicity of a particular region of a Rv3616c protein sequence can lead to improved expression without substantial detrimental impact to immunogenic properties. The modified Rv3616c proteins are of use as TB antigens, in particular as latent TB antigens.

Several of the proteins which are strongly expressed during the early stages of *Mycobacterium* infection have been shown to provide strong protective efficacy in animal vaccination models. However, vaccination with antigens which are highly expressed during the early stages of infection may not provide an optimal immune response for dealing with later stages of infection. Adequate control during latent infection may require T cells which are specific for the particular antigens which are expressed at that time.

Post-exposure vaccines which directly target the dormant persistent bacteria may aid in protecting against TB reactivation, thereby enhancing TB control, or even enabling clearance of the infection. A vaccine targeting latent TB could therefore significantly and economically reduce global TB infection rates.

Subunit vaccines based on late stage antigens could also be utilised in combination with early stage antigens to provide a multiphase vaccine. Alternatively, late stage antigens could be used to complement and improve BCG vaccination (either by boosting the BCG response or through the development of advanced recombinant BCG strains).

While macrophages have been shown to act as the principal effectors of *Mycobacterium* immunity, T cells are the predominant inducers of such immunity. The essential role of T cells in protection against tuberculosis is illustrated by the increased rates of TB reactivation in human immunodeficiency virus infected individuals, due to the associated depletion of CD4+ T cells. Furthermore, adoptive transfer of CD4+ T cells taken at the height of the primary immune response to *M. tuberculosis* has been shown to confer protection against *M. tuberculosis* in T cell deficient mice (Orme et al *J. Exp. Med.* 1983 158:74-83).

*Mycobacterium*-reactive CD4+ T cells have been shown to be potent producers of γ-interferon (IFN-γ), which, in turn, has been shown to trigger the anti-mycobacterial effects of macrophages in mice (Flynn et al. *J. Exp. Med.* 1993 178:2249-2254). While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, interleukin-12 (IL-12) has been shown to play a role in stimulating resistance to *M. tuberculosis* infection. For a review of the immunology of *M. tuberculosis* infection, see Chan & Kaufmann, *Tuberculosis: Pathogenesis, Protection and Control* (Bloom ed., 1994), *Tuberculosis* (2nd ed., Rom and Garay, eds., 2003), and *Harrison's Principles of Internal Medicine*, Chapter 150, pp. 953-966 (16th ed., Braunwald, et al., eds., 2005).

Diagnosis of latent TB infection is commonly achieved using the tuberculin skin test, which involves intradermal exposure to tuberculin protein-purified derivative (PPD). Antigen-specific T cell responses result in measurable induration at the injection site by 48-72 hours after injection, which indicates exposure to mycobacterial antigens. Sensitivity and specificity have, however, been a problem with this test, and individuals vaccinated with BCG cannot always be easily distinguished from infected individuals (this is particularly important in light of the fact that BCG does not protect against latent infection). In general, individuals who have received BCG but are not infected by *M. tuberculosis* show a PPD reaction below 10 mm in diameter whereas people who have a PPD reaction above 10 mm in diameter are considered to have been infected by *M. tuberculosis*. However, this rule is not applicable to individuals with immunosuppression due to HIV infection, which may result in a PPD reaction below 10 mm in diameter); or in endemic countries, where people infected by non-tuberculosis mycobacteria can show a PPD reaction above 10 mm in diameter.

Progress over recent years has seen the development of in vitro T cell based assays, based on interferon-gamma release and using antigens which are more specific to *M. tuberculosis* than PPD, namely ESAT-6 and CFP-10. These high specificity tests appear to be at least as sensitive as the tuberculin skin test and also demonstrate less cross-reactivity due to BCG vaccination. See Pai M et al *Expert Rev. Mol. Diagn.* 2006 6(3):413-422 for a recent review of latent TB diagnosis. However, since ESAT-6/CFP-10 are early stage antigens, assays based on ESAT-6/CFP-10 may only perform optimally in recently infected people. Consequently, the identification of antigens specifically associated with latent tuberculosis may aid the development of more sensitive assays that could ensure detection of longer-term latent infections.

There remains a need for effective strategies for the treatment and prevention of tuberculosis, in particular the treatment and prevention of latent TB and the prevention of reactivation of TB.

Recently, a range of *M. tuberculosis* vaccine candidates have been proposed based on a bioinformatics analysis of the whole genome *M. tuberculosis* genome (Zvi et al. *BMC Medical Genetics* 2008 1:18) and on the testing of differentially expressed proteins in actively and latently infected individuals (Schuck S D et al. *PLoS ONE* 2009 4(5):e5590).

Rv3616c, also known as Mtb40, HTCC1 and EspA, is involved in the *Mycobacterium tuberculosis* ESX-1 secretion system (Woodsworth et al. *Infection and Immunity* 2008 76(9):4199-4205). Rv3616c has previously been implicated in the immune responses associated with tuberculosis (see, for example, WO98/53075). Al-Attiyah et al. *Clin. Exp. Immunol.* 2004 138:139-144 have shown that Rv3616c is well recognised (through PMBC proliferation and IFN-gamma production) by pulmonary tuberculosis patients. Mustafa et al. *Infect. Immun.* 2006 74(8):4566-4572 have investigated the recognition of Rv3616c by *M. bovis* infected and BCG vaccinated cattle.

International patent application PCT/EP2009/059580, published as WO2010/010177, describes the identification of Rv3616c as an antigen associated with the latent stage of TB infection.

International patent application WO2010/121618 proposes the use of constitutively expressed proteins and the genes encoding them for immunological compositions such as vaccines, including EspA (i.e. Rv3616c).

Vaccine antigens are desirably produced having their wild-type sequence, thus ensuring that the immunological responses solicited by the vaccine correspond closely to those required to counter infection by a pathogen. Nevertheless, efficient production of antigens is an important factor in reducing the costs associated with vaccine manufacture. Consequently, modified antigens which are conveniently expressed at high levels but which avoid any detrimental impact on immunogenicity could provide a substantial benefit. The present invention seeks to provide modified Rv3616c antigens which address this and other issues.

Without being limited by theory, amino acid residues 134-183 of the *Mycobacterium tuberculosis* H37Rv strain Rv3616c are thought to correspond to a potential transmembrane region, a low complexity region and a coiled-coil. The disruption of one, two or all three of these structural elements enables the resultant modified Rv3616c protein sequence to be expressed at improved levels.

Consequently, in its broadest aspect the present invention provides a modified Rv3616c protein in which the hydrophobicity of the amino acid residues corresponding to residues 134-183 of the H37Rv sequence has been disrupted, suitably a modified Rv3616c protein in which the hydrophobicity of the amino acid residues corresponding to residues 135-154 of the H37Rv sequence is disrupted.

By the term 'disrupting the hydrophobicity' is meant a sequence modification which results in a sufficiently reduced hydrophobicity such that the modified Rv3616c protein sequence may be expressed more efficiently.

Desirably, the extent of modifications relative to the wild-type sequence should be kept to a minimum, to reduce the likelihood of any detrimental impact on immunogenicity.

As used herein, a 'direct peptide linkage' is a peptide linkage in which two peptides are linked via peptide bonds directly to each other and without an intervening amino acid sequence. An 'indirect peptide linkage' is a peptide linkage in which two peptides are linked via peptide bonds to a third, intervening peptide.

In the context of the present invention, four main approaches exist for disrupting the hydrophobicity—namely, separating hydrophobic residues, deleting hydrophobic residues, substituting hydrophobic residues with hydrophilic residues and adding hydrophilic residues. The skilled person will recognise that a combination of such approaches may also be utilised. However, as mentioned previously the extent of the sequence modifications should ideally be minimised to avoid unnecessary detrimental impact on immunogenicity.

Separating hydrophobic residues may be achieved by splitting an Rv3616c protein sequence at a location between the amino acids corresponding to residues 133 to 184 of SEQ ID No: 1 into an N-terminal and a C-terminal fragment, followed by rearranging such portions such that the N-terminal fragment is located in the C-terminal region of the modified Rv3616c protein and the C-terminal fragment is located in the N-terminal region of the modified Rv3616c protein.

In one aspect of the invention there is provided a modified Rv3616c protein, said modified Rv3616c protein comprising a first polypeptide and a second polypeptide, the first polypeptide being located towards the C-terminus of the modified Rv3616c protein relative to the second polypeptide, and wherein:
  (i) the first polypeptide is a sequence having at least 90% identity to residues 1-133 of SEQ ID No: 1; and
  (ii) the second polypeptide is a sequence having at least 90% identity to residues 184-392 of SEQ ID No: 1;
wherein the first and second polypeptides are directly or indirectly linked.

In some embodiments the modified Rv3616c protein consists essentially of, or alternatively consists of, a first polypeptide and a second polypeptide, the first polypeptide being located towards the C-terminus of the modified Rv3616c protein relative to the second polypeptide, and wherein:
  (i) the first polypeptide is a sequence having at least 90% identity to residues 1-133 of SEQ ID No: 1; and
  (ii) the second polypeptide is a sequence having at least 90% identity to residues 184-392 of SEQ ID No: 1;
wherein the first and second polypeptides are directly or indirectly linked.

The first polypeptide may be a sequence having at least 95% identity to residues 1-133 of SEQ ID No: 1, such as at least 97% identity, at least 98% identity, at least 99% identity or even 100% identical.

The second polypeptide may be a sequence having at least 95% identity to residues 184-392 of SEQ ID No: 1, such as at least 97% identity, at least 98% identity, at least 99% identity or even 100% identical.

Suitably, the first polypeptide may be a sequence having at least 90% identity to residues 1-134 of SEQ ID No: 1, in particular at least 95% identity, such as at least 97% identity, at least 98% identity, at least 99% identity or even 100% identical.

Suitably, the second polypeptide may be a sequence having at least 90% identity to residues 155-392 of SEQ ID No: 1, in particular at least 95% identity, such as at least 97% identity, at least 98% identity, at least 99% identity or even 100% identical.

Suitably the modified Rv3616c protein of the first aspect does not comprise a sequence having at least 90% identity to full length SEQ ID No: 1. Suitably, the modified Rv3616c protein of the first aspect is less than 500 amino acids long, such as less than 450 amino acids long, in particular less than 400 amino acids long.

The peptide linkage may be direct. The peptide linkage may alternatively be indirect.

In a second aspect of the invention there is provided a modified Rv3616c protein, said modified Rv3616c protein comprising a first polypeptide and a second polypeptide, the first polypeptide being located towards the C-terminus of the modified Rv3616c protein relative to the second polypeptide, and wherein:
  (iii) the first polypeptide is a contiguous sequence of at least 100 amino acids within residues 1-133 of SEQ ID No: 1; and
  (iv) the second polypeptide is a contiguous sequence of at least 155 amino acids within residues 184-392 of SEQ ID No: 1;

wherein the first and second polypeptides are directly or indirectly linked.

In some embodiments the modified Rv3616c protein consists essentially of, or alternatively consists of, a first polypeptide and a second polypeptide, the first polypeptide being located towards the C-terminus of the modified Rv3616c protein relative to the second polypeptide, and wherein:
  (i) the first polypeptide is a contiguous sequence of at least 100 amino acids within residues 1-133 of SEQ ID No: 1; and
  (ii) the second polypeptide is a contiguous sequence of at least 155 amino acids within residues 184-392 of SEQ ID No: 1;
wherein the first and second polypeptides are directly or indirectly linked.

The first polypeptide may be a contiguous sequence of at least 110 amino acids within residues 1-133 of SEQ ID No: 1, such as at least 120 amino acids or at least 130 amino acids, for example residues 1-133.

The second polypeptide may be a contiguous sequence of at least 180 amino acids within residues 184-392 of SEQ ID No: 1, such as at least 190 amino acids or at least 200 amino acids, for example residues 184-392.

Suitably, the first polypeptide may be a contiguous sequence of at least 100 amino acids within residues 1-134 of SEQ ID No: 1, in particular at least 110 amino acids, such as at least 120 amino acids or at least 130 amino acids, for example residues 1-134.

Suitably, the second polypeptide may be a contiguous sequence of at least 175 amino acids within residues 155-392 of SEQ ID No: 1, in particular at least 200 amino acids such as at least 210 amino acids or at least 220 amino acids, for example residues 155-392. Embodiments wherein the second polypeptide is a contiguous sequence of at least 235 amino acids within residues 155-392 of SEQ ID No: 1 are also of interest.

Suitably the modified Rv3616c protein of the second aspect does not comprise a contiguous sequence of more than 259 amino acids from SEQ ID No: 1. Alternatively, the modified Rv3616c protein of the second aspect does not comprise a contiguous sequence of more than 257 amino acids, a contiguous sequence of more than 255 amino acids or a contiguous sequence of more than 253 amino acids. Suitably the modified Rv3616c protein of the second aspect is less than 500 amino acids long, such as less than 450 amino acids long, in particular less than 400 amino acids long.

The peptide linkage may either be a direct or indirect linkage.

Examples of the first and second aspects include modified Rv3616c proteins wherein the first and second polypeptide correspond to the N-terminal and C-terminal fragments resulting from splitting an Rv3616c sequence at a location between the amino acids corresponding to residues 135-154 in SEQ ID No: 1, e.g. the residues 138-139 or 152-153, e.g. the residues 138-139 or 152-153 where the peptide linkage is direct. Suitably when the first and second polypeptides are rearranged, the start methionine is left at the N-terminus of the modified Rv3616c protein. See for example SEQ ID Nos: 179 and 180 which illustrate this type of arrangement.

Deleting hydrophobic residues may be achieved through the removal of at least one amino acid corresponding to residues 134 to 183 of SEQ ID No: 1. Deleted residues may be non-contiguous, and/or contiguous.

Suitably, deleting hydrophobic residues may be achieved through the removal of at least two amino acids corresponding to residues 134 to 183 of SEQ ID No: 1. Deleting hydrophobic residues may also be achieved through the removal of at least three amino acids corresponding to residues 134 to 183 of SEQ ID No: 1.

Deleted residues may be non-contiguous, and/or contiguous.

It may be noted that the wild-type Rv3616c sequences contain a Cys residue at location 138. Suitably, this Cys residue is deleted or replaced (e.g. C138Q).

In a third aspect of the invention there is provided a modified Rv3616c protein, said protein comprising or, alternatively, consisting essentially or consisting of, a Rv3616c sequence in which at least one amino acid (e.g. at least 2) has been deleted from the region corresponding to residues 134-183 in SEQ ID No:1.

The modified Rv3616c protein may comprise or, alternatively, consists essentially or consist of, a Rv3616c sequence in which a contiguous portion of at least 3 amino acids (e.g. at least 4) has been deleted from the region corresponding to residues 134-183 in SEQ ID No:1.

Of particular interest are modified Rv3616c proteins comprising a Rv3616c sequence in which at least 1 amino acid (e.g. at least 2) has been deleted from the region corresponding to residues 135-154 in SEQ ID No:1. Other sequences of interest are modified Rv3616c proteins comprising a Rv3616c sequence in which a contiguous portion of at least 3 amino acids (e.g. at least 4) has been deleted from the region corresponding to residues 135-154 in SEQ ID No:1.

The deleted contiguous portion may be at least 5 amino acids (e.g. 5 to 30, such as 5 to 20 or 5 to 15), especially at least 6 amino acids (e.g. 6 to 30, such as 6 to 20 or 6 to 15), in particular at least 7 amino acids (e.g. 7 to 30, such as 7 to 20 or 7 to 15), such as at least 8 amino acids (e.g. 8 to 30, such as 8 to 20 or 8 to 15), or at least 10 amino acids (e.g. 10 to 30, such as 10 to 20 or 10 to 15).

In certain embodiments the deleted contiguous portion may be:
  4 amino acids, such as those corresponding to residues 142-145 in SEQ ID No:1;
  5 amino acids, such as those corresponding to residues 135-139 in SEQ ID No:1;
  6 amino acids, such as those corresponding to residues 149-154 in SEQ ID No:1;
  8 amino acids, such as those corresponding to residues 138-145 in SEQ ID No:1 or residues 145-152 in SEQ ID No:1;
  11 amino acids, such as those corresponding to residues 150-160 in SEQ ID No:1;
  17 amino acids, such as those corresponding to residues 166-182 in SEQ ID No:1;
  19 amino acids, such as those corresponding to residues 136-154 in SEQ ID No:1;
  31 amino acids, such as those corresponding to residues 136-166 in SEQ ID No:1; or
  48 amino acids, such as those corresponding to residues 136-183 in SEQ ID No:1.

In other embodiments the deleted contiguous portion may be 3 to 10 amino acid residues, such as 4 to 10, for example 4 to 8. The particular number of deleted amino acids may be 3, 4, 5, 6, 7, 8, 9 or 10, especially 4, 5, 6 or 8.

In other embodiments the deleted portion may be those corresponding to residues 135-138 in SEQ ID No: 1, residues 136-138 in SEQ ID No: 1, residues 137-138 in SEQ ID No: 1, residues 138-140 in SEQ ID No: 1, residues 138-141 in SEQ ID No: 1, residues 152-154 in SEQ ID No: 1 or the deletion of residues 149-151 in SEQ ID No: 1.

A fourth aspect of the invention provides a modified Rv3616c protein, said protein comprising a first polypeptide and a second polypeptide, the first polypeptide being located towards the N-terminus relative to the second polypeptide, and wherein:
- (iii) the first polypeptide is a contiguous sequence of at least 100 amino acids within residues 1-133 of SEQ ID No: 1; and
- (iv) the second polypeptide is a contiguous sequence of at least 155 amino acids within residues 184-392 of SEQ ID No: 1;

wherein the first and second polypeptides are directly or indirectly linked via a third polypeptide, said third polypeptide corresponding to residues 134-183 in SEQ ID No:1 in which at least 1 amino acid (e.g. at least 2) has been deleted.

In some embodiments the modified Rv3616c protein consists essentially of, or alternatively consists of, a first polypeptide and a second polypeptide, the first polypeptide being located towards the N-terminus relative to the second polypeptide, and wherein:
- (i) the first polypeptide is a contiguous sequence of at least 100 amino acids within residues 1-133 of SEQ ID No: 1; and
- (ii) the second polypeptide is a contiguous sequence of at least 155 amino acids within residues 184-392 of SEQ ID No: 1;

wherein the first and second polypeptides are directly or indirectly linked via a third polypeptide, said third polypeptide corresponding to residues 134-183 in SEQ ID No:1 in which at least 1 amino acid (e.g. at least 2) has been deleted.

Of particular interest are proteins comprising, or alternatively consisting essentially or consisting of, a first polypeptide and a second polypeptide, the first polypeptide being located towards the N-terminus relative to the second polypeptide, and wherein:
- (i) the first polypeptide is a contiguous sequence of at least 100 amino acids within residues 1-133 of SEQ ID No: 1; and
- (ii) the second polypeptide is a contiguous sequence of at least 155 amino acids within residues 184-392 of SEQ ID No: 1;

wherein the first and second polypeptides are directly or indirectly linked via a third polypeptide, said third polypeptide corresponding to residues 134-183 in SEQ ID No:1 in which at least a contiguous portion of at least 3 amino acids (e.g. at least 4) has been deleted.

The first polypeptide may be a contiguous sequence of at least 110 amino acids within residues 1-133 of SEQ ID No: 1, such as at least 120 amino acids or at least 130 amino acids (for example residues 1-133).

The second polypeptide may be a contiguous sequence of at least 180 amino acids within residues 184-392 of SEQ ID No: 1, such as at least 190 amino acids or at least 200 amino acids (for example residues 184-392).

The deleted contiguous portion from the residues corresponding to 134-183 in SEQ ID No:1 may be at least 5 amino acids (e.g. 5 to 30, such as 5 to 20 or 5 to 15), especially at least 6 amino acids (e.g. 6 to 30, such as 6 to 20 or 6 to 15), in particular at least 7 amino acids (e.g. 7 to 30, such as 7 to 20 or 7 to 15), such as at least 8 amino acids (e.g. 8 to 30, such as 8 to 20 or 8 to 15), or at least 10 amino acids (e.g. 10 to 30, such as 10 to 20 or 10 to 15).

In certain embodiments the deleted contiguous portion from the residues corresponding to 134-183 in SEQ ID No:1 may be:
- 4 amino acids, such as those corresponding to residues 142-145 in SEQ ID No:1;
- 5 amino acids, such as those corresponding to residues 135-139 in SEQ ID No:1;
- 6 amino acids, such as those corresponding to residues 149-154 in SEQ ID No:1;
- 8 amino acids, such as those corresponding to residues 138-145 in SEQ ID No:1 or residues 145-152 in SEQ ID No:1;
- 11 amino acids, such as those corresponding to residues 150-160 in SEQ ID No:1;
- 17 amino acids, such as those corresponding to residues 166-182 in SEQ ID No:1;
- 19 amino acids, such as those corresponding to residues 136-154 in SEQ ID No:1;
- 31 amino acids, such as those corresponding to residues 136-166 in SEQ ID No:1; or
- 48 amino acids, such as those corresponding to residues 136-183 in SEQ ID No:1.

In other embodiments the deleted contiguous portion from the residues corresponding to 134-183 in SEQ ID No:1 may be may be 3 to 10 amino acid residues, such as 4 to 10, for example 4 to 8. The particular number of deleted amino acids may be 3, 4, 5, 6, 7, 8, 9 or 10, especially 4, 5, 6 or 8.

In other embodiments the deleted contiguous portion from the residues corresponding to 134-183 in SEQ ID No:1 may be those corresponding to residues 135-138 in SEQ ID No: 1, residues 136-138 in SEQ ID No: 1, residues 137-138 in SEQ ID No: 1, residues 138-140 in SEQ ID No: 1, residues 138-141 in SEQ ID No: 1, residues 152-154 in SEQ ID No: 1 or the deletion of residues 149-151 in SEQ ID No: 1.

The first polypeptide and second polypeptide will in some embodiments be directly linked. In other embodiments the first polypeptide and second polypeptide will be indirectly linked via a third polypeptide. The third polypeptide may correspond to residues 134-183 in SEQ ID No: 1 wherein deletion has occurred at a single contiguous portion of at least 3 amino acids (e.g. at least 4). Additionally, the third polypeptide may correspond to residues 134-183 in SEQ ID No: 1 wherein deletions have occurred at a plurality of distinct locations (e.g. 1-10, such as 1-5, in particular 1 or 2 locations), each deletion being of 1-10, such as 1-5 amino acid residues.

Suitably the third polypeptide is 48 amino acids or fewer (e.g. 10-48, such as 20-48 or 30-48 residues), such as 46 amino acids or fewer (e.g. 10-46, such as 20-46 or 30-46 residues), 44 amino acids or fewer (e.g. 10-44, such as 20-44 or 30-44 residues), or 42 amino acids or fewer (e.g. 10-42, such as 20-42 or 30-42 residues).

A fifth aspect of the invention provides modified Rv3616c proteins comprising a first polypeptide and a second polypeptide, the first polypeptide being located towards the N-terminus relative to the second polypeptide, and wherein:
- (iii) the first polypeptide is a contiguous sequence of at least 100 amino acids within residues 1-134 of SEQ ID No: 1; and
- (iv) the second polypeptide is a contiguous sequence of at least 175 amino acids within residues 155-392 of SEQ ID No: 1;

wherein the first and second polypeptides are either directly linked or indirectly linked via a third polypeptide, wherein said third polypeptide corresponds to residues 135-154 in SEQ ID No:1 in which at least 1 amino acid (e.g. at least 2) has been deleted.

In some embodiments the modified Rv3616c protein consists essentially of, or alternatively consists of, a first polypeptide and a second polypeptide, the first polypeptide being located towards the N-terminus relative to the second polypeptide, and wherein:
- (i) the first polypeptide is a contiguous sequence of at least 100 amino acids within residues 1-134 of SEQ ID No: 1; and (ii) the second polypeptide is a contiguous sequence of at least 175 amino acids within residues 155-392 of SEQ ID No: 1;

wherein the first and second polypeptides are either directly linked or indirectly linked via a third polypeptide, wherein said third polypeptide corresponds to residues 135-154 in SEQ ID No:1 in which at least 1 amino acid (e.g. at least 2) has been deleted.

Of particular interest are proteins comprising, or alternatively consisting essentially or consisting of, a first polypeptide and a second polypeptide, the first polypeptide being located towards the N-terminus relative to the second polypeptide, and wherein:
(i) the first polypeptide is a contiguous sequence of at least 100 amino acids within residues 1-134 of SEQ ID No: 1; and
(ii) the second polypeptide is a contiguous sequence of at least 175 amino acids within residues 155-392 of SEQ ID No: 1;

wherein the first and second polypeptides are either directly linked or indirectly linked via a third polypeptide, wherein said third polypeptide corresponds to residues 135-154 in SEQ ID No:1 in which at least a contiguous portion of at least 3 amino acids (e.g. at least 4) has been deleted.

The first polypeptide may also be a contiguous sequence of at least 110 amino acids within residues 1-134 of SEQ ID No: 1, such as at least 120 amino acids or at least 130 amino acids, for example residues 1-134.

The second polypeptide may also be a contiguous sequence of at least 200 amino acids within residues 155-392 of SEQ ID No: 1, such as at least 210 amino acids or at least 220 amino acids, for example residues 155-392. Embodiments wherein the second polypeptide is a contiguous sequence of at least 235 amino acids within residues 155-392 of SEQ ID No: 1 are also of interest.

The deleted contiguous portion from the residues corresponding to 135-154 in SEQ ID No: 1 may be at least 5 amino acids (e.g. 5 to 20, such as 5 to 15 or 5 to 10), especially at least 6 amino acids (e.g. 6 to 20, such as 6 to 15 or 6 to 10), in particular at least 7 amino acids (e.g. 7 to 20, such as 7 to 15 or 7 to 10), such as at least 8 amino acids (e.g. 8 to 20, such as 8 to 15 or 8 to 10), or at least 10 amino acids (e.g. 10 to 20, such as 10 to 15).

In certain embodiments the deleted contiguous portion from the residues corresponding to 135-154 in SEQ ID No: 1 may be:
  4 amino acids, such as those corresponding to residues 142-145 in SEQ ID No:1;
  6 amino acids, such as those corresponding to residues 149-154 in SEQ ID No:1;
  8 amino acids, such as those corresponding to residues 138-145 in SEQ ID No:1 or residues 145-152 in SEQ ID No:1;
  11 amino acids, such as those corresponding to residues 150-160 in SEQ ID No:1; or
  19 amino acids, such as those corresponding to residues 136-154 in SEQ ID No:1.

In other embodiments the deleted contiguous portion from the residues corresponding to 135-154 may be 3 to 10 amino acid residues, such as 4 to 10, for example 4 to 8. The particular number of deleted amino acids may be 3, 4, 5, 6, 7, 8, 9 or 10, especially 4, 5, 6 or 8.

In other embodiments the deleted contiguous portion from the residues corresponding to 135-154 in SEQ ID No: 1 may be those corresponding to residues 135-138 in SEQ ID No: 1, residues 136-138 in SEQ ID No: 1, residues 137-138 in SEQ ID No: 1, residues 138-140 in SEQ ID No: 1, residues 138-141 in SEQ ID No: 1, residues 152-154 in SEQ ID No: 1 or the deletion of residues 149-151 in SEQ ID No: 1.

The first polypeptide and second polypeptide may in some embodiments be directly linked. In other embodiments the first polypeptide and second polypeptide may be indirectly linked via a third polypeptide. The third polypeptide may correspond to residues 135-154 in SEQ ID No: 1 wherein deletion has occurred at a single contiguous portion of at least 3 amino acids (e.g. at least 4). Additionally, the third polypeptide may correspond to residues 135-154 in SEQ ID No: 1 wherein deletions have occurred at a plurality of distinct locations (e.g. 1-10, such as 1-5, in particular 1 or 2 locations), each deletion being of 1-10, such as 1-5 amino acid residues.

Suitably the third polypeptide is 20 amino acids or fewer (e.g. 5-20, such as 10-20 residues), such as 18 amino acids or fewer (e.g. 5-18, such as 10-18 residues), 16 amino acids or fewer (e.g. 5-16, such as 10-16 residues), or 14 amino acids or fewer (e.g. 5-14, such as 10-14 residues).

A sixth aspect of the invention provides a modified Rv3616c protein, said protein comprising a first polypeptide and a second polypeptide, the first polypeptide being located towards the N-terminus relative to the second polypeptide, and wherein:
(iii) the first polypeptide is a sequence having at least 90% identity to residues 1-133 of SEQ ID No: 1; and
(iv) the second polypeptide is a sequence having at least 90% identity to residues 184-392 of SEQ ID No: 1;
wherein the first and second polypeptides are directly linked or indirectly linked via a third polypeptide, said third polypeptide having at least 90% identity to a sequence corresponding to residues 134-183 in SEQ ID No:1 in which a contiguous portion of at least 3 amino acids (e.g. at least 4) has been deleted.

In some embodiments the modified Rv3616c protein consists essentially of, or alternatively consists of, a first polypeptide and a second polypeptide, the first polypeptide being located towards the N-terminus relative to the second polypeptide, and wherein:
(i) the first polypeptide is a sequence having at least 90% identity to residues 1-133 of SEQ ID No: 1; and
(ii) the second polypeptide is a sequence having at least 90% identity to residues 184-392 of SEQ ID No: 1;
wherein the first and second polypeptides are directly linked or indirectly linked via a third polypeptide, said third polypeptide having at least 90% identity to a sequence corresponding to residues 134-183 in SEQ ID No:1 in which a contiguous portion of at least 3 amino acids (e.g. at least 4) has been deleted.

The first polypeptide may be a sequence having at least 95% identity to residues 1-133 of SEQ ID No: 1, such as at least 97% identity, at least 98% identity, at least 99% identity or even 100% identical.

The second polypeptide may be a sequence having at least 95% identity to residues 184-392 of SEQ ID No: 1, such as at least 97% identity, at least 98% identity, at least 99% identity or even 100% identical.

The first polypeptide and second polypeptide may in some embodiments be directly linked. In other embodiments the first polypeptide and second polypeptide will be indirectly linked via a third polypeptide. The third polypeptide may be a sequence having at least 95% identity to a sequence corresponding to residues 134-183 in SEQ ID No:1 in which a contiguous portion of at least 3 amino acids (e.g. at least 4) has been deleted, such as at least 97% identity, at least 98% identity, at least 99% identity or even 100% identical.

The contiguous portion deleted from the residues corresponding to 134-183 in SEQ ID No: 1 may be at least 5 amino acids (e.g. 5 to 30, such as 5 to 20 or 5 to 15), especially at least 6 amino acids (e.g. 6 to 30, such as 6 to 20 or 6 to 15), in particular at least 7 amino acids (e.g. 7 to 30, such as 7 to 20 or 7 to 15), such as at least 8 amino acids (e.g. 8 to 30, such as 8 to 20 or 8 to 15), or at least 10 amino acids (e.g. 10 to 30, such as 10 to 20 or 10 to 15).

In certain embodiments the contiguous portion deleted from the residues corresponding to 134-183 in SEQ ID No: 1 may be:
- 4 amino acids, such as those corresponding to residues 142-145 in SEQ ID No:1;
- 5 amino acids, such as those corresponding to residues 135-139 in SEQ ID No:1;
- 6 amino acids, such as those corresponding to residues 149-154 in SEQ ID No:1;
- 8 amino acids, such as those corresponding to residues 138-145 in SEQ ID No:1 or residues 145-152 in SEQ ID No:1;
- 11 amino acids, such as those corresponding to residues 150-160 in SEQ ID No:1;
- 17 amino acids, such as those corresponding to residues 166-182 in SEQ ID No:1;
- 19 amino acids, such as those corresponding to residues 136-154 in SEQ ID No:1;
- 31 amino acids, such as those corresponding to residues 136-166 in SEQ ID No:1; or
- 48 amino acids, such as those corresponding to residues 136-183 in SEQ ID No:1.

In other embodiments the deleted contiguous portion may be 3 to 10 amino acid residues, such as 4 to 10, for example 4 to 8. The particular number of deleted amino acids may be 3, 4, 5, 6, 7, 8, 9 or 10, especially 4, 5, 6 or 8.

In other embodiments the contiguous portion deleted from the residues corresponding to 134-183 in SEQ ID No: 1 may be those corresponding to residues 135-138 in SEQ ID No: 1, residues 136-138 in SEQ ID No: 1, residues 137-138 in SEQ ID No: 1, residues 138-140 in SEQ ID No: 1, residues 138-141 in SEQ ID No: 1, residues 152-154 in SEQ ID No: 1 or the deletion of residues 149-151 in SEQ ID No: 1.

Suitably the third polypeptide is 48 amino acids or fewer (e.g. 10-48, such as 20-48 or 30-48 residues), such as 46 amino acids or fewer (e.g. 10-46, such as 20-46 or 30-46 residues), 44 amino acids or fewer (e.g. 10-44, such as 20-44 or 30-44 residues), or 42 amino acids or fewer (e.g. 10-42, such as 20-42 or 30-42 residues).

A seventh aspect of the invention provides modified Rv3616c proteins comprising a first polypeptide and a second polypeptide, the first polypeptide being located towards the N-terminus relative to the second polypeptide, and wherein:

(i) the first polypeptide is a sequence having at least 90% identity to residues 1-134 of SEQ ID No: 1; and (ii) the second polypeptide is a sequence having at least 90% identity to residues 155-392 of SEQ ID No: 1;

wherein the first and second polypeptides are either directly linked or indirectly linked via a third polypeptide, said third polypeptide having at least 80% identity to a sequence corresponding to residues 135-154 in SEQ ID No:1 in which a contiguous portion of at least 3 amino acids (e.g. at least 4) has been deleted.

In some embodiments the modified Rv3616c protein consists essentially of, or alternatively consists of, a first polypeptide and a second polypeptide, the first polypeptide being located towards the N-terminus relative to the second polypeptide, and wherein:

(i) the first polypeptide is a sequence having at least 90% identity to residues 1-134 of SEQ ID No: 1; and (ii) the second polypeptide is a sequence having at least 90% identity to residues 155-392 of SEQ ID No: 1;

wherein the first and second polypeptides are either directly linked or indirectly linked via a third polypeptide, said third polypeptide having at least 80% identity to a sequence corresponding to residues 135-154 in SEQ ID No:1 in which a contiguous portion of at least 3 amino acids (e.g. at least 4) has been deleted.

The first polypeptide may be a sequence having at least 95% identity to residues 1-134 of SEQ ID No: 1, such as at least 97% identity, at least 98% identity, at least 99% identity or even 100% identical.

The second polypeptide may be a sequence having at least 95% identity to residues 155-392 of SEQ ID No: 1, such as at least 97% identity, at least 98% identity, at least 99% identity or even 100% identical.

The first polypeptide and second polypeptide will in some embodiments be directly linked. In other embodiments the first polypeptide and second polypeptide will be indirectly linked via a third polypeptide. The third polypeptide may be a sequence having at least 90% identity to a sequence corresponding to residues 135-154 in SEQ ID No:1 in which a contiguous portion of at least 3 amino acids (e.g. at least 4) has been deleted, such as at least 95% identity, at least 98% identity, at least 99% identity or even 100% identical.

The contiguous portion deleted contiguous portion from the residues corresponding to 135-154 in SEQ ID No: 1 may be at least 5 amino acids (e.g. 5 to 20, such as 5 to 15 or 5 to 10), especially at least 6 amino acids (e.g. 6 to 20, such as 6 to 15 or 6 to 10), in particular at least 7 amino acids (e.g. 7 to 20, such as 7 to 15 or 7 to 10), such as at least 8 amino acids (e.g. 8 to 20, such as 8 to 15 or 8 to 10), or at least 10 amino acids (e.g. 10 to 20, such as 10 to 15).

In certain embodiments the contiguous portion deleted contiguous portion from the residues corresponding to 135-154 in SEQ ID No: 1 may be:

- 4 amino acids, such as those corresponding to residues 142-145 in SEQ ID No:1;
- 6 amino acids, such as those corresponding to residues 149-154 in SEQ ID No:1;
- 8 amino acids, such as those corresponding to residues 138-145 in SEQ ID No:1 or residues 145-152 in SEQ ID No:1;
- 11 amino acids, such as those corresponding to residues 150-160 in SEQ ID No:1; or
- 19 amino acids, such as those corresponding to residues 136-154 in SEQ ID No:1.

In other embodiments the deleted contiguous portion may be 3 to 10 amino acid residues, such as 4 to 10, for example 4 to 8. The particular number of deleted amino acids may be 3, 4, 5, 6, 7, 8, 9 or 10, especially 4, 5, 6 or 8.

In other embodiments the contiguous portion deleted contiguous portion from the residues corresponding to 135-154 in SEQ ID No: 1 may be those corresponding to residues 135-138 in SEQ ID No: 1, residues 136-138 in SEQ ID No: 1, residues 137-138 in SEQ ID No: 1, residues 138-140 in SEQ ID No: 1, residues 138-141 in SEQ ID No: 1, residues 152-154 in SEQ ID No: 1 or the deletion of residues 149-151 in SEQ ID No: 1.

Suitably the third polypeptide is 20 amino acids or fewer (e.g. 5-20, such as 10-20 residues), such as 18 amino acids or fewer (e.g. 5-18, such as 10-18 residues), 16 amino acids or fewer (e.g. 5-16, such as 10-16 residues), or 14 amino acids or fewer (e.g. 5-14, such as 10-14 residues).

Substituting hydrophobic residues may be achieved through the replacement of at least one (e.g. at least 2) amino acid corresponding to residues 134 to 183 of SEQ ID No: 1 with a hydrophilic residue. In this regard, suitable hydrophilic residues will typically be Gln (Q), Asp (D), Glu (E), Asn (N), His (H), Lys (K), Arg (R), Ser (S) or Thr (T).

Of particular interest is the replacement of at least one (e.g. at least 2) amino acid corresponding to residues 135 to 154 of SEQ ID No: 1 with a hydrophilic residue. In this regard, suitable hydrophilic residues will typically be Gln (Q), Asp (D), Glu (E), Asn (N), His (H), Lys (K), Arg (R), Ser (S) or Thr (T).

Substituted residues may be non-contiguous, although are suitably contiguous.

In a eighth aspect of the invention there is provided a modified Rv3616c protein, said protein comprising a Rv3616c sequence in which a contiguous portion of at least 3 amino acids (e.g. at least 4) from the region corresponding to residues 134-183 in SEQ ID No: 1 has been substituted with hydrophilic residues.

In some embodiments the modified Rv3616c protein consists essentially of, or alternatively consists of a Rv3616c sequence in which a contiguous portion of at least 3 amino acids (e.g. at least 4) from the region corresponding to residues 134-183 in SEQ ID No: 1 has been substituted with hydrophilic residues.

Of particular interest are modified Rv3616c proteins comprising an Rv3616c sequence in which a contiguous portion of at least 3 amino acids (e.g. at least 4) from the region corresponding to residues 135-154 in SEQ ID No: 1 has been substituted with hydrophilic residues.

The substituted contiguous portion may be at least 5 amino acids (e.g. 5 to 30, such as 5 to 20 or 5 to 15), especially at least 6 amino acids (e.g. 6 to 30, such as 6 to 20 or 6 to 15), in particular at least 7 amino acids (e.g. 7 to 30, such as 7 to 20 or 7 to 15), such as at least 8 amino acids (e.g. 8 to 30, such as 8 to 20 or 8 to 15), or at least 10 amino acids (e.g. 10 to 30, such as 10 to 20 or 10 to 15).

In certain embodiments the substituted contiguous portion may be:
  4 amino acids, such as those corresponding to residues 142-145 in SEQ ID No:1;
  5 amino acids, such as those corresponding to residues 135-139 in SEQ ID No:1;
  6 amino acids, such as those corresponding to residues 149-154 in SEQ ID No:1;
  8 amino acids, such as those corresponding to residues 138-145 in SEQ ID No:1 or residues 145-152 in SEQ ID No:1;
  11 amino acids, such as those corresponding to residues 150-160 in SEQ ID No:1;
  17 amino acids, such as those corresponding to residues 166-182 in SEQ ID No:1;
  19 amino acids, such as those corresponding to residues 136-154 in SEQ ID No:1;
  31 amino acids, such as those corresponding to residues 136-166 in SEQ ID No:1; or
  48 amino acids, such as those corresponding to residues 136-183 in SEQ ID No:1.

In other embodiments the substituted contiguous portion may be 3 to 10 amino acid residues, such as 4 to 10, for example 4 to 8. The particular number of substituted amino acids may be 3, 4, 5, 6, 7, 8, 9 or 10, especially 4, 5, 6 or 8.

In other embodiments the substituted portion may be those corresponding to residues 135-138 in SEQ ID No: 1, residues 136-138 in SEQ ID No: 1, residues 137-138 in SEQ ID No: 1, residues 138-140 in SEQ ID No: 1, residues 138-141 in SEQ ID No: 1, residues 152-154 in SEQ ID No: 1 or the deletion of residues 149-151 in SEQ ID No: 1.

Disrupting the hydrophobicity may also be achieved by adding hydrophilic residues, e.g. the addition of at least one hydrophilic amino acid residue (e.g. at least 2, such as 2-10) at a location between those residues corresponding to residues 133 to 184 of SEQ ID No: 1. Suitably, at least 3 hydrophilic residues may be added (e.g. 3 to 20, such as 3 to 15, especially 3 to 10), such as at least 4 residues (e.g. 4 to 20, such as 4 to 15, especially 4 to 10), in particular at least 5 residues (e.g. 5 to 20, such as 5 to 15, especially 5 to 10), optionally at least 6 residues (e.g. 6 to 20, such as 6 to 15, especially 6 to 10). In this regard, suitable hydrophilic residues will typically be Gln (Q), Asp (D), Glu (E), Asn (N), His (H), Lys (K), Arg (R), Ser (S) or Thr (T).

The additional hydrophilic residues will typically be located between those residues corresponding to residues 133 to 184 of SEQ ID No: 1, especially between those residues corresponding to residues 134 to 155 of SEQ ID No: 1 (such as between those residues corresponding to residues 135 to 154 of SEQ ID No: 1).

The additional hydrophilic residues may be distributed at different positions between those residues corresponding to residues 133 to 184 of SEQ ID No: 1 (e.g. 1-10 locations, such as 1-5, in particular 1 or 2 locations), each location having 1-10 additional hydrophilic residues, such as 1-5 additional residues. The additional hydrophilic residues will suitably be located in one contiguous group.

In particular embodiments of the modified Rv3616c proteins described in the various aspects above, the modified Rv3616c protein is not SEQ ID No: 162 (Rv3616cΔ150-160). In other embodiments the modified Rv3616c protein does not comprise SEQ ID No: 162 (Rv3616cΔ150-160).

Modified Rv3616c proteins may be based on a wild-type Rv3616c protein sequence from any strain of *M. tuberculosis*. For example, any one of SEQ ID Nos: 3-7, in particular any one of SEQ ID Nos: 3-6, may be substituted for SEQ ID No:1 in the foregoing embodiments.

Proteins of the various aspects discussed above are collectively referred to herein as modified Rv3616c proteins. Also provided are such modified Rv3616c proteins for use as medicaments, such as a medicament for the treatment or prevention of TB.

A further aspect of the invention relates to a method for inducing an immune response in a subject, comprising the administration of a modified Rv3616c protein.

A further aspect of the invention relates to a method for the treatment, amelioration or prevention of TB comprising the administration of a safe and effective amount of a modified Rv3616c protein to a subject in need thereof, wherein said polypeptide induces an immune response. In a further aspect, the method further comprises inducing an immune response against *Mycobacterium tuberculosis*.

A further aspect of the invention relates to a method for the treatment, amelioration, delaying or prevention of tuberculosis reactivation comprising the administration of an effective amount of a modified Rv3616c protein to a subject in need thereof, wherein said polypeptide induces and immune response. In a further aspect, the method further comprises inducing an immune response against *Mycobacterium tuberculosis*.

The use of a modified Rv3616c protein in the manufacture of a medicament for the treatment, amelioration or prevention of TB, represents another aspect of the invention.

The present invention provides a polynucleotide comprising a nucleic acid sequence encoding a modified Rv3616c protein. Also provided is a polynucleotide comprising a nucleic acid sequence encoding a modified Rv3616c protein for use as a medicament, such as a medicament for the treatment, amelioration or prevention of TB.

A further aspect of the invention relates to a method for inducing an immune response in a subject, comprising the administration of a polynucleotide comprising a nucleic acid sequence encoding a modified Rv3616c protein.

A further aspect of the invention relates to a method for the treatment, amelioration or prevention of TB comprising the administration of a safe and effective amount of a polynucleotide comprising a nucleic acid sequence encoding a modified Rv3616c protein to a subject in need thereof, wherein said polynucleotide induces an immune response. In a further aspect, the present invention provides a method for inducing an immune response against *Mycobacterium tuberculosis*.

A further aspect of the invention relates to a method for the treatment, amelioration, delaying or prevention of tuberculosis reactivation comprising the administration of an effective amount of a polynucleotide comprising a nucleic acid sequence encoding a modified Rv3616c protein to a subject in need thereof, wherein said polypeptide induces and immune response. In a further aspect, the method further comprises inducing an immune response against *Mycobacterium tuberculosis*.

Use of a polynucleotide comprising a nucleic acid sequence encoding a polypeptide comprising a modified Rv3616c protein in the manufacture of a medicament for the treatment, amelioration or prevention of TB, represents another aspect of the invention.

Additionally, there is provided a pharmaceutical composition comprising:
(a) a modified Rv3616c protein; or
(b) a polynucleotide comprising a nucleic acid sequence encoding a modified Rv3616c protein;
and
(c) a pharmaceutically acceptable carrier or excipient.

Further, there is provided an immunogenic composition comprising:
(a) a modified Rv3616c protein; or
(b) a polynucleotide comprising a nucleic acid sequence encoding a modified Rv3616c protein;
and
(c) a non-specific immune response enhancer.

Also provided is an expression vector comprising a nucleic acid sequence encoding a modified Rv3616c protein.

Host cells, transformed with said expression vector, form a further aspect of the invention. Additionally provided is a host cell which recombinantly expresses a modified Rv3616c protein.

Further, there is provided a method for the production of a modified Rv3616c protein; said method comprising the step of recombinantly expressing said polypeptide within a host cell.

Also provided are diagnostic kits comprising:
(a) a modified Rv3616c protein;
(b) apparatus sufficient to contact said modified Rv3616c protein with a sample (e.g. whole blood or more suitably PBMC) from an individual; and
(c) means to quantify the T cell response of the sample.

Another aspect of the invention relates to a diagnostic kit comprising:
(a) a modified Rv3616c protein; and
(b) apparatus sufficient to contact said modified Rv3616c protein with the dermal cells of a patient.

A further aspect of the invention relates to a method for detecting *Mycobacterium tuberculosis* infection in a subject comprising:

(a) contacting a sample from said subject with a modified Rv3616c protein; and
(b) detecting in the biological sample the presence of antibodies that bind to the modified Rv3616c protein.

The invention also provides a diagnostic kit comprising:
(a) a modified Rv3616c protein, which protein is optionally immobilised on a solid support; and
(b) a detection reagent.

In one embodiment the subject receiving a modified Rv3616c protein, polynucleotide or composition according the invention may have active tuberculosis (e.g. active infection by *M. tuberculosis*). In a second embodiment the subject may have latent tuberculosis (e.g. dormant infection by *M. tuberculosis*). In a third embodiment the subject may be free from tuberculosis (e.g. free from infection by *M. tuberculosis*).

A subject receiving a modified Rv3616c protein, polynucleotide or composition according to the invention may have previously been vaccinated for tuberculosis (e.g. vaccinated against infection by *M. tuberculosis*), such as having been vaccinated with a *Bacillus* Calmette-Guerin (BCG). Alternatively, a subject receiving a polypeptide, polynucleotide or composition of the invention may have not been previously vaccinated for tuberculosis (e.g. not vaccinated against infection by *M. tuberculosis*), such as not having been vaccinated with a *Bacillus* Calmette-Guerin (BCG).

A modified Rv3616c protein, polynucleotide or composition according the invention may be provided for the purpose of:
treating active tuberculosis;
preventing active tuberculosis (such as by administering to a subject who is uninfected, or alternatively a subject who has latent infection);
treating latent tuberculosis;
preventing latent tuberculosis; or
preventing or delaying reactivation of tuberculosis (especially the delay of TB reactivation, for example by a period of months, years or even indefinitely).

There is also provided a method for the treatment of latent TB comprising the steps:
(i) identifying a subject as having a latent TB infection (e.g. by PPD or T cell based assays); and
(ii) administering to said subject a safe and effective amount of a modified Rv3616c protein or polynucleotide encoding a modified Rv3616c protein (such as in the form of a pharmaceutical composition or immunogenic composition).

Also provided is the use of a polypeptide of the present invention in the manufacture of a diagnostic kit for the identification of TB (e.g. latent TB) in a test subject.

The term "*Mycobacterium* species of the tuberculosis complex" includes those species traditionally considered as causing the disease tuberculosis, as well as *Mycobacterium* environmental and opportunistic species that cause tuberculosis and lung disease in immune compromised patients, such as patients with AIDS, e.g., *M. tuberculosis, M. bovis*, or *M. africanum*, BCG, *M. avium, M. intracellulare, M. celatum, M. genavense, M. haemophilum, M. kansasii, M. simiae, M. vaccae, M. fortuitum*, and *M. scrofulaceum* (see, e.g., *Harrison's Principles of Internal Medicine*, Chapter 150, pp. 953-966 (16th ed., Braunwald, et al., eds., 2005). The present invention is particularly directed to infection with *M. tuberculosis*.

The term "active infection" refers to an infection (e.g. infection by *M. tuberculosis*) with manifested disease symptoms and/or lesions (suitably with manifested disease symptoms).

The terms "inactive infection", "dormant infection" or "latent infection" refer to an infection (e.g. infection by *M. tuberculosis*) without manifested disease symptoms and/or lesions (suitably without manifested disease symptoms). A subject with latent infection will suitably be one which tests positive for infection (e.g. by PPD or T cell based assays) but which has not demonstrated the disease symptoms and/or lesions which are associated with an active infection.

The term "primary tuberculosis" refers to clinical illness (e.g., manifestation of disease symptoms) directly following infection (e.g. infection by *M. tuberculosis*). See, *Harrison's Principles of Internal Medicine*, Chapter 150, pp. 953-966 (16th ed., Braunwald, et al., eds., 2005).

The terms "secondary tuberculosis" or "postprimary tuberculosis" refer to the reactivation of a dormant, inactive or latent infection (e.g. infection by *M. tuberculosis*). See, *Harrison's Principles of Internal Medicine*, Chapter 150, pp. 953-966 (16th ed., Braunwald, et al., eds., 2005).

The term "tuberculosis reactivation" refers to the later manifestation of disease symptoms in an individual that tests positive for infection (e.g. in a tuberculin skin test, suitably in an in vitro T cell based assay) test but does not have apparent disease symptoms. Suitably the individual will not have been re-exposed to infection. The positive diagnostic test indicates that the individual is infected, however, the individual may or may not have previously manifested active disease symptoms that had been treated sufficiently to bring the tuberculosis into an inactive or latent state. It will be recognised that methods for the prevention, delay or treatment of tuberculosis reactivation can be initiated in an individual manifesting active symptoms of disease.

The term "drug resistant" tuberculosis refers to an infection (e.g. infection by *M. tuberculosis*) wherein the infecting strain is not held static or killed (i.e. is resistant to) one or more of so-called "front-line" chemotherapeutic agents effective in treating tuberculosis (e.g., isoniazid, rifampin, ethambutol, streptomycin and pyrazinamide).

The term "multi-drug resistant" tuberculosis refers to an infection (e.g. infection by *M. tuberculosis*) wherein the infecting strain is resistant to two or more of "front-line" chemotherapeutic agents effective in treating tuberculosis.

A "chemotherapeutic agent" refers to a pharmacological agent known and used in the art to treat tuberculosis (e.g. infection by *M. tuberculosis*). Exemplified pharmacological agents used to treat tuberculosis include, but are not limited to amikacin, aminosalicylic acid, capreomycin, cycloserine, ethambutol, ethionamide, isoniazid, kanamycin, pyrazinamide, rifamycins (i.e., rifampin, rifapentine and rifabutin), streptomycin, ofloxacin, ciprofloxacin, clarithromycin, azithromycin and fluoroquinolones. "First-line" or "Frontline" chemotherapeutic agents used to treat tuberculosis that is not drug resistant include isoniazid, rifampin, ethambutol, streptomycin and pyrazinamide. "Second-line" chemotherapeutic agents used to treat tuberculosis that has demonstrated drug resistance to one or more "first-line" drugs include ofloxacin, ciprofloxacin, ethionamide, aminosalicylic acid, cycloserine, amikacin, kanamycin and capreomycin. Such pharmacological agents are reviewed in Chapter 48 of *Goodman and Gilman's The Pharmacological Basis of Therapeutics*, Hardman and Limbird eds., 2001.

The terms "polypeptide", "peptide" and "protein" are used interchangeably herein to refer to a polymer of amino acid residues. Naturally occurring amino acids are those encoded by the genetic code, as well as those amino acids that are later modified, e.g., hydroxyproline, γ-carboxyglutamate, and O-phosphoserine. Suitably a polypeptide according to the present invention will consist only of naturally occurring amino acid residues, especially those amino acids encoded by the genetic code.

"Nucleic acid" refers to deoxyribonucleotides or ribonucleotides and polymers thereof in either single- or double-stranded form. The term nucleic acid is used interchangeably with gene, cDNA, mRNA, oligonucleotide, and polynucleotide.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

By the term 'Rv3616c protein sequence' as used herein is meant the Rv3616c polypeptide sequence provided in SEQ ID No: 1 or a homologue thereof from a *Mycobacterium* species of the tuberculosis complex, e.g., a species such as *M. tuberculosis*, *M. bovis*, or *M. africanum*, or a *Mycobacterium* species that is environmental or opportunistic and that causes opportunistic infections such as lung infections in immune compromised hosts (e.g., patients with AIDS), e.g., BCG, *M. avium*, *M. intracellulare*, *M. celatum*, *M. genavense*, *M. haemophilum*, *M. kansasii*, *M. simiae*, *M. vaccae*, *M. fortuitum*, and *M. scrofulaceum* (see, e.g., *Harrison's Principles of Internal Medicine*, Chapter 150, pp. 953-966, 16th ed., Braunwald, et al., eds., 2005).

To ensure a high efficacy rate among vaccinated hosts, the components of a vaccine should be well conserved among the stains of clinical significance. Suitably, the Rv3616c protein is derived from *M. tuberculosis* H37Rv (i.e. the polypeptide sequence provided in SEQ ID No: 1) or a homologue thereof from another *M. tuberculosis* strain (such as CDC1551, F11, Haarlem A and C strains). Strains of *M. tuberculosis* which are associated with drug resistance (e.g. MDR or especially XDR) are a particularly valuable basis for the wild-type Rv3616c protein sequence. Strains of interest include:

CDC1551—transmissible and virulent strain

Haarlem family (such as Haarlem A)—Drug resistant strains found in crowded human populations. Members of the Haarlem family of *M. tuberculosis* strains have been found in many parts of the world. The first representative of the family was discovered in Haarlem, The Netherlands.

KZN4207—Drug sensitive isolate from patients in KwaZulu-Natal, South Africa

KZN1435—Multiple drug resistant (MDR) isolate from patients in KwaZulu-Natal, South Africa KZN605—Extensively drug resistant (XDR) isolate from patients in KwaZulu-Natal, South Africa C—Highly transmitted in New York City. In one study this strain was found to be more common among injection drug users and resistant to reactive nitrogen intermediates (Friedman et al. *J. Infect. Dis.* 1997 176(2):478-84)

94_M4241A—Isolated in San Francisco in 1994 from a patient born in China. This strain was previously analysed by genomic deletion analysis (Gagneux et al., *PNAS* 2006 103(8):2869-2873).

02_1987—Isolated in San Francisco in 2002 from a patient born in South Korea. This strain was previously analyzed by genomic deletion analysis (Gagneux et al., *PNAS* 2006 103(8):2869-2873).

T92—Isolated in San Francisco in 1999 from a patient born in The Philippines. This strain was published in Hirsh et al. *PNAS* 2004 101:4871-4876).

T85—Isolated in San Francisco in 1998 from a patient born in China. This strain was published in Hirsh et al. *PNAS* 2004 101:4871-4876).

EAS054—Isolated in San Francisco in 1993 from a patient born in India. This strain was previously analyzed by genomic deletion analysis (Gagneux et al., *PNAS* 2006 103(8):2869-2873).

Gagneux et al., *PNAS* 2006 103(8):2869-2873 and Herbert et al. Infect. Immun. 2007 75(12):5798-5805 provide valuable background on the range of *M. tuberculosis* strains which are known to exist.

Most suitably, the Rv3616c protein is selected from the polypeptide sequences provided in SEQ ID Nos: 1 and 3-7, in particular SEQ ID Nos: 1 and 3-6, such as SEQ ID No: 1. An alignment of SEQ ID Nos: 1 and 3-7 is provided in FIG. 15.

Modified Rv3616c proteins of particular interest are those comprising (e.g. consisting of) SEQ ID Nos: 161-169.

Polynucleotides of particular interest are those derived from the wild-type sequences corresponding to the *M. tuberculosis* strains discussed above, such as those derived from SEQ ID No: 2 or its related *E. coli* codon optimised SEQ ID No: 160.

Combinations

A sequence containing the modified Rv3616c proteins (or associated polynucleotides) of the present invention can further comprise other components designed to enhance their immunogenicity or to improve these antigens in other respects. For example, improved isolation of the polypeptide antigens may be facilitated through the addition of a stretch of histidine residues (commonly known as a his-tag) towards one end of the antigen.

The term "his-tag" refers to a string of histidine residues, typically six residues, that are inserted within the reference sequence. To minimise disruption of the activity associated with the reference sequence, a his-tag is typically inserted at the N-terminus, usually immediately after the initiating methionine residue, or else at the C-terminus. They are usually heterologous to the native sequence but are incorporated since they facilitate isolation by improving the protein binding to immobilised metal affinity chromatography resins (IMAC). Generally speaking the presence or absence of a his-tag is not of significance from the point of view of eliciting a desirable immune response against the reference protein. However, to avoid the risk of an adverse reaction against the his-tag itself, it is considered best to minimise the length of the his-tag e.g. to four or fewer residues, in particular two residues, or to exclude the use of a his-tag entirely.

To improve the magnitude and/or breadth of the elicited immune response compositions, polypeptides (and nucleic acids encoding them) can be prepared which comprise multiple modified Rv3616c sequences and/or additional heterologous polypeptides or the polynucleotides encoding them from *Mycobacterium* species (in particular *M. tuberculosis*).

One skilled in the art will recognise that when a number of components are utilised in combination, the precise presentation can be varied. For example, a modified Rv3616c sequence component and an additional copy of the antigen or an additional heterologous antigen component could be presented:

(1) as two individual polypeptide components;
(2) as a fusion protein comprising both polypeptide components;
(3) as one polypeptide and one polynucleotide component;
(4) as two individual polynucleotide components;
(5) as a single polynucleotide encoding two individual polypeptide components; or
(6) as a single polynucleotide encoding a fusion protein comprising both polypeptide components.

This flexibility applies equally to situations where three or more components are used in combination. However, for convenience, it is often desirable that when a number of components are present they are contained within a single fusion protein or a polynucleotide encoding a single fusion protein. In one embodiment of the invention all antigen components are provided as polypeptides (e.g. within a single fusion protein). In an alternative embodiment of the invention all antigen components are provided as polynucleotides (e.g. a single polynucleotide, such as one encoding a single fusion protein).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Fusion polypeptide" or "fusion protein" refers to a protein having at least two heterologous polypeptides (e.g. at least two *Mycobacterium* sp. polypeptides) covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. This term also refers to conservatively modified variants, polymorphic variants, alleles, mutants, immunogenic fragments, and interspecies homologs of the antigens that make up the fusion protein. *Mycobacterium tuberculosis* antigens are described in Cole et al., *Nature* 393:537 (1998), which discloses the entire *Mycobacterium tuberculosis* genome. Antigens from other *Mycobacterium* species that correspond to *M. tuberculosis* antigens can be identified, e.g., using sequence comparison algorithms, as described herein, or other methods known to those of skill in the art, e.g., hybridisation assays and antibody binding assays.

The term "fused" refers to the covalent linkage between two polypeptides in a fusion protein. The polypeptides are typically joined via a peptide bond, either directly to each other or via an amino acid linker. Optionally, the peptides can be joined via non-peptide covalent linkages known to those of skill in the art.

Figure 2:
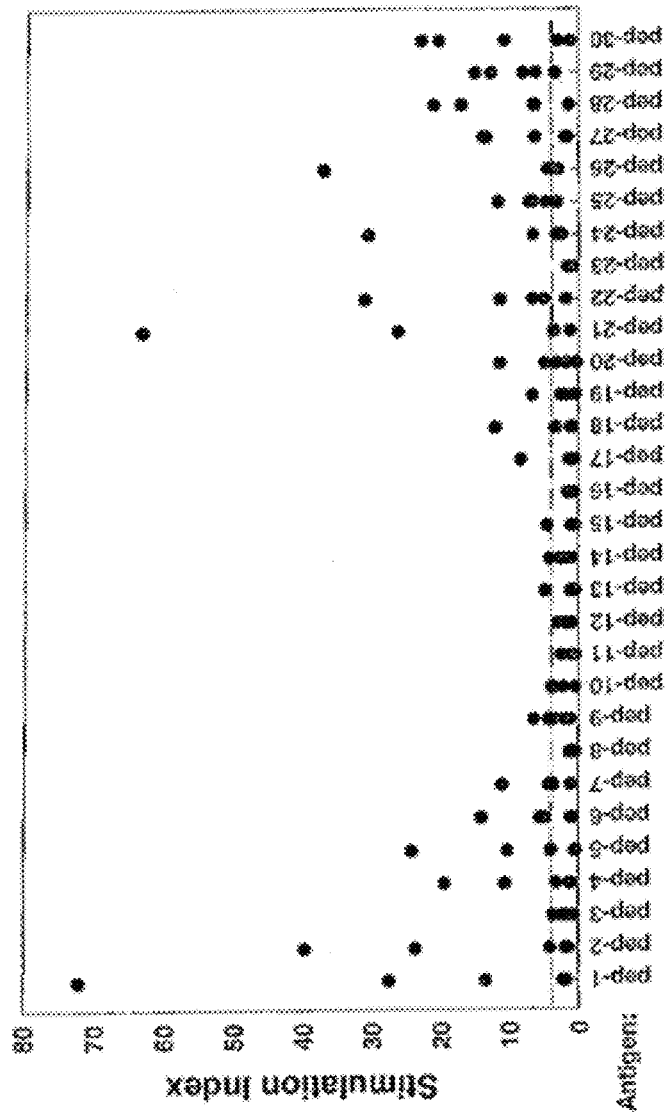
FIG. 2: PBMC responses to Rv3616c peptides.

Exemplary *M. tuberculosis* antigens which may be combined with a modified Rv3616c sequence include one or more of (e.g. 1 to 5, such as 1 to 3, in particular 1) the following:

(i) Mtb8.4 (also known as DPV and Rv1174c), the polypeptide sequence of which is described in SEQ ID No: 102 of WO97/09428 (cDNA in SEQ ID No: 101) and in Coler et al *Journal of Immunology* 1998 161: 2356-2364. Of particular interest is the mature Mtb8.4 sequence which is absent the leading signal peptide (i.e. amino acid residues 15-96 from SEQ ID No: 102 of WO97/09428). The full-length polypeptide sequence of Mtb8.4 is shown in SEQ ID No: 8;

(ii) Mtb9.8 (also known as MSL and Rv0287), the polypeptide sequence of which is described in SEQ ID No: 109 of WO98/53075 (fragments of MSL are disclosed in SEQ ID Nos: 110-124 of WO98/53075, SEQ ID Nos: 119 and 120 being of particular interest) and also in Coler et al *Vaccine* 2009 27:223-233 (in particular the reactive fragments shown in FIG. 2 therein). The full-length polypeptide sequence for Mtb9.8 is shown in SEQ ID No: 9;

(iii) Mtb9.9 (also known as Mtb9.9A, MTI, MTI-A and Rv1793) the polypeptide sequence of which is described in SEQ ID No: 19 of WO98/53075 and in Alderson et al *Journal of Experimental Medicine* 2000 7:551-559 (fragments of MTI are disclosed in SEQ ID Nos: 17 and 51-66 of WO98/53075, SEQ ID Nos: 17, 51, 52, 53, 56 and 62-65 being of particular interest). A number of polypeptide variants of MTI are described in SEQ ID Nos: 21, 23, 25, 27, 29 and 31 of WO98/53075 and in Alderson et al *Journal of Experimental Medicine* 2000 7:551-559. The full-length polypeptide sequence for Mtb9.9 is shown in SEQ ID No: 10;

(iv) Ra12 (also known as Mtb32A C-terminal antigen) the polypeptide sequence of which is described in SEQ ID No: 10 of WO01/98460 and in Skeiky et al *Journal of Immunology* 2004 172:7618-7682. The full-length polypeptide sequence for Ra12 is shown in SEQ ID No: 11;

(v) Ra35 (also known as Mtb32A N-terminal antigen) the polypeptide sequence of which is described in SEQ ID No: 8 of WO01/98460 and in Skeiky et al *Journal of Immunology* 2004 172:7618-7682. The full-length polypeptide sequence for Ra35 is shown in SEQ ID No: 12;

(vi) TbH9 (also known as Mtb39, Mtb39A, TbH9FL and Rv1196) the polypeptide sequence of which is described in SEQ ID No: 107 of WO97/09428, and also in Dillon et al *Infection and Immunity* 1999 67(6):2941-2950 and Skeiky et al *Journal of Immunology* 2004 172:7618-7682. The full-length polypeptide sequence for TbH9 is shown in SEQ ID No: 13;

(vii) Mtb41 (also known as MTCC2 and Rv0915c) the polypeptide sequence of which is described in SEQ ID No: 142 of WO98/53075 (cDNA in SEQ ID No: 140) and in Skeiky et al *Journal of Immunology* 2000 165: 7140-7149. The full-length polypeptide sequence for Mtb41 is shown in SEQ ID No: 14;

(viii) ESAT-6 (also known as esxA and Rv3875) the polypeptide sequence of which is described in SEQ ID No: 103 of WO97/09428 (cDNA in SEQ ID No: 104) and in Sorensen et al *Infection and Immunity* 1995 63(5): 1710-1717. The full-length polypeptide sequence for ESAT-6 is shown in SEQ ID No: 15;

(ix) Ag85 complex antigens (e.g. Ag85A, also known as fbpA and Rv3804c; or Ag85B, also known as fbpB and Rv1886c) which are discussed, for example, in Content et al *Infection and Immunity* 1991 59:3205-3212 and in Huygen et al *Nature Medicine* 1996 2(8):893-898. The full-length polypeptide sequence for Ag85A is shown in SEQ ID No: 16 (the mature protein of residues 43-338, i.e. lacking the signal peptide, being of particular interest). The full-length polypeptide sequence for Ag85B is shown in SEQ ID No: 17 (the mature protein of residues 41-325, i.e. lacking the signal peptide, being of particular interest);

(x) Alpha-crystallin (also known as hspX and Rv2031c) which is described in Verbon et al *Journal of Bacteriology* 1992 174:1352-1359 and Friscia et al *Clinical and Experimental Immunology* 1995 102:53-57 (of particular interest are the fragments corresponding to residues 71-91, 21-40, 91-110 and 111-130)). The full-length polypeptide sequence for alpha-crystallin is shown in SEQ ID No: 18;

(xi) Mpt64 (also known as Rv1980c) which is described in Roche et al *Scandinavian Journal of Immunology* 1996 43:662-670. The full-length polypeptide sequence for MPT64 is shown in SEQ ID No: 19 (the mature protein of residues 24-228, i.e. lacking the signal peptide, being of particular interest):

(xii) Mtb32A, the polypeptide sequence of which is described in SEQ ID No: 2 (full-length) and residues 8-330 of SEQ ID No: 4 (mature) of WO01/98460, especially variants having at least one of the catalytic triad mutated (e.g. the catalytic serine residue, which may for example be mutated to alanine). The full-length polypeptide sequence for Mtb32A is shown in SEQ ID No: 20. The mature form of Mtb32A having a Ser/Ala mutation is shown in SEQ ID No: 21;

(xiii) TB10.4, the full-length polypeptide sequence for TB10.4 is shown in SEQ ID No: 22;

(xiv) Rv1753c, the full-length polypeptide sequence for Rv1753c from *Mycobacterium tuberculosis* H37Rv is shown in SEQ ID No: 157;

(xv) Rv2386c, the full-length polypeptide sequence for Rv2386c from *Mycobacterium tuberculosis* H37Rv is shown in SEQ ID No: 158; and/or (xvi) Rv2707c, the full-length polypeptide sequence for Rv2707c from *Mycobacterium tuberculosis* H37Rv is shown in SEQ ID No: 159.

or combinations thereof, such as:

(a) a combination of Ra12, TbH9 and Ra35 components, for example in the form of a fusion protein, such as Mtb72f. The polypeptide sequence of Mtb72f is described in SEQ ID No: 6 of WO2006/117240 (cDNA in SEQ ID No: 5) and in Skeiky et al *Journal of Immunology* 2004 172:7618-7682 (where it incorporates an optional His-tag to aid purification, when utilised in the present invention suitably Mtb72f is absent the optional histidine residues). The polypeptide sequence for Mtb72f is shown in SEQ ID No: 23;

(b) a combination of Ra12, TbH9 and Ser/Ala mutated Ra35 (i.e. where the catalytic serine residue has been replaced with alanine) components, for example in the form of a fusion protein, such as M72. The polypeptide sequence of M72 is described in SEQ ID No: 4 of WO2006/117240 (cDNA in SEQ ID No: 3) where it incorporates an optional double histidine to aid manufacture, when utilised in the present invention M72 may also incorporate a double histidine though suitably M72 is absent the optional double histidine (i.e. residues 4-725 from SEQ ID No: 4 of WO2006/117240 are of particular interest). The polypeptide sequence for M72 is shown in SEQ ID No: 24;

(c) a combination of Mtb8.4, Mtb9.8, Mtb9.9 and Mtb41 components, for example in the form of a fusion protein, such as Mtb71f. The polypeptide sequence of Mtb71f is described in SEQ ID No: 16 of WO99/051748 (cDNA in SEQ ID No: 15), where it incorporates an optional His-tag to aid purification, when utilised in the present invention suitably Mtb71f corresponds to amino acid residues 9-710 of SEQ ID NO: 16 from WO99/051748. The polypeptide sequence for Mtb71f is shown in SEQ ID No: 25;

(d) a combination of Mtb72f or M72 (suitably without optional histidine residues to aid expression) with Mtb9.8 and Mtb9.9, for example in a fusion protein. The polypeptide sequence for an M72-Mtb9.9-Mtb9.8 fusion is shown in SEQ ID No: 26 (M92 fusion), when used in the present invention, the M72-Mtb9.9-Mtb9.8 fusion may optionally incorporate a double histidine following the initiating methionine residue to aid manufacture;

(e) a combination of Mtb72f or M72 (suitably without optional histidine residues to aid expression) with Ag85B, for example in a fusion protein, such Mtb103f. The polypeptide sequence of Mtb103f is described in SEQ ID No: 18 of WO03/070187 (cDNA in SEQ ID No: 10), where it incorporates an optional His-tag to aid purification, when utilised in the present invention suitably Mtb103f corresponds to amino acid residues 8-1016 of SEQ ID No: 18 from WO03/070187. Also of particular interest is M103, i.e. Mtb103f incorporating a Ser/Ala mutation in the Ra35 component, when utilised in the present invention suitably M103 corresponds to amino acid residues 8-1016 of SEQ ID No: 18 from WO03/070187 wherein the Ser residue at position 710 has been replaced with Ala. The polypeptide sequence for M103 is shown in SEQ ID No: 27, when used in the present invention, the M72-Mtb9.9-Mtb9.8 fusion may optionally incorporate a double histidine following the initiating methionine residue to aid manufacture;

(f) a combination of Mtb72f or M72 (suitably without optional histidine residues to aid expression) with Mtb41, for example in a fusion protein, such Mtb114f. The polypeptide sequence of Mtb114f is described in SEQ ID No: 16 of WO03/070187 (cDNA in SEQ ID No: 9), where it incorporates an optional His-tag to aid purification, when utilised in the present invention suitably Mtb114f corresponds to amino acid residues 8-1154 of SEQ ID No: 16 from WO03/070187. Also of particular interest is M114, i.e. Mtb114f incorporating a Ser/Ala mutation in the Ra35 component, when utilised in the present invention suitably M114 corresponds to amino acid residues 8-1154 of SEQ ID No: 16 from WO03/070187 wherein the Ser residue at position 710 has been replaced with Ala. The polypeptide sequence for M114 is shown in SEQ ID No: 28, when used in the present invention, the M72-Mtb9.9-Mtb9.8 fusion may optionally incorporate a double histidine following the initiating methionine residue to aid manufacture;

(g) a combination of Ag85B and ESAT-6 components, such as in a fusion described in Doherty et al *Journal of Infectious Diseases* 2004 190:2146-2153; and/or (h) a combination of Ag85B and TB10.4 components, such as in a fusion described in Dietrich et al *Journal of Immunology* 2005 174(10):6332-6339 190:2146-2153.

Combinations of a modified Rv3616c sequence component and an Rv1753c component are of particular interest. Obviously such combinations could optionally contain other additional antigen components (e.g. an M72 component).

Another combination of interest comprises a modified Rv3616c sequence component and an M72 component.

A further combination of interest comprises a modified Rv3616c sequence component and an Rv2386c component.

Other combinations of interest include those comprising a modified Rv3616c sequence component and an Rv2707c component.

An additional combination of interest comprises a modified Rv3616c sequence component and an alpha-crystallin component.

The skilled person will recognise that combinations need not rely upon the specific sequences described in above in (i)-(xvi) and (a)-(h), and that conservatively modified variants (e.g. having at least 70% identity, such as at least 80% identity, in particular at least 90% identity and especially at least 95% identity) or immunogenic fragments (e.g. at least 20% of the full length antigen, such as at least 50% of the antigen, in particular at least 70% and especially at least 80%) of the described sequences can be used to achieve the same practical effect.

Each of the above individual antigen sequences is also disclosed in Cole et al *Nature* 1998 393:537-544 and Camus *Microbiology* 2002 148:2967-2973. The genome of *M. tuberculosis* H37Rv is publicly available, for example at the Welcome Trust Sanger Institute website (www.sanger.ac.uk/Projects/M_tuberculosis/) and elsewhere.

Many of the above antigens are also disclosed in U.S. patent application Ser. Nos. 08/523,435, 08/523,436, 08/658,800, 08/659,683, 08/818,111, 08/818,112, 08/942,341, 08/942,578, 08/858,998, 08/859,381, 09/056,556, 09/072,596, 09/072,967, 09/073,009, 09/073,010, 09/223,040, 09/287,849 and in PCT patent applications PCT/US98/10407, PCT/US98/10514, PCT/US99/03265, PCT/US99/03268, PCT/US99/07717, WO97/09428 and WO97/09429, WO98/16645, WO98/16646, each of which is herein incorporated by reference.

The compositions, polypeptides, and nucleic acids of the invention can also comprise additional polypeptides from other sources. For example, the compositions and fusion proteins of the invention can include polypeptides or nucleic acids encoding polypeptides, wherein the polypeptide enhances expression of the antigen, e.g., NS1, an influenza virus protein (see, e.g. WO99/40188 and WO93/04175).

The nucleic acids of the invention can be engineered based on codon preference in a species of choice, e.g., humans (in the case of in vivo expression) or a particular bacterium (in the case of polypeptide production). SEQ ID No: 160 for example, provides a codon optimised polynucleotide for the expression of Rv3616c from H37Rv in *E. coli*.

The modified Rv3616c sequence component may also be administered with one or more chemotherapeutic agents effective against tuberculosis (e.g. *M. tuberculosis* infection). Examples of such chemotherapeutic agents include, but are not limited to, amikacin, aminosalicylic acid, capreomycin, cycloserine, ethambutol, ethionamide, isoniazid, kanamycin, pyrazinamide, rifamycins (i.e., rifampin, rifapentine and rifabutin), streptomycin, ofloxacin, ciprofloxacin, clarithromycin, azithromycin and fluoroquinolones. Such chemotherapy is determined by the judgment of the treating physician using preferred drug combinations. "First-line" chemotherapeutic agents used to treat tuberculosis (e.g. *M. tuberculosis* infection) that is not drug resistant include isoniazid, rifampin, ethambutol, streptomycin and pyrazinamide. "Second-line" chemotherapeutic agents used to treat tuberculosis (e.g. *M. tuberculosis* infection) that has demonstrated drug resistance to one or more "first-line" drugs include ofloxacin, ciprofloxacin, ethionamide, aminosalicylic acid, cycloserine, amikacin, kanamycin and capreomycin.

Conventional chemotherapeutic agents are generally administered over a relatively long period (ca. 9 months). Combination of conventional chemotherapeutic agents with the administration of a modified Rv3616c sequence component according to the present invention may enable the chemotherapeutic treatment period to be reduced (e.g. to 8 months, 7 months, 6 months, 5 months, 4 months, 3 months or less) without a decrease in efficacy.

Of particular interest is the use of a modified Rv3616c sequence component in conjunction with *Bacillus* Calmette-Guerin (BCG). For example, in the form of a modified BCG which recombinantly expresses a modified Rv3616c protein. Alternatively, the modified Rv3616c sequence component may be used to enhance the response of a subject to BCG vaccination, either by co-administration or by boosting a previous BCG vaccination. When used to enhance the response of a subject to BCG vaccination, the modified Rv3616c sequence component may obviously be provided in the form of a polypeptide or a polynucleotide (optionally in conjunction with additional antigenic components as described above).

The skilled person will recognise that combinations of components need not be administered together and may be applied: separately or in combination; at the same time, sequentially or within a short period; though the same or through different routes. Nevertheless, for convenience it is generally desirable (where administration regimes are compatible) to administer a combination of components as a single composition.

The polypeptides, polynucleotides and compositions of the present invention will usually be administered to humans, but may be expected to be effective in other mammals including domestic mammals (e.g., dogs, cats, rabbits, rats, mice, guinea pigs, hamsters, chinchillas) and agricultural mammals (e.g., cows, pigs, sheep, goats, horses).

Variants

T cell epitopes are short contiguous stretches of amino acids which are recognised by T cells (e.g. CD4+ or CD8+ T cells). Identification of T cell epitopes may be achieved through epitope mapping experiments which are well known to the person skilled in the art (see, for example, Paul, *Fundamental Immunology*, 3rd ed., 243-247 (1993); Beiβbarth et al *Bioinformatics* 2005 21(Suppl. 1):i29-i37). Alternatively, epitopes may be predicted or mapped using the approaches discussed in the Examples.

In a diverse out-bred population, such as humans, different HLA types mean that particular epitopes may not be recognised by all members of the population. As a result of the crucial involvement of the T cell response in tuberculosis, to maximise the level of recognition and scale of immune response, an optimal modified Rv3616c protein is one which contains the majority (or suitably all) T cell epitopes intact.

"Variants" or "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences.

Due to the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations lead to "silent" or "degenerate" variants, which are one species of conservatively modified variations. Every nucleic acid sequence herein which encodes a polypeptide also describes every possible silent variation of the nucleic acid. One of skill will recognise that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

Non-silent variations are those which result in a change in the encoded amino acid sequence (either though the substitution, deletion or addition of amino acid residues). Those skilled in the art will recognise that a particular polynucleotide sequence may contain both silent and non-silent conservative variations.

In respect of variants of a protein sequence, the skilled person will recognise that individual substitutions, deletions or additions to polypeptide, which alters, adds or deletes a single amino acid or a small percentage of amino acids is a "conservatively modified variant" where the alteration(s) results in the substitution of an amino acid with a functionally similar amino acid or the substitution/deletion/addition of residues which do not substantially impact the biological function of the variant.

Conservative substitution tables providing functionally similar amino acids are well known in the art. Such conservatively modified variants are in addition to and do not exclude polymorphic variants, interspecies homologs, and alleles of the invention.

In general, such conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* 1984).

Suitably such substitutions do not occur in the region of an epitope, and do not therefore have a significant impact on the immunogenic properties of the antigen.

Protein variants may also include those wherein additional amino acids are inserted compared to the reference sequence. Suitably such insertions do not occur in the region of an epitope, and do not therefore have a significant impact on the immunogenic properties of the antigen. One example of insertions includes a short stretch of histidine residues (e.g. 2-6 residues) to aid expression and/or purification of the antigen in question.

Protein variants include those wherein amino acids have been deleted compared to the reference sequence. Suitably such deletions do not occur in the region of an epitope, and do not therefore have a significant impact on the immunogenic properties of the antigen.

The skilled person will recognise that a particular protein variant may comprise substitutions, deletions and additions (or any combination thereof).

The terms "identical" or percent "identity," in the context of two or more nucleic acids or polypeptide sequences, refer to two or more sequences or sub-sequences that are the same or have a specified percentage of amino acid residues or nucleotides that are the same (i.e., 70% identity, optionally 75%, 80%, 85%, 90%, 95%, 98% or 99% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 25 to about 50 amino acids or nucleotides in length, or optionally over a region that is 75-100 amino acids or nucleotides in length. Suitably, the comparison is performed over a window corresponding to the entire length of the reference sequence (as opposed to the variant sequence).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, references to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

In any event, variants of a polypeptide sequence will have essentially the same activity as the reference sequence (in the case of polynucleotides, variant polynucleotide sequences will encode a polypeptide which has essentially the same activity as the reference sequence). By essentially the same activity is meant at least 50%, suitably at least 75% and especially at least 90% activity of the reference sequence in an in vitro restimulation assay of PBMC or whole blood with specific antigens (e.g. restimulation for a period of between several hours to up to two weeks, such as up to one day, 1 day to 1 week or 1 to 2 weeks) that measures the activation of the cells via lymphoproliferation, production of cytokines in the supernatant of culture (measured by ELISA, CBA etc) or characterisation of T and B cell responses by intra and extra-cellular staining (e.g. using antibodies specific to immune markers, such as CD3, CD4, CD8, IL2, TNFa, IFNg, CD40L, CD69 etc) followed by analysis with a flowcytometer. Suitably, by essentially the same activity is meant at least 50%, suitably at least 75% and especially at least 90% activity of the reference sequence in a T cell proliferation and/or IFN-gamma production assay.

As will be understood by those skilled in the art, the polynucleotides of use in this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognised by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a *Mycobacterium* antigen or a portion thereof) or may comprise a variant, or a biological or functional equivalent of such a sequence. Polynucleotide variants may contain one or more substitutions, additions, deletions and/or insertions, such that the immunogenicity of the encoded polypeptide is not diminished relative to the reference protein.

Polynucleotide Identification and Characterisation

Polynucleotides may be identified, prepared and/or manipulated using any of a variety of well established techniques. For example, a polynucleotide may be identified, as described in more detail below, by screening a microarray of cDNAs. Such screens may be performed, for example, using a Synteni microarray (Palo Alto, Calif.) according to the manufacturer's instructions (and essentially as described by Schena et al., *Proc. Natl. Acad. Sci. USA* 93:10614-10619 (1996) and Heller et al., *Proc. Natl. Acad. Sci. USA* 94:2150-2155 (1997)). Alternatively, polynucleotides may be amplified from cDNA prepared from cells expressing the proteins described herein, such as *M. tuberculosis* cells. Such polynucleotides may be amplified via polymerase chain reaction (PCR). For this approach, sequence-specific primers may be designed based on the sequences provided herein, and may be purchased or synthesised.

An amplified portion of a polynucleotide may be used to isolate a full length gene from a suitable library (e.g., a *M. tuberculosis* cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridisation techniques, a partial sequence may be labeled (e.g., by nick-translation or end-labeling with $^{32}P$) using well known techniques. A bacterial or bacteriophage library is then generally screened by hybridising filters containing denatured bacterial colonies (or lawns containing phage plaques) with the labeled probe (see Sambrook et al., *Molecular Cloning: A Laboratory Manual* (2000)). Hybridising colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then be assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22-30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186 (1988)), which uses restriction enzymes to generate a fragment in the known region of the gene. The fragment is then circularised by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridises to a polyA region or vector sequence, to identify sequences that are 5' and 3' of a known sequence. Additional techniques include capture PCR (Lagerstrom et al., *PCR Methods Applic.* 1:111-19 (1991)) and walking PCR (Parker et al., *Nucl. Acids. Res.* 19:3055-60 (1991)). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

Polynucleotide sequences or fragments thereof which encode polypeptides, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

Natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognised by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesised, in whole or in part, using chemical methods well known in the art (see Caruthers, M. H. et al., *Nucl. Acids Res. Symp. Ser*. pp. 215-223 (1980), Horn et al., *Nucl. Acids Res. Symp. Ser*. pp. 225-232 (1980)). Alternatively, the protein itself may be produced using chemical methods to synthesize the amino acid sequence of a polypeptide, or a portion thereof. For example, peptide synthesis can be performed using various solid-phase techniques (Roberge et al., *Science* 269:202-204 (1995)) and automated synthesis may be achieved, for example, using the ABI 431A Peptide Synthesizer (Perkin Elmer, Palo Alto, Calif.).

A newly synthesised peptide may be substantially purified by preparative high performance liquid chromatography (e.g., Creighton, *Proteins, Structures and Molecular Principles* (1983)) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into an appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., *Molecular Cloning, A Laboratory Manual* (2000), and Ausubel et al., *Current Protocols in Molecular Biology* (updated annually).

A variety of expression vector/host systems may be utilised to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke &Schuster, *J. Biol. Chem.* 264:5503-5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. Other vectors containing constitutive or inducible promoters include GAP, PGK, GAL and ADH. For reviews, see Ausubel et al. (supra) and Grant et al., *Methods Enzymol.* 153:516-544 (1987) and Romas et al. *Yeast* 8 423-88 (1992).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in *McGraw Hill Yearbook of Science and Technology* pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, S. frugiperda cells or Trichoplusia larvae in which the polypeptide of interest may be expressed (Engelhard et al., Proc. Natl. Acad. Sci. U.S.A. 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, Proc. Natl. Acad. Sci. U.S.A. 81:3655-3659 (1984)). In addition, transcription enhancers, such as the Rous sarcoma virus (RSV) enhancer, may be used to increase expression in mammalian host cells. Methods and protocols for working with adenovirus vectors are reviewed in Wold, Adenovirus Methods and Protocols, 1998. Additional references regarding use of adenovirus vectors can be found in Adenovirus: A Medical Dictionary, Bibliography, and Annotated Research Guide to Internet References, 2004.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., Results Probl. Cell Differ. 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., Cell 11:223-32 (1977)) and adenine phosphoribosyltransferase (Lowy et al., Cell 22:817-23 (1990)) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler et al., Proc. Natl. Acad. Sci. U.S.A. 77:3567-70 (1980)); npt, which confers resistance to the aminoglycosides, neomycin and G-418 (Colbere-Garapin et al., J. Mol. Biol. 150:1-14 (1981)); and als or pat, which confer resistance to chlorsulfuron and phosphinotricin acetyltransferase, respectively (Murry, supra). Additional selectable genes have been described, for example, trpB, which allows cells to utilise indole in place of tryptophan, or hisD, which allows cells to utilise histinol in place of histidine (Hartman & Mulligan, Proc. Natl. Acad. Sci. U.S.A. 85:8047-51 (1988)). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., Methods Mol. Biol. 55:121-131 (1995)).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridisations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilising monoclonal antibodies reactive to two non-interfering epitopes on a given polypeptide may be preferred for some applications, but a competitive binding assay may also be employed. These and other assays are described, among other places, in Hampton et al., Serological Methods, a Laboratory Manual (1990) and Maddox et al., J. Exp. Med. 158:1211-1216 (1983).

A wide variety of labels and conjugation techniques are known by those skilled in the art and may be used in various nucleic acid and amino acid assays. Means for producing labelled hybridisation or PCR probes for detecting sequences related to polynucleotides include oligolabeling, nick translation, end-labelling or PCR amplification using a labelled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilised immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilised metal ion affinity chromatography) as described in Porath et al., *Prot. Exp. Purif.* 3:263-281 (1992) while the enterokinase cleavage site provides a means for purifying the desired polypeptide from the fusion protein. A discussion of vectors which contain fusion proteins is provided in Kroll et al., *DNA Cell Biol.* 12:441-453 (1993)).

In Vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesised.

The expression vector comprises a genetically engineered form of an adenovirus. Knowledge of the genetic organisation of adenovirus, a 36 kb, linear, double-stranded DNA virus, allows substitution of large pieces of adenoviral DNA with foreign sequences up to 7 kb (Grunhaus & Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titre, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Racher et al. (1995) have disclosed improved methods for culturing 293 cells and propagating adenovirus. In one format, natural cell aggregates are grown by inoculating individual cells into 1 liter siliconised spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titres, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus & Horwitz, 1992; Graham & Prevec, 1992). Recently, animal studies suggested that recombinant adenovirus could be used for gene therapy (Stratford-Perricaudet & Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993).

Adenovirus vectors may originate from human adenovirus. Alternatively they may originate from adenovirus of other species e.g. chimpanzee which may have the advantage that the viral vectors are not neutralised by antibodies against human adenovirus circulating in many human subjects (see e.g.: Tatsis N et al Gene *Therapy* 2006 13:421-429).

Adenovirus type 35, which is relatively uncommon and therefore there are low levels of pre-existing immunity to the vector itself, has been used as a delivery system in certain tuberculosis vaccines which are being developed (see for example, Radosevic et al *Infection and Immunity* 2007 75(8): 4105-4115). Adenovirus type 35 may also be of particular value in the present invention as a delivery vector.

2. Retroviruses

The retroviruses are a group of single-stranded RNA viruses characterised by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas & Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

3. Adeno-Associated Viruses

AAV (Ridgeway, 1988; Hermonat & Muzycska, 1984) is a parovirus, discovered as a contamination of adenoviral stocks. It is a ubiquitous virus (antibodies are present in 85% of the US human population) that has not been linked to any disease. It is also classified as a dependovirus, because its replication is dependent on the presence of a helper virus, such as adenovirus. Five serotypes have been isolated, of which AAV-2 is the best characterised. AAV has a single-stranded linear DNA that is encapsidated into capsid proteins VP1, VP2 and VP3 to form an icosahedral virion of 20 to 24 nm in diameter (Muzyczka & McLaughlin, 1988).

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat & Muzyczka, 1984).

There are several factors that prompted researchers to study the possibility of using rAAV as an expression vector. One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering antisense constructs.

AAV is also a good choice of delivery vehicles due to its safety. There is a relatively complicated rescue mechanism: not only wild type adenovirus but also AAV genes are required to mobilise rAAV. Likewise, AAV is not pathogenic and not associated with any disease. The removal of viral coding sequences minimises immune reactions to viral gene expression, and therefore, rAAV does not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, 1988; Coupar et al., 1988), lentiviruses, polio viruses and herpes viruses may be employed. Other poxvirus derived vectors, such as fowlpox derived vectors, may also be expected to be of use. They offer several attractive features for various mammalian cells (Friedmann, 1989; Ridgeway, 1988; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titres of the recombinant virus were used to infect primary duckling hepatocytes. Stable CAT gene expression was detected for at least 24 days after transfection (Chang et al., 1991).

Additional 'viral' vectors include virus like particles (VLPs) and phages.

5. Non-Viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronisation with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed, for example, by any method which physically or chemically permeabilises the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty & Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated.

Bacteria may also be utilised as a delivery method (e.g. listeria, see WO2004/11048) and in particular BCG.

Polypeptide Compositions

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Shorter polypeptides may also be generated by synthetic means, using techniques well known to those of ordinary skill in the art. For example, such polypeptides may be synthesised using any of the commercially available solid-phase techniques, such as the Merrifield solid-phase synthesis method, where amino acids are sequentially added to a growing amino acid chain. See Merrifield, *J. Am. Chem. Soc.* 85:2149-2146 (1963). Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple modified Rv3616c proteins as described herein, or that comprises at least one modified Rv3616c proteins as described herein and an unrelated sequence such as those described in (i) to (xvi) and (a) to (g) above.

A fusion partner may, for example, assist in providing T helper epitopes (an immunological fusion partner), preferably T helper epitopes recognised by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the fusion partners by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46 (1985); Murphy et al., *Proc. Natl. Acad. Sci. USA* 83:8258-8262 (1986); U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798 (1992)). Within a preferred embodiment, a repeat portion of LYTA may be incorporated into a fusion protein. A repeat portion is found in the C-terminal region starting at residue 178. A particularly preferred repeat portion incorporates residues 188-305.

Pharmaceutical Compositions

In additional embodiments, the polynucleotide or polypeptide compositions disclosed herein may be formulated in pharmaceutically-acceptable or physiologically-acceptable solutions for administration to a cell or an animal, either alone, or in combination with one or more other modalities of therapy. Compositions may be presented in powder form (e.g. freeze-dried) for reconstitution shortly before use, such dry compositions generally are more stable during storage.

Pharmaceutical compositions may comprise a fusion protein or a polynucleotide encoding a fusion protein, in combination with a pharmaceutically-acceptable carrier or excipient.

It will also be understood that, if desired, the nucleic acid segment (e.g., RNA or DNA) that expresses a polypeptide as disclosed herein may be administered in combination with other agents as well, such as, e.g., other proteins or polypeptides or various pharmaceutically-active agents, including chemotherapeutic agents effective against a *M. tuberculosis* infection. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesised as described herein. Likewise, such compositions may further comprise substituted or derivatised RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation. Other routes of administration include via the mucosal surfaces.

Typically, formulations comprising a therapeutically effective amount deliver about 0.01 ug to about 1000 ug of modified Rv3616c polypeptide per administration, more typically about 0.1 ug to about 100 ug of polypeptide per administration (e.g. 0.5 to 50 ug). In respect of polynucleotide compositions, these typically deliver about 10 ug to about 20 mg of the inventive polynucleotide per administration, more typically about 0.1 mg to about 10 mg of the inventive polynucleotide per administration Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

1. Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavouring agent, such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active component, sucrose as a sweetening agent methyl and propylparabens as preservatives, a dye and flavouring, such as cherry or orange flavour. Of course, any material used in preparing any dosage unit form should be pharmaceutically pure and substantially non-toxic in the amounts employed. In addition, the active components may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

2. Injectable Delivery

In general it may be desirable to deliver the pharmaceutical compositions disclosed herein parenterally, intravenously, intramuscularly, intradermally, or even intraperitoneally as described in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington's Pharmaceutical Sciences, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

3. Nasal and Buccal Delivery

In certain embodiments, the pharmaceutical compositions may be delivered by intranasal sprays, buccal sprays, inhalation, and/or other aerosol delivery vehicles. Methods for delivering genes, nucleic acids, and peptide compositions directly to the lungs eg via nasal and buccal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon & Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath & Martin, 1986; Heath et al., 1986; Balazsovits et al., 1989; Fresta & Puglisi, 1996), radiotherapeutic agents (Pikul et al., 1987), enzymes (Imaizumi et al., 1990a; Imaizumi et al., 1990b), viruses (Faller & Baltimore, 1984), transcription factors and allosteric effectors (Nicolau & Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori & Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention. Such particles may be are easily made, as described (Couvreur et al., 1980; 1988; zur Muhlen et al., 1998; Zambaux et al. 1998; Pinto-Alphandry et al., 1995 and U.S. Pat. No. 5,145,684, specifically incorporated herein by reference in its entirety).

Skin patches may also be utilised for transcutaneous delivery.

Immunogenic Compositions

In certain embodiments of the present invention, immunogenic compositions are provided. The immunogenic compositions will comprise one or more modified Rv3616c sequences (polypeptides or polynucleotides) as those discussed above, in combination with an immunostimulant.

Immunogenic compositions may also comprise a fusion protein or a polynucleotide encoding a fusion protein, in combination with a pharmaceutically-acceptable carrier or excipient.

An immunostimulant may be any substance that enhances or potentiates an immune response (antibody and/or cell-mediated) to an exogenous antigen. Examples of immunostimulants include adjuvants.

Preparation of immunogenic compositions is generally described in, for example, Powell & Newman, eds., *Vaccine Design* (the subunit and adjuvant approach) (1995). Pharmaceutical compositions and immunogenic compositions within the scope of the present invention may also contain other compounds, which may be biologically active or inactive. For example, one or more immunogenic portions of other *M. tuberculosis* antigens may be present, either incorporated into a fusion polypeptide or as a separate component, within the pharmaceutical or immunogenic composition.

Illustrative immunogenic compositions may contain a polynucleotide (e.g. DNA) encoding one or more of the polypeptides as described above, such that the polypeptide is generated in situ (thereby eliciting an immune response). As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198 (1998), and references cited therein. Appropriate nucleic acid expression systems contain the necessary DNA sequences for expression in the patient (such as a suitable promoter and terminating signal). Bacterial delivery systems involve the administration of a bacterium host cell (for example, a *Mycobacterium, Bacillus* or *Lactobacillus* strain, including *Bacillus*-Calmette-Guerrin or *Lactococcus lactis*) that expresses the polypeptide (e.g. on its cell surface or secretes the polypeptide) (see, for example, Ferreira, et al., *An Acad Bras Cienc* (2005) 77:113-124; and Raha, et al., *Appl Microbiol Biotechnol* (2005) PubMedID 15635459). In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317-321 (1989); Flexner et al., *Ann. N.Y. Acad. Sci.* 569:86-103 (1989); Flexner et al., *Vaccine* 8:17-21 (1990); U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627 (1988); Rosenfeld et al., *Science* 252:431-434 (1991); Kolls et al., *Proc. Natl. Acad. Sci. USA* 91:215-219 (1994); Kass-Eisler et al., *Proc. Natl. Acad. Sci. USA* 90:11498-11502 (1993); Guzman et al., *Circulation* 88:2838-2848 (1993); and Guzman et al., *Cir. Res.* 73:1202-1207 (1993). Techniques for incorporating DNA into such expression systems are well known to those of ordinary skill in the art. The DNA may also be "naked," as described, for example, in Ulmer et al., *Science* 259:1745-1749 (1993) and reviewed by Cohen, *Science* 259:1691-1692 (1993). The uptake of naked DNA may be increased by coating the DNA onto biodegradable beads, which are efficiently transported into the cells. It will be apparent that a immunogenic composition may comprise both a polynucleotide and a polypeptide component. Such immunogenic composition may provide for an enhanced immune response.

It will be apparent that an immunogenic composition may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the immunogenic compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the immunogenic compositions of this invention. For example, an adjuvant may be included. An adjuvant refers to the components in a vaccine or therapeutic composition that increase the specific immune response to the antigen (see, e.g., Edelman, *AIDS Res. Hum Retroviruses* 8:1409-1411 (1992)). Adjuvants induce immune responses of the Th1-type and Th-2 type response. Th1-type cytokines (e.g., IFN-γ, IL-2, and IL-12) tend to favour the induction of cell-mediated immune response to an administered antigen, while Th-2 type cytokines (e.g., IL-4, IL-5, Il-6, IL-10) tend to favour the induction of humoral immune responses.

Within the immunogenic compositions provided herein, the adjuvant composition is preferably designed to induce an immune response predominantly of the Th1 type.

Suitable adjuvant compositions include oil in water emulsions. In particular an oil in water emulsion which comprises 0.5-10 mg metabolisable oil (e.g. squalene), 0.5-11 mg tocol (e.g. alpha-tocopherol) and 0.1-4 mg emulsifying agent (e.g. polyoxyethylene sorbitan monooleate) per human dose. See, for example, WO2008/043774 which is hereby incorporated by reference.

An alternative adjuvant comprises an immunologically active saponin fraction derived from the bark of Quillaja Saponaria Molina (such as the HPLC purified fraction known as QS21, as described in U.S. Pat. No. 5,057,540) presented in the form of a liposome and a lipopolysaccharide (such as 3-de-O-acylated monophosphoryl lipid A). These compositions may further comprise a sterol (e.g. cholesterol), such as wherein the ratio of saponin:sterol is from 1:1 to 1:100 w/w (e.g. the ratio of saponin:sterol is from 1:1 to 1:10 w/w). Particularly suitable are those adjutants wherein said QS21 and said 3-de-O-acylated monophosphoryl lipid A are present at ratio of QS21:3D-MPL of 1:1 w/w and both are present in a human dose at a level of below 30 ug. Such adjuvant compositions are described, for example, in WO2007/068907 and US2008279926, which are hereby incorporated by reference.

Other adjuvant systems of interest include those based on aluminium salts in conjunction with the lipopolysaccharide 3-de-O-acylated monophosphoryl lipid A. The antigen and 3-de-O-acylated monophosphoryl lipid A may be co-adsorbed to the same metallic salt particles or may be adsorbed to distinct metallic salt particles. See, for example, WO00/23105, U.S. Pat. No. 7,357,936 and US20080226672A1, which are hereby incorporated by reference, which describe immunogenic compositions comprising an antigen bound to a first metallic salt particle (in particular aluminium phosphate or aluminium hydroxide) and 3-de-O-acylated monophosphoryl lipid A which is bound to a second metallic salt particle (in particular aluminium phosphate or aluminium hydroxide).

Any immunogenic composition provided herein may be prepared using well known methods that result in a combination of antigen, immune response enhancer and a suitable carrier or excipient (as necessary).

Any of a variety of delivery vehicles may be employed within pharmaceutical compositions and immunogenic compositions to facilitate production of an antigen-specific immune response.

Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response and/or to be immunologically compatible with the receiver (i.e., matched HLA haplotype). APCs may generally be isolated from any of a variety of biological fluids and organs, and may be autologous, allogeneic, syngeneic or xenogeneic cells.

Certain embodiments of the present invention use dendritic cells or progenitors thereof as antigen-presenting cells. Dendritic cells are highly potent APCs (Banchereau & Steinman, *Nature* 392:245-251 (1998)) and have been shown to be effective as a physiological adjuvant for eliciting prophylactic or therapeutic immunity (see Timmerman & Levy, *Ann. Rev. Med.* 50:507-529 (1999)). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within an immunogenic composition (see Zitvogel et al., *Nature Med.* 4:594-600 (1998)).

Dendritic cells and progenitors may be obtained from peripheral blood, bone marrow, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorised as "immature" and "mature" cells, which allows a simple way to discriminate between two well characterised phenotypes. However, this nomenclature should not be construed to exclude all possible intermediate stages of differentiation. Immature dendritic cells are characterised as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a protein (or portion or other variant thereof) such that the polypeptide, is expressed on the cell surface. Such transfection may take place ex vivo, and a pharmaceutical composition or immunogenic composition comprising such transfected cells may then be used, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and Cell Biology* 75:456-460 (1997). Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Immunogenic compositions and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, an immunogenic composition or pharmaceutical composition may be stored in a freeze-dried condition requiring only the addition of a sterile liquid carrier immediately prior to use.

In some embodiments, a "priming" or first administration of a modified Rv3616c protein (including fusion proteins), or polynucleotide encoding said protein, is followed by one or more "boosting" or subsequent administrations of a modified Rv3616c protein (including fusion proteins) or polynucleotide encoding said protein ("prime and boost" method). For instance, a first administration with a modified Rv3616c polypeptide (including fusion proteins) or polynucleotide encoding said protein is followed by one or more subsequent administrations of a modified Rv3616c polypeptide (including fusion proteins) or polynucleotide encoding said polypeptide.

In one embodiment, a first administration with a modified Rv3616c protein or polynucleotide is followed by one or more subsequent administrations of a modified Rv3616c protein. In one embodiment, a first administration with a modified Rv3616c protein or polynucleotide is followed by one or more subsequent administrations of a modified Rv3616c polynucleotide. Usually the first or "priming" administration and the second or "boosting" administration are given about 2-12 weeks apart, or up to 4-6 months apart. Subsequent "booster" administrations are given about 6 months apart, or as long as 1, 2, 3, 4 or 5 years apart. Conventional booster treatment (e.g., a protein priming administration followed by a protein boosting administration) may also useful be in preventing or treating tuberculosis (e.g. preventing or treating latent tuberculosis, in particular preventing or delay tuberculosis reactivation).

Diagnostics

In another aspect, this invention provides methods for using one or more of the modified Rv3616c proteins described above to diagnose tuberculosis, such as latent tuberculosis (for example using T cell response based assays or antibody based assays of conventional format).

For example, there is provided a method for determining latent *M. tuberculosis* infection in an individual comprising:
(a) obtaining a sample from the individual;
(b) contacting said sample with a modified Rv3616c protein;
(c) quantifying the sample response.

The sample may for example be whole blood or purified cells. Suitably the sample will contain peripheral blood mononucleated cells (PBMC). In one embodiment of the invention the individual will be seropositive. In a second embodiment of the invention the individual will be seronegative.

Suitably the individual will not previously have been vaccinated against *M. tuberculosis* infection (e.g. suitably the individual will not previously have been vaccinated with a BCG).

The sample response may be quantified by a range of means known to those skilled in the art, including the monitoring of lymphocyte proliferation or the production of specific cytokines or antibodies. For example, T-cell ELISPOT may be used to monitor cytokines such as interferon gamma (IFNγ), interleukin 2 (IL2) and interleukin 5 (IL5). B-cell ELLISPOT may be used to monitor the stimulation of *M. tuberculosis* specific antigens. The cellular response may also be characterised by the use of by intra- and extra-cellular staining and analysis by a flow cytometer.

Methods of quantifying a sample proliferation response include:
(i) pulsing cultured cells with a radiolabel (e.g. tritiated thymidine) and monitoring tritium uptake (e.g. gas scintillation);
(ii) carboxyfluorsecein diacetate succinimidyl ester (CFSE) labelling and fluorescence monitoring of cell division using flow cytometry.

Quantifying a sample cytokine response includes in particular the monitoring of interferon gamma production.

When using such quantification methods, a positive response to an antigen may be defined by a signal to noise ratio (S/N ratio) of at least 2:1 (for example, at least 3:1 or at least 5:1).

In a further aspect of the present invention methods are provided to diagnose latent *M. tuberculosis* infection using a skin test. As used herein, a "skin test" is any assay performed directly on a patient in which a delayed-type hypersensitivity (DTH) reaction (such as swelling, reddening or dermatitis) is measured following intradermal injection of a modified Rv153c protein as described above. Such injection may be achieved using any suitable device sufficient to contact the antigen combinations with dermal cells of the patient, such as a tuberculin syringe or 1 mL syringe. The reaction is measured after a period of time, for example at least 48 hours after injection, especially 48-72 hours.

The DTH reaction is a cell-mediated immune response, which is greater in patients that have been exposed previously to the test antigen. The response may be measured visually, using a ruler. In general, a response that is greater than about 0.5 cm in diameter, especially greater than about 1.0 cm in diameter, is a positive response, indicative of prior *M. tuberculosis* infection, which may or may not be manifested as an active disease.

For use in a skin test, the modified Rv3616c protein component is suitably formulated as a pharmaceutical composition containing a physiologically acceptable carrier. Suitably, the carrier employed in such pharmaceutical compositions is a saline solution with appropriate preservatives, such as phenol and/or Tween 80™.

The present invention further provides kits for use within any of the above diagnostic methods. Such kits typically comprise two or more components necessary for performing a diagnostic assay. Components may be compounds, reagents, containers and/or equipment. For example, one container within a kit may contain a modified Rv3616c protein. Such protein may be provided attached to a support material. Such kits may also, contain a detection reagent that contains a reporter group suitable for direct or indirect detection of antibody binding.

Other diagnostics kits include those designed for the detection of cell mediated responses (which may, for example, be of use in the diagnostic methods of the present invention). Such kits will typically comprise:
(i) apparatus for obtaining an appropriate cell sample from a subject;
(ii) means for stimulating said cell sample with an Rv3616c polypeptide (or variant thereof, immunogenic fragments thereof, or DNA encoding such polypeptides);
(iii) means for detecting or quantifying the cellular response to stimulation.

Suitable means for quantifying the cellular response include a B-cell ELISPOT kit or alternatively a T-cell ELISPOT kit, which are known to those skilled in the art.

One possible kit comprises:
(a) a polypeptide of the invention; and
(b) a detection reagent suitable for direct or indirect detection of antibody binding.

Of particular interest are diagnostic kits tailored for quantifying T cell responses:

A diagnostic kit comprising:
(a) a polypeptide of the invention; and
(b) apparatus sufficient to contact said polypeptide with the dermal cells of an individual.

A diagnostic kit comprising:
(a) a polypeptide of the invention;
(b) apparatus sufficient to contact said polypeptide with a sample (e.g. whole blood or more suitably PBMC) from an individual; and
(c) means to quantify the T cell response (e.g. proliferation or IFN-gamma production).

EXAMPLES

The following examples are provided by way of illustration only and not by way of limitation. Those of skill in the art will readily recognize a variety of noncritical parameters that could be changed or modified to yield essentially similar results.

Example 1

Identification of Rv3616c as a Latent TB Vaccine Target

The gene Rv3616c encodes for a conserved hypothetical alanine and glycine rich protein.

Rv3616c was selected based on a genome-wide analysis of *Mycobacterium tuberculosis* genes associated with dormancy phase maintenance and infectivity as in Murphy and Brown *BMC. Infect. Dis.* 2007 7:84-99. Potential dormancy phase gene targets in *Mycobacterium tuberculosis* were prioritised through a bioinformatics meta-analysis of published genome-wide DNA microarray datasets of bacterial gene expression under simulated dormancy conditions. Subcellular localisation of *M. tuberculosis* proteins encoded by genes, was subsequently carried out on the entire genome to identify vaccine targets.

Briefly, experimental conditions in the dormancy models were quite varied so a zero to five scoring system was developed to normalise these data based upon two criteria: 1) the relevance of the experimental conditions to the dormant state and 2) the rank order of expression. The maximum score for a particular experimental dataset was adjusted based on potential relevance to the clinical occurrence of dormancy phase *M. tuberculosis* infections. Table 1 shows the data sets collected for Step 1 together with the adjusted maximum scores for each dataset. Additional datasets on gene essentiality for growth were obtained from published studies using transposon-based knockout experiments (TraSH). Genes which had no effect on growth received a score of zero.

sion in the experimental condition versus cells in log-phase liquid culture). The highest scoring gene received the maximum score for that particular dataset (listed in column 3 of Table 1. (e.g. 5, 4 . . . , 1 point)). The score was decreased by 0.005 points for each gene in order until zero, or the end of the data set was reached. Thus when the maximum score was 4 points, the 100th ranked gene would receive a score of 3.500. For a maximum score of 5 points, 1000 genes or 25% of the *M. tuberculosis* genome received a score. For experiments where data from multiple time points were collected, the maximum score across all time points was used as the final score.

In Step 3 scores for each gene in each of the experimental conditions were collected into a Microsoft Access database. Reference fields were added to facilitate prioritisation, such as the Refseq ID, Genbank function, Genbank note, Tuberculist classification, and KEGG and Sanger Center links. By combining the data from different studies and sources, a consensus view was reached about the particular genes and pathways most critical for survival in the dormant state.

In Step 4, a prioritised list of therapeutic targets was derived utilising the top 400 scoring genes (~10% of the genome) supplemented by expert computational and manual analysis of biochemical pathways, enzymology, drug tractability, homology to human genes and other prior knowledge. The great majority of the high scoring genes come from the subset where two or three of the groups intersect.

In Step 5, the identification of subcellular localisation of *M. tuberculosis* proteins encoded by genes, was carried out on

TABLE 1

Sources, experimental models, and scoring criteria for *M. tuberculosis* DNA microarray gene expression and genome-wide gene knock-out (growth phase essentiality).

| Reference | Experimental model | Timepoint: Maximum score[a] |
|---|---|---|
| Belts J C et al. *Mol. Microbiol.* 2002 43: 717-731 | Starvation under controlled $O_2$ | 96 h: 3<br>24 h: 2<br>4 h: 1 |
| Hampshire T et al. *Tuberculosis.(Edinb.)* 2004 84: 228-238 | Nutrient depletion under controlled $O_2$ | 62 and 75 d: 5<br>49 d: 4<br>18 d: 2 |
| Muttucumaru D G et al. *Tuberculosis.(Edinb.)* 2004 84: 239-246 | Wayne model of hypoxia[#] | 14 d (NRP-2): 4<br>7 d (NRP-1): 2 |
| Voskuil M I et al. *Tuberculosis.(Edinb.)* 2004 84: 218-227 | Wayne model of hypoxia[#] | 30 and 80 d: 5<br>14 and 20 d: 4<br>10 and 12 d: 3<br>6 and 8 d: 2 |
| Schnappinger D et al. *J. Exp. Med.* 2003 198: 693-704 | Infection of mouse macrophages, +/− γ-INF | 24 and 48 h: 5 |
| Karakousis P C et al. *J. Exp. Med.* 2004 200: 647-657 | Hollow fiber subcutaneous implant in mice | 10 d: 3 |
| Talaat A M et al. *Proc. Natl. Acad. Sci. U.S.A* 2004, 101: 4602-4607 | Infection of mice. MTB harvested from lung[b] | 28 d: 3 |
| Sassetti C M et al. *Mol. Microbiol.* 2003 48: 77-84 | TraSH mutated libraries grown on solid media | 14 d: 5 |
| Rengarajan J et al. *Proc. Natl. Acad. Sci. U.S.A* 2005, 102: 8327-8332 | Infection of mouse macrophages, +/− γ-INF with TraSH mutated libraries of *M. tuberculosis* | 7 d: 5 |
| Sassetti C M et al. *Proc. Natl. Acad. Sci. U.S.A* 2003 100: 12989-12994 | C57BL/6J mice infected with TraSH mutated libraries of *M. tuberculosis* | 7, 14, 28 and 56 d: 5 |

[a]Maximum score based on relevance as a dormancy model; h = hour; d = day..
[b]Ratio of *M. tuberculosis* from Balb/c lung to MTB in aerated culture for 28 d.
[#]Wayne L G and Hayes L G *Infect. Immun.* 1996 64: 2062-2069

Step 2—In applying the second criterion, the rank order of gene expression, gene scores from each dataset were ordered from highest to lowest based on expression ratio (fold expres- the entire genome. The heuristic used for membrane protein prediction is described in Chalker et al. *J. Bacteriol.* 2001 183:1259-1268. Average hydropathy profiles (H) (von Heijne G J. Mol. Biol. 1992 225:487-494) were generated using GES hydropathy values (Engelman D M et al. Annu. Rev. Biophys. Biophys. Chem. 1986 15:321-353) weighted using a trapezoid window. Using a process similar to the initial steps of the TopPred II algorithm (Claros M G et al. Comput. Appl. Biosci. 1994 10:685-686), helical transmembrane segments (TMS) were predicted for each peptide sequence by selecting 19 amino acids centered on the highest H value (MaxH), masking these from further consideration, and repeating the process until no peaks with a H of >0.5 remained. Subcellular locations were assigned based on the peak MaxH value, number of segments with a H of >1.0, and distribution and peak H values of the putative TMS. A MaxH cutoff of 1.15 was chosen to maximize the discrimination between two SwissProtein release 34 test datasets containing transmembrane and cytoplasmic proteins, respectively (Boyd D et al. Protein Sci. 1998 7:201-205). Proteins with a MaxH of <1.15 were classified as cytoplasmic, while those with a MaxH of >1.15 and at least three possible TMS were classified as membrane proteins. Anchored proteins were defined as having exactly two TMS, one starting before amino acid (aa) 35 and one having a H of >1.15 with the other having a H not lower than 0.5. SignalP with Gram positive settings was specifically used for M. bacterium to identify secreted proteins amongst those classified as either cytoplasmic or "unknown" in the heuristic analysis (Nielsen H et al. Protein Eng. 1997 10:1-6).

Rv3616c ranked very high as a vaccine antigen according to several criteria:
(i) Rv3616c is consistently up-regulated across all models of dormancy. Among the entire suite of 3999 genes scored in the meta-analysis, Rv3616c was ranked in the top quartile of overexpressed genes across all dormancy models. The up-regulated score for Rv3616c was 6.52 which favourably compared with the top gene score of 22.28.
(ii) Rv3616c ranked as being highly essential for survival in the mouse spleen infection model (scoring 4.945, out of a possible scoring of 5).
(iii) Subcellular localisation predicted that Rv3616c protein is a membrane bound protein and thus has significant extracellular exposure, indicating suitability as a vaccine target.
(iv) Rv3616c can a elicit protective response against initial tuberculosis challenge.
(v) Rv3616c is broadly recognised as an antigen.

Example 2

Rv3616c Epitope Prediction

Method

T cell epitope prediction was based on the following approaches:

| Prediction | Name | URL/References |
| --- | --- | --- |
| CD4 and CD8 | Multipred | website: antigen.i2r.a-star.edu.sg/multipred/<br>Zhang, G. L., Khan, A. M., Srinivasan, K. N., August, J. T. and Brusic, V. (2005) "MULTIPRED: a computational system for prediction of promiscuous HLA binding peptides" Nucleic Acids Res. 33, W172-W179. |
|  | SVMHC | website: www-bs.informatik.uni-tuebingen.de/SVMHC<br>"Prediction of MHC class I binding peptides, using SVMHC." Pierre Dönnes and Arne Elofsson in: BMC Bioinformatics 2002 3: 25 |
| CD4 | ProPred | website: www.imtech.res.in/raghava/propred/<br>Singh, H. and Raghava, G. P. S. (2001) "ProPred: Prediction of HLA-DR binding sites." Bioinformatics, 17(12), 1236-37. |
|  | Tepitope2 | In house program based on:<br>H. Bian, J. Hammer (2004) "Discovery of promiscuous HLA-II-restricted T cell epitopes with TEPITOPE." Methods 34: 468-75 |
| CD8 | nHLA | website: www.imtech.res.in/raghava/nhlapred/<br>Bhasin M. and Raghava G P S (2006) "A hybrid approach for predicting promiscuous MHC class I restricted T cell epitopes"; J. Biosci. 32: 31-42 |
|  | NetCTL | website: www.cbs.dtu.dk/services/NetCTL/<br>"An integrative approach to CTL epitope prediction. A combined algorithm integrating MHC-I binding, TAP transport efficiency, and proteasomal cleavage predictions." Larsen M. V., Lundegaard C., Kasper Lamberth, Buus S,. Brunak S., Lund O., and Nielsen M. European Journal of Immunology. 35(8): 2295-303. 2005 |
|  | Epijen | website: www.jenner.ac.uk/EpiJen/<br>Doytchinova, I. A., P. Guan, D. R. Flower. "EpiJen: a server for multi-step T cell epitope prediction." BMC Bioinformatics, 2006, 7, 131. |
|  | Syfpeithi | website: www.syfpeithi.de/Scripts/MHCServer.dll/EpitopePrediction.htm<br>Hans-Georg Rammensee, Jutta Bachmann, Niels Nikolaus Emmerich, Oskar Alexander Bachor, Stefan Stevanovic: "SYFPEITHI: database for MHC ligands and peptide motifs." Immunogenetics (1999) 50: 213-219 |
|  | PredTAP | website: antigen.i2r.a-star.edu.sg/predTAP/<br>Zhang, G. L., Petrovsky, N., Kwoh, C. K., August, J. T. and Brusic, V. (2006) "PRED$^{TAP}$: a system for prediction of peptide binding to the human transporter associated with antigen processing." Immunome Res. 2(1), 3. |

| Prediction Name | URL/References |
|---|---|
| PAPROC | website: paproc2.de/paproc1/paproc1.html
C. Kuttler, A. K. Nussbaum, T. P. Dick, H.-G. Rammensee, H. Schild, K. P. Hadeler, "An algorithm for the prediction of proteasomal cleavages", J. Mol. Biol. 298 (2000), 417-429
A. K. Nussbaum, C. Kuttler, K. P. Hadeler, H.-G. Rammensee, H. Schild, "PAProC: A Prediction Algorithm for Proteasomal Cleavages available on the WWW", Immunogenetics 53 (2001), 87-94 |

TABLE 2

Putative Rv3616c human CD4+ T cell epitopes

| Putative CD4 epitope number | Amino acid position | Epitope sequence | SEQ ID No: | HLA allele |
|---|---|---|---|---|
| 1 | 5 | FIIDPTISA | SEQ ID No: 29 | DRB1_0301, DRB1_0401, DRB1_1101 |
| 2 | 31 | ILYSSLEYF | SEQ ID No: 30 | DRB1_0301 |
| 3 | 36 | LEYFEKALE | SEQ ID No: 31 | DRB1_1301 |
| 4 | 63 | YAGKNRNHV | SEQ ID No: 32 | DRB1_0801 |
| 5 | 87 | LIHDQANAV | SEQ ID No: 33 | DRB1_0301, DRB1_0401 |
| 6 | 111 | FVRPVAVDL | SEQ ID No: 34 | DRB1_0101 |
| 7 | 119 | LTYIPVVGH | SEQ ID No: 35 | DRB1_0401 |
| 8 | 121 | YIPVVGHAL | SEQ ID No: 36 | DRB1_0101 |
| 9 | 151 | YLVVKTLIN | SEQ ID No: 37 | DRB1_0401 |
| 10 | 152 | LVVKTLINA | SEQ ID No: 38 | DRB1_1301 |
| 11 | 154 | VKTLINATQ | SEQ ID No: 39 | DRB1_0401 |
| 12 | 164 | LKLLAKLAE | SEQ ID No: 40 | DRB1_0301, DRB1_0801, DRB1_1101, DRB1_1301 |
| 13 | 173 | LVAAAIADI | SEQ ID No: 41 | DRB1_0301, DRB1_1101, DRB1_1301 |
| 14 | 181 | IISDVADII | SEQ ID No: 42 | DRB1_0301 |
| 15 | 197 | WEFITNALN | SEQ ID No: 43 | DRB1_0401 |
| 16 | 252 | LFGAAGLSA | SEQ ID No: 44 | DRB1_1501 |
| 17 | 264 | LAHADSLAS | SEQ ID No: 45 | DRB1_0401 |
| 18 | 270 | LASSASLPA | SEQ ID No: 46 | DRB1_0401 |
| 19 | 288 | FGGLPSLAQ | SEQ ID No: 47 | DRB1_0401 |

TABLE 3

Putative Rv3616c human CD8+ T cell epitopes

| Putative CD8 epitope number | Amino acid position | Epitope sequence | SEQ ID No: | HLA allele |
|---|---|---|---|---|
| 1 | 5 | FIIDPTISA | SEQ ID No: 48 | A2 |
| 2 | 6 | IIDPTISAI | SEQ ID No: 49 | A_0101, A2 |
| 3 | 9 | PTISAIDGL | SEQ ID No: 50 | A2, A_0201, B7, B8 |
| 4 | 10 | TISAIDGLY | SEQ ID No: 51 | A1, A_0101, A3, A_0301 |
| 5 | 12 | SAIDGLYDL | SEQ ID No: 52 | A2, B_3501 |
| 6 | 13 | AIDGLYDLL | SEQ ID No: 53 | A_0101, A_0201, B44 |
| 7 | 17 | LYDLLGIGI | SEQ ID No: 54 | A24 |
| 8 | 25 | IPNQGGILY | SEQ ID No: 55 | B7, A_0101, B_3501, B51 |
| 9 | 30 | GILYSSLEY | SEQ ID No: 56 | A1, A_0101, A3, A_0301 |
| 10 | 33 | YSSLEYFEK | SEQ ID No: 57 | A1, A_0301 |
| 11 | 35 | SLEYFEKAL | SEQ ID No: 58 | A_0201, B7, Cw_0401, Cw_0602 |
| 12 | 38 | YFEKALEEL | SEQ ID No: 59 | A24, A_2402, B8, Cw_0401, Cw_0602 |

TABLE 3-continued

Putative Rv3616c human CD8+ T cell epitopes

| Putative CD8 epitope number | Amino acid position | Epitope sequence | SEQ ID No: | HLA allele |
|---|---|---|---|---|
| 13 | 39 | FEKALEELA | SEQ ID No: 60 | B44, B_4403 |
| 14 | 69 | NHVNFFQEL | SEQ ID No: 61 | A24, Cw_0602 |
| 15 | 76 | ELADLDRQL | SEQ ID No: 62 | A_0201 |
| 16 | 77 | LADLDRQLI | SEQ ID No: 63 | A_0101, B51 |
| 17 | 79 | DLDRQLISL | SEQ ID No: 64 | A_0101, A_0201 |
| 18 | 80 | LDRQLISLI | SEQ ID No: 65 | A24, B7, B51 |
| 19 | 94 | AVQTTRDIL | SEQ ID No: 66 | B7 |
| 20 | 103 | EGAKKGLEF | SEQ ID No: 67 | A24, B7 |
| 21 | 107 | KGLEFVRPV | SEQ ID No: 68 | A_0201, B51 |
| 22 | 108 | GLEFVRPVA | SEQ ID No: 69 | A_0101, A_0301 |
| 23 | 109 | LEFVRPVAV | SEQ ID No: 70 | B44 |
| 24 | 111 | FVRPVAVDL | SEQ ID No: 71 | B7, B8, B_3501 |
| 25 | 113 | RPVAVDLTY | SEQ ID No: 72 | B7, A_0101, B_3501, B51 |
| 26 | 116 | AVDLTYIPV | SEQ ID No: 73 | A2, A_0201 |
| 27 | 120 | TYIPVVGHA | SEQ ID No: 74 | A24 |
| 28 | 121 | YIPVVGHAL | SEQ ID No: 75 | A_0101, A2, A_0201, B7, B8 |
| 29 | 129 | LSAAFQAPF | SEQ ID No: 76 | A1, B7, B_3501 |
| 30 | 130 | SAAFQAPFC | SEQ ID No: 77 | A_0201 |
| 31 | 131 | AAFQAPFCA | SEQ ID No: 78 | A_0301, B_3501 |
| 32 | 133 | FQAPFCAGA | SEQ ID No: 79 | A2, A_0201 |
| 33 | 135 | APFCAGAMA | SEQ ID No: 80 | B7, B_3501 |
| 34 | 136 | PFCAGAMAV | SEQ ID No: 81 | A3 |
| 35 | 141 | AMAVVGGAL | SEQ ID No: 82 | A2, A_0201, A24, B7 |
| 36 | 143 | AVVGGALAY | SEQ ID No: 83 | A1, A3, A_0301, B7 |
| 37 | 147 | GALAYLVVK | SEQ ID No: 84 | A3, A_0301 |
| 38 | 149 | LAYLVVKTL | SEQ ID No: 85 | B8, B44, B51 |
| 39 | 150 | AYLVVKTLI | SEQ ID No: 86 | A24 |
| 40 | 155 | KTLINATQL | SEQ ID No: 87 | A_0201, A2, A_0301, A24 |
| 41 | 156 | TLINATQLL | SEQ ID No: 88 | A2, A_0201, A3, A_0101, Cw_0401 |
| 42 | 158 | INATQLLKL | SEQ ID No: 89 | B7, B8, Cw_0602 |
| 43 | 159 | NATQLLKLL | SEQ ID No: 90 | A_2402, B7, B_3501, B44, Cw_0401, Cw_0602 |
| 44 | 162 | QLLKLLAKL | SEQ ID No: 91 | A2, A_0201, A_0301, A_2402, B8, Cw_0401, Cw_0602 |
| 45 | 165 | KLLAKLAEL | SEQ ID No: 92 | A2, A_0201, A_0301, B7, B8, Cw_0602 |

TABLE 3-continued

Putative Rv3616c human CD8+ T cell epitopes

| Putative CD8 epitope number | Amino acid position | Epitope sequence | SEQ ID No: | HLA allele |
|---|---|---|---|---|
| 46 | 166 | LLAKLAELV | SEQ ID No: 93 | A2, A_0201, A_0101, B8 |
| 47 | 169 | KLAELVAAA | SEQ ID No: 94 | A2 |
| 48 | 170 | LAELVAAAI | SEQ ID No: 95 | A1, A24, B51 |
| 49 | 173 | LVAAAIADI | SEQ ID No: 96 | B7, B51 |
| 50 | 177 | AIADIISDV | SEQ ID No: 97 | A2, A_0201, Cw_0602 |
| 51 | 178 | IADIISDVA | SEQ ID No: 98 | A_0101, B_3501 |
| 52 | 182 | ISDVADIIK | SEQ ID No: 99 | A1, A_0301 |
| 53 | 192 | TLGEVWEFI | SEQ ID No: 100 | A2, A_0201 |
| 54 | 199 | FITNALNGL | SEQ ID No: 101 | A2 |
| 55 | 202 | NALNGLKEL | SEQ ID No: 102 | B51, A_2402, B_3501, Cw_0602 |
| 56 | 213 | KLTGWVTGL | SEQ ID No: 103 | A2, A_0201 |
| 57 | 214 | LTGWVTGLF | SEQ ID No: 104 | A1, A_0101, A24 |
| 58 | 225 | GWSNLESFF | SEQ ID No: 105 | A24 |
| 59 | 228 | NLESFFAGV | SEQ ID No: 106 | A2, A_0201 |
| 60 | 231 | SFFAGVPGL | SEQ ID No: 107 | A2, A_0201, A24, Cw_0401 |
| 61 | 238 | GLTGATSGL | SEQ ID No: 108 | A2, A_0201 |
| 62 | 246 | LSQVTGLFG | SEQ ID No: 109 | A1, B8 |
| 63 | 247 | SQVTGLFGA | SEQ ID No: 110 | A2 |
| 64 | 258 | LSASSGLAH | SEQ ID No: 111 | A1, A3, B7, B8 |
| 65 | 260 | ASSGLAHAD | SEQ ID No: 112 | A1, A3, A_0301 |
| 66 | 262 | SGLAHADSL | SEQ ID No: 113 | A_0201 |
| 67 | 263 | GLAHADSLA | SEQ ID No: 114 | A_0101, A_0201, A_0301 |
| 68 | 269 | SLASSASLP | SEQ ID No: 115 | A_0201, A_0301 |
| 69 | 271 | ASSASLPAL | SEQ ID No: 116 | B7 |
| 70 | 286 | SGFGGLPSL | SEQ ID No: 117 | A2, A_0201, B51 |
| 71 | 291 | LPSLAQVHA | SEQ ID No: 118 | B7, B_3501, B51 |
| 72 | 298 | HAASTRQAL | SEQ ID No: 119 | B7, B8, B_3501 |
| 73 | 301 | STRQALRPR | SEQ ID No: 120 | A3, A_0301 |
| 74 | 307 | RPRADGPVG | SEQ ID No: 121 | B7, B_0702, B8, B51 |
| 75 | 319 | EQVGGQSQL | SEQ ID No: 122 | B7, B44 |
| 76 | 350 | GASKGTTTK | SEQ ID No: 123 | A3, A_0301 |
| 77 | 351 | ASKGTTTKK | SEQ ID No: 124 | A3, A_0301 |
| 78 | 353 | KGTTTKKYS | SEQ ID No: 125 | A_0301, B8 |
| 79 | 368 | TEDAERAPV | SEQ ID No: 126 | B44 |

As can be seen from Tables 2 and 3, Rv3616c contains a number of predicted CD4+ and CD8 T cell epitopes. Furthermore, this information suggests that the protein carries epitopes that can be recognised by HLAs which occur worldwide (that is HLAs from Caucasian, African, Asian or Latin-American individuals—see website at www.allelefrequencies.net).

Example 3

Rv3616c Epitope Identification

A range of 30 overlapping peptides covering the full length of Rv3616c were prepared (see FIG. 1 for details and SEQ ID Nos: 127-156) and tested for their ability to stimulate PBMC from four PPD+ donors.

The data, shown in FIG. 2, reveals that peptides 1-7 and 17-30 were immunogenic for these individuals. These peptides are suitably present within the sequence of the modified Rv3616c proteins of the invention.

It should be noted that peptides 8-16 (amino acid residues 92-215) may be immunogenic in other individuals of differing HLA type.

Example 4

Rv3616c H37Rv Homologues

Rv3616c sequences from a number of *M. tuberculosis* strains and BCG were identified using BLASTP searches of GenBank (H37Rv reference sequence accession number NP_218133.1):

| Strain | Accession Number | % identity |
|---|---|---|
| CDC1551 | NP_338263.1 | 99 |
| F11 | YP_001289574.1 | 99 |
| Haarlem | ZP_02248979.1 | 99 |
| C | ZP_00877472.1 | 99 |
| BCG | YP_979759.1 | 99 |

Alignment of the homologue sequences indicates a high level of identity.

Biological Assays
Quantification of T Cell Responses to Rv3616c

Polypeptides may be screened for their ability to activate T-cells (induction of proliferation and/or production of cytokines) in peripheral blood mononuclear cell (PBMC) or in whole blood preparations from infected (such as latently infected) individuals.

Latently infected individuals are usually identified by a skin test that has a diameter above 10 mm and without symptoms, with no Mtb positive culture, with a negative sputum negative and with no lesion (as detected by chest X-Ray).

A range of in vitro assays can be used based on PBMC samples or whole blood: after restimulation in presence of the antigen (or variant/immunogenic fragment thereof as appropriate) the proliferation of the cells may be determined (as measured by CFSE/flow cytometry) or the production of cytokines quantified (present in the supernatant of cultured cells and measured by ELISA, or, after intracellular staining of CD4 and CD8 T cells and analysis by flow cytometry).

For example, PBMC samples may be obtained from heparinised whole blood by Ficoll-Hypaque density gradient centrifugation following standard procedures. The cells may then be washed and cryopreserved in liquid nitrogen until testing (for further details see Lalvani A et al. *J. Infect. Dis.* 1999 180:1656-1664).

T Cell Proliferation

The specific immune response may be characterised by performing lymphocyte proliferation analysis using the tritiated thymidine. This technique assesses the cellular expansion upon in vitro stimulation to an antigen. In practice, cell proliferation is determined by estimating incorporation of tritiated-thymidine into DNA, a process closely related to underlying changes in cell number.

More suitably, lymphocyte proliferation may be performed using the succinimidyl ester of carboxyfluorsecein diacetate (CFSE). CFSE spontaneously and irreversibly couples to both intracellular and cell surface proteins by reaction with lysine side chains and other available amine groups. When lymphocyte cells divide, CFSE labelling is distributed equally between the daughter cells, which are therefore half as fluorescent as the parents. As a result, halving of cellular fluorescence intensity marks each successive generation in a population of proliferating cells and is readily followed by flow cytometry (for further details see Hodgkins, P D et al *J. Exp. Med.* 1996 184:277-281).

Practically, after thawing, PMBC may be washed and stained with CFSE before being cultivated ($2 \times 10^5$ cells) for 72 hrs with 10 ug/ml of antigen in culture media (RPMI-1640 supplemented with glutamine, non essential amino acid, pyruvate and heat inactivated human AB serum). Cells may then harvested and their phenotype characterised using surface staining to identify memory CD8 and CD4+ T-Cells. Subsequently, flow cytometry analysis can be used to indicate the extent of lymphocyte proliferation in response to each antigen (proportion of cells with decreased CFSE intensity upon in vitro stimulation).

Cytokine Production

IFN-γ production (or the production of other cytokines such as e.g. IL2, TNF-alpha, IL5, IL12 etc) may be measured using an enzyme-linked immunosorbent assay (ELISA). ELISA plates may be coated with a mouse monoclonal antibody directed to human IFN-γ (PharMingen, San Diego, Calif.) in PBS for four hours at room temperature. Wells are then blocked with PBS containing 5% (W/V) non-fat dried milk for 1 hour at room temperature. The plates are then washed, for example, six times in PBS/0.2% TWEEN-20 and samples diluted 1:2 in culture medium in the ELISA plates are incubated overnight at room temperature. The plates are again washed and a polyclonal rabbit anti-human IFN-γ serum, for example, diluted 1:3000 in PBS/10% normal goat serum may be added to each well. The plates are then incubated for two hours at room temperature, washed and horseradish peroxidase-coupled anti-rabbit IgG (Sigma Chemical So., St. Louis, Mo.) may be added, for example, at a 1:2000 dilution in PBS/5% non-fat dried milk. After a further two hour incubation at room temperature, the plates are washed and TMB substrate added. The reaction may be stopped after 20 min with 1 N sulfuric acid. Optical density can then be determined at 450 nm using 570 nm as a reference wavelength. Typically, fractions that result in both replicates giving an OD two fold greater than the mean OD from cells cultured in medium alone may be considered positive.

Example 5

Immunogenicity of Rv3616c in CB6F1 Mice

The immunogenicity of the antigen was evaluated in CB6F1 mice (first generation cross of BALB/c and C57BL/6 mice).

CB6F1 mice were immunised intramuscularly three times (on day 0, day 14 and day 28) with 0.5 ug of protein antigen in combination with the Adjuvant System AS01E (a liposomal adjuvant formulation comprising 3D-MPL and QS21).

The experimental design was as follows:

| Group | Day 0 | Day 14 | Day 28 |
|---|---|---|---|
| 1 | 0.5 ug Rv3616c/AS01E | 0.5 ug Rv3616c/AS01E | 0.5 ug Rv3616c/AS01E |

A total of 24 mice were used in the protocol group.

Peripheral blood lymphocytes (PBL) were collected and pooled on day 21 (i.e. 7 days post second immunisation) and day 35 (i.e. 7 days post third immunisation) and the antigen-specific CD4 & CD8 T cell responses (as determined by CD4 or CD8 T cells producing IL-2 and/or IFN-gamma and/or TNF-alpha) were measured by flow cytometry after overnight in vitro restimulation with pools of 15mer peptides covering the sequences of interest. The detection of mouse T cells that express IL-2 and/or IFN-gamma and/or TNF-alpha was done by using short-term antigen-driven in vitro amplification of cytokine expression.

Briefly, PharmLyse solution (BD-Pharmingen) was added to heparinised mouse peripheral blood in order to lyse the red blood cells. The PBLs (Peripheral Blood Lymphocytes) obtained were washed and then incubated in the presence of a pool of 15-mer peptides—overlapping by 11 amino acids—covering the sequence of the antigen of interest and of 1 ug/ml of antibodies to CD28 and CD49d (BD-Pharmingen). Each 15-mer peptide was used at a final concentration of 1 ug/ml. Medium controls were also stimulated with antibodies to CD28 and CD49d.

The cytokine secretion blocking compound brefeldin-A (BD-Pharmingen) was added 2 h after the onset of the cultures at 37° C., 5% $CO_2$ and the cells maintained at 37° C., 5% $CO_2$ for 4 additional hours followed by overnight incubation at +4° C.

Cells were then harvested and stained with Pacific Blue-coupled anti-CD4 (BD—clone RM4-5, BD-Pharmingen) and peridinin chlorophyll A protein (PerCp) cyanin5.5 (Cy5.5)-coupled anti-CD8 alpha (clone 53-6.7, BD-Pharmingen) antibodies.

Cells were then washed, fixed, permeabilised (Cytofix-cytoperm kit, BD-Pharmingen) and stained with allophycocyanin-coupled anti-IFN-g antibodies (clone XMG1.2, BDP-harmingen), fluorescein isothiocyanate (FITC)-coupled anti-IL-2 antibodies (clone JES 6-5H4, Beckman Coulter) and phycoerythrin (PE)-coupled anti-TNF alpha antibodies (clone MP6-XT22, BD-Pharmingen). After final washes, stained cells were analysed on a LSR II flow cytometer (Beckton-Dickinson). A minimum number of 10,000 cells were acquired in the CD8+ subset. For further background see Walzer T et al *Cell Immunol.* 2000 206(1):16-25 and Maecker H T et al *J. Immunol. Methods* 2001 255(1-2):27-40.

As negative controls, some cells were also cultured overnight in vitro in culture medium (unstimulated). The antigen-specific responses were calculated by subtracting the average cytokine response produced by unstimulated cells from the average cytokine response produced by the peptide-stimulated cells.

At each timepoint and for each group, the data was collected from 4 pools of 6 mice each. The data below is presented as the % of CD4 or CD8 T cells producing IL-2 and/or IFN-gamma and/or TNF-alpha. Each individual pool of mice is plotted (triangles) as well as the average value of the group (bar).

FIG. 3 shows that on day 21 (i.e. 7 days post second immunisation), Rv3616c-specific CD4 and CD8 T cell responses are detected in mice immunised with 0.5 ug of Rv3616c/AS01E.

Figure 4:
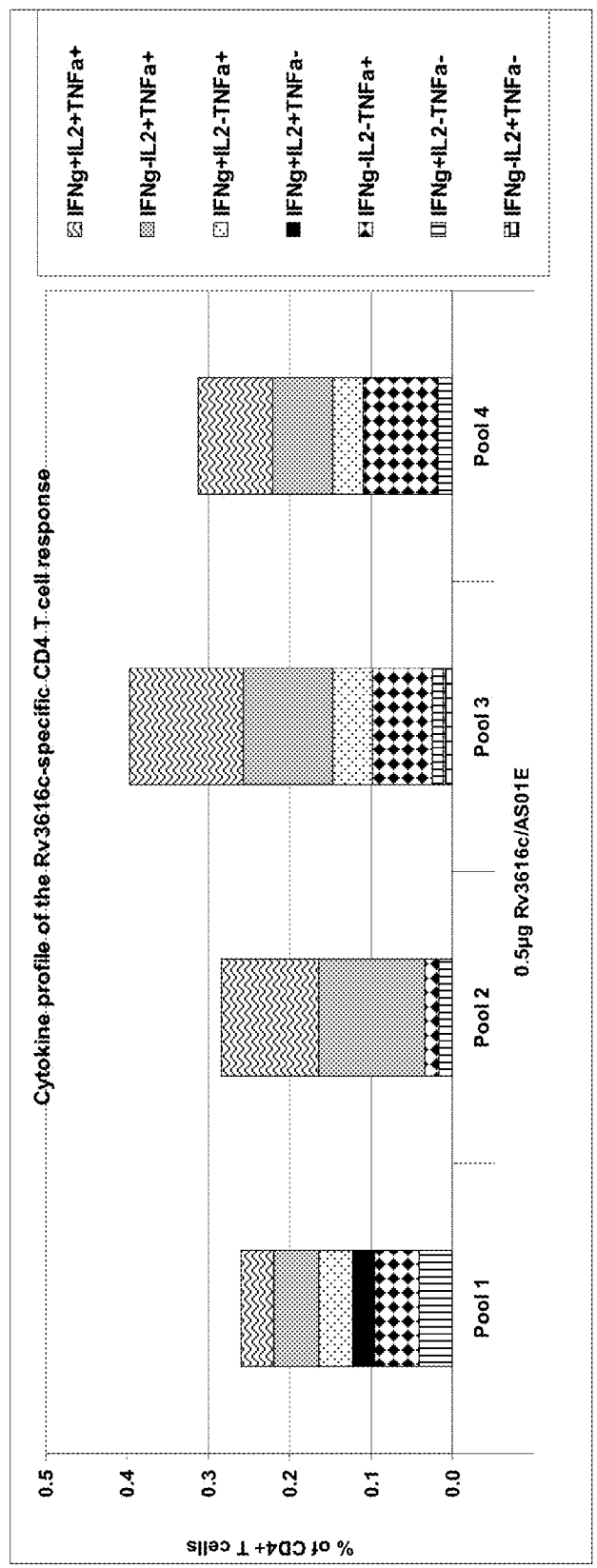
FIG. 4: Cytokine profile at day 21 (i.e. 7 days post second immunisation) of the antigen specific CD4 response in immunised CB6F1 mice.

FIG. 4 shows the cytokine profile of CD4 T cell response from the Rv3616c peptide pool-stimulated PBL (not medium removed) on day 21 (i.e. 7 days post second immunisation).

Figure 5:
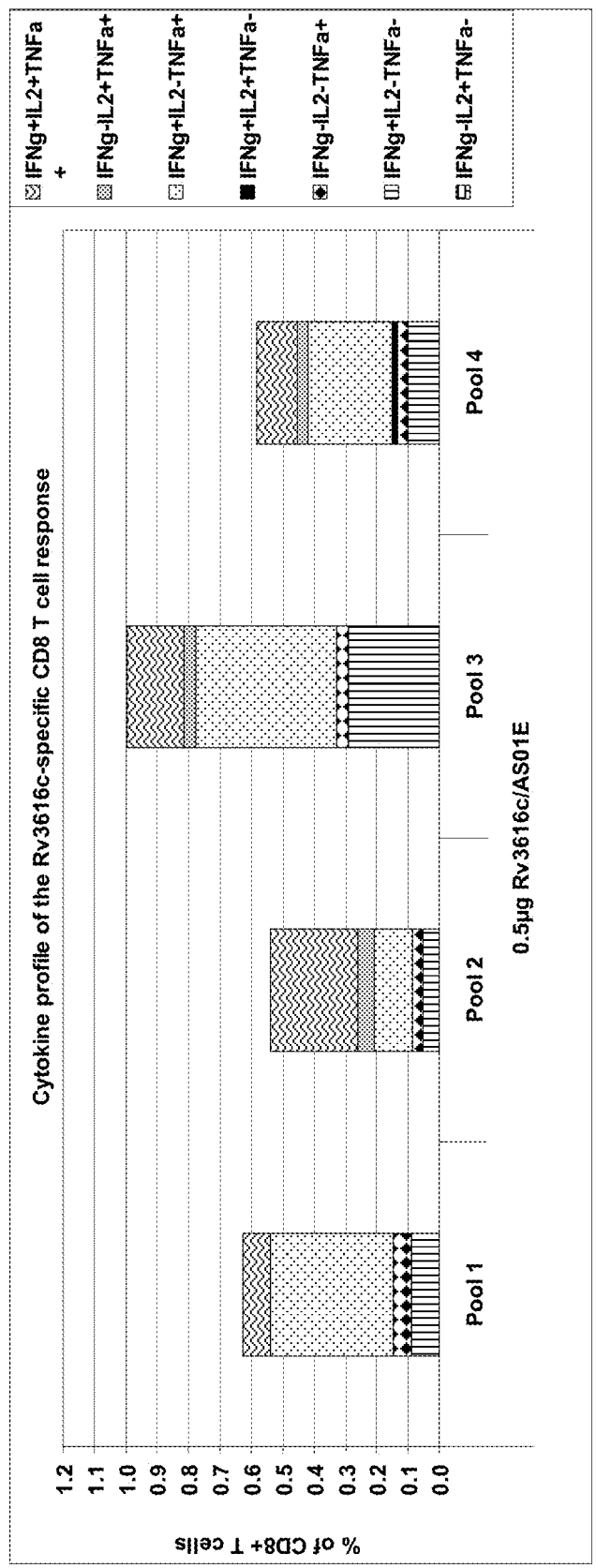
FIG. 5: Cytokine profile at day 21 (i.e. 7 days post second immunisation) of the antigen specific CD8 response in immunised CB6F1 mice.

FIG. 5 shows the cytokine profile of CD8 T cell response from the Rv3616c peptide pool-stimulated PBL (not medium removed) on day 21 (i.e. 7 days post second immunisation).

FIG. 6 shows that on day 35 (i.e. 7 days post third immunisation), Rv3616c-specific CD4 and CD8 T cell responses are detected in mice immunised with 0.5 ug of Rv3616c/AS01E. The third dose increases the CD4 T cell response but not the CD8 T cell response. Due to technical difficulties, data was only available for a single pool.

Figure 7:
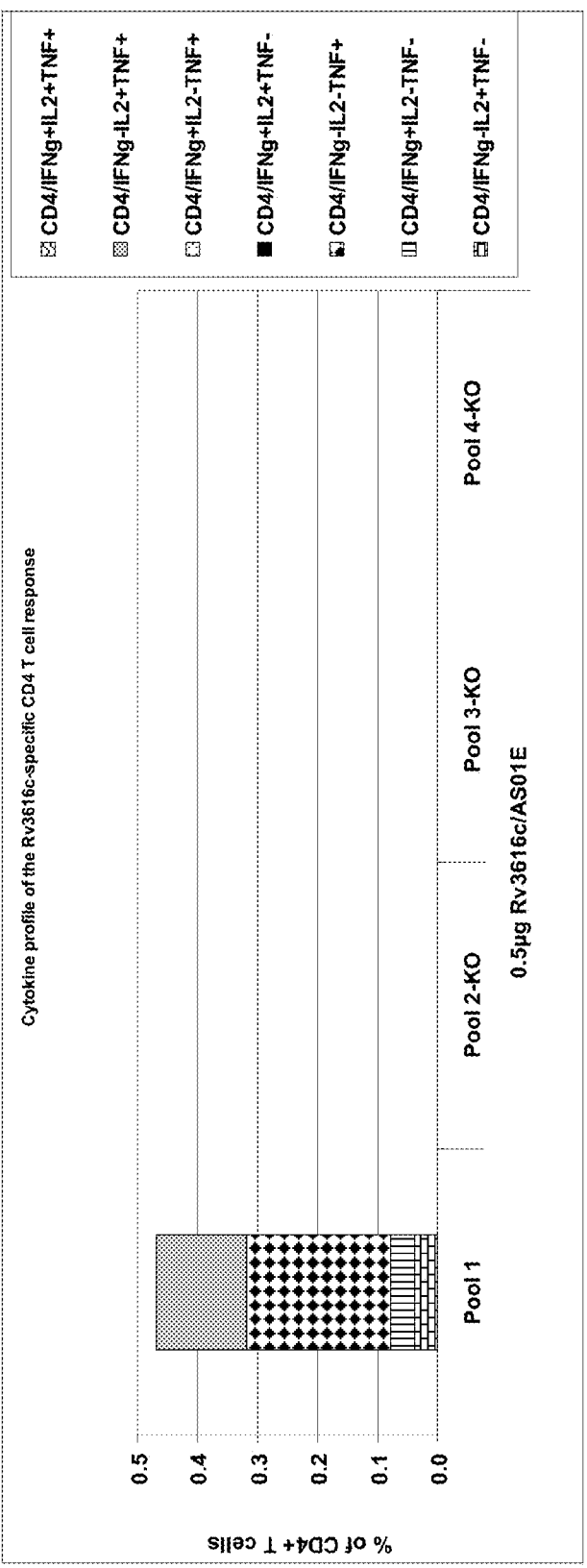
FIG. 7: Cytokine profile at day 35 (i.e. 7 days post third immunisation) of the antigen specific CD4 response in immunised CB6F1 mice.

FIG. 7 shows the cytokine profile of CD4 T cell response from the Rv3616c peptide pool-stimulated PBL (not medium removed) on day 35 (i.e. 7 days post third immunisation). Due to technical difficulties, data was only available for a single pool.

Figure 8:
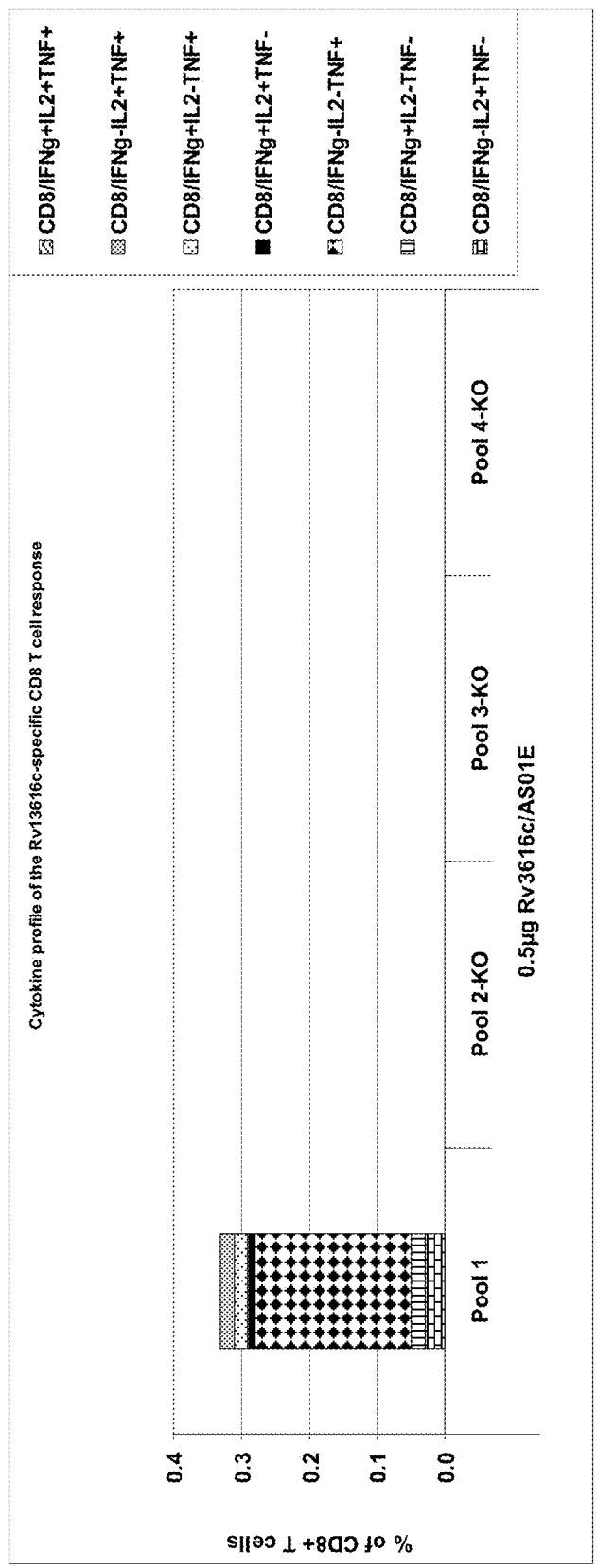
FIG. 8: Cytokine profile at day 35 (i.e. 7 days post third immunisation) of the antigen specific CD8 response in immunised CB6F1 mice.

FIG. 8 shows the cytokine profile of CD8 T cell response from the Rv3616c peptide pool-stimulated PBL (not medium removed) on day 35 (i.e. 7 days post third immunisation). Due to technical difficulties, data was only available for a single pool.

Example 6

Immunogenicity of Rv3616c in C57BL/6 Mice

The immunogenicity of the antigen was also evaluated in C57BL/6 mice.

C57BL/6 mice were immunised intramuscularly three times (on day 0, day 14 and day 28) with 1 ug protein antigen in combination with a the Adjuvant System AS01E (a liposomal adjuvant formulation comprising 3D-MPL and QS21).

The experimental design was the following:

| Group | Day 0 | Day 14 | Day 28 |
|---|---|---|---|
| 1 | 1 ug Rv3616c/AS01E | 1 ug Rv3616c/AS01E | 1 ug Rv3616c/AS01E |

Peripheral blood lymphocytes (PBL) were collected and pooled on day 21 (i.e. 7 days post second immunisation) and day 35 (i.e. 7 days post third immunisation) and the antigen-specific CD4 & CD8 T cell responses (as determined by CD4 or CD8 T cells producing IL-2 and/or IFN-gamma and/or TNF-alpha) were measured by flow cytometry after overnight in vitro restimulation with pools of 15mer peptides covering the sequences of interest. The procedure followed was as described previously.

As negative controls, some cells were also cultured overnight in vitro in culture medium (unstimulated). The antigen-specific responses were calculated by subtracting the average cytokine response produced by unstimulated cells from the average cytokine response produced by the peptide-stimulated cells.

At each timepoint and for each group, the data was collected from 4 pools of 6 mice each. The data below is presented as the % of CD4 or CD8 T cells producing IL-2 and/or IFN-gamma and/or TNF-alpha. Each individual pool of mice is plotted (triangles) as well as the average value of the group (bar).

FIG. 9 shows that on day 21 (i.e. 7 days post second immunisation), Rv3616c-specific CD4 and CD8 T cell responses are detected in mice immunised with 1 ug of Rv3616c/AS01E, although the antigen-specific CD8 T cell response is very low (cytokine profile data is therefore not shown).

Figure 10:
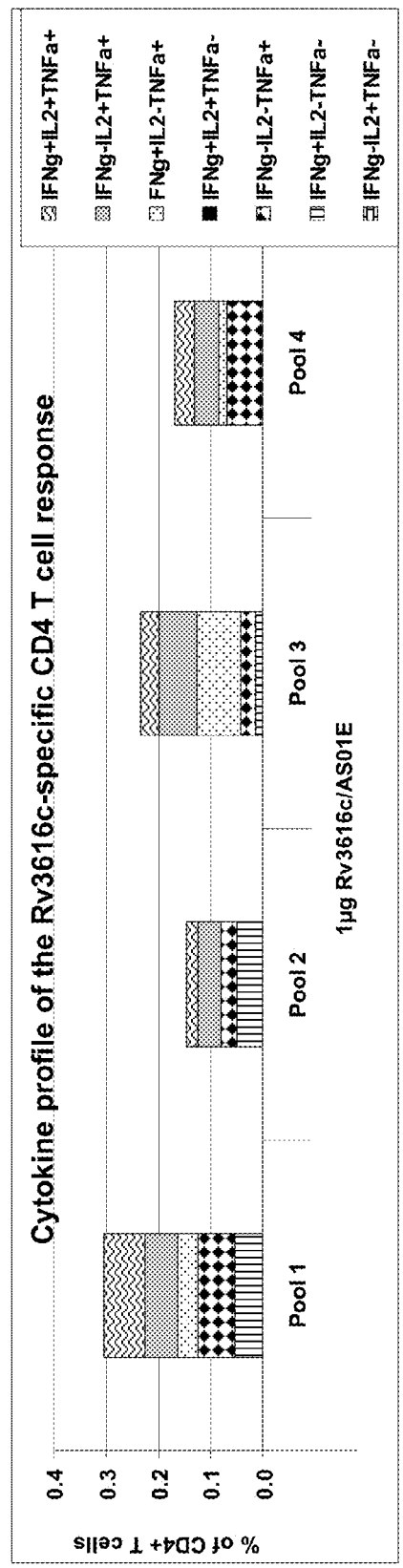
FIG. 10: Cytokine profile at day 21 (i.e. 7 days post second immunisation) of the antigen specific CD4 response in immunised C57BL/6 mice.

FIG. 10 shows the cytokine profile of CD4 T cell response from the Rv3616c peptide pool-stimulated PBL (not medium removed) on day 21 (i.e. 7 days post second immunisation).

FIG. 11 shows that on day 35 (i.e. 7 days post third immunisation), Rv3616c-specific CD4 and CD8 T cell responses are detected in mice immunised with 1 ug of Rv3616c/AS01E. A third immunisation dose increases the CD4 T cell responses but only slightly the CD8 T cell response.

Figure 12:
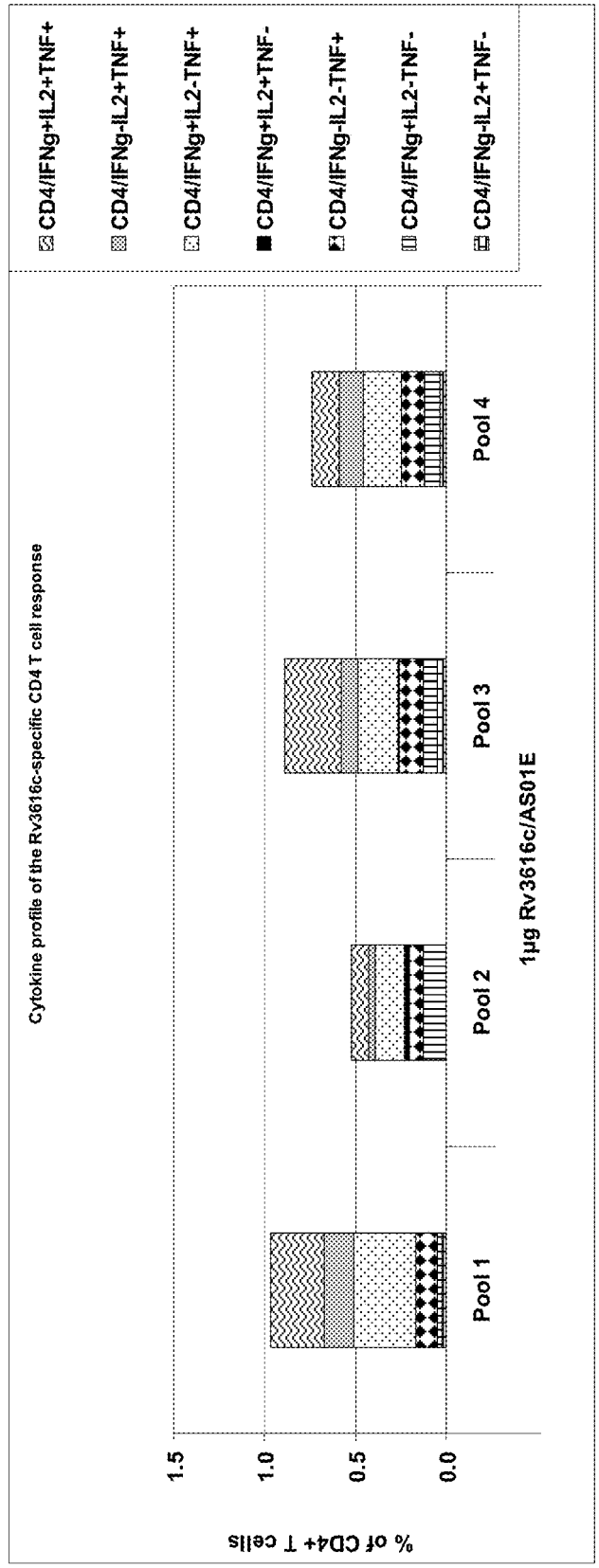
FIG. 12: Cytokine profile at day 35 (i.e. 7 days post third immunisation) of the antigen specific CD4 response in immunised C57BL/6 mice.

FIG. 12 shows the cytokine profile of CD4 T cell response from the Rv3616c peptide pool-stimulated PBL (not medium removed) on day 35 (i.e. 7 days post third immunisation).

Figure 13:
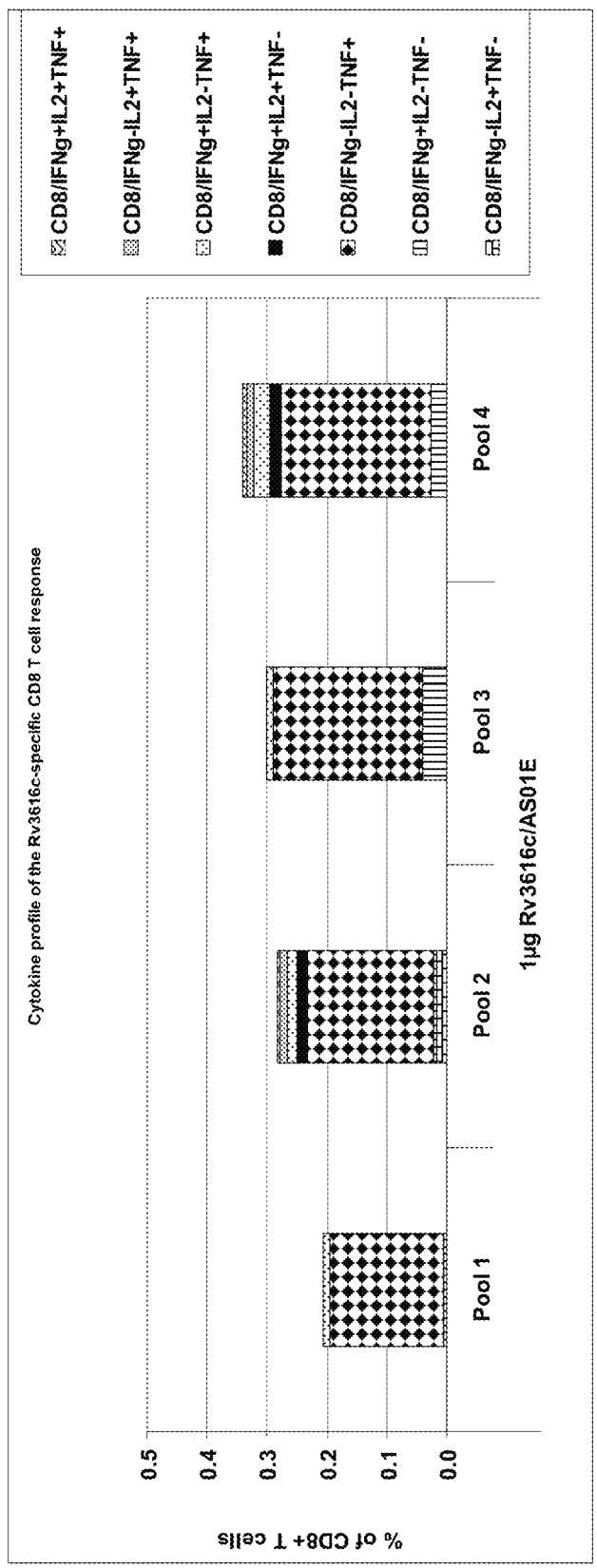
FIG. 13: Cytokine profile at day 35 (i.e. 7 days post third immunisation) of the antigen specific CD8 response in immunised C57BL/6 mice.

FIG. 13 shows the cytokine profile of CD8 T cell response from the Rv3616c peptide pool-stimulated PBL (not medium removed) on day 35 (i.e. 7 days post third immunisation).

Example 7

In Vitro Recognition of Rv3616c by PBMC from Humans with Latent TB

Experiments were performed in order to assess the peripheral T cell response specific to the inventive antigen in 4 TB naïve healthy adults (PPD skin test=0 mm) and 8 TB latently Infected healthy adults (PPD skin test=15 mm or above) from South Africa

| PPD Skin Test Data | |
|---|---|
| Individual ID Number | Induration diameter (mm) |
| 4 | 0 |
| 5 | 0 |
| 33 | 0 |
| 38 | 0 |
| 36 | 15 |
| 46 | 15 |
| 13 | 15 |
| 7 | 16 |
| 58 | 25 |
| 74 | 26 |
| 8 | 53 |
| 60 | 55 |

The cell-mediated immune (CMI) response was assessed by measuring cytokines on isolated peripheral blood mononuclear cells (PBMCs) by intracellular cytokine staining (ICS) assay.

ICS carried out was an adaptation of previously described methodology (see Von Eschen et al, *Hum. Vaccin.* 2009 5(7)). PBMCs were stimulated in vitro by one pool of 15-mer peptides—overlapping by 11 amino acids—covering the entire sequence of the antigen of interest. Cells were stimulated with peptides for 2 hours, further cultured overnight in the presence of Brefeldin A, processed for ICS and analysed using flow cytometry. The frequencies of the antigen-specific CD3+CD4+ or CD3+CD8+ T cells expressing IFN-gamma and/or TNF-alpha and/or IL-17 were measured. Medium-stimulated cell responses were subtracted from the responses obtained in peptide pools stimulated cells.

ICS: Antibodies
  Anti-CD3 PO (Invitrogen—cat CD0330)
  Anti-CD4 PB (BD—cat 558116)
  Anti-CD8 APC-H7 (BD—cat 641400)
  Anti-IFNg AF700 (BD-Pharmingen—cat 557995)
  Anti-TNF PE-Cy7 (BD-Pharmingen—cat 557647)
  Anti-IL17 AF647 (BD-Pharmingen—cat 51-7178-71)

Figure 14:
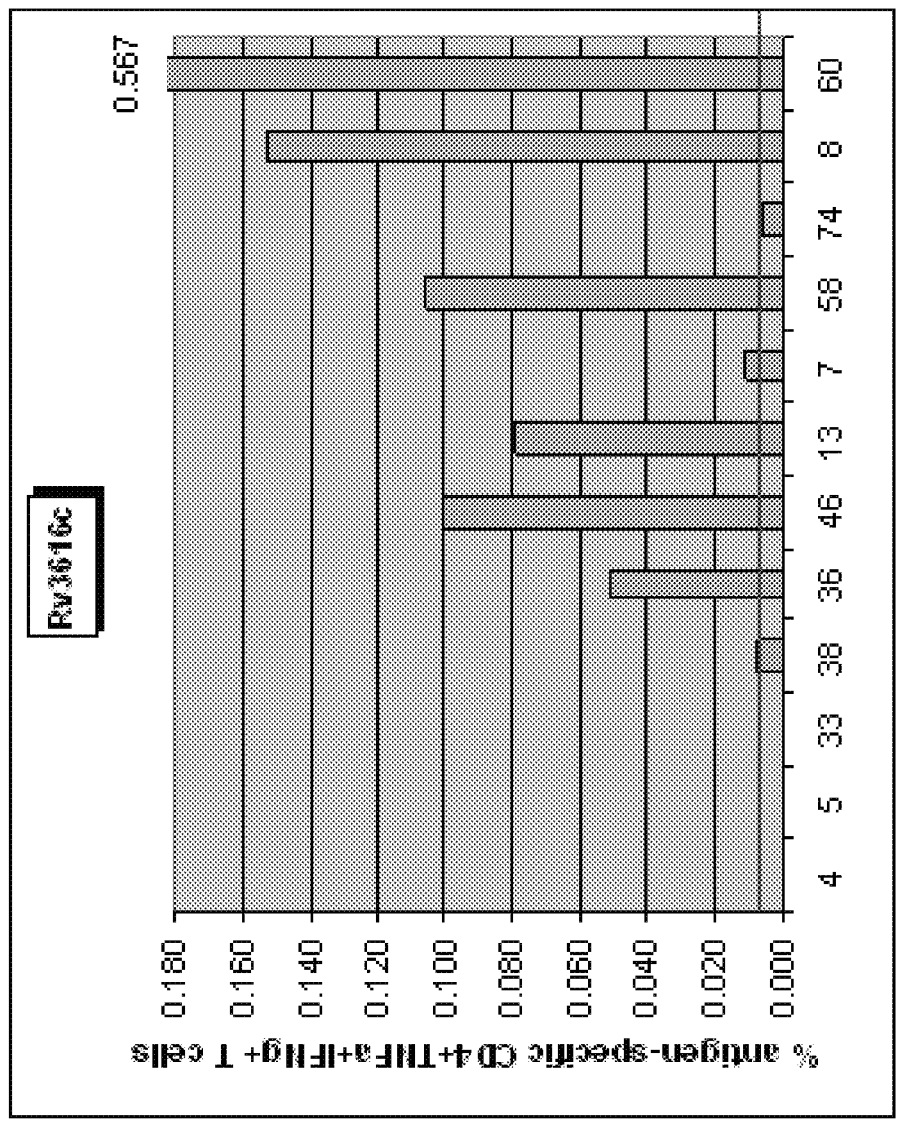
FIG. 14: Antigen-specific CD4 T cell responses in naive and latently infected humans.

The results are presented as number of antigen-specific CD3+CD4+ T cells expressing TNF-alpha and IFN-gamma, per million of CD3+CD4+ T cells since these cells represent the main population of the antigen-specific CD4 T cells (the background response level due to the medium is removed). No antigen-specific CD3+CD8+ T cells were detected. FIG. 14 shows that an antigen-specific CD4 T cell response is measured in 6 out of 8 latently infected individuals (not in individuals number 7 and 74) when compared to the non-specific CD4 T cell response measured in the naïve individuals.

Example 8

Production of Modified Rv3616c Sequences (i) Cloning

The *Mycobacterium tuberculosis* H37Rv Rv3616 nucleotide sequence was codon-optimized for expression in *E. coli* and gene synthesised. The insert obtained following subcloning was cloned into pET21 b+ (Novagen) using a NdeI restriction site at the N-terminus and a XhoI restriction site at the C-terminus. To generate the modified Rv3616c constructs, a series of PCR amplications using different primers was performed in order to delete specific nucleotide residues within the Rv3616c. The modified inserts were then cloned into pET26b+ and/or pET19b (Novagen).

| Clone to be generated | Primers used |
|---|---|
| pET26_Rv3616Δ136-183His | CAN1001/1004 |
| | CAN1003/1002 |
| pET26_Rv3616Δ150-160His | CAN1001/1006 |
| | CAN1005/1002 |
| pET26_Rv3616Δ136-154His | CAN1001/1008 |
| | CAN1007/1002 |
| pET26_Rv3616Δ166-182His | CAN1001/1010 |
| | CAN1009/1002 |
| pET19_Rv3616Δ136-183His | CAN1001/1004 |
| | CAN1003/1002 |
| pET19_Rv3616Δ150-160His | CAN1001/1006 |
| | CAN1005/1002 |
| pET19_Rv3616Δ136-154His | CAN1001/1008 |
| | CAN1007/1002 |
| pET19_Rv3616Δ166-182His | CAN1001/1010 |
| | CAN1009/1002 |
| pET26_Rv3616Δ135-139His | CAN1001/1065 |
| | CAN1064/1002 |
| pET26_Rv3616Δ142-145His | CAN1001/1067 |
| | CAN1066/1002 |
| pET26_Rv3616Δ145-152His | CAN1001/1069 |
| | CAN1068/1002 |
| pET26_Rv3616Δ138-145His | CAN1001/1071 |
| | CAN1070/1002 |
| pET26_Rv3616Δ149-154His | CAN1001/1073 |
| | CAN1072/1002 |

| Primer | primer sequence | Restriction site |
|---|---|---|
| CAN1001 | ggaattccatatgagccgtgcctttattattgatccgac | NdeI |

| Primer | primer sequence | Restriction site |
|---|---|---|
| CAN1002 | ccg ctc gag cac cac att gcg aac cag aac | XhoI |
| CAN1003 | ctg agc gca gca ttt cag gca ccg atg tgg ccg ata tta tta aag | nil |
| CAN1004 | ctttaataatatcggccacatcggt gcctgaaatgctgcgctcag | nil |
| CAN1005 | gttgtgggtggtgtctgacccagc tgctgaaactg | nil |
| CAN1006 | cagtttcagcagctgggtcagagca ccacccacaac | nil |
| CAN1007 | ctgagcgcagcatttcaggcgaaaa ccctgattaatgcaac | nil |
| CAN1008 | gttgcattaatcagggttttcgcct gaaatgctgcgctcag | nil |
| CAN1009 | gcaacccagctgctgaaatccgatg tggccgatattattaaag | nil |
| CAN1010 | ctttaataatatcggccacatcgga tttcagcagctgggttgc | nil |
| CAN1064 | ctgagcgcagcatttcagggtgcaa tggcagttgtg | nil |
| CAN1065 | cacaactgccattgcaccctgaaat gctgcgctcag | nil |
| CAN1066 | caatggcagttgtgggtggtgctaa aaccctgattaatgcaac | nil |
| CAN1067 | gttgcattaatcagggttttagcac cacccacaactgccattg | nil |
| CAN1068 | ccgttttgtgccggtgcaggtggtg ctctggcatatc | nil |
| CAN1069 | gatatgccagagcaccacctgcacc ggcacaaaacgg | nil |
| CAN1070 | gccggtgcaatggcagttgttgtga aaaccctgattaatg | nil |
| CAN1071 | cattaatcagggttttcacaacaac tgccattgcaccggc | nil |
| CAN1072 | gcatttcaggcaccgtttggtggtg ctctggcatatc | nil |
| CAN1073 | gatatgccagagcaccaccaaacgg tgcctgaaatgc | nil |

(ii) Expression of the Recombinant Proteins
Host Strain:
T7 Express competent *E. coli* (New England Biolabs): enhanced BL21 derivative.
Transformation of *Escherichia coli* T7 Express with plasmid DNA was carried out by standard methods with CaCl$_2$-treated cells (Hanahan D. <<Plasmid transformation by Simanis.>> in Glover, D. M. (Ed), DNA cloning. IRL Press London. (1985): p. 109-135).

| Recombinant plasmids ID | Host strain | Plate agar |
|---|---|---|
| pET21_Rv3616His | T7 Express[A] | LB agar plate with phytone and 100 µg/ml Carbenicillin[B] |
| pET26_Rv3616Δ136-183His | T7 Express[A] | LB agar plate with phytone and 100 µg/ml Kanamycin[C] |
| pET26_Rv3616Δ150-160His | T7 Express[A] | LB agar plate with phytone and 100 µg/ml Kanamycin[C] |
| pET26_Rv3616Δ136-154His | T7 Express[A] | LB agar plate with phytone and 100 µg/ml Kanamycin[C] |
| pET26_Rv3616Δ166-182His | T7 Express[A] | LB agar plate with phytone and 100 µg/ml Kanamycin[C] |
| pET19_Rv3616Δ136-183His | T7 Express[A] | LB agar plate with phytone and 100 µg/ml Carbenicillin[B] |
| pET19_Rv3616Δ150-160His | T7 Express[A] | LB agar plate with phytone and 100 µg/ml Carbenicillin[B] |
| pET19_Rv3616Δ136-154His | T7 Express[A] | LB agar plate with phytone and 100 µg/ml Carbenicillin[B] |
| pET19_Rv3616Δ166-182His | T7 Express[A] | LB agar plate with phytone and 100 µg/ml Carbenicillin[B] |
| pET26_Rv3616Δ135-139His | T7 Express[A] | LB agar plate with phytone and 100 µg/ml Kanamycin[C] |
| pET26_Rv3616Δ142-145His | T7 Express[A] | LB agar plate with phytone and 100 µg/ml Kanamycin[C] |
| pET26_Rv3616Δ145-152His | T7 Express[A] | LB agar plate with phytone and 100 µg/ml Kanamycin[C] |
| pET26_Rv3616Δ138-145His | T7 Express[A] | LB agar plate with phytone and 100 µg/ml Kanamycin[C] |
| pET26_Rv3616Δ149-154His | T7 Express[A] | LB agar plate with phytone and 100 µg/ml Kanamycin[C] |

[A]NEB (catalogue number: C2566H)
[B]Teknova, CA, USA (catalogue number L1092)
[C]Teknova, CA, USA (catalogue number L1096)

Confluent agar plate inoculated with transformed *E. coli* T7 Express+plasmid was used to inoculate 800 ml of LB broth APS+50 µg/ml of antibiotic to obtain O.D.$_{600nm}$ between 0.05-0.1. Cultures were incubated at 37° C., 250 RPM to an O.D.$_{600nm}$ around 0.8.

Expression of the recombinant protein was induced by addition of 1 mM final of isopropyl β-D-1-thiogalactopyranoside (IPTG; EMD Chemicals Inc) to the growing culture medium. Induction was maintained for 3 hours at 37° C. (or overnight at 16° C.).

(iii) Purification

Bacterial culture was centrifuged 15 min, 4° C. at 8000 g. Bacterial culture pellets were resuspended in Lysis buffer (20 mM Tris buffer (pH 8.0) and a mixture of protease inhibitors cocktail (Complete EDTA-free). Bacteria were lysed with the Constant Cell disruption system (Constant System). Soluble (supernatant) and insoluble (pellet) components were separated by centrifugation at 20000 g for 20 min at 4° C.

The insoluble components (pellets) were resolubilised in 20 mM HEPES buffer containing 6M guanidine HCl, 500 mM NaCl, 10 mM imidazole pH8.0. The supernatant was then loaded on a 5 ml IMAC column (BioRad). After washes, elution was performed using a 20 mM HEPES buffer (pH 8.0) containing 6M Guanidine-HCl, 500 mM NaCl, and 250 mM imidazole.

Two dialysis steps were performed in membrane 12-14000 MWCO (SpectraPor): primary in a 8M urea buffer containing 20 mM HEPES, 150 mM NaCl at pH 8.0 followed by a second dialysis in PBS, 4M urea pH7.4.

(iv) SDS-PAGE

Samples from non-induced and induced cultures were collected to determine the expression profile and analyzed by SDS-PAGE.

Figure 17:
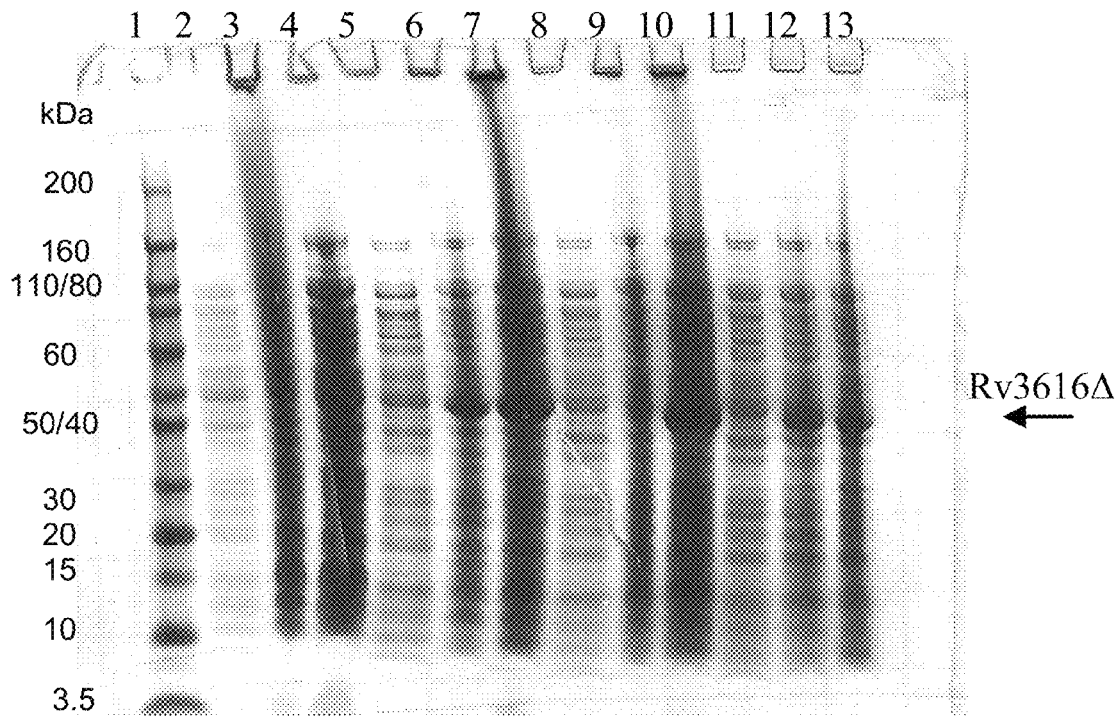
FIG. 17: SDS-PAGE results of initial antigen expression experiments.
Figure 18:
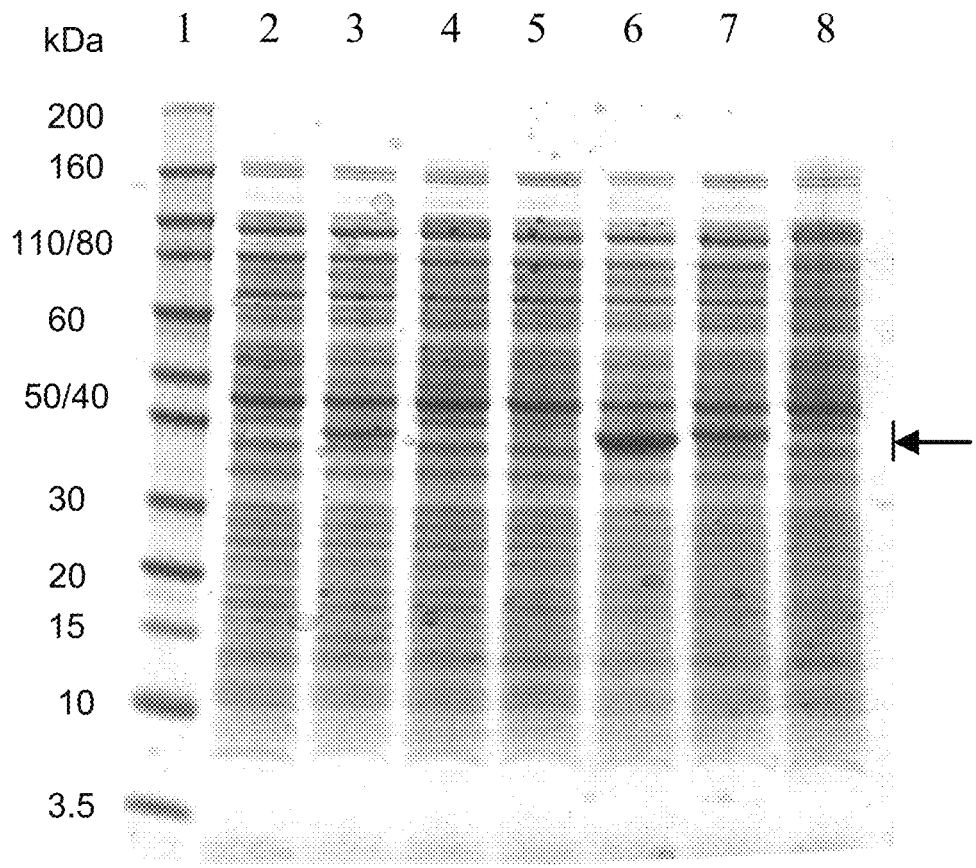
FIG. 18: SDS-PAGE results of further antigen expression experiments.

Briefly, samples were treated with NUPAGE 4xLDS Sample buffer (Invitrogen), reduced using 0.05M DTT and heated at 70° C. for 10 min. Samples were then centrifuged at maximum speed for 2 minutes and loaded on NUPAGE Novex 4-12% Bis-Tris gel (Invitrogen). The migration was performed at 200V for 35 minutes in 1× NUPAGE MES Running Buffer (Invitrogen) and the gel was stained to allow visualization of the separated proteins, the results of which are shown in FIGS. 17 and 18.

When compared to the H37Rv wild-type expression, the constructs Rv3616Δ138-145, Rv3616Δ136-154, Rv3616Δ150-160, Rv3616Δ166-182, Rv3616Δ149-154 and Rv3616Δ135-139 are notably improved.

The construct Rv3616Δ136-183 contained an erroneous STOP codon within the sequence, consequently expression of the sequence did not proceed as intended.

Example 9

Further Production of Modified Rv3616c Sequences

Using analogous methodology to that described in Example 8, wherein the BL21 (DE3) strain was used in place of T7Express and confluent agar plate was used to inoculate 25 ml of LB broth APS with antibiotic, three expression runs were performed (starting from the same transformation plate) in respect of a range of modified Rv3616c constructs.

Figure 19:
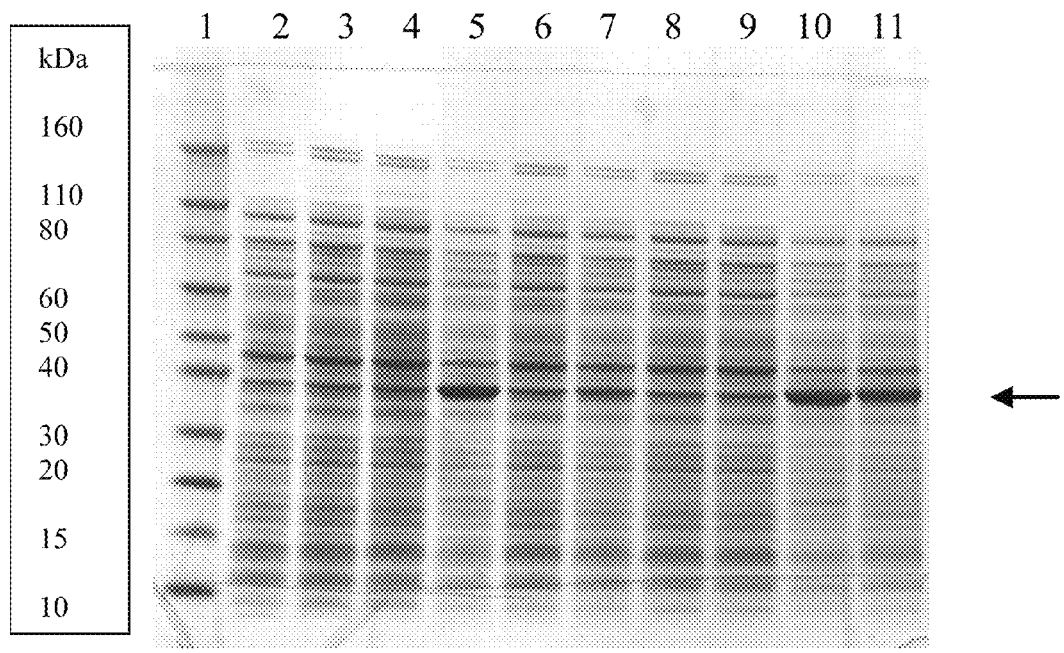
FIG. 19: SDS-PAGE results of additional antigen expression experiments.

The products of the expression runs were analysed by SDS-PAGE and a representative gel from one of the expression runs is provided in FIG. 19. Rv3616Δ138-145 was found to offer the best protein expression, followed closely by Rv3616Δ149-154 and Rv3616Δ136-154, with Rv3616Δ135-139 also showing good expression.

Quantification of the band corresponding to the target protein was performed using ImageQuant TL software. Briefly, the SDS-PAGE gels were stained using InstantBlue staining (Novexin) and scanned with a UVP BioImaging System in TIFF files format. The bands were then analysed using ImageQuantTL 7.0 software from GE Healthcare. The Rv3616 non-induced protein being used as control for negative expression as no reactivity with anti-his tag Ab was observed.

| Construct | Band %: Gel 1 | Band %: Gel 2 | Band %: Gel 3 | Band % average |
|---|---|---|---|---|
| non induced Rv3616 | 9 | 8 | 7 | 8 |
| Rv3616 | 8 | 8 | 8 | 8 |
| Rv3616Δ150-160 | 8 | 10 | 12 | 10 |
| Rv3616Δ136-154 | 22 | 28 | 29 | 26 |
| Rv3616Δ166-182 | 10 | 10 | 9 | 10 |
| Rv3616Δ135-139 | 15 | 16 | 17 | 16 |
| Rv3616Δ142-145 | 9 | 9 | 8 | 9 |
| Rv3616Δ145-152 | 10 | 9 | 10 | 10 |
| Rv3616Δ149-154 | 26 | 28 | 31 | 28 |
| Rv3616Δ138-145 | 23 | 25 | 21 | 23 |

Band %: measure of the band's Volume divided by the Total Volume of all the bands in the lane.

In band percentage, the Rv3616Δ149-154, Rv3616Δ138-145 and Rv3616Δ136-154 proteins are all expressed at notably higher levels compared to the natural sequence or the known Rv3616Δ150-160 construct. Rv3616Δ135-139 was also expressed at a high level.

Example 10

Immunogenicity of Rv3616Δ138-145 in CB6F1 Mice

The immunogenicity of Rv3616Δ138-145 was evaluated in CB6F1 mice.

CB6F1 mice were immunised intramuscularly three times (on day 0, day 14 and day 28) with 50 ul of test vaccine containing a dose range (8 ug, 2 ug and 0.5 ug) of Rv3616Δ138-145 in combination with the Adjuvant System AS01E (a liposomal adjuvant formulation comprising 3D-MPL and QS21). The formulations also contained urea (4M) and arginine (500 mM).

The experimental design was the following:

| Group | Day 0 | Day 14 | Day 28 |
|---|---|---|---|
| 1 | 8 ug Rv3616Δ138-145/AS01E | 8 ug Rv3616Δ138-145/AS01E | 8 ug Rv3616Δ138-145/AS01E |
| 2 | 2 ug Rv3616Δ138-145/AS01E | 2 ug Rv3616Δ138-145/AS01E | 2 ug Rv3616Δ138-145/AS01E |
| 3 | 0.5 ug Rv3616Δ138-145/AS01E | 0.5 ug Rv3616Δ138-145/AS01E | 0.5 ug Rv3616Δ138-145/AS01E |

A total of 20 mice were used in each immunisation group. 10 mice received saline as a negative control group (data not shown).

Peripheral blood lymphocytes (PBL) were collected & pooled on days 21 (i.e. 7 days post second immunisation) and 35 (i.e. 7 days post third immunisation) and the antigen-specific CD4 & CD8 T cell responses (as determined by CD4 or CD8 T cells producing IL-2 and/or IFN-gamma and/or TNF-alpha) were measured by flow cytometry after a 6 hour in vitro restimulation with pools of 15mer peptides covering the full Rv3616c antigen sequence. The detection of mouse T cells that express IL-2 and/or IFN-gamma and/or TNF-alpha was done by using short-term antigen-driven in vitro amplification of cytokine expression.

Briefly, PharmLyse solution (BD-Pharmingen) was added to heparinised mouse peripheral blood in order to lyse red blood cells. The PBLs (Peripheral Blood Lymphocytes) obtained were washed and then incubated in the presence of a pool of 15-mer peptides—overlapping by 11 amino acids—covering the sequence of the antigen of interest and of 1 ug/ml of antibodies to CD28 and CD49d (BD-Pharmingen). Each 15-mer peptide was used at a final concentration of 1 ug/ml. Medium controls wells were also stimulated with antibodies to CD28 and CD49d.

The cytokine secretion blocking compound brefeldin-A (BD-Pharmingen) was added 2 h after the onset of the cultures at 37° C., 5% $CO_2$ and the cells maintained at 37° C., 5% $CO_2$ for 4 additional hours followed by overnight storage at +4° C.

Cells were then harvested and stained with Pacific Blue-coupled anti-CD4 (clone RM4-5, BD-Pharmingen) and peridinin chlorophyll A protein (PerCp) cyanin5.5 (Cy5.5)-coupled anti-CD8 alpha (clone 53-6.7, BD-Pharmingen) antibodies.

Cells were then washed, fixed, permeabilised (Cytofix-cytoperm kit, BD-Pharmingen) and stained with allophycocyanin-coupled anti IFN-gamma antibodies (clone XMG1.2, BD-Pharmingen), fluorescein isothiocyanate (FITC)-coupled anti IL-2 antibodies (clone JES 6-5H4, BD-Pharmingen) and phycoerythrin (PE)-coupled anti-TNF alpha antibodies (clone MP6-XT22, BD-Pharmingen). After final washes, stained cells were analysed on a LSRII flow cytometer (Becton-Dickinson). A minimum of 10,000 cells were acquired in the CD8+ subset.

As negative controls, some cells were also cultured for 6 h in vitro in culture medium (unstimulated). The antigen-specific responses were calculated by subtracting the average cytokine response produced by unstimulated cells from the average cytokine response produced by the peptide-stimulated cells.

At each timepoint and for each group, the data was collected from 4 pools of 5 mice each and the data presented as the % of CD4 or CD8 T cells producing IL-2 and/or IFN-gamma and/or TNF-alpha. Each individual pool of mice is plotted (closed diamonds) as well as the median value of the group (bar).

The results are shown in FIGS. 20 to 25.

Figure 20:
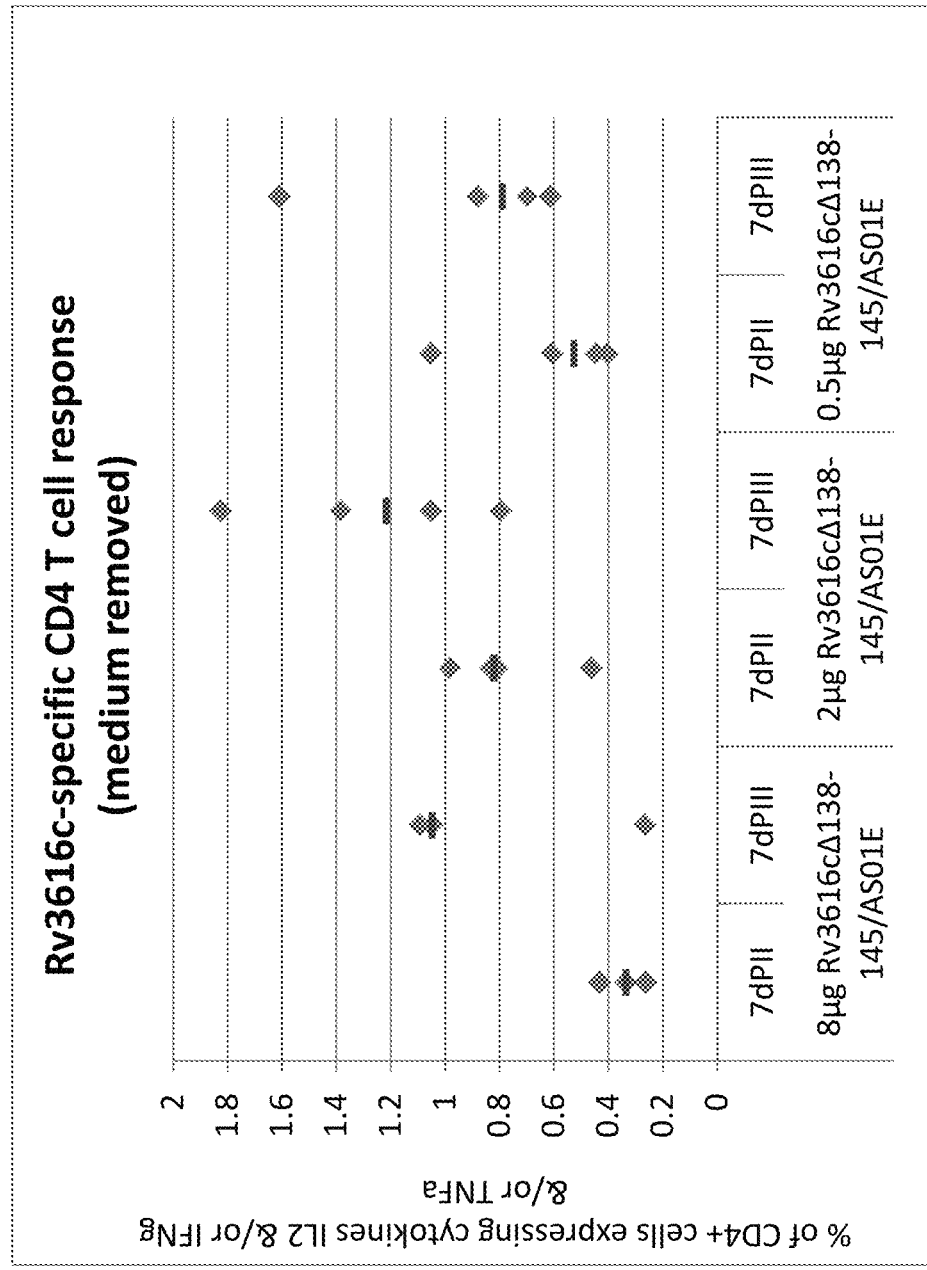
FIG. 20: Percentage of CD4 cells from immunised mice expressing IFN-gamma and/or IL-2 and/or TNF-alpha cytokines at 7 days post second and 7 days post third immunisations with Rv3616Δ138-145.
Figure 22:
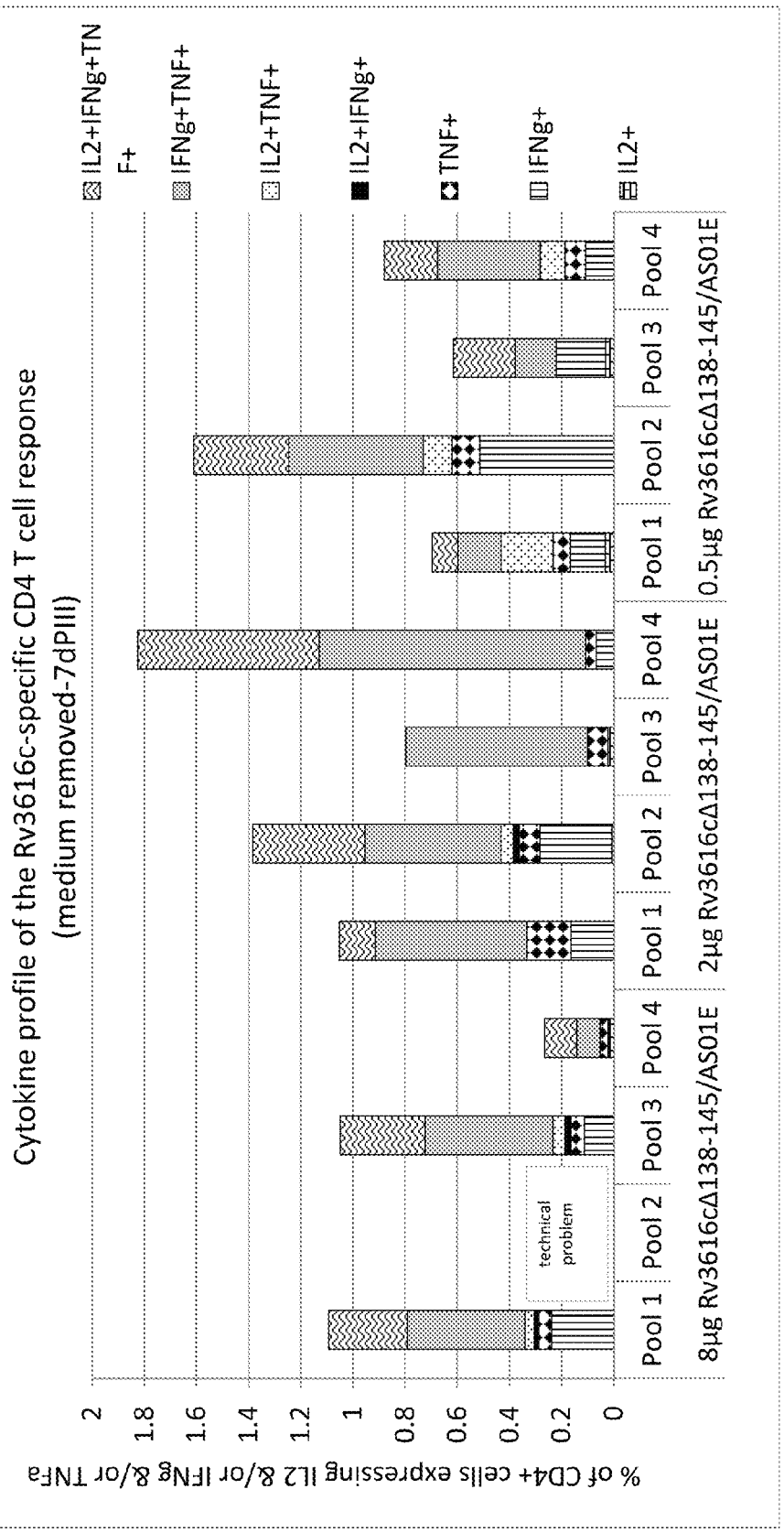
FIG. 22: Cytokine profile of the Rv3616 specific CD4 T cell response at 7 days post third immunisation with Rv3616Δ138-145.

FIG. 20 shows that at both timepoints (7dPII & 7dPIII), Rv3616c-specific CD4 T cell responses are detected in mice immunised with either dose of Rv3616Δ138-145/AS01E. The levels of Rv3616c-specific T cell responses are higher at the 7dPIII timepoint when compared to the 7dPII timepoint. Cyotokine profiles of the CD4 T cell response from the Rv3616c peptide pool-stimulated PBL (medium removed) are shown in FIGS. 21 (7dPII) and 22 (7dPIII).

Figure 23:
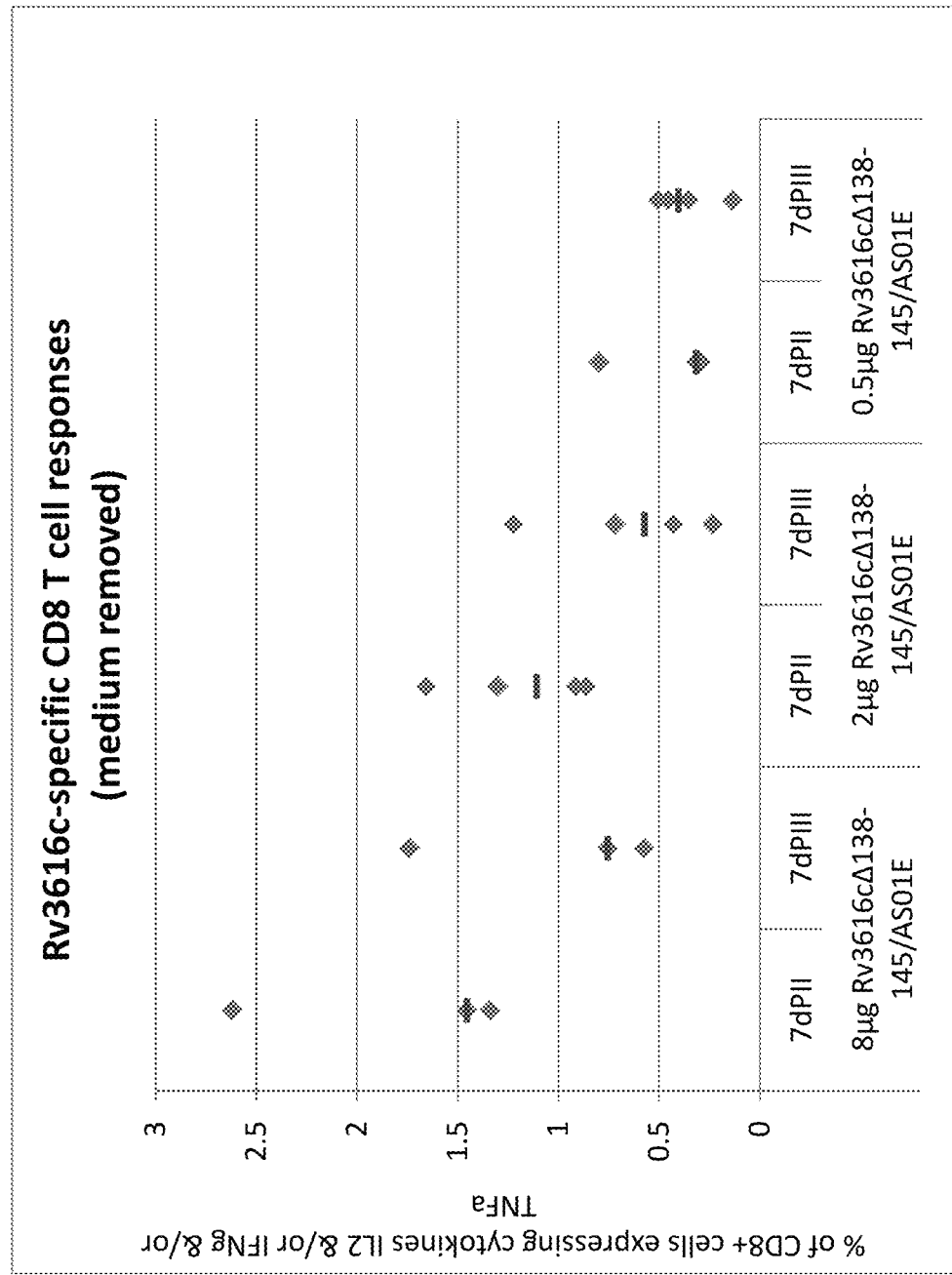
FIG. 23: Percentage of CD8 cells from immunised mice expressing IFN-gamma and/or IL-2 and/or TNF-alpha cytokines at 7 days post second and 7 days post third immunisations with Rv3616Δ138-145.
Figure 24:
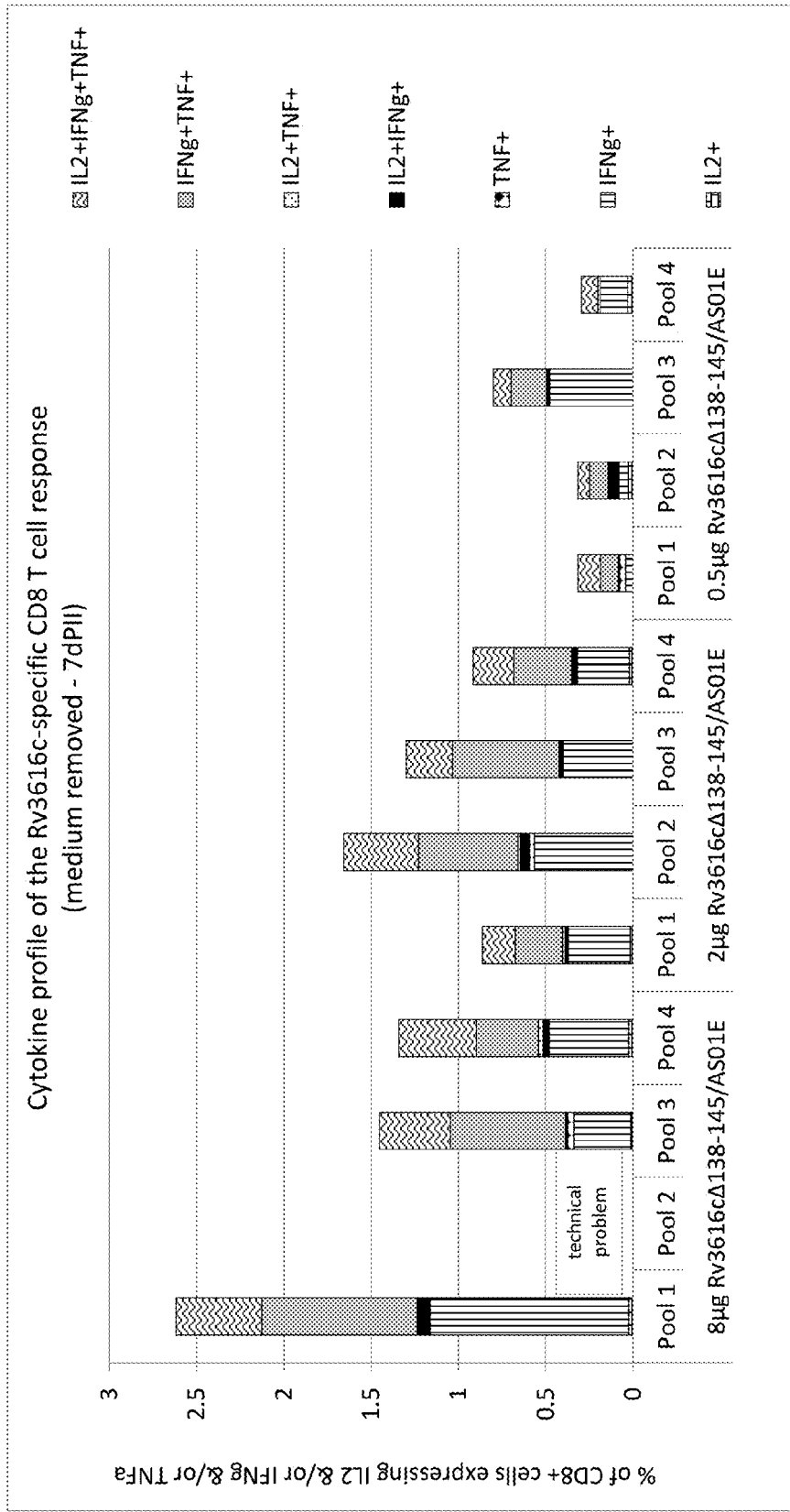
FIG. 24: Cytokine profile of the Rv3616 specific CD8 T cell response at 7 days post second immunisation with Rv3616Δ138-145.
Figure 25:
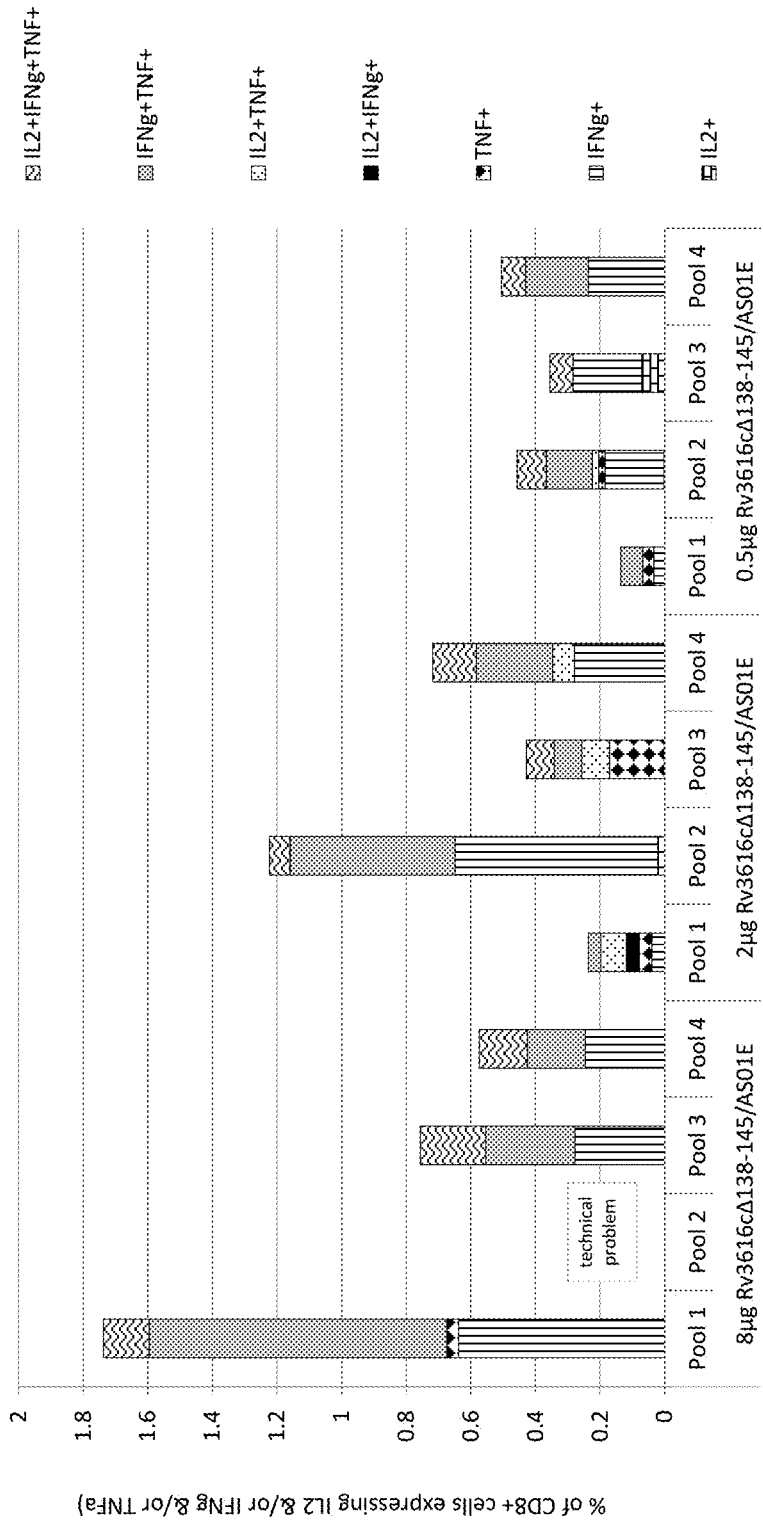
FIG. 25: Cytokine profile of the Rv3616 specific CD8 T cell response at 7 days post third immunisation with Rv3616Δ138-145.

FIG. 23 shows that at both timepoints (7dPII & 7dPIII), Rv3616c-specific CD8 T cell responses are detected in mice immunised with either dose of Rv3616Δ138-145/AS01E. The levels of Rv3616c-specific T cell responses are higher at the 7dPII timepoint when compared to the 7dPIII timepoint. Cyotokine profiles of the CD8 T cell response from the Rv3616c peptide pool-stimulated PBL (medium removed) are shown in FIGS. 24 (7dPII) and 25 (7dPIII).

In conclusion it may be noted that the Rv3616c antigen is capable of eliciting an immune response in both CB6F1 and C57BL/6 mice. Furthermore, the profile of cytokine production indicates that a large proportion of antigen-specific T-cells express a plurality of Th1 associated cytokines (i.e. a polyfunctional T-cell response is elicited). Importantly both CD4 and CD8 antigen-specific T-cells are present after immunisation, CD8 cells may be particularly important in a latent TB scenario. The relevance of Rv3616c to human infection is confirmed by the high level of recognition in latently infected individuals from South Africa and the absence of responses in naive subjects. Rv3616c may therefore be expected to be of substantial value in the prevention, treatment and diagnosis of tuberculosis infection (especially latent tuberculosis infection).

A number of modified Rv3616c proteins have been prepared which clearly demonstrate expression equal to or better than the corresponding H37Rv wild-type sequence, or to the Rv3616Δ150-160 sequence of the prior art. The immunogenicity of Rv3616Δ138-145/AS01E was confirmed in CB6F1 mice.

Constructs demonstrating good expression characteristics while maintaining the immunogenicity of the wild-type sequence are key to the production of commercially viable vaccine products. The new modified Rv3616c proteins may be of great value in the commercial production of Rv3616c compositions, such as vaccines.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All references referred to in this application, including patents and patent applications, are incorporated herein by reference to the fullest extent possible as if each individual publication or patent application were specifically and individually indicated to be incorporated by reference.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:

1. A polynucleotide comprising a nucleic acid sequence encoding a modified *mycobacterium* Rv3616c protein, said modified *mycobacterium* Rv3616c protein comprising a first polypeptide and a second polypeptide, the first polypeptide being located towards the N-terminus relative to the second polypeptide, and wherein:
   (i) the first polypeptide has at least 98% identity to residues 1-134 of SEQ ID No: 1; and
   (ii) the second polypeptide has at least 98% identity to residues 155-392 of SEQ ID No: 1;
   wherein the first and second polypeptides are (A) directly linked or (B) indirectly linked via a third polypeptide having at least 80% identity to a sequence corresponding to residues 135-154 in SEQ ID No:1 in which a contiguous portion of at least 3 amino acids has been deleted.

2. The polynucleotide according to claim 1, wherein the second polypeptide has at least 99% identity to residues 155-392 of SEQ ID No: 1.

3. The polynucleotide according to claim 2, wherein the third polypeptide is a sequence having at least 95% identity to a sequence corresponding to residues 135-154 in SEQ ID No:1 in which a contiguous portion of at least 3 amino acids has been deleted.

4. The polynucleotide according to claim 1, wherein the third polypeptide is a sequence having at least 95% identity to a sequence corresponding to residues 135-154 in SEQ ID No:1 in which a contiguous portion of at least 3 amino acids has been deleted.

5. The polynucleotide according to claim 1, said polynucleotide further comprising a nucleic acid sequence encoding an additional heterologous polypeptide, wherein said polynucleotide encodes a fusion protein comprising the modified *mycobacterium* Rv3616c protein and the additional heterologous polypeptide.

6. A pharmaceutical composition comprising:
(a) a polynucleotide according to claim 1; and
(b) a pharmaceutically acceptable carrier or excipient.

7. An immunogenic composition comprising:
(a) a polynucleotide according to claim 1; and
(b) a non-specific immune response enhancer.

8. A polynucleotide comprising a nucleic acid sequence encoding a protein comprising the amino acid sequence of any one of SEQ ID Nos: 163, 165, 166, 167, 168, 169, 179 and 180.

9. The polynucleotide of claim 8, encoding a protein comprising the amino acid sequence of SEQ ID No: 163.

10. The polynucleotide of claim 8, encoding a protein comprising the amino acid sequence of SEQ ID No: 165.

11. The polynucleotide of claim 8, encoding a protein comprising the amino acid sequence of SEQ ID No: 166.

12. The polynucleotide of claim 8, encoding a protein comprising the amino acid sequence of SEQ ID No: 167.

13. The polynucleotide of claim 8, encoding a protein comprising the amino acid sequence of SEQ ID No: 168.

14. The polynucleotide of claim 8, encoding a protein comprising the amino acid sequence of SEQ ID No: 169.

15. The polynucleotide of claim 8, encoding a protein comprising the amino acid sequence of SEQ ID No: 179.

16. The polynucleotide of claim 8, encoding a protein comprising the amino acid sequence of SEQ ID No: 180.

17. The polynucleotide of claim 8, comprising a nucleic acid sequence encoding a protein consisting of the amino acid sequence of any one of SEQ ID Nos: 163, 165, 166, 167, 168, 169, 179 or 180.

18. The polynucleotide of claim 8, encoding a protein consisting of the amino acid sequence of SEQ ID No: 163.

19. The polynucleotide of claim 17, encoding a protein consisting of the amino acid sequence of SEQ ID No: 165.

20. The polynucleotide of claim 17, encoding a protein consisting of the amino acid sequence of SEQ ID No: 166.

21. The polynucleotide of claim 17, encoding a protein consisting of the amino acid sequence of SEQ ID No: 167.

22. The polynucleotide of claim 17, encoding a protein consisting of the amino acid sequence of SEQ ID No: 168.

23. The polynucleotide of claim 17, encoding a protein consisting of the amino acid sequence of SEQ ID No: 169.

24. The polynucleotide of claim 17, encoding a protein consisting of the amino acid sequence of SEQ ID No: 179.

25. The polynucleotide of claim 17, encoding a protein consisting the of amino acid sequence of SEQ ID No: 180.

* * * * *

SEQUENCE LISTING

```
<160> NUMBER OF SEQ ID NOS: 180

<210> SEQ ID NO 1
<211> LENGTH: 392
<212> TYPE: PRT
<213> ORGANISM: Mycobacterium tuberculosis
<220> FEATURE:
<221> NAME/KEY: MISC_FEATURE
<223> OTHER INFORMATION: Strain H37Rv

<400> SEQUENCE: 1

Met Ser Arg Ala Phe Ile Ile Asp Pro Thr Ile Ser Ala Ile Asp Gly
 1               5                  10                  15

Leu Tyr Asp Leu Leu Gly Ile Gly Ile Pro Asn Gln Gly Gly Ile Leu
            20                  25                  30

Tyr Ser Ser Leu Glu Tyr Phe Glu Lys Ala Leu Glu Glu Leu Ala Ala
        35                  40                  45

Ala Phe Pro Gly Asp Gly Trp Leu Gly Ser Ala Ala Asp Lys Tyr Ala
    50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
            100                 105                 110
```

Arg Pro Val Ala Val Asp Leu Thr Tyr Ile Pro Val Gly His Ala
    115                 120                 125

Leu Ser Ala Ala Phe Gln Ala Pro Phe Cys Ala Gly Ala Met Ala Val
    130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Thr
            180                 185                 190

Leu Gly Glu Val Trp Glu Phe Ile Thr Asn Ala Leu Asn Gly Leu Lys
    195                 200                 205

Glu Leu Trp Asp Lys Leu Thr Gly Trp Val Thr Gly Leu Phe Ser Arg
    210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
            260                 265                 270

Ser Ala Ser Leu Pro Ala Leu Ala Gly Ile Gly Gly Ser Gly Phe
    275                 280                 285

Gly Gly Leu Pro Ser Leu Ala Gln Val His Ala Ala Ser Thr Arg Gln
    290                 295                 300

Ala Leu Arg Pro Arg Ala Asp Gly Pro Val Gly Ala Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Met His Pro Ser Ser Gly Ala Ser
            340                 345                 350

Lys Gly Thr Thr Thr Lys Lys Tyr Ser Glu Gly Ala Ala Ala Gly Thr
    355                 360                 365

Glu Asp Ala Glu Arg Ala Pro Val Glu Ala Asp Ala Gly Gly Gly Gln
    370                 375                 380

Lys Val Leu Val Arg Asn Val Val
385                 390

<210> SEQ ID NO 2
<211> LENGTH: 1179
<212> TYPE: DNA
<213> ORGANISM: Mycobacterium tuberculosis
<220> FEATURE:
<221> NAME/KEY: misc_feature
<223> OTHER INFORMATION: Strain H37Rv

<400> SEQUENCE: 2
atgagcagag cgttcatcat cgatccaacg atcagtgcca ttgacggctt gtacgacctt      60
ctggggattg aatacccaa ccaaggggt atcctttact cctcactaga gtacttcgaa      120
aaagccctgg aggagctggc agcagcgttt ccgggtgatg ctggttagg ttcggccgcg      180 gacaaatacg ccggcaaaaa ccgcaaccac gtgaattttt ccaggaact ggcagacctc      240 gatcgtcagc tcatcagcct gatccacgac caggccaacg cggtccagac gacccgcgac      300
atcctggagg gcgccaagaa aggtctcgag ttcgtgcgcc cggtggctgt ggacctgacc      360
tacatcccgg tcgtcgggca cgccctatcg gccgccttcc aggcgccgtt ttgcgcgggc      420

-continued

```
gcgatggccg tagtgggcgg cgcgcttgcc tacttggtcg tgaaaacgct gatcaacgcg      480
actcaactcc tcaaattgct tgccaaattg gcggagttgg tcgcggccgc cattgcggac      540
atcatttcgg atgtggcgga catcatcaag ggcaccctcg agaagtgtg  ggagttcatc      600 acaaacgcgc tcaacggcct gaaagagctt tgggacaagc tcacggggtg ggtgaccgga      660
ctgttctctc gagggtggtc gaacctggag tccttctttg cgggcgtccc cggcttgacc      720
ggcgcgacca gcggcttgtc gcaagtgact ggcttgttcg gtgcggccgg tctgtccgca      780
tcgtcgggct tggctcacgc ggatagcctg gcgagctcag ccagcttgcc cgccctggcc      840
ggcattgggg gcgggtccgg ttttgggggc ttgccgagcc tggctcaggt ccatgccgcc      900
tcaactcggc aggcgctacg gccccgagct gatggcccgg tcgcgccgc  tgccgagcag      960 gtcggcgggc agtcgcagct ggtctccgcg cagggttccc aaggtatggg cggacccgta     1020
ggcatgggcg gcatgcaccc ctcttcgggg gcgtcgaaag ggacgacgac gaagaagtac     1080
tcggaaggcg cggcggcggg cactgaagac gccgagcgcg cgccagtcga agctgacgcg     1140
ggcggtgggc aaaaggtgct ggtacgaaac gtcgtctaa                            1179
```

<210> SEQ ID NO 3
<211> LENGTH: 392
<212> TYPE: PRT
<213> ORGANISM: Mycobacterium tuberculosis
<220> FEATURE:
<221> NAME/KEY: MISC_FEATURE
<223> OTHER INFORMATION: Strain CDC1551

<400> SEQUENCE: 3

```
Met Ser Arg Ala Phe Ile Ile Asp Pro Thr Ile Ser Ala Ile Asp Gly
  1               5                  10                  15

Leu Tyr Asp Leu Leu Gly Ile Gly Ile Pro Asn Gln Gly Gly Ile Leu
             20                  25                  30

Tyr Ser Ser Leu Glu Tyr Phe Glu Lys Ala Leu Glu Glu Leu Ala Ala
         35                  40                  45

Ala Phe Pro Gly Asp Gly Trp Leu Gly Ser Ala Ala Asp Lys Tyr Ala
     50                  55                  60

Gly Lys Asn Arg Asn His Val Asn Phe Gln Glu Leu Ala Asp Leu
 65                  70                  75                  80

Asp Arg Gln Leu Ile Ser Leu Ile His Asp Gln Ala Asn Ala Val Gln
                 85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Gly His Ala
            115                 120                 125

Leu Ser Ala Ala Phe Gln Ala Pro Phe Cys Ala Gly Ala Met Ala Val
    130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Ile
            180                 185                 190

Leu Gly Glu Val Trp Glu Phe Ile Thr Asn Ala Leu Asn Gly Leu Lys
        195                 200                 205

Glu Leu Trp Asp Lys Leu Thr Gly Trp Val Thr Gly Leu Phe Ser Arg
    210                 215                 220
```

```
Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
                260                 265                 270

Ser Ala Ser Leu Pro Ala Leu Ala Gly Ile Gly Gly Ser Gly Phe
            275                 280                 285

Gly Gly Leu Pro Ser Leu Ala Gln Val His Ala Ala Ser Thr Arg Gln
        290                 295                 300

Ala Leu Arg Pro Arg Ala Asp Gly Pro Val Gly Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Gly Met His Pro Ser Ser Gly Ala Ser
                340                 345                 350

Lys Gly Thr Thr Thr Lys Lys Tyr Ser Glu Gly Ala Ala Ala Gly Thr
                355                 360                 365

Glu Asp Ala Glu Arg Ala Pro Val Glu Ala Asp Ala Gly Gly Gly Gln
370                 375                 380

Lys Val Leu Val Arg Asn Val Val
385                 390

<210> SEQ ID NO 4
<211> LENGTH: 392
<212> TYPE: PRT
<213> ORGANISM: Mycobacterium tuberculosis
<220> FEATURE:
<221> NAME/KEY: MISC_FEATURE
<223> OTHER INFORMATION: Strain F11

<400> SEQUENCE: 4

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
                20                  25                  30

Tyr Ser Ser Leu Glu Tyr Phe Glu Lys Ala Leu Glu Glu Leu Ala Ala
                35                  40                  45

Ala Phe Pro Gly Asp Gly Trp Leu Gly Ser Ala Ala Asp Lys Tyr Ala
            50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
                100                 105                 110

Arg Pro Val Ala Val Asp Leu Thr Tyr Ile Pro Val Val Gly His Ala
            115                 120                 125

Leu Ser Ala Ala Phe Gln Ala Pro Phe Cys Ala Gly Ala Met Ala Val
            130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Ile
            180                 185                 190
```

```
Leu Gly Glu Val Trp Glu Phe Ile Thr Asn Ala Leu Asn Gly Leu Lys
        195                 200                 205

Glu Leu Trp Asp Lys Leu Thr Gly Trp Val Thr Gly Leu Phe Ser Arg
        210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
                260                 265                 270

Ser Ala Ser Leu Pro Ala Leu Ala Gly Ile Gly Gly Ser Gly Phe
                275                 280                 285

Gly Gly Leu Pro Ser Leu Ala Gln Val His Ala Ala Ser Thr Arg Gln
                290                 295                 300

Ala Leu Arg Pro Arg Ala Asp Gly Pro Val Gly Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Met His Pro Ser Ser Gly Ala Ser
                340                 345                 350

Lys Gly Thr Thr Thr Lys Lys Tyr Ser Glu Gly Ala Ala Ala Gly Thr
                355                 360                 365

Glu Asp Ala Glu Arg Ala Pro Val Glu Ala Asp Ala Gly Gly Gly Gln
        370                 375                 380

Lys Val Leu Val Arg Asn Val Val
385                 390

<210> SEQ ID NO 5
<211> LENGTH: 392
<212> TYPE: PRT
<213> ORGANISM: Mycobacterium tuberculosis
<220> FEATURE:
<221> NAME/KEY: MISC_FEATURE
<223> OTHER INFORMATION: Strain Haarlem A

<400> SEQUENCE: 5

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
                20                  25                  30

Tyr Ser Ser Leu Glu Tyr Phe Glu Lys Ala Leu Glu Glu Leu Ala Ala
                35                  40                  45

Ala Phe Pro Gly Asp Gly Trp Leu Gly Ser Ala Asp Lys Tyr Ala
        50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
                100                 105                 110

Arg Pro Val Ala Val Asp Leu Thr Tyr Ile Pro Val Val Gly His Ala
                115                 120                 125

Leu Ser Ala Ala Phe Gln Ala Pro Phe Cys Ala Gly Ala Met Ala Val
                130                 135                 140

Val Gly Gly Ala Leu Ala Tyr Leu Val Val Lys Thr Leu Ile Asn Ala
```

```
                145                 150                 155                 160
        Thr Gln Leu Leu Lys Leu Leu Ala Lys Leu Ala Glu Leu Val Ala Ala
                    165                 170                 175

Ala Ile Ala Asp Ile Ile Ser Asp Val Ala Asp Ile Ile Lys Gly Ile
                    180                 185                 190

Leu Gly Glu Val Trp Glu Phe Ile Thr Asn Ala Leu Asn Gly Leu Lys
                    195                 200                 205

Glu Leu Trp Asp Lys Leu Thr Gly Trp Val Thr Gly Leu Phe Ser Arg
                    210                 215                 220

Gly Trp Ser Asn Leu Glu Ser Phe Phe Ala Gly Val Pro Gly Leu Thr
        225                 230                 235                 240

Gly Ala Thr Ser Gly Leu Ser Gln Val Thr Gly Leu Phe Gly Ala Ala
                    245                 250                 255

Gly Leu Ser Ala Ser Ser Gly Leu Ala His Ala Asp Ser Leu Ala Ser
                    260                 265                 270

Ser Ala Ser Leu Pro Ala Leu Ala Gly Ile Gly Gly Ser Gly Phe
                    275                 280                 285

Gly Gly Leu Pro Ser Leu Ala Gln Val His Ala Ala Ser Thr Arg Gln
                    290                 295                 300

Ala Leu Arg Pro Arg Ala Asp Gly Pro Val Gly Ala Ala Ala Glu Gln
        305                 310                 315                 320

Val Gly Gly Gln Ser Gln Leu Val Ser Ala Gln Gly Ser Gln Gly Met
                    325                 330                 335

Gly Gly Pro Val Gly Met Gly Gly Met His Pro Ser Ser Gly Ala Ser
                    340                 345                 350

Lys Gly Thr Thr Thr Lys Lys Tyr Ser Glu Gly Ala Ala Ala Gly Thr
                    355                 360                 365

Glu Asp Ala Glu Arg Ala Pro Val Glu Ala Asp Ala Gly Gly Gly Gln
                    370                 375                 380

Lys Val Leu Val Arg Asn Val Val
        385                 390

<210> SEQ ID NO 6
<211> LENGTH: 392
<212> TYPE: PRT
<213> ORGANISM: Mycobacterium tuberculosis
<220> FEATURE:
<221> NAME/KEY: MISC_FEATURE
<223> OTHER INFORMATION: Strain C

<400> SEQUENCE: 6

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
                20                  25                  30

Tyr Ser Ser Leu Glu Tyr Phe Glu Lys Ala Leu Glu Glu Leu Ala Ala
            35                  40                  45

Ala Phe Pro Gly Asp Gly Trp Leu Gly Ser Ala Ala Asp Lys Tyr Ala
        50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
                100                 105                 110
```

```
Arg Pro Val Ala Val Asp Leu Thr Tyr Ile Pro Val Gly His Ala
            115                 120                 125

Leu Ser Ala Ala Phe Gln Ala Pro Phe Cys Ala Gly Ala Met Ala Val
130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Ile
            180                 185                 190

Leu Gly Glu Val Trp Glu Phe Ile Thr Asn Ala Leu Asn Gly Leu Lys
        195                 200                 205

Glu Leu Trp Asp Lys Leu Thr Gly Trp Val Thr Gly Leu Phe Ser Arg
210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
            260                 265                 270

Ser Ala Ser Leu Pro Ala Leu Ala Gly Ile Gly Gly Gly Ser Gly Phe
        275                 280                 285

Gly Gly Leu Pro Ser Leu Ala Gln Val His Ala Ala Ser Thr Arg Gln
290                 295                 300

Ala Leu Arg Pro Arg Ala Asp Gly Pro Val Gly Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Met His Pro Ser Ser Gly Ala Ser
            340                 345                 350

Lys Gly Thr Thr Thr Lys Lys Tyr Ser Glu Gly Ala Ala Ala Gly Thr
        355                 360                 365

Glu Asp Ala Glu Arg Ala Pro Val Glu Ala Asp Ala Gly Gly Gly Gln
370                 375                 380

Lys Val Leu Val Arg Asn Val Val
385                 390
```

<210> SEQ ID NO 7
<211> LENGTH: 392
<212> TYPE: PRT
<213> ORGANISM: Mycobacterium bovis
<220> FEATURE:
<221> NAME/KEY: MISC_FEATURE
<223> OTHER INFORMATION: Strain BCG

<400> SEQUENCE: 7

```
Met Ser Arg Val Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
            20                  25                  30

Tyr Ser Ser Leu Glu Tyr Phe Glu Lys Ala Leu Glu Glu Leu Ala Ala
        35                  40                  45

Ala Phe Pro Gly Asp Gly Trp Leu Gly Ser Ala Ala Asp Lys Tyr Ala
    50                  55                  60

Gly Lys Asn Arg Asn His Val Asn Phe Phe Gln Glu Leu Ala Asp Leu
65                  70                  75                  80
```

```
Asp Arg Gln Leu Ile Ser Leu Ile His Asp Gln Ala Asn Ala Val Gln
                 85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
            115                 120                 125

Leu Ser Ala Ala Phe Gln Ala Pro Phe Cys Ala Gly Ala Met Ala Val
            130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Ile
                180                 185                 190

Leu Gly Glu Val Trp Glu Phe Ile Thr Asn Ala Leu Asn Gly Leu Lys
            195                 200                 205

Glu Leu Trp Asp Lys Leu Thr Gly Trp Val Thr Gly Leu Phe Ser Arg
            210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
                260                 265                 270

Ser Ala Ser Leu Pro Ala Leu Ala Gly Ile Gly Gly Ser Gly Phe
                275                 280                 285

Gly Gly Leu Pro Ser Leu Ala Gln Val His Ala Ser Thr Arg Gln
290                 295                 300

Ala Leu Arg Pro Arg Ala Asp Gly Pro Val Gly Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Gly Met His Pro Ser Ser Gly Ala Ser
            340                 345                 350

Lys Gly Thr Thr Thr Lys Lys Tyr Ser Glu Gly Ala Ala Ala Gly Thr
            355                 360                 365

Glu Asp Ala Glu Arg Ala Pro Val Glu Ala Asp Ala Gly Gly Gly Gln
            370                 375                 380

Lys Val Leu Val Arg Asn Val Val
385                 390

<210> SEQ ID NO 8
<211> LENGTH: 110
<212> TYPE: PRT
<213> ORGANISM: Mycobacterium tuberculosis
<220> FEATURE:
<221> NAME/KEY: mat_peptide
<222> LOCATION: (29)..(110)

<400> SEQUENCE: 8

Met Arg Leu Ser Leu Thr Ala Leu Ser Ala Gly Val Gly Ala Val Ala
                -25                 -20                 -15

Met Ser Leu Thr Val Gly Ala Gly Val Ala Ser Ala Asp Pro Val Asp
            -10                  -5                  -1   1

Ala Val Ile Asn Thr Thr Cys Asn Tyr Gly Gln Val Val Ala Ala Leu
```

```
                5                  10                 15                 20
Asn Ala Thr Asp Pro Gly Ala Ala Gln Phe Asn Ala Ser Pro Val
                25                 30                 35

Ala Gln Ser Tyr Leu Arg Asn Phe Leu Ala Pro Pro Pro Gln Arg
                40                 45                 50

Ala Ala Met Ala Ala Gln Leu Gln Ala Val Pro Gly Ala Ala Gln Tyr
                55                 60                 65

Ile Gly Leu Val Glu Ser Val Ala Gly Ser Cys Asn Asn Tyr
 70                 75                 80

<210> SEQ ID NO 9
<211> LENGTH: 97
<212> TYPE: PRT
<213> ORGANISM: Mycobacterium tuberculosis

<400> SEQUENCE: 9

Met Ser Leu Leu Asp Ala His Ile Pro Gln Leu Val Ala Ser Gln Ser
 1               5                  10                 15

Ala Phe Ala Ala Lys Ala Gly Leu Met Arg His Thr Ile Gly Gln Ala
                20                 25                 30

Glu Gln Ala Ala Met Ser Ala Gln Ala Phe His Gln Gly Glu Ser Ser
                35                 40                 45

Ala Ala Phe Gln Ala Ala His Ala Arg Phe Val Ala Ala Ala Lys
 50                 55                 60

Val Asn Thr Leu Leu Asp Val Ala Gln Ala Asn Leu Gly Glu Ala Ala
 65                 70                 75                 80

Gly Thr Tyr Val Ala Ala Asp Ala Ala Ala Ser Thr Tyr Thr Gly
                85                 90                 95

Phe

<210> SEQ ID NO 10
<211> LENGTH: 94
<212> TYPE: PRT
<213> ORGANISM: Mycobacterium tuberculosis

<400> SEQUENCE: 10

Met Thr Ile Asn Tyr Gln Phe Gly Asp Val Asp Ala His Gly Ala Met
 1               5                  10                 15

Ile Arg Ala Gln Ala Ala Ser Leu Glu Ala Glu His Gln Ala Ile Val
                20                 25                 30

Arg Asp Val Leu Ala Ala Gly Asp Phe Trp Gly Gly Ala Gly Ser Val
                35                 40                 45

Ala Cys Gln Glu Phe Ile Thr Gln Leu Gly Arg Asn Phe Gln Val Ile
 50                 55                 60

Tyr Glu Gln Ala Asn Ala His Gly Gln Lys Val Gln Ala Ala Gly Asn
 65                 70                 75                 80

Asn Met Ala Gln Thr Asp Ser Ala Val Gly Ser Ser Trp Ala
                85                 90

<210> SEQ ID NO 11
<211> LENGTH: 132
<212> TYPE: PRT
<213> ORGANISM: Mycobacterium tuberculosis

<400> SEQUENCE: 11

Thr Ala Ala Ser Asp Asn Phe Gln Leu Ser Gln Gly Gly Gln Gly Phe
 1               5                  10                 15
```

```
Ala Ile Pro Ile Gly Gln Ala Met Ala Ile Ala Gly Gln Ile Arg Ser
            20                  25                  30

Gly Gly Gly Ser Pro Thr Val His Ile Gly Pro Thr Ala Phe Leu Gly
        35                  40                  45

Leu Gly Val Val Asp Asn Asn Gly Asn Gly Ala Arg Val Gln Arg Val
 50                  55                  60

Val Gly Ser Ala Pro Ala Ala Ser Leu Gly Ile Ser Thr Gly Asp Val
 65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Thr Trp
            100                 105                 110

Gln Thr Lys Ser Gly Gly Thr Arg Thr Gly Asn Val Thr Leu Ala Glu
            115                 120                 125

Gly Pro Pro Ala
        130

<210> SEQ ID NO 12
<211> LENGTH: 195
<212> TYPE: PRT
<213> ORGANISM: Mycobacterium tuberculosis

<400> SEQUENCE: 12

Ala Pro Pro Ala Leu Ser Gln Asp Arg Phe Ala Asp Phe Pro Ala Leu
 1               5                  10                  15

Pro Leu Asp Pro Ser Ala Met Val Ala Gln Val Gly Pro Gln Val Val
            20                  25                  30

Asn Ile Asn Thr Lys Leu Gly Tyr Asn Asn Ala Val Gly Ala Gly Thr
        35                  40                  45

Gly Ile Val Ile Asp Pro Asn Gly Val Val Leu Thr Asn Asn His Val
 50                  55                  60

Ile Ala Gly Ala Thr Asp Ile Asn Ala Phe Ser Val Gly Ser Gly Gln
 65                  70                  75                  80

Thr Tyr Gly Val Asp Val Val Gly Tyr Asp Arg Thr Gln Asp Val Ala
                85                  90                  95

Val Leu Gln Leu Arg Gly Ala Gly Gly Leu Pro Ser Ala Ala Ile Gly
            100                 105                 110

Gly Gly Val Ala Val Gly Glu Pro Val Val Ala Met Gly Asn Ser Gly
            115                 120                 125

Gly Gln Gly Gly Thr Pro Arg Ala Val Pro Gly Arg Val Val Ala Leu
        130                 135                 140

Gly Gln Thr Val Gln Ala Ser Asp Ser Leu Thr Gly Ala Glu Glu Thr
145                 150                 155                 160

Leu Asn Gly Leu Ile Gln Phe Asp Ala Ala Ile Gln Pro Gly Asp Ser
                165                 170                 175

Gly Gly Pro Val Val Asn Gly Leu Gly Gln Val Val Gly Met Asn Thr
            180                 185                 190

Ala Ala Ser
        195

<210> SEQ ID NO 13
<211> LENGTH: 391
<212> TYPE: PRT
<213> ORGANISM: Mycobacterium tuberculosis

<400> SEQUENCE: 13
```

```
Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Gln Met Trp
            20                  25                  30

Asp Ser Val Ala Ser Asp Leu Phe Ser Ala Ala Ser Ala Phe Gln Ser
                35                  40                  45

Val Val Trp Gly Leu Thr Val Gly Ser Trp Ile Gly Ser Ser Ala Gly
50                  55                  60

Leu Met Val Ala Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Val Ile Ala
                100                 105                 110

Glu Asn Arg Ala Glu Leu Met Ile Leu Ile Ala Thr Asn Leu Leu Gly
            115                 120                 125

Gln Asn Thr Pro Ala Ile Ala Val Asn Glu Ala Glu Tyr Gly Glu Met
    130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Val Glu Glu Ala Ser
                180                 185                 190

Asp Thr Ala Ala Ala Asn Gln Leu Met Asn Asn Val Pro Gln Ala Leu
            195                 200                 205

Gln Gln Leu Ala Gln Pro Thr Gln Gly Thr Thr Pro Ser Ser Lys Leu
    210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
    275                 280                 285

Met Ser Ser Leu Gly Ser Ser Leu Gly Ser Ser Gly Leu Gly Gly Gly
290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Glu Arg Gly Pro Gly
            340                 345                 350

Gln Met Leu Gly Gly Leu Pro Val Gly Gln Met Gly Ala Arg Ala Gly
    355                 360                 365

Gly Gly Leu Ser Gly Val Leu Arg Val Pro Pro Arg Pro Tyr Val Met
370                 375                 380

Pro His Ser Pro Ala Ala Gly
385                 390

<210> SEQ ID NO 14
<211> LENGTH: 423
<212> TYPE: PRT
```

<213> ORGANISM: Mycobacterium tuberculosis

<400> SEQUENCE: 14

```
Met Asp Phe Gly Leu Leu Pro Pro Glu Val Asn Ser Ser Arg Met Tyr
1               5                   10                  15

Ser Gly Pro Gly Pro Glu Ser Met Leu Ala Ala Ala Ala Ala Trp Asp
            20                  25                  30

Gly Val Ala Ala Glu Leu Thr Ser Ala Ala Val Ser Tyr Gly Ser Val
        35                  40                  45

Val Ser Thr Leu Ile Val Glu Pro Trp Met Gly Pro Ala Ala Ala Ala
    50                  55                  60

Met Ala Ala Ala Ala Thr Pro Tyr Val Gly Trp Leu Ala Ala Thr Ala
65                  70                  75                  80

Ala Leu Ala Lys Glu Thr Ala Thr Gln Ala Arg Ala Ala Ala Glu Ala
                85                  90                  95

Phe Gly Thr Ala Phe Ala Met Thr Val Pro Pro Ser Leu Val Ala Ala
            100                 105                 110

Asn Arg Ser Arg Leu Met Ser Leu Val Ala Ala Asn Ile Leu Gly Gln
        115                 120                 125

Asn Ser Ala Ala Ile Ala Ala Thr Gln Ala Glu Tyr Ala Glu Met Trp
    130                 135                 140

Ala Gln Asp Ala Ala Val Met Tyr Ser Tyr Glu Gly Ala Ser Ala Ala
145                 150                 155                 160

Ala Ser Ala Leu Pro Pro Phe Thr Pro Pro Val Gln Gly Thr Gly Pro
                165                 170                 175

Ala Gly Pro Ala Ala Ala Ala Ala Ala Thr Gln Ala Ala Gly Ala Gly
            180                 185                 190

Ala Val Ala Asp Ala Gln Ala Thr Leu Ala Gln Leu Pro Pro Gly Ile
        195                 200                 205

Leu Ser Asp Ile Leu Ser Ala Leu Ala Ala Asn Ala Asp Pro Leu Thr
    210                 215                 220

Ser Gly Leu Leu Gly Ile Ala Ser Thr Leu Asn Pro Gln Val Gly Ser
225                 230                 235                 240

Ala Gln Pro Ile Val Ile Pro Thr Pro Ile Gly Glu Leu Asp Val Ile
                245                 250                 255

Ala Leu Tyr Ile Ala Ser Ile Ala Thr Gly Ser Ile Ala Leu Ala Ile
            260                 265                 270

Thr Asn Thr Ala Arg Pro Trp His Ile Gly Leu Tyr Gly Asn Ala Gly
        275                 280                 285

Gly Leu Gly Pro Thr Gln Gly His Pro Leu Ser Ser Ala Thr Asp Glu
    290                 295                 300

Pro Glu Pro His Trp Gly Pro Phe Gly Gly Ala Ala Pro Val Ser Ala
305                 310                 315                 320

Gly Val Gly His Ala Ala Leu Val Gly Ala Leu Ser Val Pro His Ser
                325                 330                 335

Trp Thr Thr Ala Ala Pro Glu Ile Gln Leu Ala Val Gln Ala Thr Pro
            340                 345                 350

Thr Phe Ser Ser Ser Ala Gly Ala Asp Pro Thr Ala Leu Asn Gly Met
        355                 360                 365

Pro Ala Gly Leu Leu Ser Gly Met Ala Leu Ala Ser Leu Ala Ala Arg
    370                 375                 380

Gly Thr Thr Gly Gly Gly Gly Thr Arg Ser Gly Thr Ser Thr Asp Gly
385                 390                 395                 400
```

Gln Glu Asp Gly Arg Lys Pro Pro Val Val Ile Arg Glu Gln Pro
                405                 410                 415

Pro Pro Gly Asn Pro Pro Arg
            420

<210> SEQ ID NO 15
<211> LENGTH: 95
<212> TYPE: PRT
<213> ORGANISM: Mycobacterium tuberculosis
<220> FEATURE:
<221> NAME/KEY: INIT_MET
<222> LOCATION: (1)..(1)
<220> FEATURE:
<221> NAME/KEY: mat_peptide
<222> LOCATION: (2)..(95)

<400> SEQUENCE: 15

Met Thr Glu Gln Gln Trp Asn Phe Ala Gly Ile Glu Ala Ala Ala Ser
-1   1               5                  10                  15

Ala Ile Gln Gly Asn Val Thr Ser Ile His Ser Leu Leu Asp Glu Gly
                20                  25                  30

Lys Gln Ser Leu Thr Lys Leu Ala Ala Ala Trp Gly Gly Ser Gly Ser
                35                  40                  45

Glu Ala Tyr Gln Gly Val Gln Gln Lys Trp Asp Ala Thr Ala Thr Glu
            50                  55                  60

Leu Asn Asn Ala Leu Gln Asn Leu Ala Arg Thr Ile Ser Glu Ala Gly
65                  70                  75

Gln Ala Met Ala Ser Thr Glu Gly Asn Val Thr Gly Met Phe Ala
80                  85                  90

<210> SEQ ID NO 16
<211> LENGTH: 338
<212> TYPE: PRT
<213> ORGANISM: Mycobacterium tuberculosis
<220> FEATURE:
<221> NAME/KEY: mat_peptide
<222> LOCATION: (43)..(338)

<400> SEQUENCE: 16

Met Gln Leu Val Asp Arg Val Arg Gly Ala Val Thr Gly Met Ser Arg
        -40                 -35                 -30

Arg Leu Val Val Gly Ala Val Gly Ala Ala Leu Val Ser Gly Leu Val
        -25                 -20                 -15

Gly Ala Val Gly Gly Thr Ala Thr Ala Gly Ala Phe Ser Arg Pro Gly
-10                 -5                  -1   1                5

Leu Pro Val Glu Tyr Leu Gln Val Pro Ser Pro Ser Met Gly Arg Asp
                10                  15                  20

Ile Lys Val Gln Phe Gln Ser Gly Gly Ala Asn Ser Pro Ala Leu Tyr
                25                  30                  35

Leu Leu Asp Gly Leu Arg Ala Gln Asp Asp Phe Ser Gly Trp Asp Ile
            40                  45                  50

Asn Thr Pro Ala Phe Glu Trp Tyr Asp Gln Ser Gly Leu Ser Val Val
55                  60                  65                  70

Met Pro Val Gly Gly Gln Ser Ser Phe Tyr Ser Asp Trp Tyr Gln Pro
                75                  80                  85

Ala Cys Gly Lys Ala Gly Cys Gln Thr Tyr Lys Trp Glu Thr Phe Leu
                90                  95                  100

Thr Ser Glu Leu Pro Gly Trp Leu Gln Ala Asn Arg His Val Lys Pro
            105                 110                 115

```
Thr Gly Ser Ala Val Val Gly Leu Ser Met Ala Ala Ser Ser Ala Leu
    120             125                 130

Thr Leu Ala Ile Tyr His Pro Gln Gln Phe Val Tyr Ala Gly Ala Met
135             140                 145                 150

Ser Gly Leu Leu Asp Pro Ser Gln Ala Met Gly Pro Thr Leu Ile Gly
                155                 160                 165

Leu Ala Met Gly Asp Ala Gly Tyr Lys Ala Ser Asp Met Trp Gly
            170                 175                 180

Pro Lys Glu Asp Pro Ala Trp Gln Arg Asn Asp Pro Leu Leu Asn Val
                185                 190                 195

Gly Lys Leu Ile Ala Asn Asn Thr Arg Val Trp Val Tyr Cys Gly Asn
    200                 205                 210

Gly Lys Pro Ser Asp Leu Gly Gly Asn Asn Leu Pro Ala Lys Phe Leu
215                 220                 225                 230

Glu Gly Phe Val Arg Thr Ser Asn Ile Lys Phe Gln Asp Ala Tyr Asn
                235                 240                 245

Ala Gly Gly Gly His Asn Gly Val Phe Asp Phe Pro Asp Ser Gly Thr
                250                 255                 260

His Ser Trp Glu Tyr Trp Gly Ala Gln Leu Asn Ala Met Lys Pro Asp
                265                 270                 275

Leu Gln Arg Ala Leu Gly Ala Thr Pro Asn Thr Gly Pro Ala Pro Gln
    280                 285                 290

Gly Ala
295

<210> SEQ ID NO 17
<211> LENGTH: 325
<212> TYPE: PRT
<213> ORGANISM: Mycobacterium tuberculosis
<220> FEATURE:
<221> NAME/KEY: mat_peptide
<222> LOCATION: (41)..(325)

<400> SEQUENCE: 17

Met Thr Asp Val Ser Arg Lys Ile Arg Ala Trp Gly Arg Arg Leu Met
-40             -35                 -30                 -25

Ile Gly Thr Ala Ala Ala Val Val Leu Pro Gly Leu Val Gly Leu Ala
                -20                 -15                 -10

Gly Gly Ala Ala Thr Ala Gly Ala Phe Ser Arg Pro Gly Leu Pro Val
            -5                  -1  1                   5

Glu Tyr Leu Gln Val Pro Ser Pro Ser Met Gly Arg Asp Ile Lys Val
    10                  15                  20

Gln Phe Gln Ser Gly Gly Asn Asn Ser Pro Ala Val Tyr Leu Leu Asp
25                  30                  35                  40

Gly Leu Arg Ala Gln Asp Asp Tyr Asn Gly Trp Asp Ile Asn Thr Pro
                45                  50                  55

Ala Phe Glu Trp Tyr Tyr Gln Ser Gly Leu Ser Ile Val Met Pro Val
                60                  65                  70

Gly Gly Gln Ser Ser Phe Tyr Ser Asp Trp Tyr Ser Pro Ala Cys Gly
    75                  80                  85

Lys Ala Gly Cys Gln Thr Tyr Lys Trp Glu Thr Phe Leu Thr Ser Glu
    90                  95                  100

Leu Pro Gln Trp Leu Ser Ala Asn Arg Ala Val Lys Pro Thr Gly Ser
105                 110                 115                 120

Ala Ala Ile Gly Leu Ser Met Ala Gly Ser Ser Ala Met Ile Leu Ala
                125                 130                 135
```

```
Ala Tyr His Pro Gln Gln Phe Ile Tyr Ala Gly Ser Leu Ser Ala Leu
            140                 145                 150

Leu Asp Pro Ser Gln Gly Met Gly Pro Ser Leu Ile Gly Leu Ala Met
        155                 160                 165

Gly Asp Ala Gly Gly Tyr Lys Ala Ala Asp Met Trp Gly Pro Ser Ser
    170                 175                 180

Asp Pro Ala Trp Glu Arg Asn Asp Pro Thr Gln Gln Ile Pro Lys Leu
185                 190                 195                 200

Val Ala Asn Asn Thr Arg Leu Trp Val Tyr Cys Gly Asn Gly Thr Pro
                205                 210                 215

Asn Glu Leu Gly Gly Ala Asn Ile Pro Ala Glu Phe Leu Glu Asn Phe
                220                 225                 230

Val Arg Ser Ser Asn Leu Lys Phe Gln Asp Ala Tyr Asn Ala Ala Gly
                235                 240                 245

Gly His Asn Ala Val Phe Asn Phe Pro Pro Asn Gly Thr His Ser Trp
                250                 255                 260

Glu Tyr Trp Gly Ala Gln Leu Asn Ala Met Lys Gly Asp Leu Gln Ser
265                 270                 275                 280

Ser Leu Gly Ala Gly
            285

<210> SEQ ID NO 18
<211> LENGTH: 144
<212> TYPE: PRT
<213> ORGANISM: Mycobacterium tuberculosis
<220> FEATURE:
<221> NAME/KEY: INIT_MET
<222> LOCATION: (1)..(1)
<220> FEATURE:
<221> NAME/KEY: mat_peptide
<222> LOCATION: (2)..(144)

<400> SEQUENCE: 18

Met Ala Thr Thr Leu Pro Val Gln Arg His Pro Arg Ser Leu Phe Pro
 -1  1               5                  10                  15

Glu Phe Ser Glu Leu Phe Ala Ala Phe Pro Ser Phe Ala Gly Leu Arg
                20                  25                  30

Pro Thr Phe Asp Thr Arg Leu Met Arg Leu Glu Asp Glu Met Lys Glu
            35                  40                  45

Gly Arg Tyr Glu Val Arg Ala Glu Leu Pro Gly Val Asp Pro Asp Lys
        50                  55                  60

Asp Val Asp Ile Met Val Arg Asp Gly Gln Leu Thr Ile Lys Ala Glu
65                  70                  75

Arg Thr Glu Gln Lys Asp Phe Asp Gly Arg Ser Glu Phe Ala Tyr Gly
80                  85                  90                  95

Ser Phe Val Arg Thr Val Ser Leu Pro Val Gly Ala Asp Glu Asp Asp
                100                 105                 110

Ile Lys Ala Thr Tyr Asp Lys Gly Ile Leu Thr Val Ser Val Ala Val
            115                 120                 125

Ser Glu Gly Lys Pro Thr Glu Lys His Ile Gln Ile Arg Ser Thr Asn
        130                 135                 140

<210> SEQ ID NO 19
<211> LENGTH: 228
<212> TYPE: PRT
<213> ORGANISM: Mycobacterium tuberculosis
<220> FEATURE:
<221> NAME/KEY: mat_peptide
```

<222> LOCATION: (24)..(228)

<400> SEQUENCE: 19

Met Arg Ile Lys Ile Phe Met Leu Val Thr Ala Val Val Leu Leu Cys
        -20                 -15                 -10

Cys Ser Gly Val Ala Thr Ala Ala Pro Lys Thr Tyr Cys Glu Glu Leu
         -5              -1   1               5

Lys Gly Thr Asp Thr Gly Gln Ala Cys Gln Ile Gln Met Ser Asp Pro
 10              15                  20                  25

Ala Tyr Asn Ile Asn Ile Ser Leu Pro Ser Tyr Tyr Pro Asp Gln Lys
             30                  35                  40

Ser Leu Glu Asn Tyr Ile Ala Gln Thr Arg Asp Lys Phe Leu Ser Ala
             45                  50                  55

Ala Thr Ser Ser Thr Pro Arg Glu Ala Pro Tyr Glu Leu Asn Ile Thr
             60                  65                  70

Ser Ala Thr Tyr Gln Ser Ala Ile Pro Pro Arg Gly Thr Gln Ala Val
 75              80                  85

Val Leu Lys Val Tyr Gln Asn Ala Gly Gly Thr His Pro Thr Thr Thr
 90              95                 100                 105

Tyr Lys Ala Phe Asp Trp Asp Gln Ala Tyr Arg Lys Pro Ile Thr Tyr
            110                 115                 120

Asp Thr Leu Trp Gln Ala Asp Thr Asp Pro Leu Pro Val Val Phe Pro
            125                 130                 135

Ile Val Gln Gly Glu Leu Ser Lys Gln Thr Gly Gln Gln Val Ser Ile
            140                 145                 150

Ala Pro Asn Ala Gly Leu Asp Pro Val Asn Tyr Gln Asn Phe Ala Val
            155                 160                 165

Thr Asn Asp Gly Val Ile Phe Phe Asn Pro Gly Glu Leu Pro
170              175                 180                 185

Glu Ala Ala Gly Pro Thr Gln Val Leu Val Pro Arg Ser Ala Ile Asp
            190                 195                 200

Ser Met Leu Ala
        205

<210> SEQ ID NO 20
<211> LENGTH: 355
<212> TYPE: PRT
<213> ORGANISM: Mycobacterium tuberculosis
<220> FEATURE:
<221> NAME/KEY: mat_peptide
<222> LOCATION: (33)..(355)

<400> SEQUENCE: 20

Met Ser Asn Ser Arg Arg Arg Ser Leu Arg Trp Ser Trp Leu Leu Ser
        -30                 -25                 -20

Val Leu Ala Ala Val Gly Leu Gly Leu Ala Thr Ala Pro Ala Gln Ala
        -15                 -10                  -5              -1

Ala Pro Pro Ala Leu Ser Gln Asp Arg Phe Ala Asp Phe Pro Ala Leu
  1               5                  10                  15

Pro Leu Asp Pro Ser Ala Met Val Ala Gln Val Gly Pro Gln Val Val
             20                  25                  30

Asn Ile Asn Thr Lys Leu Gly Tyr Asn Asn Ala Val Gly Ala Gly Thr
             35                  40                  45

Gly Ile Val Ile Asp Pro Asn Gly Val Val Leu Thr Asn Asn His Val
 50                  55                  60

Ile Ala Gly Ala Thr Asp Ile Asn Ala Phe Ser Val Gly Ser Gly Gln

```
                65                  70                  75                  80
Thr Tyr Gly Val Asp Val Gly Tyr Asp Arg Thr Gln Asp Val Ala
                    85                  90                  95
Val Leu Gln Leu Arg Gly Ala Gly Leu Pro Ser Ala Ala Ile Gly
                100                 105                 110
Gly Gly Val Ala Val Gly Glu Pro Val Ala Met Gly Asn Ser Gly
                115                 120                 125
Gly Gln Gly Gly Thr Pro Arg Ala Val Pro Gly Arg Val Val Ala Leu
130                 135                 140
Gly Gln Thr Val Gln Ala Ser Asp Ser Leu Thr Gly Ala Glu Glu Thr
145                 150                 155                 160
Leu Asn Gly Leu Ile Gln Phe Asp Ala Ala Ile Gln Pro Gly Asp Ser
                165                 170                 175
Gly Gly Pro Val Val Asn Gly Leu Gly Gln Val Val Gly Met Asn Thr
                180                 185                 190
Ala Ala Ser Asp Asn Phe Gln Leu Ser Gln Gly Gly Gln Gly Phe Ala
                195                 200                 205
Ile Pro Ile Gly Gln Ala Met Ala Ile Ala Gly Gln Ile Arg Ser Gly
                210                 215                 220
Gly Gly Ser Pro Thr Val His Ile Gly Pro Thr Ala Phe Leu Gly Leu
225                 230                 235                 240
Gly Val Val Asp Asn Asn Gly Asn Gly Ala Arg Val Gln Arg Val Val
                245                 250                 255
Gly Ser Ala Pro Ala Ala Ser Leu Gly Ile Ser Thr Gly Asp Val Ile
                260                 265                 270
Thr Ala Val Asp Gly Ala Pro Ile Asn Ser Ala Thr Ala Met Ala Asp
                275                 280                 285
Ala Leu Asn Gly His His Pro Gly Asp Val Ile Ser Val Thr Trp Gln
                290                 295                 300
Thr Lys Ser Gly Gly Thr Arg Thr Gly Asn Val Thr Leu Ala Glu Gly
305                 310                 315                 320
Pro Pro Ala

<210> SEQ ID NO 21
<211> LENGTH: 323
<212> TYPE: PRT
<213> ORGANISM: Artificial Sequence
<220> FEATURE:
<223> OTHER INFORMATION: Ser/Ala mutant of mature Mtb32A

<400> SEQUENCE: 21

Ala Pro Pro Ala Leu Ser Gln Asp Arg Phe Ala Asp Phe Pro Ala Leu
1               5                   10                  15
Pro Leu Asp Pro Ser Ala Met Val Ala Gln Val Gly Pro Gln Val Val
                20                  25                  30
Asn Ile Asn Thr Lys Leu Gly Tyr Asn Asn Ala Val Gly Ala Gly Thr
                35                  40                  45
Gly Ile Val Ile Asp Pro Asn Gly Val Val Leu Thr Asn Asn His Val
                50                  55                  60
Ile Ala Gly Ala Thr Asp Ile Asn Ala Phe Ser Val Gly Ser Gly Gln
65                  70                  75                  80
Thr Tyr Gly Val Asp Val Val Gly Tyr Asp Arg Thr Gln Asp Val Ala
                85                  90                  95
Val Leu Gln Leu Arg Gly Ala Gly Gly Leu Pro Ser Ala Ala Ile Gly
                100                 105                 110
```

Gly Gly Val Ala Val Gly Glu Pro Val Val Ala Met Gly Asn Ser Gly
            115                 120                 125

Gly Gln Gly Gly Thr Pro Arg Ala Val Pro Gly Arg Val Val Ala Leu
        130                 135                 140

Gly Gln Thr Val Gln Ala Ser Asp Ser Leu Thr Gly Ala Glu Glu Thr
145                 150                 155                 160

Leu Asn Gly Leu Ile Gln Phe Asp Ala Ala Ile Gln Pro Gly Asp Ala
                165                 170                 175

Gly Gly Pro Val Val Asn Gly Leu Gly Gln Val Val Gly Met Asn Thr
            180                 185                 190

Ala Ala Ser Asp Asn Phe Gln Leu Ser Gln Gly Gly Gln Gly Phe Ala
        195                 200                 205

Ile Pro Ile Gly Gln Ala Met Ala Ile Ala Gly Gln Ile Arg Ser Gly
    210                 215                 220

Gly Gly Ser Pro Thr Val His Ile Gly Pro Thr Ala Phe Leu Gly Leu
225                 230                 235                 240

Gly Val Val Asp Asn Asn Gly Asn Gly Ala Arg Val Gln Arg Val Val
                245                 250                 255

Gly Ser Ala Pro Ala Ala Ser Leu Gly Ile Ser Thr Gly Asp Val Ile
            260                 265                 270

Thr Ala Val Asp Gly Ala Pro Ile Asn Ser Ala Thr Ala Met Ala Asp
        275                 280                 285

Ala Leu Asn Gly His His Pro Gly Asp Val Ile Ser Val Thr Trp Gln
    290                 295                 300

Thr Lys Ser Gly Gly Thr Arg Thr Gly Asn Val Thr Leu Ala Glu Gly
305                 310                 315                 320

Pro Pro Ala

<210> SEQ ID NO 22
<211> LENGTH: 96
<212> TYPE: PRT
<213> ORGANISM: Mycobacterium tuberculosis

<400> SEQUENCE: 22

Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Lys Trp Gly Gly
                85                  90                  95

<210> SEQ ID NO 23
<211> LENGTH: 723
<212> TYPE: PRT
<213> ORGANISM: Artificial Sequence
<220> FEATURE:
<223> OTHER INFORMATION: Mtb72f

<400> SEQUENCE: 23

Met Thr Ala Ala Ser Asp Asn Phe Gln Leu Ser Gln Gly Gly Gln Gly

-continued

```
1               5                   10                  15
Phe Ala Ile Pro Ile Gly Gln Ala Met Ala Ile Ala Gly Gln Ile Arg
                20                  25                  30

Ser Gly Gly Gly Ser Pro Thr Val His Ile Gly Pro Thr Ala Phe Leu
                35              40                  45

Gly Leu Gly Val Val Asp Asn Gly Asn Gly Ala Arg Val Gln Arg
    50                  55                  60

Val Val Gly Ser Ala Pro Ala Ser Leu Gly Ile Ser Thr Gly Asp
65                  70              75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
                100             105                 110

Trp Gln Thr Lys Ser Gly Gly Thr Arg Thr Gly Asn Val Thr Leu Ala
                115                 120                 125

Glu Gly Pro Pro Ala Glu Phe Met Val Asp Phe Gly Ala Leu Pro Pro
                130                 135             140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
                180                 185                 190

Trp Ile Gly Ser Ser Ala Gly Leu Met Val Ala Ala Ser Pro Tyr
    195                 200                 205

Val Ala Trp Met Ser Val Thr Ala Gly Gln Ala Glu Leu Thr Ala Ala
    210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                245                 250                 255

Ile Ala Thr Asn Leu Leu Gly Gln Asn Thr Pro Ala Ile Ala Val Asn
                260                 265                 270

Glu Ala Glu Tyr Gly Glu Met Trp Ala Gln Asp Ala Ala Ala Met Phe
    275                 280                 285

Gly Tyr Ala Ala Ala Thr Ala Thr Ala Thr Ala Thr Leu Leu Pro Phe
    290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Ala Asn Gln Leu Met
                325                 330                 335

Asn Asn Val Pro Gln Ala Leu Gln Gln Leu Ala Gln Pro Thr Gln Gly
                340                 345                 350

Thr Thr Pro Ser Ser Lys Leu Gly Gly Leu Trp Lys Thr Val Ser Pro
                355                 360                 365

His Arg Ser Pro Ile Ser Asn Met Val Ser Met Ala Asn Asn His Met
                370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                405                 410                 415

Ala Gln Asn Gly Val Arg Ala Met Ser Ser Leu Gly Ser Ser Leu Gly
                420                 425                 430
```

```
Ser Ser Gly Leu Gly Gly Val Ala Ala Asn Leu Gly Arg Ala Ala
        435                 440                 445

Ser Val Gly Ser Leu Ser Val Pro Gln Ala Trp Ala Ala Asn Gln
    450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
                485                 490                 495

Gln Met Gly Ala Arg Ala Gly Gly Leu Ser Gly Val Leu Arg Val
            500                 505                 510

Pro Pro Arg Pro Tyr Val Met Pro His Ser Pro Ala Ala Gly Asp Ile
            515                 520                 525

Ala Pro Pro Ala Leu Ser Gln Asp Arg Phe Ala Asp Phe Pro Ala Leu
530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
                565                 570                 575

Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
            595                 600                 605

Thr Tyr Gly Val Asp Val Val Gly Tyr Asp Arg Thr Gln Asp Val Ala
    610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
                645                 650                 655

Gly Gln Gly Gly Thr Pro Arg Ala Val Pro Gly Arg Val Val Ala Leu
            660                 665                 670

Gly Gln Thr Val Gln Ala Ser Asp Ser Leu Thr Gly Ala Glu Glu Thr
            675                 680                 685

Leu Asn Gly Leu Ile Gln Phe Asp Ala Ala Ile Gln Pro Gly Asp Ser
        690                 695                 700

Gly Gly Pro Val Val Asn Gly Leu Gly Gln Val Val Gly Met Asn Thr
705                 710                 715                 720

Ala Ala Ser

<210> SEQ ID NO 24
<211> LENGTH: 723
<212> TYPE: PRT
<213> ORGANISM: Artificial Sequence
<220> FEATURE:
<223> OTHER INFORMATION: M72

<400> SEQUENCE: 24

Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60
```

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Thr Ala Met
            85                  90                  95

Ala Asp Ala Leu Asn Gly His His Pro Gly Asp Val Ile Ser Val Thr
                100                 105                 110

Trp Gln Thr Lys Ser Gly Gly Thr Arg Thr Gly Asn Val Thr Leu Ala
            115                 120                 125

Glu Gly Pro Pro Ala Glu Phe Met Val Asp Phe Gly Ala Leu Pro Pro
130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
                180                 185                 190

Trp Ile Gly Ser Ser Ala Gly Leu Met Val Ala Ala Ser Pro Tyr
            195                 200                 205

Val Ala Trp Met Ser Val Thr Ala Gly Gln Ala Glu Leu Thr Ala Ala
210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
            275                 280                 285

Gly Tyr Ala Ala Ala Thr Ala Thr Ala Thr Thr Leu Leu Pro Phe
290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Ala Asn Gln Leu Met
                325                 330                 335

Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
            355                 360                 365

His Arg Ser Pro Ile Ser Asn Met Val Ser Met Ala Asn Asn His Met
            370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Ala Gln Ala Val Gln Thr Ala
                405                 410                 415

Ala Gln Asn Gly Val Arg Ala Met Ser Ser Leu Gly Ser Ser Leu Gly
            420                 425                 430

Ser Ser Gly Leu Gly Gly Gly Val Ala Ala Asn Leu Gly Arg Ala Ala
            435                 440                 445

Ser Val Gly Ser Leu Ser Val Pro Gln Ala Trp Ala Ala Ala Asn Gln
            450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly

```
                    485                 490                 495
Gln Met Gly Ala Arg Ala Gly Gly Leu Ser Gly Val Leu Arg Val
                500                 505                 510

Pro Pro Arg Pro Tyr Val Met Pro His Ser Pro Ala Ala Gly Asp Ile
            515                 520                 525

Ala Pro Pro Ala Leu Ser Gln Asp Arg Phe Ala Asp Phe Pro Ala Leu
    530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
                565                 570                 575

Gly Ile Val Ile Asp Pro Asn Gly Val Val Leu Thr Asn Asn His Val
                580                 585                 590

Ile Ala Gly Ala Thr Asp Ile Asn Ala Phe Ser Val Ser Gly Gln
                595                 600                 605

Thr Tyr Gly Val Asp Val Gly Tyr Asp Arg Thr Gln Asp Val Ala
                610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
                645                 650                 655

Gly Gln Gly Gly Thr Pro Arg Ala Val Pro Gly Arg Val Val Ala Leu
                660                 665                 670

Gly Gln Thr Val Gln Ala Ser Asp Ser Leu Thr Gly Ala Glu Glu Thr
                675                 680                 685

Leu Asn Gly Leu Ile Gln Phe Asp Ala Ala Ile Gln Pro Gly Asp Ala
            690                 695                 700

Gly Gly Pro Val Val Asn Gly Leu Gly Gln Val Val Gly Met Asn Thr
705                 710                 715                 720

Ala Ala Ser

<210> SEQ ID NO 25
<211> LENGTH: 702
<212> TYPE: PRT
<213> ORGANISM: Artificial Sequence
<220> FEATURE:
<223> OTHER INFORMATION: Mtb71f

<400> SEQUENCE: 25

Asp Pro Val Asp Ala Val Ile Asn Thr Thr Cys Asn Tyr Gly Gln Val
1               5                   10                  15

Val Ala Ala Leu Asn Ala Thr Asp Pro Gly Ala Ala Ala Gln Phe Asn
                20                  25                  30

Ala Ser Pro Val Ala Gln Ser Tyr Leu Arg Asn Phe Leu Ala Ala Pro
            35                  40                  45

Pro Pro Gln Arg Ala Ala Met Ala Ala Gln Leu Gln Ala Val Pro Gly
        50                  55                  60

Ala Ala Gln Tyr Ile Gly Leu Val Glu Ser Val Ala Gly Ser Cys Asn
65                  70                  75                  80

Asn Tyr Glu Leu Met Thr Ile Asn Tyr Gln Phe Gly Asp Val Asp Ala
                85                  90                  95

His Gly Ala Met Ile Arg Ala Gln Ala Ala Ser Leu Glu Ala Glu His
            100                 105                 110

Gln Ala Ile Val Arg Asp Val Leu Ala Ala Gly Asp Phe Trp Gly Gly
        115                 120                 125
```

```
Ala Gly Ser Val Ala Cys Gln Glu Phe Ile Thr Gln Leu Gly Arg Asn
            130                 135                 140

Phe Gln Val Ile Tyr Glu Gln Ala Asn Ala His Gly Gln Lys Val Gln
145                 150                 155                 160

Ala Ala Gly Asn Asn Met Ala Gln Thr Asp Ser Ala Val Gly Ser Ser
                165                 170                 175

Trp Ala Thr Ser Met Ser Leu Leu Asp Ala His Ile Pro Gln Leu Val
            180                 185                 190

Ala Ser Gln Ser Ala Phe Ala Ala Lys Ala Gly Leu Met Arg His Thr
        195                 200                 205

Ile Gly Gln Ala Glu Gln Ala Ala Met Ser Ala Gln Ala Phe His Gln
    210                 215                 220

Gly Glu Ser Ser Ala Ala Phe Gln Ala Ala His Ala Arg Phe Val Ala
225                 230                 235                 240

Ala Ala Ala Lys Val Asn Thr Leu Leu Asp Val Ala Gln Ala Asn Leu
                245                 250                 255

Gly Glu Ala Ala Gly Thr Tyr Val Ala Ala Asp Ala Ala Ala Ala Ser
            260                 265                 270

Thr Tyr Thr Gly Phe Asp Ile Met Asp Phe Gly Leu Leu Pro Pro Glu
        275                 280                 285

Val Asn Ser Ser Arg Met Tyr Ser Gly Pro Gly Pro Glu Ser Met Leu
    290                 295                 300

Ala Ala Ala Ala Ala Trp Asp Gly Val Ala Ala Glu Leu Thr Ser Ala
305                 310                 315                 320

Ala Val Ser Tyr Gly Ser Val Val Ser Thr Leu Ile Val Glu Pro Trp
                325                 330                 335

Met Gly Pro Ala Ala Ala Met Ala Ala Ala Thr Pro Tyr Val
            340                 345                 350

Gly Trp Leu Ala Ala Thr Ala Ala Leu Ala Lys Glu Thr Ala Thr Gln
        355                 360                 365

Ala Arg Ala Ala Ala Glu Ala Phe Gly Thr Ala Phe Ala Met Thr Val
    370                 375                 380

Pro Pro Ser Leu Val Ala Ala Asn Arg Ser Arg Leu Met Ser Leu Val
385                 390                 395                 400

Ala Ala Asn Ile Leu Gly Gln Asn Ser Ala Ala Ile Ala Ala Thr Gln
                405                 410                 415

Ala Glu Tyr Ala Glu Met Trp Ala Gln Asp Ala Ala Val Met Tyr Ser
            420                 425                 430

Tyr Glu Gly Ala Ser Ala Ala Ser Ala Leu Pro Pro Phe Thr Pro
        435                 440                 445

Pro Val Gln Gly Thr Gly Pro Ala Gly Pro Ala Ala Ala Ala Ala
450                 455                 460

Thr Gln Ala Ala Gly Ala Gly Ala Val Ala Asp Ala Gln Ala Thr Leu
465                 470                 475                 480

Ala Gln Leu Pro Pro Gly Ile Leu Ser Asp Ile Leu Ser Ala Leu Ala
                485                 490                 495

Ala Asn Ala Asp Pro Leu Thr Ser Gly Leu Leu Gly Ile Ala Ser Thr
            500                 505                 510

Leu Asn Pro Gln Val Gly Ser Ala Gln Pro Ile Val Ile Pro Thr Pro
        515                 520                 525

Ile Gly Glu Leu Asp Val Ile Ala Leu Tyr Ile Ala Ser Ile Ala Thr
    530                 535                 540
```

```
Gly Ser Ile Ala Leu Ala Ile Thr Asn Thr Ala Arg Pro Trp His Ile
545                 550                 555                 560

Gly Leu Tyr Gly Asn Ala Gly Leu Gly Pro Thr Gln Gly His Pro
            565                 570                 575

Leu Ser Ser Ala Thr Asp Glu Pro Glu Pro His Trp Gly Pro Phe Gly
            580                 585                 590

Gly Ala Ala Pro Val Ser Ala Gly Val Gly His Ala Ala Leu Val Gly
            595                 600                 605

Ala Leu Ser Val Pro His Ser Trp Thr Thr Ala Ala Pro Glu Ile Gln
            610                 615                 620

Leu Ala Val Gln Ala Thr Pro Thr Phe Ser Ser Ser Ala Gly Ala Asp
625                 630                 635                 640

Pro Thr Ala Leu Asn Gly Met Pro Ala Gly Leu Leu Ser Gly Met Ala
            645                 650                 655

Leu Ala Ser Leu Ala Ala Arg Gly Thr Thr Gly Gly Gly Thr Arg
            660                 665                 670

Ser Gly Thr Ser Thr Asp Gly Gln Glu Asp Gly Arg Lys Pro Pro Val
            675                 680                 685

Val Val Ile Arg Glu Gln Pro Pro Gly Asn Pro Pro Arg
    690                 695                 700

<210> SEQ ID NO 26
<211> LENGTH: 920
<212> TYPE: PRT
<213> ORGANISM: Artificial Sequence
<220> FEATURE:
<223> OTHER INFORMATION: M72-Mtb9.9-Mtb9.8

<400> SEQUENCE: 26

Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
            35                  40                  45

Gly Leu Gly Val Val Asp Asn Asn Gly Asn Gly Ala Arg Val Gln Arg
    50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
            85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
            115                 120                 125

Glu Gly Pro Pro Ala Glu Phe Met Val Asp Phe Gly Ala Leu Pro Pro
130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
            165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ala Ser Pro Tyr
            195                 200                 205
```

```
Val Ala Trp Met Ser Val Thr Ala Gly Gln Ala Glu Leu Thr Ala Ala
    210                 215                 220
Gln Val Arg Val Ala Ala Ala Tyr Glu Thr Ala Tyr Gly Leu Thr
225                 230                 235                 240
Val Pro Pro Val Ile Ala Glu Asn Arg Ala Glu Leu Met Ile Leu
            245                 250                 255
Ile Ala Thr Asn Leu Leu Gly Gln Asn Thr Pro Ala Ile Ala Val Asn
        260                 265                 270
Glu Ala Glu Tyr Gly Glu Met Trp Ala Gln Asp Ala Ala Met Phe
            275                 280                 285
Gly Tyr Ala Ala Ala Thr Ala Thr Ala Thr Leu Leu Pro Phe
290                 295                 300
Glu Glu Ala Pro Glu Met Thr Ser Ala Gly Leu Leu Glu Gln Ala
305                 310                 315                 320
Ala Ala Val Glu Glu Ala Ser Asp Thr Ala Ala Asn Gln Leu Met
            325                 330                 335
Asn Asn Val Pro Gln Ala Leu Gln Gln Leu Ala Gln Pro Thr Gln Gly
        340                 345                 350
Thr Thr Pro Ser Ser Lys Leu Gly Gly Leu Trp Lys Thr Val Ser Pro
        355                 360                 365
His Arg Ser Pro Ile Ser Asn Met Val Ser Met Ala Asn Asn His Met
        370                 375                 380
Ser Met Thr Asn Ser Gly Val Ser Met Thr Asn Thr Leu Ser Ser Met
385                 390                 395                 400
Leu Lys Gly Phe Ala Pro Ala Ala Ala Gln Ala Val Gln Thr Ala
            405                 410                 415
Ala Gln Asn Gly Val Arg Ala Met Ser Ser Leu Gly Ser Ser Leu Gly
        420                 425                 430
Ser Ser Gly Leu Gly Gly Val Ala Ala Asn Leu Gly Arg Ala Ala
        435                 440                 445
Ser Val Gly Ser Leu Ser Val Pro Gln Ala Trp Ala Ala Ala Asn Gln
        450                 455                 460
Ala Val Thr Pro Ala Ala Arg Ala Leu Pro Leu Thr Ser Leu Thr Ser
465                 470                 475                 480
Ala Ala Glu Arg Gly Pro Gly Gln Met Leu Gly Gly Leu Pro Val Gly
            485                 490                 495
Gln Met Gly Ala Arg Ala Gly Gly Leu Ser Gly Val Leu Arg Val
            500                 505                 510
Pro Pro Arg Pro Tyr Val Met Pro His Ser Pro Ala Ala Gly Asp Ile
        515                 520                 525
Ala Pro Pro Ala Leu Ser Gln Asp Arg Phe Ala Asp Phe Pro Ala Leu
530                 535                 540
Pro Leu Asp Pro Ser Ala Met Val Ala Gln Val Gly Pro Gln Val Val
545                 550                 555                 560
Asn Ile Asn Thr Lys Leu Gly Tyr Asn Asn Ala Val Gly Ala Gly Thr
            565                 570                 575
Gly Ile Val Ile Asp Pro Asn Gly Val Val Leu Thr Asn Asn His Val
            580                 585                 590
Ile Ala Gly Ala Thr Asp Ile Asn Ala Phe Ser Val Gly Ser Gly Gln
            595                 600                 605
Thr Tyr Gly Val Asp Val Val Gly Tyr Asp Arg Thr Gln Asp Val Ala
        610                 615                 620
Val Leu Gln Leu Arg Gly Ala Gly Gly Leu Pro Ser Ala Ala Ile Gly
```

```
                625                 630                 635                 640
Gly Gly Val Ala Val Gly Glu Pro Val Ala Met Gly Asn Ser Gly
                645                 650                 655
Gly Gln Gly Gly Thr Pro Arg Ala Val Pro Gly Arg Val Val Ala Leu
                660                 665                 670
Gly Gln Thr Val Gln Ala Ser Asp Ser Leu Thr Gly Ala Glu Glu Thr
                675                 680                 685
Leu Asn Gly Leu Ile Gln Phe Asp Ala Ala Ile Gln Pro Gly Asp Ala
                690                 695                 700
Gly Gly Pro Val Val Asn Gly Leu Gly Gln Val Val Gly Met Asn Thr
705                 710                 715                 720
Ala Ala Ser Ser Thr Met Thr Ile Asn Tyr Gln Phe Gly Asp Val Asp
                725                 730                 735
Ala His Gly Ala Met Ile Arg Ala Gln Ala Ala Ser Leu Glu Ala Glu
                740                 745                 750
His Gln Ala Ile Val Arg Asp Val Leu Ala Ala Gly Asp Phe Trp Gly
                755                 760                 765
Gly Ala Gly Ser Val Ala Cys Gln Glu Phe Ile Thr Gln Leu Gly Arg
                770                 775                 780
Asn Phe Gln Val Ile Tyr Glu Gln Ala Asn Ala His Gly Gln Lys Val
785                 790                 795                 800
Gln Ala Ala Gly Asn Asn Met Ala Gln Thr Asp Ser Ala Val Gly Ser
                805                 810                 815
Ser Trp Ala Thr Ser Met Ser Leu Leu Asp Ala His Ile Pro Gln Leu
                820                 825                 830
Val Ala Ser Gln Ser Ala Phe Ala Ala Lys Ala Gly Leu Met Arg His
                835                 840                 845
Thr Ile Gly Gln Ala Glu Gln Ala Ala Met Ser Ala Gln Ala Phe His
                850                 855                 860
Gln Gly Glu Ser Ser Ala Ala Phe Gln Ala Ala His Ala Arg Phe Val
865                 870                 875                 880
Ala Ala Ala Ala Lys Val Asn Thr Leu Leu Asp Val Ala Gln Ala Asn
                885                 890                 895
Leu Gly Glu Ala Ala Gly Thr Tyr Val Ala Ala Asp Ala Ala Ala Ala
                900                 905                 910
Ser Thr Tyr Thr Gly Phe Pro Trp
                915                 920

<210> SEQ ID NO 27
<211> LENGTH: 1010
<212> TYPE: PRT
<213> ORGANISM: Artificial Sequence
<220> FEATURE:
<223> OTHER INFORMATION: M103

<400> SEQUENCE: 27

Met Thr Ala Ala Ser Asp Asn Phe Gln Leu Ser Gln Gly Gly Gln Gly
1                   5                   10                  15
Phe Ala Ile Pro Ile Gly Gln Ala Met Ala Ile Ala Gly Gln Ile Arg
                20                  25                  30
Ser Gly Gly Gly Ser Pro Thr Val His Ile Gly Pro Thr Ala Phe Leu
                35                  40                  45
Gly Leu Gly Val Val Asp Asn Asn Gly Asn Gly Ala Arg Val Gln Arg
                50                  55                  60
Val Val Gly Ser Ala Pro Ala Ala Ser Leu Gly Ile Ser Thr Gly Asp
```

-continued

```
            65                  70                  75                  80
Val Ile Thr Ala Val Asp Gly Ala Pro Ile Asn Ser Ala Thr Ala Met
                85                  90                  95
Ala Asp Ala Leu Asn Gly His His Pro Gly Asp Val Ile Ser Val Thr
                100                 105                 110
Trp Gln Thr Lys Ser Gly Gly Thr Arg Thr Gly Asn Val Thr Leu Ala
                115                 120                 125
Glu Gly Pro Pro Ala Glu Phe Met Val Asp Phe Gly Ala Leu Pro Pro
            130                 135                 140
Glu Ile Asn Ser Ala Arg Met Tyr Ala Gly Pro Gly Ser Ala Ser Leu
145                 150                 155                 160
Val Ala Ala Ala Gln Met Trp Asp Ser Val Ala Ser Asp Leu Phe Ser
                165                 170                 175
Ala Ala Ser Ala Phe Gln Ser Val Val Trp Gly Leu Thr Val Gly Ser
                180                 185                 190
Trp Ile Gly Ser Ser Ala Gly Leu Met Val Ala Ala Ser Pro Tyr
                195                 200                 205
Val Ala Trp Met Ser Val Thr Ala Gly Gln Ala Glu Leu Thr Ala Ala
            210                 215                 220
Gln Val Arg Val Ala Ala Ala Tyr Glu Thr Ala Tyr Gly Leu Thr
225                 230                 235                 240
Val Pro Pro Pro Val Ile Ala Glu Asn Arg Ala Glu Leu Met Ile Leu
                245                 250                 255
Ile Ala Thr Asn Leu Leu Gly Gln Asn Thr Pro Ala Ile Ala Val Asn
                260                 265                 270
Glu Ala Glu Tyr Gly Glu Met Trp Ala Gln Asp Ala Ala Ala Met Phe
                275                 280                 285
Gly Tyr Ala Ala Ala Thr Ala Thr Ala Thr Ala Thr Leu Leu Pro Phe
            290                 295                 300
Glu Glu Ala Pro Glu Met Thr Ser Ala Gly Gly Leu Leu Glu Gln Ala
305                 310                 315                 320
Ala Ala Val Glu Glu Ala Ser Asp Thr Ala Ala Ala Asn Gln Leu Met
                325                 330                 335
Asn Asn Val Pro Gln Ala Leu Gln Gln Leu Ala Gln Pro Thr Gln Gly
                340                 345                 350
Thr Thr Pro Ser Ser Lys Leu Gly Gly Leu Trp Lys Thr Val Ser Pro
                355                 360                 365
His Arg Ser Pro Ile Ser Asn Met Val Ser Met Ala Asn Asn His Met
                370                 375                 380
Ser Met Thr Asn Ser Gly Val Ser Met Thr Asn Thr Leu Ser Ser Met
385                 390                 395                 400
Leu Lys Gly Phe Ala Pro Ala Ala Ala Gln Ala Val Gln Thr Ala
                405                 410                 415
Ala Gln Asn Gly Val Arg Ala Met Ser Ser Leu Gly Ser Ser Leu Gly
                420                 425                 430
Ser Ser Gly Leu Gly Gly Val Ala Ala Asn Leu Gly Arg Ala Ala
                435                 440                 445
Ser Val Gly Ser Leu Ser Val Pro Gln Ala Trp Ala Ala Ala Asn Gln
                450                 455                 460
Ala Val Thr Pro Ala Ala Arg Ala Leu Pro Leu Thr Ser Leu Thr Ser
465                 470                 475                 480
Ala Ala Glu Arg Gly Pro Gly Gln Met Leu Gly Gly Leu Pro Val Gly
                485                 490                 495
```

```
Gln Met Gly Ala Arg Ala Gly Gly Leu Ser Gly Val Leu Arg Val
            500                 505                 510

Pro Pro Arg Pro Tyr Val Met Pro His Ser Pro Ala Ala Gly Asp Ile
            515                 520                 525

Ala Pro Pro Ala Leu Ser Gln Asp Arg Phe Ala Asp Phe Pro Ala Leu
            530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
                565                 570                 575

Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
            595                 600                 605

Thr Tyr Gly Val Asp Val Val Gly Tyr Asp Arg Thr Gln Asp Val Ala
            610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
                645                 650                 655

Gly Gln Gly Gly Thr Pro Arg Ala Val Pro Gly Arg Val Val Ala Leu
            660                 665                 670

Gly Gln Thr Val Gln Ala Ser Asp Ser Leu Thr Gly Ala Glu Glu Thr
            675                 680                 685

Leu Asn Gly Leu Ile Gln Phe Asp Ala Ala Ile Gln Pro Gly Asp Ala
            690                 695                 700

Gly Gly Pro Val Val Asn Gly Leu Gly Gln Val Val Gly Met Asn Thr
705                 710                 715                 720

Ala Ala Ser Ser Gly Phe Ser Arg Pro Gly Leu Pro Val Glu Tyr Leu
                725                 730                 735

Gln Val Pro Ser Pro Ser Met Gly Arg Asp Ile Lys Val Gln Phe Gln
            740                 745                 750

Ser Gly Gly Asn Asn Ser Pro Ala Val Tyr Leu Leu Asp Gly Leu Arg
            755                 760                 765

Ala Gln Asp Asp Tyr Asn Gly Trp Asp Ile Asn Thr Pro Ala Phe Glu
            770                 775                 780

Trp Tyr Tyr Gln Ser Gly Leu Ser Ile Val Met Pro Val Gly Gly Gln
785                 790                 795                 800

Ser Ser Phe Tyr Ser Asp Trp Tyr Ser Pro Ala Cys Gly Lys Ala Gly
                805                 810                 815

Cys Gln Thr Tyr Lys Trp Glu Thr Phe Leu Thr Ser Glu Leu Pro Gln
            820                 825                 830

Trp Leu Ser Ala Asn Arg Ala Val Lys Pro Thr Gly Ser Ala Ala Ile
            835                 840                 845

Gly Leu Ser Met Ala Gly Ser Ser Ala Met Ile Leu Ala Ala Tyr His
            850                 855                 860

Pro Gln Gln Phe Ile Tyr Ala Gly Ser Leu Ser Ala Leu Leu Asp Pro
865                 870                 875                 880

Ser Gln Gly Met Gly Pro Ser Leu Ile Gly Leu Ala Met Gly Asp Ala
                885                 890                 895

Gly Gly Tyr Lys Ala Ala Asp Met Trp Gly Pro Ser Ser Asp Pro Ala
            900                 905                 910
```

-continued

```
Trp Glu Arg Asn Asp Pro Thr Gln Gln Ile Pro Lys Leu Val Ala Asn
            915                 920                 925

Asn Thr Arg Leu Trp Val Tyr Cys Gly Asn Gly Thr Pro Asn Glu Leu
        930                 935                 940

Gly Gly Ala Asn Ile Pro Ala Glu Phe Leu Glu Asn Phe Val Arg Ser
945                 950                 955                 960

Ser Asn Leu Lys Phe Gln Asp Ala Tyr Asn Ala Ala Gly Gly His Asn
                965                 970                 975

Ala Val Phe Asn Phe Pro Pro Asn Gly Thr His Ser Trp Glu Tyr Trp
            980                 985                 990

Gly Ala Gln Leu Asn Ala Met Lys Gly Asp Leu Gln Ser Ser Leu Gly
        995                1000                1005

Ala Gly
    1010

<210> SEQ ID NO 28
<211> LENGTH: 1148
<212> TYPE: PRT
<213> ORGANISM: Artificial Sequence
<220> FEATURE:
<223> OTHER INFORMATION: M114

<400> SEQUENCE: 28

Met Thr Ala Ala Ser Asp Asn Phe Gln Leu Ser Gln Gly Gly Gln Gly
1               5                  10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
        115                 120                 125

Glu Gly Pro Pro Ala Glu Phe Met Val Asp Phe Gly Ala Leu Pro Pro
130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ser Pro Tyr
        195                 200                 205

Val Ala Trp Met Ser Val Thr Ala Gly Gln Ala Glu Leu Thr Ala Ala
210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                245                 250                 255
```

```
Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
            275                 280                 285

Gly Tyr Ala Ala Ala Thr Ala Thr Ala Thr Ala Thr Leu Leu Pro Phe
            290                 295                 300

Glu Glu Ala Pro Glu Met Thr Ser Ala Gly Leu Leu Glu Gln Ala
305                 310                 315                 320

Ala Ala Val Glu Glu Ala Ser Asp Thr Ala Ala Asn Gln Leu Met
            325                 330                 335

Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
            355                 360                 365

His Arg Ser Pro Ile Ser Asn Met Val Ser Met Ala Asn Asn His Met
            370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
            405                 410                 415

Ala Gln Asn Gly Val Arg Ala Met Ser Ser Leu Gly Ser Ser Leu Gly
            420                 425                 430

Ser Ser Gly Leu Gly Gly Val Ala Ala Asn Leu Gly Arg Ala Ala
            435                 440                 445

Ser Val Gly Ser Leu Ser Val Pro Gln Ala Trp Ala Ala Asn Gln
            450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
            485                 490                 495

Gln Met Gly Ala Arg Ala Gly Gly Leu Ser Gly Val Leu Arg Val
            500                 505                 510

Pro Pro Arg Pro Tyr Val Met Pro His Ser Pro Ala Ala Gly Asp Ile
            515                 520                 525

Ala Pro Pro Ala Leu Ser Gln Asp Arg Phe Ala Asp Phe Pro Ala Leu
            530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
            565                 570                 575

Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
            595                 600                 605

Thr Tyr Gly Val Asp Val Val Gly Tyr Asp Arg Thr Gln Asp Val Ala
            610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Ala Met Gly Asn Ser Gly
            645                 650                 655

Gly Gln Gly Gly Thr Pro Arg Ala Val Pro Gly Arg Val Val Ala Leu
            660                 665                 670

Gly Gln Thr Val Gln Ala Ser Asp Ser Leu Thr Gly Ala Glu Glu Thr
```

```
              675                 680                 685
Leu Asn Gly Leu Ile Gln Phe Asp Ala Ala Ile Gln Pro Gly Asp Ala
    690                 695                 700
Gly Gly Pro Val Val Asn Gly Leu Gly Gln Val Val Gly Met Asn Thr
705                 710                 715                 720
Ala Ala Ser Ser Thr Met Asp Phe Gly Leu Leu Pro Pro Glu Val Asn
                725                 730                 735
Ser Ser Arg Met Tyr Ser Gly Pro Gly Pro Glu Ser Met Leu Ala Ala
                740                 745                 750
Ala Ala Ala Trp Asp Gly Val Ala Ala Glu Leu Thr Ser Ala Ala Val
                755                 760                 765
Ser Tyr Gly Ser Val Val Ser Thr Leu Ile Val Glu Pro Trp Met Gly
    770                 775                 780
Pro Ala Ala Ala Ala Met Ala Ala Ala Thr Pro Tyr Val Gly Trp
785                 790                 795                 800
Leu Ala Ala Thr Ala Ala Leu Ala Lys Glu Thr Ala Thr Gln Ala Arg
                805                 810                 815
Ala Ala Ala Glu Ala Phe Gly Thr Ala Phe Ala Met Thr Val Pro Pro
                820                 825                 830
Ser Leu Val Ala Ala Asn Arg Ser Arg Leu Met Ser Leu Val Ala Ala
                835                 840                 845
Asn Ile Leu Gly Gln Asn Ser Ala Ala Ile Ala Ala Thr Gln Ala Glu
850                 855                 860
Tyr Ala Glu Met Trp Ala Gln Asp Ala Ala Val Met Tyr Ser Tyr Glu
865                 870                 875                 880
Gly Ala Ser Ala Ala Ala Ser Ala Leu Pro Pro Phe Thr Pro Pro Val
                885                 890                 895
Gln Gly Thr Gly Pro Ala Gly Pro Ala Ala Ala Ala Ala Ala Thr Gln
                900                 905                 910
Ala Ala Gly Ala Gly Ala Val Ala Asp Ala Gln Ala Thr Leu Ala Gln
                915                 920                 925
Leu Pro Pro Gly Ile Leu Ser Asp Ile Leu Ser Ala Leu Ala Ala Asn
    930                 935                 940
Ala Asp Pro Leu Thr Ser Gly Leu Leu Gly Ile Ala Ser Thr Leu Asn
945                 950                 955                 960
Pro Gln Val Gly Ser Ala Gln Pro Ile Val Ile Pro Thr Pro Ile Gly
                965                 970                 975
Glu Leu Asp Val Ile Ala Leu Tyr Ile Ala Ser Ile Ala Thr Gly Ser
                980                 985                 990
Ile Ala Leu Ala Ile Thr Asn Thr Ala Arg Pro Trp His Ile Gly Leu
    995                 1000                1005
Tyr Gly Asn Ala Gly Gly Leu Gly Pro Thr Gln Gly His Pro Leu
    1010                1015                1020
Ser Ser Ala Thr Asp Glu Pro Glu Pro His Trp Gly Pro Phe Gly
    1025                1030                1035
Gly Ala Ala Pro Val Ser Ala Gly Val Gly His Ala Ala Leu Val
    1040                1045                1050
Gly Ala Leu Ser Val Pro His Ser Trp Thr Thr Ala Ala Pro Glu
    1055                1060                1065
Ile Gln Leu Ala Val Gln Ala Thr Pro Thr Phe Ser Ser Ser Ala
    1070                1075                1080
Gly Ala Asp Pro Thr Ala Leu Asn Gly Met Pro Ala Gly Leu Leu
    1085                1090                1095
```

Ser Gly Met Ala Leu Ala Ser Leu Ala Ala Arg Gly Thr Thr Gly
    1100            1105                1110

Gly Gly Gly Thr Arg Ser Gly Thr Ser Thr Asp Gly Gln Glu Asp
    1115            1120                1125

Gly Arg Lys Pro Pro Val Val Val Ile Arg Glu Gln Pro Pro Pro
    1130            1135                1140

Gly Asn Pro Pro Arg
    1145

<210> SEQ ID NO 29
<211> LENGTH: 9
<212> TYPE: PRT
<213> ORGANISM: Mycobacterium tuberculosis

<400> SEQUENCE: 29

Phe Ile Ile Asp Pro Thr Ile Ser Ala
1               5

<210> SEQ ID NO 30
<211> LENGTH: 9
<212> TYPE: PRT
<213> ORGANISM: Mycobacterium tuberculosis

<400> SEQUENCE: 30

Ile Leu Tyr Ser Ser Leu Glu Tyr Phe
1               5

<210> SEQ ID NO 31
<211> LENGTH: 9
<212> TYPE: PRT
<213> ORGANISM: Mycobacterium tuberculosis

<400> SEQUENCE: 31

Leu Glu Tyr Phe Glu Lys Ala Leu Glu
1               5

<210> SEQ ID NO 32
<211> LENGTH: 9
<212> TYPE: PRT
<213> ORGANISM: Mycobacterium tuberculosis

<400> SEQUENCE: 32

Tyr Ala Gly Lys Asn Arg Asn His Val
1               5

<210> SEQ ID NO 33
<211> LENGTH: 9
<212> TYPE: PRT
<213> ORGANISM: Mycobacterium tuberculosis

<400> SEQUENCE: 33

Leu Ile His Asp Gln Ala Asn Ala Val
1               5

<210> SEQ ID NO 34
<211> LENGTH: 9
<212> TYPE: PRT
<213> ORGANISM: Mycobacterium tuberculosis

<400> SEQUENCE: 34

Phe Val Arg Pro Val Ala Val Asp Leu
1               5

```
<210> SEQ ID NO 35
<211> LENGTH: 9
<212> TYPE: PRT
<213> ORGANISM: Mycobacterium tuberculosis

<400> SEQUENCE: 35

Leu Thr Tyr Ile Pro Val Val Gly His
1               5

<210> SEQ ID NO 36
<211> LENGTH: 9
<212> TYPE: PRT
<213> ORGANISM: Mycobacterium tuberculosis

<400> SEQUENCE: 36

Tyr Ile Pro Val Val Gly His Ala Leu
1               5

<210> SEQ ID NO 37
<211> LENGTH: 9
<212> TYPE: PRT
<213> ORGANISM: Mycobacterium tuberculosis

<400> SEQUENCE: 37

Tyr Leu Val Val Lys Thr Leu Ile Asn
1               5

<210> SEQ ID NO 38
<211> LENGTH: 9
<212> TYPE: PRT
<213> ORGANISM: Mycobacterium tuberculosis

<400> SEQUENCE: 38

Leu Val Val Lys Thr Leu Ile Asn Ala
1               5

<210> SEQ ID NO 39
<211> LENGTH: 9
<212> TYPE: PRT
<213> ORGANISM: Mycobacterium tuberculosis

<400> SEQUENCE: 39

Val Lys Thr Leu Ile Asn Ala Thr Gln
1               5

<210> SEQ ID NO 40
<211> LENGTH: 9
<212> TYPE: PRT
<213> ORGANISM: Mycobacterium tuberculosis

<400> SEQUENCE: 40

Leu Lys Leu Leu Ala Lys Leu Ala Glu
1               5

<210> SEQ ID NO 41
<211> LENGTH: 9
<212> TYPE: PRT
<213> ORGANISM: Mycobacterium tuberculosis

<400> SEQUENCE: 41

Leu Val Ala Ala Ala Ile Ala Asp Ile
1               5

<210> SEQ ID NO 42
```

```
<211> LENGTH: 9
<212> TYPE: PRT
<213> ORGANISM: Mycobacterium tuberculosis

<400> SEQUENCE: 42

Ile Ile Ser Asp Val Ala Asp Ile Ile
1               5

<210> SEQ ID NO 43
<211> LENGTH: 9
<212> TYPE: PRT
<213> ORGANISM: Mycobacterium tuberculosis

<400> SEQUENCE: 43

Trp Glu Phe Ile Thr Asn Ala Leu Asn
1               5

<210> SEQ ID NO 44
<211> LENGTH: 9
<212> TYPE: PRT
<213> ORGANISM: Mycobacterium tuberculosis

<400> SEQUENCE: 44

Leu Phe Gly Ala Ala Gly Leu Ser Ala
1               5

<210> SEQ ID NO 45
<211> LENGTH: 9
<212> TYPE: PRT
<213> ORGANISM: Mycobacterium tuberculosis

<400> SEQUENCE: 45

Leu Ala His Ala Asp Ser Leu Ala Ser
1               5

<210> SEQ ID NO 46
<211> LENGTH: 9
<212> TYPE: PRT
<213> ORGANISM: Mycobacterium tuberculosis

<400> SEQUENCE: 46

Leu Ala Ser Ser Ala Ser Leu Pro Ala
1               5

<210> SEQ ID NO 47
<211> LENGTH: 9
<212> TYPE: PRT
<213> ORGANISM: Mycobacterium tuberculosis

<400> SEQUENCE: 47

Phe Gly Gly Leu Pro Ser Leu Ala Gln
1               5

<210> SEQ ID NO 48
<211> LENGTH: 9
<212> TYPE: PRT
<213> ORGANISM: Mycobacterium tuberculosis

<400> SEQUENCE: 48

Phe Ile Ile Asp Pro Thr Ile Ser Ala
1               5

<210> SEQ ID NO 49
<211> LENGTH: 9
<212> TYPE: PRT
```

<213> ORGANISM: Mycobacterium tuberculosis

<400> SEQUENCE: 49

Ile Ile Asp Pro Thr Ile Ser Ala Ile
1               5

<210> SEQ ID NO 50
<211> LENGTH: 9
<212> TYPE: PRT
<213> ORGANISM: Mycobacterium tuberculosis

<400> SEQUENCE: 50

Pro Thr Ile Ser Ala Ile Asp Gly Leu
1               5

<210> SEQ ID NO 51
<211> LENGTH: 9
<212> TYPE: PRT
<213> ORGANISM: Mycobacterium tuberculosis

<400> SEQUENCE: 51

Thr Ile Ser Ala Ile Asp Gly Leu Tyr
1               5

<210> SEQ ID NO 52
<211> LENGTH: 9
<212> TYPE: PRT
<213> ORGANISM: Mycobacterium tuberculosis

<400> SEQUENCE: 52

Ser Ala Ile Asp Gly Leu Tyr Asp Leu
1               5

<210> SEQ ID NO 53
<211> LENGTH: 9
<212> TYPE: PRT
<213> ORGANISM: Mycobacterium tuberculosis

<400> SEQUENCE: 53

Ala Ile Asp Gly Leu Tyr Asp Leu Leu
1               5

<210> SEQ ID NO 54
<211> LENGTH: 9
<212> TYPE: PRT
<213> ORGANISM: Mycobacterium tuberculosis

<400> SEQUENCE: 54

Leu Tyr Asp Leu Leu Gly Ile Gly Ile
1               5

<210> SEQ ID NO 55
<211> LENGTH: 9
<212> TYPE: PRT
<213> ORGANISM: Mycobacterium tuberculosis

<400> SEQUENCE: 55

Ile Pro Asn Gln Gly Gly Ile Leu Tyr
1               5

<210> SEQ ID NO 56
<211> LENGTH: 9
<212> TYPE: PRT
<213> ORGANISM: Mycobacterium tuberculosis

```
<400> SEQUENCE: 56

Gly Ile Leu Tyr Ser Ser Leu Glu Tyr
1               5

<210> SEQ ID NO 57
<211> LENGTH: 9
<212> TYPE: PRT
<213> ORGANISM: Mycobacterium tuberculosis

<400> SEQUENCE: 57

Tyr Ser Ser Leu Glu Tyr Phe Glu Lys
1               5

<210> SEQ ID NO 58
<211> LENGTH: 9
<212> TYPE: PRT
<213> ORGANISM: Mycobacterium tuberculosis

<400> SEQUENCE: 58

Ser Leu Glu Tyr Phe Glu Lys Ala Leu
1               5

<210> SEQ ID NO 59
<211> LENGTH: 9
<212> TYPE: PRT
<213> ORGANISM: Mycobacterium tuberculosis

<400> SEQUENCE: 59

Tyr Phe Glu Lys Ala Leu Glu Glu Leu
1               5

<210> SEQ ID NO 60
<211> LENGTH: 9
<212> TYPE: PRT
<213> ORGANISM: Mycobacterium tuberculosis

<400> SEQUENCE: 60

Phe Glu Lys Ala Leu Glu Glu Leu Ala
1               5

<210> SEQ ID NO 61
<211> LENGTH: 9
<212> TYPE: PRT
<213> ORGANISM: Mycobacterium tuberculosis

<400> SEQUENCE: 61

Asn His Val Asn Phe Phe Gln Glu Leu
1               5

<210> SEQ ID NO 62
<211> LENGTH: 9
<212> TYPE: PRT
<213> ORGANISM: Mycobacterium tuberculosis

<400> SEQUENCE: 62

Glu Leu Ala Asp Leu Asp Arg Gln Leu
1               5

<210> SEQ ID NO 63
<211> LENGTH: 9
<212> TYPE: PRT
<213> ORGANISM: Mycobacterium tuberculosis

<400> SEQUENCE: 63
```

```
Leu Ala Asp Leu Asp Arg Gln Leu Ile
1               5

<210> SEQ ID NO 64
<211> LENGTH: 9
<212> TYPE: PRT
<213> ORGANISM: Mycobacterium tuberculosis

<400> SEQUENCE: 64

Asp Leu Asp Arg Gln Leu Ile Ser Leu
1               5

<210> SEQ ID NO 65
<211> LENGTH: 9
<212> TYPE: PRT
<213> ORGANISM: Mycobacterium tuberculosis

<400> SEQUENCE: 65

Leu Asp Arg Gln Leu Ile Ser Leu Ile
1               5

<210> SEQ ID NO 66
<211> LENGTH: 9
<212> TYPE: PRT
<213> ORGANISM: Mycobacterium tuberculosis

<400> SEQUENCE: 66

Ala Val Gln Thr Thr Arg Asp Ile Leu
1               5

<210> SEQ ID NO 67
<211> LENGTH: 9
<212> TYPE: PRT
<213> ORGANISM: Mycobacterium tuberculosis

<400> SEQUENCE: 67

Glu Gly Ala Lys Lys Gly Leu Glu Phe
1               5

<210> SEQ ID NO 68
<211> LENGTH: 9
<212> TYPE: PRT
<213> ORGANISM: Mycobacterium tuberculosis

<400> SEQUENCE: 68

Lys Gly Leu Glu Phe Val Arg Pro Val
1               5

<210> SEQ ID NO 69
<211> LENGTH: 9
<212> TYPE: PRT
<213> ORGANISM: Mycobacterium tuberculosis

<400> SEQUENCE: 69

Gly Leu Glu Phe Val Arg Pro Val Ala
1               5

<210> SEQ ID NO 70
<211> LENGTH: 9
<212> TYPE: PRT
<213> ORGANISM: Mycobacterium tuberculosis

<400> SEQUENCE: 70

Leu Glu Phe Val Arg Pro Val Ala Val
1               5
```

```
<210> SEQ ID NO 71
<211> LENGTH: 9
<212> TYPE: PRT
<213> ORGANISM: Mycobacterium tuberculosis

<400> SEQUENCE: 71

Phe Val Arg Pro Val Ala Val Asp Leu
1               5

<210> SEQ ID NO 72
<211> LENGTH: 9
<212> TYPE: PRT
<213> ORGANISM: Mycobacterium tuberculosis

<400> SEQUENCE: 72

Arg Pro Val Ala Val Asp Leu Thr Tyr
1               5

<210> SEQ ID NO 73
<211> LENGTH: 9
<212> TYPE: PRT
<213> ORGANISM: Mycobacterium tuberculosis

<400> SEQUENCE: 73

Ala Val Asp Leu Thr Tyr Ile Pro Val
1               5

<210> SEQ ID NO 74
<211> LENGTH: 9
<212> TYPE: PRT
<213> ORGANISM: Mycobacterium tuberculosis

<400> SEQUENCE: 74

Thr Tyr Ile Pro Val Val Gly His Ala
1               5

<210> SEQ ID NO 75
<211> LENGTH: 9
<212> TYPE: PRT
<213> ORGANISM: Mycobacterium tuberculosis

<400> SEQUENCE: 75

Tyr Ile Pro Val Val Gly His Ala Leu
1               5

<210> SEQ ID NO 76
<211> LENGTH: 9
<212> TYPE: PRT
<213> ORGANISM: Mycobacterium tuberculosis

<400> SEQUENCE: 76

Leu Ser Ala Ala Phe Gln Ala Pro Phe
1               5

<210> SEQ ID NO 77
<211> LENGTH: 9
<212> TYPE: PRT
<213> ORGANISM: Mycobacterium tuberculosis

<400> SEQUENCE: 77

Ser Ala Ala Phe Gln Ala Pro Phe Cys
1               5
```

-continued

<210> SEQ ID NO 78
<211> LENGTH: 9
<212> TYPE: PRT
<213> ORGANISM: Mycobacterium tuberculosis

<400> SEQUENCE: 78

Ala Ala Phe Gln Ala Pro Phe Cys Ala
1 5

<210> SEQ ID NO 79
<211> LENGTH: 9
<212> TYPE: PRT
<213> ORGANISM: Mycobacterium tuberculosis

<400> SEQUENCE: 79

Phe Gln Ala Pro Phe Cys Ala Gly Ala
1 5

<210> SEQ ID NO 80
<211> LENGTH: 9
<212> TYPE: PRT
<213> ORGANISM: Mycobacterium tuberculosis

<400> SEQUENCE: 80

Ala Pro Phe Cys Ala Gly Ala Met Ala
1 5

<210> SEQ ID NO 81
<211> LENGTH: 9
<212> TYPE: PRT
<213> ORGANISM: Mycobacterium tuberculosis

<400> SEQUENCE: 81

Pro Phe Cys Ala Gly Ala Met Ala Val
1 5

<210> SEQ ID NO 82
<211> LENGTH: 9
<212> TYPE: PRT
<213> ORGANISM: Mycobacterium tuberculosis

<400> SEQUENCE: 82

Ala Met Ala Val Val Gly Gly Ala Leu
1 5

<210> SEQ ID NO 83
<211> LENGTH: 9
<212> TYPE: PRT
<213> ORGANISM: Mycobacterium tuberculosis

<400> SEQUENCE: 83

Ala Val Val Gly Gly Ala Leu Ala Tyr
1 5

<210> SEQ ID NO 84
<211> LENGTH: 9
<212> TYPE: PRT
<213> ORGANISM: Mycobacterium tuberculosis

<400> SEQUENCE: 84

Gly Ala Leu Ala Tyr Leu Val Val Lys
1 5

<210> SEQ ID NO 85
<211> LENGTH: 9

<212> TYPE: PRT
<213> ORGANISM: Mycobacterium tuberculosis

<400> SEQUENCE: 85

Leu Ala Tyr Leu Val Val Lys Thr Leu
1               5

<210> SEQ ID NO 86
<211> LENGTH: 9
<212> TYPE: PRT
<213> ORGANISM: Mycobacterium tuberculosis

<400> SEQUENCE: 86

Ala Tyr Leu Val Val Lys Thr Leu Ile
1               5

<210> SEQ ID NO 87
<211> LENGTH: 9
<212> TYPE: PRT
<213> ORGANISM: Mycobacterium tuberculosis

<400> SEQUENCE: 87

Lys Thr Leu Ile Asn Ala Thr Gln Leu
1               5

<210> SEQ ID NO 88
<211> LENGTH: 9
<212> TYPE: PRT
<213> ORGANISM: Mycobacterium tuberculosis

<400> SEQUENCE: 88

Thr Leu Ile Asn Ala Thr Gln Leu Leu
1               5

<210> SEQ ID NO 89
<211> LENGTH: 9
<212> TYPE: PRT
<213> ORGANISM: Mycobacterium tuberculosis

<400> SEQUENCE: 89

Ile Asn Ala Thr Gln Leu Leu Lys Leu
1               5

<210> SEQ ID NO 90
<211> LENGTH: 9
<212> TYPE: PRT
<213> ORGANISM: Mycobacterium tuberculosis

<400> SEQUENCE: 90

Asn Ala Thr Gln Leu Leu Lys Leu Leu
1               5

<210> SEQ ID NO 91
<211> LENGTH: 9
<212> TYPE: PRT
<213> ORGANISM: Mycobacterium tuberculosis

<400> SEQUENCE: 91

Gln Leu Leu Lys Leu Leu Ala Lys Leu
1               5

<210> SEQ ID NO 92
<211> LENGTH: 9
<212> TYPE: PRT
<213> ORGANISM: Mycobacterium tuberculosis

<400> SEQUENCE: 92

Lys Leu Leu Ala Lys Leu Ala Glu Leu
1               5

<210> SEQ ID NO 93
<211> LENGTH: 9
<212> TYPE: PRT
<213> ORGANISM: Mycobacterium tuberculosis

<400> SEQUENCE: 93

Leu Leu Ala Lys Leu Ala Glu Leu Val
1               5

<210> SEQ ID NO 94
<211> LENGTH: 9
<212> TYPE: PRT
<213> ORGANISM: Mycobacterium tuberculosis

<400> SEQUENCE: 94

Lys Leu Ala Glu Leu Val Ala Ala Ala
1               5

<210> SEQ ID NO 95
<211> LENGTH: 9
<212> TYPE: PRT
<213> ORGANISM: Mycobacterium tuberculosis

<400> SEQUENCE: 95

Leu Ala Glu Leu Val Ala Ala Ala Ile
1               5

<210> SEQ ID NO 96
<211> LENGTH: 9
<212> TYPE: PRT
<213> ORGANISM: Mycobacterium tuberculosis

<400> SEQUENCE: 96

Leu Val Ala Ala Ala Ile Ala Asp Ile
1               5

<210> SEQ ID NO 97
<211> LENGTH: 9
<212> TYPE: PRT
<213> ORGANISM: Mycobacterium tuberculosis

<400> SEQUENCE: 97

Ala Ile Ala Asp Ile Ile Ser Asp Val
1               5

<210> SEQ ID NO 98
<211> LENGTH: 9
<212> TYPE: PRT
<213> ORGANISM: Mycobacterium tuberculosis

<400> SEQUENCE: 98

Ile Ala Asp Ile Ile Ser Asp Val Ala
1               5

<210> SEQ ID NO 99
<211> LENGTH: 9
<212> TYPE: PRT
<213> ORGANISM: Mycobacterium tuberculosis

<400> SEQUENCE: 99

```
Ile Ser Asp Val Ala Asp Ile Ile Lys
1               5
```

<210> SEQ ID NO 100
<211> LENGTH: 9
<212> TYPE: PRT
<213> ORGANISM: Mycobacterium tuberculosis

<400> SEQUENCE: 100

```
Thr Leu Gly Glu Val Trp Glu Phe Ile
1               5
```

<210> SEQ ID NO 101
<211> LENGTH: 9
<212> TYPE: PRT
<213> ORGANISM: Mycobacterium tuberculosis

<400> SEQUENCE: 101

```
Phe Ile Thr Asn Ala Leu Asn Gly Leu
1               5
```

<210> SEQ ID NO 102
<211> LENGTH: 9
<212> TYPE: PRT
<213> ORGANISM: Mycobacterium tuberculosis

<400> SEQUENCE: 102

```
Asn Ala Leu Asn Gly Leu Lys Glu Leu
1               5
```

<210> SEQ ID NO 103
<211> LENGTH: 9
<212> TYPE: PRT
<213> ORGANISM: Mycobacterium tuberculosis

<400> SEQUENCE: 103

```
Lys Leu Thr Gly Trp Val Thr Gly Leu
1               5
```

<210> SEQ ID NO 104
<211> LENGTH: 9
<212> TYPE: PRT
<213> ORGANISM: Mycobacterium tuberculosis

<400> SEQUENCE: 104

```
Leu Thr Gly Trp Val Thr Gly Leu Phe
1               5
```

<210> SEQ ID NO 105
<211> LENGTH: 9
<212> TYPE: PRT
<213> ORGANISM: Mycobacterium tuberculosis

<400> SEQUENCE: 105

```
Gly Trp Ser Asn Leu Glu Ser Phe Phe
1               5
```

<210> SEQ ID NO 106
<211> LENGTH: 9
<212> TYPE: PRT
<213> ORGANISM: Mycobacterium tuberculosis

<400> SEQUENCE: 106

```
Asn Leu Glu Ser Phe Phe Ala Gly Val
```

```
1               5

<210> SEQ ID NO 107
<211> LENGTH: 9
<212> TYPE: PRT
<213> ORGANISM: Mycobacterium tuberculosis

<400> SEQUENCE: 107

Ser Phe Phe Ala Gly Val Pro Gly Leu
1               5

<210> SEQ ID NO 108
<211> LENGTH: 9
<212> TYPE: PRT
<213> ORGANISM: Mycobacterium tuberculosis

<400> SEQUENCE: 108

Gly Leu Thr Gly Ala Thr Ser Gly Leu
1               5

<210> SEQ ID NO 109
<211> LENGTH: 9
<212> TYPE: PRT
<213> ORGANISM: Mycobacterium tuberculosis

<400> SEQUENCE: 109

Leu Ser Gln Val Thr Gly Leu Phe Gly
1               5

<210> SEQ ID NO 110
<211> LENGTH: 9
<212> TYPE: PRT
<213> ORGANISM: Mycobacterium tuberculosis

<400> SEQUENCE: 110

Ser Gln Val Thr Gly Leu Phe Gly Ala
1               5

<210> SEQ ID NO 111
<211> LENGTH: 9
<212> TYPE: PRT
<213> ORGANISM: Mycobacterium tuberculosis

<400> SEQUENCE: 111

Leu Ser Ala Ser Ser Gly Leu Ala His
1               5

<210> SEQ ID NO 112
<211> LENGTH: 9
<212> TYPE: PRT
<213> ORGANISM: Mycobacterium tuberculosis

<400> SEQUENCE: 112

Ala Ser Ser Gly Leu Ala His Ala Asp
1               5

<210> SEQ ID NO 113
<211> LENGTH: 9
<212> TYPE: PRT
<213> ORGANISM: Mycobacterium tuberculosis

<400> SEQUENCE: 113

Ser Gly Leu Ala His Ala Asp Ser Leu
1               5
```

```
<210> SEQ ID NO 114
<211> LENGTH: 9
<212> TYPE: PRT
<213> ORGANISM: Mycobacterium tuberculosis

<400> SEQUENCE: 114

Gly Leu Ala His Ala Asp Ser Leu Ala
1               5

<210> SEQ ID NO 115
<211> LENGTH: 9
<212> TYPE: PRT
<213> ORGANISM: Mycobacterium tuberculosis

<400> SEQUENCE: 115

Ser Leu Ala Ser Ser Ala Ser Leu Pro
1               5

<210> SEQ ID NO 116
<211> LENGTH: 9
<212> TYPE: PRT
<213> ORGANISM: Mycobacterium tuberculosis

<400> SEQUENCE: 116

Ala Ser Ser Ala Ser Leu Pro Ala Leu
1               5

<210> SEQ ID NO 117
<211> LENGTH: 9
<212> TYPE: PRT
<213> ORGANISM: Mycobacterium tuberculosis

<400> SEQUENCE: 117

Ser Gly Phe Gly Gly Leu Pro Ser Leu
1               5

<210> SEQ ID NO 118
<211> LENGTH: 9
<212> TYPE: PRT
<213> ORGANISM: Mycobacterium tuberculosis

<400> SEQUENCE: 118

Leu Pro Ser Leu Ala Gln Val His Ala
1               5

<210> SEQ ID NO 119
<211> LENGTH: 9
<212> TYPE: PRT
<213> ORGANISM: Mycobacterium tuberculosis

<400> SEQUENCE: 119

His Ala Ala Ser Thr Arg Gln Ala Leu
1               5

<210> SEQ ID NO 120
<211> LENGTH: 9
<212> TYPE: PRT
<213> ORGANISM: Mycobacterium tuberculosis

<400> SEQUENCE: 120

Ser Thr Arg Gln Ala Leu Arg Pro Arg
1               5

<210> SEQ ID NO 121
```

```
<211> LENGTH: 9
<212> TYPE: PRT
<213> ORGANISM: Mycobacterium tuberculosis

<400> SEQUENCE: 121

Arg Pro Arg Ala Asp Gly Pro Val Gly
1               5

<210> SEQ ID NO 122
<211> LENGTH: 9
<212> TYPE: PRT
<213> ORGANISM: Mycobacterium tuberculosis

<400> SEQUENCE: 122

Glu Gln Val Gly Gly Gln Ser Gln Leu
1               5

<210> SEQ ID NO 123
<211> LENGTH: 9
<212> TYPE: PRT
<213> ORGANISM: Mycobacterium tuberculosis

<400> SEQUENCE: 123

Gly Ala Ser Lys Gly Thr Thr Thr Lys
1               5

<210> SEQ ID NO 124
<211> LENGTH: 9
<212> TYPE: PRT
<213> ORGANISM: Mycobacterium tuberculosis

<400> SEQUENCE: 124

Ala Ser Lys Gly Thr Thr Thr Lys Lys
1               5

<210> SEQ ID NO 125
<211> LENGTH: 9
<212> TYPE: PRT
<213> ORGANISM: Mycobacterium tuberculosis

<400> SEQUENCE: 125

Lys Gly Thr Thr Thr Lys Lys Tyr Ser
1               5

<210> SEQ ID NO 126
<211> LENGTH: 9
<212> TYPE: PRT
<213> ORGANISM: Mycobacterium tuberculosis

<400> SEQUENCE: 126

Thr Glu Asp Ala Glu Arg Ala Pro Val
1               5

<210> SEQ ID NO 127
<211> LENGTH: 20
<212> TYPE: PRT
<213> ORGANISM: Mycobacterium tuberculosis

<400> SEQUENCE: 127

Met Ser Arg Ala Phe Ile Ile Asp Pro Thr Ile Ser Ala Ile Asp Gly
1               5                   10                  15

Leu Tyr Asp Leu
            20
```

-continued

<210> SEQ ID NO 128
<211> LENGTH: 20
<212> TYPE: PRT
<213> ORGANISM: Mycobacterium tuberculosis

<400> SEQUENCE: 128

Ile Asp Gly Leu Tyr Asp Leu Leu Gly Ile Gly Ile Pro Asn Gln Gly
1               5                   10                  15

Gly Ile Leu Tyr
            20

<210> SEQ ID NO 129
<211> LENGTH: 20
<212> TYPE: PRT
<213> ORGANISM: Mycobacterium tuberculosis

<400> SEQUENCE: 129

Asn Gln Gly Gly Ile Leu Tyr Ser Ser Leu Glu Tyr Phe Glu Lys Ala
1               5                   10                  15

Leu Glu Glu Leu
            20

<210> SEQ ID NO 130
<211> LENGTH: 20
<212> TYPE: PRT
<213> ORGANISM: Mycobacterium tuberculosis

<400> SEQUENCE: 130

Glu Lys Ala Leu Glu Glu Leu Ala Ala Ala Phe Pro Gly Asp Gly Trp
1               5                   10                  15

Leu Gly Ser Ala
            20

<210> SEQ ID NO 131
<211> LENGTH: 20
<212> TYPE: PRT
<213> ORGANISM: Mycobacterium tuberculosis

<400> SEQUENCE: 131

Asp Gly Trp Leu Gly Ser Ala Ala Asp Lys Tyr Ala Gly Lys Asn Arg
1               5                   10                  15

Asn His Val Asn
            20

<210> SEQ ID NO 132
<211> LENGTH: 20
<212> TYPE: PRT
<213> ORGANISM: Mycobacterium tuberculosis

<400> SEQUENCE: 132

Lys Asn Arg Asn His Val Asn Phe Phe Gln Glu Leu Ala Asp Leu Asp
1               5                   10                  15

Arg Gln Leu Ile
            20

<210> SEQ ID NO 133
<211> LENGTH: 20
<212> TYPE: PRT
<213> ORGANISM: Mycobacterium tuberculosis

<400> SEQUENCE: 133

Asp Leu Asp Arg Gln Leu Ile Ser Leu Ile His Asp Gln Ala Asn Ala
1               5                   10                  15

Val Gln Thr Thr
            20

<210> SEQ ID NO 134
<211> LENGTH: 20
<212> TYPE: PRT
<213> ORGANISM: Mycobacterium tuberculosis

<400> SEQUENCE: 134

Ala Asn Ala Val Gln Thr Thr Arg Asp Ile Leu Glu Gly Ala Lys Lys
1               5                   10                  15

Gly Leu Glu Phe
            20

<210> SEQ ID NO 135
<211> LENGTH: 20
<212> TYPE: PRT
<213> ORGANISM: Mycobacterium tuberculosis

<400> SEQUENCE: 135

Ala Lys Lys Gly Leu Glu Phe Val Arg Pro Val Ala Val Asp Leu Thr
1               5                   10                  15

Tyr Ile Pro Val
            20

<210> SEQ ID NO 136
<211> LENGTH: 27
<212> TYPE: PRT
<213> ORGANISM: Mycobacterium tuberculosis

<400> SEQUENCE: 136

Phe Val Arg Pro Val Ala Val Asp Leu Thr Tyr Ile Pro Val Val Gly
1               5                   10                  15

His Ala Leu Ser Ala Ala Phe Gln Ala Pro Phe
            20                  25

<210> SEQ ID NO 137
<211> LENGTH: 20
<212> TYPE: PRT
<213> ORGANISM: Mycobacterium tuberculosis

<400> SEQUENCE: 137

Ala Ala Phe Gln Ala Pro Phe Cys Ala Gly Ala Met Ala Val Val Gly
1               5                   10                  15

Gly Ala Leu Ala
            20

<210> SEQ ID NO 138
<211> LENGTH: 20
<212> TYPE: PRT
<213> ORGANISM: Mycobacterium tuberculosis

<400> SEQUENCE: 138

Val Val Gly Gly Ala Leu Ala Tyr Leu Val Val Lys Thr Leu Ile Asn
1               5                   10                  15

Ala Thr Gln Leu
            20

<210> SEQ ID NO 139
<211> LENGTH: 20
<212> TYPE: PRT
<213> ORGANISM: Mycobacterium tuberculosis

<400> SEQUENCE: 139

Leu Ile Asn Ala Thr Gln Leu Leu Lys Leu Leu Ala Lys Leu Ala Glu
1               5                   10                  15

Leu Val Ala Ala
            20

<210> SEQ ID NO 140
<211> LENGTH: 20
<212> TYPE: PRT
<213> ORGANISM: Mycobacterium tuberculosis

<400> SEQUENCE: 140

Leu Ala Glu Leu Val Ala Ala Ala Ile Ala Asp Ile Ile Ser Asp Val
1               5                   10                  15

Ala Asp Ile Ile
            20

<210> SEQ ID NO 141
<211> LENGTH: 20
<212> TYPE: PRT
<213> ORGANISM: Mycobacterium tuberculosis

<400> SEQUENCE: 141

Ser Asp Val Ala Asp Ile Ile Lys Gly Thr Leu Gly Glu Val Trp Glu
1               5                   10                  15

Phe Ile Thr Asn
            20

<210> SEQ ID NO 142
<211> LENGTH: 20
<212> TYPE: PRT
<213> ORGANISM: Mycobacterium tuberculosis

<400> SEQUENCE: 142

Val Trp Glu Phe Ile Thr Asn Ala Leu Asn Gly Leu Lys Glu Leu Trp
1               5                   10                  15

Asp Lys Leu Thr
            20

<210> SEQ ID NO 143
<211> LENGTH: 20
<212> TYPE: PRT
<213> ORGANISM: Mycobacterium tuberculosis

<400> SEQUENCE: 143

Glu Leu Trp Asp Lys Leu Thr Gly Trp Val Thr Gly Leu Phe Ser Arg
1               5                   10                  15

Gly Trp Ser Asn
            20

<210> SEQ ID NO 144
<211> LENGTH: 20
<212> TYPE: PRT
<213> ORGANISM: Mycobacterium tuberculosis

<400> SEQUENCE: 144

Phe Ser Arg Gly Trp Ser Asn Leu Glu Ser Phe Phe Ala Gly Val Pro
1               5                   10                  15

Gly Leu Thr Gly
            20

<210> SEQ ID NO 145
<211> LENGTH: 20
<212> TYPE: PRT
<213> ORGANISM: Mycobacterium tuberculosis

<400> SEQUENCE: 145

Gly Val Pro Gly Leu Thr Gly Ala Thr Ser Gly Leu Ser Gln Val Thr
1               5                   10                  15

Gly Leu Phe Gly
            20

<210> SEQ ID NO 146
<211> LENGTH: 20
<212> TYPE: PRT
<213> ORGANISM: Mycobacterium tuberculosis

<400> SEQUENCE: 146

Gln Val Thr Gly Leu Phe Gly Ala Ala Gly Leu Ser Ala Ser Ser Gly
1               5                   10                  15

Leu Ala His Ala
            20

<210> SEQ ID NO 147
<211> LENGTH: 20
<212> TYPE: PRT
<213> ORGANISM: Mycobacterium tuberculosis

<400> SEQUENCE: 147

Ser Ser Gly Leu Ala His Ala Asp Ser Leu Ala Ser Ser Ala Ser Leu
1               5                   10                  15

Pro Ala Leu Ala
            20

<210> SEQ ID NO 148
<211> LENGTH: 20
<212> TYPE: PRT
<213> ORGANISM: Mycobacterium tuberculosis

<400> SEQUENCE: 148

Ala Ser Leu Pro Ala Leu Ala Gly Ile Gly Gly Ser Gly Phe Gly
1               5                   10                  15

Gly Leu Pro Ser
            20

<210> SEQ ID NO 149
<211> LENGTH: 20
<212> TYPE: PRT
<213> ORGANISM: Mycobacterium tuberculosis

<400> SEQUENCE: 149

Gly Phe Gly Gly Leu Pro Ser Leu Ala Gln Val His Ala Ala Ser Thr
1               5                   10                  15

Arg Gln Ala Leu
            20

<210> SEQ ID NO 150
<211> LENGTH: 20
<212> TYPE: PRT
<213> ORGANISM: Mycobacterium tuberculosis

<400> SEQUENCE: 150

Ala Ser Thr Arg Gln Ala Leu Arg Pro Arg Ala Asp Gly Pro Val Gly

```
1               5                   10                  15

Ala Ala Ala Glu
            20

<210> SEQ ID NO 151
<211> LENGTH: 20
<212> TYPE: PRT
<213> ORGANISM: Mycobacterium tuberculosis

<400> SEQUENCE: 151

Pro Val Gly Ala Ala Glu Gln Val Gly Gly Gln Ser Gln Leu Val
1               5                   10                  15

Ser Ala Gln Gly
            20

<210> SEQ ID NO 152
<211> LENGTH: 19
<212> TYPE: PRT
<213> ORGANISM: Mycobacterium tuberculosis

<400> SEQUENCE: 152

Gln Leu Val Ser Ala Gln Gly Ser Gln Gly Met Gly Gly Pro Val Gly
1               5                   10                  15

Met Gly Gly

<210> SEQ ID NO 153
<211> LENGTH: 20
<212> TYPE: PRT
<213> ORGANISM: Mycobacterium tuberculosis

<400> SEQUENCE: 153

Pro Val Gly Met Gly Gly Met His Pro Ser Ser Gly Ala Ser Lys Gly
1               5                   10                  15

Thr Thr Thr Lys
            20

<210> SEQ ID NO 154
<211> LENGTH: 20
<212> TYPE: PRT
<213> ORGANISM: Mycobacterium tuberculosis

<400> SEQUENCE: 154

Ser Lys Gly Thr Thr Thr Lys Lys Tyr Ser Glu Gly Ala Ala Ala Gly
1               5                   10                  15

Thr Glu Asp Ala
            20

<210> SEQ ID NO 155
<211> LENGTH: 20
<212> TYPE: PRT
<213> ORGANISM: Mycobacterium tuberculosis

<400> SEQUENCE: 155

Ala Ala Gly Thr Glu Asp Ala Glu Arg Ala Pro Val Glu Ala Asp Ala
1               5                   10                  15

Gly Gly Gly Gln
            20

<210> SEQ ID NO 156
<211> LENGTH: 20
<212> TYPE: PRT
<213> ORGANISM: Mycobacterium tuberculosis
```

<400> SEQUENCE: 156

Arg Ala Pro Val Glu Ala Asp Ala Gly Gly Gln Lys Val Leu Val
1               5                   10                  15

Arg Asn Val Val
            20

<210> SEQ ID NO 157
<211> LENGTH: 1053
<212> TYPE: PRT
<213> ORGANISM: Mycobacterium tuberculosis

<400> SEQUENCE: 157

Met Asn Phe Ser Val Leu Pro Pro Glu Ile Asn Ser Ala Leu Ile Phe
1               5                   10                  15

Ala Gly Ala Gly Pro Glu Pro Met Ala Ala Ala Thr Ala Trp Asp
                20                  25                  30

Gly Leu Ala Met Glu Leu Ala Ser Ala Ala Ser Phe Gly Ser Val
            35                  40                  45

Thr Ser Gly Leu Val Gly Gly Ala Trp Gln Gly Ala Ser Ser Ala
50                  55                  60

Met Ala Ala Ala Ala Pro Tyr Ala Ala Trp Leu Ala Ala Ala
65                  70                  75                  80

Val Gln Ala Glu Gln Thr Ala Ala Gln Ala Ala Met Ile Ala Glu
                85                  90                  95

Phe Glu Ala Val Lys Thr Ala Val Val Gln Pro Met Leu Val Ala Ala
                100                 105                 110

Asn Arg Ala Asp Leu Val Ser Leu Val Met Ser Asn Leu Phe Gly Gln
            115                 120                 125

Asn Ala Pro Ala Ile Ala Ala Ile Glu Ala Thr Tyr Glu Gln Met Trp
    130                 135                 140

Ala Ala Asp Val Ser Ala Met Ser Ala Tyr His Ala Gly Ala Ser Ala
145                 150                 155                 160

Ile Ala Ser Ala Leu Ser Pro Phe Ser Lys Pro Leu Gln Asn Leu Ala
                165                 170                 175

Gly Leu Pro Ala Trp Leu Ala Ser Gly Ala Pro Ala Ala Ala Met Thr
            180                 185                 190

Ala Ala Ala Gly Ile Pro Ala Leu Ala Gly Gly Pro Thr Ala Ile Asn
        195                 200                 205

Leu Gly Ile Ala Asn Val Gly Gly Asn Val Gly Asn Ala Asn Asn
    210                 215                 220

Gly Leu Ala Asn Ile Gly Asn Ala Asn Leu Gly Asn Tyr Asn Phe Gly
225                 230                 235                 240

Ser Gly Asn Phe Gly Asn Ser Asn Ile Gly Ser Ala Ser Leu Gly Asn
                245                 250                 255

Asn Asn Ile Gly Phe Gly Asn Leu Gly Ser Asn Asn Val Gly Val Gly
            260                 265                 270

Asn Leu Gly Asn Leu Asn Thr Gly Phe Ala Asn Thr Gly Leu Gly Asn
        275                 280                 285

Phe Gly Phe Gly Asn Thr Gly Asn Asn Ile Gly Ile Gly Leu Thr
    290                 295                 300

Gly Asn Asn Gln Ile Gly Ile Gly Gly Leu Asn Ser Gly Thr Gly Asn
305                 310                 315                 320

Phe Gly Leu Phe Asn Ser Gly Ser Gly Asn Val Gly Phe Phe Asn Ser
                325                 330                 335

```
Gly Asn Gly Asn Phe Gly Ile Gly Asn Ser Gly Asn Phe Asn Thr Gly
                340                 345                 350

Gly Trp Asn Ser Gly His Gly Asn Thr Gly Phe Phe Asn Ala Gly Ser
                355                 360                 365

Phe Asn Thr Gly Met Leu Asp Val Gly Asn Ala Asn Thr Gly Ser Leu
                370                 375                 380

Asn Thr Gly Ser Tyr Asn Met Gly Asp Phe Asn Pro Gly Ser Ser Asn
385                 390                 395                 400

Thr Gly Thr Phe Asn Thr Gly Asn Ala Asn Thr Gly Phe Leu Asn Ala
                405                 410                 415

Gly Asn Ile Asn Thr Gly Val Phe Asn Ile Gly His Met Asn Asn Gly
                420                 425                 430

Leu Phe Asn Thr Gly Asp Met Asn Asn Gly Val Phe Tyr Arg Gly Val
                435                 440                 445

Gly Gln Gly Ser Leu Gln Phe Ser Ile Thr Thr Pro Asp Leu Thr Leu
                450                 455                 460

Pro Pro Leu Gln Ile Pro Gly Ile Ser Val Pro Ala Phe Ser Leu Pro
465                 470                 475                 480

Ala Ile Thr Leu Pro Ser Leu Asn Ile Pro Ala Ala Thr Thr Pro Ala
                485                 490                 495

Asn Ile Thr Val Gly Ala Phe Ser Leu Pro Gly Leu Thr Leu Pro Ser
                500                 505                 510

Leu Asn Ile Pro Ala Ala Thr Thr Pro Ala Asn Ile Thr Val Gly Ala
                515                 520                 525

Phe Ser Leu Pro Gly Leu Thr Leu Pro Ser Leu Asn Ile Pro Ala Ala
                530                 535                 540

Thr Thr Pro Ala Asn Ile Thr Val Gly Ala Phe Ser Leu Pro Gly Leu
545                 550                 555                 560

Thr Leu Pro Ser Leu Asn Ile Pro Ala Ala Thr Thr Pro Ala Asn Ile
                565                 570                 575

Thr Val Gly Ala Phe Ser Leu Pro Gly Leu Thr Leu Pro Ser Leu Asn
                580                 585                 590

Ile Pro Ala Ala Thr Thr Pro Ala Asn Ile Thr Val Gly Ala Phe Ser
                595                 600                 605

Leu Pro Gly Leu Thr Leu Pro Ser Leu Asn Ile Pro Ala Ala Thr Thr
                610                 615                 620

Pro Ala Asn Ile Thr Val Ser Gly Phe Gln Leu Pro Pro Leu Ser Ile
625                 630                 635                 640

Pro Ser Val Ala Ile Pro Pro Val Thr Val Pro Pro Ile Thr Val Gly
                645                 650                 655

Ala Phe Asn Leu Pro Pro Leu Gln Ile Pro Glu Val Thr Ile Pro Gln
                660                 665                 670

Leu Thr Ile Pro Ala Gly Ile Thr Ile Gly Gly Phe Ser Leu Pro Ala
                675                 680                 685

Ile His Thr Gln Pro Ile Thr Val Gly Gln Ile Gly Val Gly Gln Phe
                690                 695                 700

Gly Leu Pro Ser Ile Gly Trp Asp Val Phe Leu Ser Thr Pro Arg Ile
705                 710                 715                 720

Thr Val Pro Ala Phe Gly Ile Pro Phe Thr Leu Gln Phe Gln Thr Asn
                725                 730                 735

Val Pro Ala Leu Gln Pro Pro Gly Gly Gly Leu Ser Phe Thr Asn
                740                 745                 750
```

-continued

```
Gly Ala Leu Ile Phe Gly Glu Phe Asp Leu Pro Gln Leu Val Val His
            755                 760                 765

Pro Tyr Thr Leu Thr Gly Pro Ile Val Ile Gly Ser Phe Phe Leu Pro
    770                 775                 780

Ala Phe Asn Ile Pro Gly Ile Asp Val Pro Ala Ile Asn Val Asp Gly
785                 790                 795                 800

Phe Thr Leu Pro Gln Ile Thr Thr Pro Ala Ile Thr Pro Glu Phe
                805                 810                 815

Ala Ile Pro Pro Ile Gly Val Gly Phe Thr Leu Pro Gln Ile Thr
                820                 825                 830

Thr Gln Glu Ile Ile Thr Pro Glu Leu Thr Ile Asn Ser Ile Gly Val
            835                 840                 845

Gly Gly Phe Thr Leu Pro Gln Ile Thr Thr Pro Pro Ile Thr Thr Pro
        850                 855                 860

Pro Leu Thr Ile Asp Pro Ile Asn Leu Thr Gly Phe Thr Leu Pro Gln
865                 870                 875                 880

Ile Thr Thr Pro Pro Ile Thr Thr Pro Pro Leu Thr Ile Asp Pro Ile
                885                 890                 895

Asn Leu Thr Gly Phe Thr Leu Pro Gln Ile Thr Thr Pro Pro Ile Thr
            900                 905                 910

Thr Pro Pro Leu Thr Ile Glu Pro Ile Gly Val Gly Phe Thr Thr
        915                 920                 925

Pro Pro Leu Thr Val Pro Gly Ile His Leu Pro Ser Thr Thr Ile Gly
    930                 935                 940

Ala Phe Ala Ile Pro Gly Gly Pro Gly Tyr Phe Asn Ser Ser Thr Ala
945                 950                 955                 960

Pro Ser Ser Gly Phe Phe Asn Ser Gly Ala Gly Gly Asn Ser Gly Phe
                965                 970                 975

Gly Asn Asn Gly Ser Gly Leu Ser Gly Trp Phe Asn Thr Asn Pro Ala
            980                 985                 990

Gly Leu Leu Gly Gly Ser Gly Tyr  Gln Asn Phe Gly Gly  Leu Ser Ser
        995                 1000                1005

Gly Phe  Ser Asn Leu Gly Ser  Gly Val Ser Gly Phe  Ala Asn Arg
    1010                1015                1020

Gly Ile  Leu Pro Phe Ser Val  Ala Ser Val Val Ser  Gly Phe Ala
    1025                1030                1035

Asn Ile  Gly Thr Asn Leu Ala  Gly Phe Phe Gln Gly  Thr Thr Ser
    1040                1045                1050
```

<210> SEQ ID NO 158
<211> LENGTH: 450
<212> TYPE: PRT
<213> ORGANISM: Mycobacterium tuberculosis

<400> SEQUENCE: 158

```
Met Ser Glu Leu Ser Val Ala Thr Gly Ala Val Ser Thr Ala Ser Ser
1               5                   10                  15

Ser Ile Pro Met Pro Ala Gly Val Asn Pro Ala Asp Leu Ala Ala Glu
            20                  25                  30

Leu Ala Ala Val Val Thr Glu Ser Val Asp Glu Asp Tyr Leu Leu Tyr
        35                  40                  45

Glu Cys Asp Gly Gln Trp Val Leu Ala Ala Gly Val Gln Ala Met Val
    50                  55                  60

Glu Leu Asp Ser Asp Glu Leu Arg Val Ile Arg Asp Gly Val Thr Arg
65                  70                  75                  80
```

```
Arg Gln Gln Trp Ser Gly Arg Pro Gly Ala Ala Leu Gly Glu Ala Val
                85                  90                  95

Asp Arg Leu Leu Leu Glu Thr Asp Gln Ala Phe Gly Trp Val Ala Phe
            100                 105                 110

Glu Phe Gly Val His Arg Tyr Gly Leu Gln Gln Arg Leu Ala Pro His
        115                 120                 125

Thr Pro Leu Ala Arg Val Phe Ser Pro Arg Thr Arg Ile Met Val Ser
    130                 135                 140

Glu Lys Glu Ile Arg Leu Phe Asp Ala Gly Ile Arg His Arg Glu Ala
145                 150                 155                 160

Ile Asp Arg Leu Leu Ala Thr Gly Val Arg Glu Val Pro Gln Ser Arg
                165                 170                 175

Ser Val Asp Val Ser Asp Asp Pro Ser Gly Phe Arg Arg Arg Val Ala
            180                 185                 190

Val Ala Val Asp Glu Ile Ala Ala Gly Arg Tyr His Lys Val Ile Leu
        195                 200                 205

Ser Arg Cys Val Glu Val Pro Phe Ala Ile Asp Phe Pro Leu Thr Tyr
    210                 215                 220

Arg Leu Gly Arg Arg His Asn Thr Pro Val Arg Ser Phe Leu Leu Gln
225                 230                 235                 240

Leu Gly Gly Ile Arg Ala Leu Gly Tyr Ser Pro Glu Leu Val Thr Ala
                245                 250                 255

Val Arg Ala Asp Gly Val Val Ile Thr Glu Pro Leu Ala Gly Thr Arg
            260                 265                 270

Ala Leu Gly Arg Gly Pro Ala Ile Asp Arg Leu Ala Arg Asp Asp Leu
        275                 280                 285

Glu Ser Asn Ser Lys Glu Ile Val Glu His Ala Ile Ser Val Arg Ser
    290                 295                 300

Ser Leu Glu Glu Ile Thr Asp Ile Ala Glu Pro Gly Ser Ala Ala Val
305                 310                 315                 320

Ile Asp Phe Met Thr Val Arg Glu Arg Gly Ser Val Gln His Leu Gly
                325                 330                 335

Ser Thr Ile Arg Ala Arg Leu Asp Pro Ser Ser Asp Arg Met Ala Ala
            340                 345                 350

Leu Glu Ala Leu Phe Pro Ala Val Thr Ala Ser Gly Ile Pro Lys Ala
        355                 360                 365

Ala Gly Val Glu Ala Ile Phe Arg Leu Asp Glu Cys Pro Arg Gly Leu
    370                 375                 380

Tyr Ser Gly Ala Val Val Met Leu Ser Ala Asp Gly Gly Leu Asp Ala
385                 390                 395                 400

Ala Leu Thr Leu Arg Ala Ala Tyr Gln Val Gly Gly Arg Thr Trp Leu
                405                 410                 415

Arg Ala Gly Ala Gly Ile Ile Glu Glu Ser Glu Pro Glu Arg Glu Phe
            420                 425                 430

Glu Glu Thr Cys Glu Lys Leu Ser Thr Leu Thr Pro Tyr Leu Val Ala
        435                 440                 445

Arg Gln
    450
```

<210> SEQ ID NO 159
<211> LENGTH: 324
<212> TYPE: PRT
<213> ORGANISM: Mycobacterium tuberculosis

<400> SEQUENCE: 159

```
Met Ser Asp Gln Val Pro Lys Pro His Arg His His Ile Trp Arg Ile
1               5                   10                  15

Thr Arg Arg Thr Leu Ser Lys Ser Trp Asp Asp Ser Ile Phe Ser Glu
            20                  25                  30

Ser Ala Gln Ala Ala Phe Trp Ser Ala Leu Ser Leu Pro Pro Leu Leu
        35                  40                  45

Leu Gly Met Leu Gly Ser Leu Ala Tyr Val Ala Pro Leu Phe Gly Pro
    50                  55                  60

Asp Thr Leu Pro Ala Ile Glu Lys Ser Ala Leu Ser Thr Ala His Ser
65                  70                  75                  80

Phe Phe Ser Pro Ser Val Val Asn Glu Ile Ile Glu Pro Thr Ile Gly
                85                  90                  95

Asp Ile Thr Asn Asn Ala Arg Gly Glu Val Ala Ser Leu Gly Phe Leu
            100                 105                 110

Ile Ser Leu Trp Ala Gly Ser Ser Ala Ile Ser Ala Phe Val Asp Ala
        115                 120                 125

Val Val Glu Ala His Asp Gln Thr Pro Leu Arg His Pro Val Arg Gln
    130                 135                 140

Arg Phe Phe Ala Leu Phe Leu Tyr Val Val Met Leu Val Phe Leu Val
145                 150                 155                 160

Ala Thr Ala Pro Val Met Val Val Gly Pro Arg Lys Val Ser Glu His
                165                 170                 175

Ile Pro Glu Ser Leu Ala Asn Leu Leu Arg Tyr Gly Tyr Tyr Pro Ala
            180                 185                 190

Leu Ile Leu Gly Leu Thr Val Gly Val Ile Leu Leu Tyr Arg Val Ala
        195                 200                 205

Leu Pro Val Pro Leu Pro Thr His Arg Leu Val Leu Gly Ala Val Leu
    210                 215                 220

Ala Ile Ala Val Phe Leu Ile Ala Thr Leu Gly Leu Arg Val Tyr Leu
225                 230                 235                 240

Ala Trp Ile Thr Arg Thr Gly Tyr Thr Tyr Gly Ala Leu Ala Thr Pro
                245                 250                 255

Ile Ala Phe Leu Leu Phe Ala Phe Phe Gly Gly Phe Ala Ile Met Leu
            260                 265                 270

Gly Ala Glu Leu Asn Ala Ala Val Gln Glu Glu Trp Pro Ala Pro Ala
        275                 280                 285

Thr His Ala His Arg Leu Gly Asn Trp Leu Lys Ala Arg Ile Gly Val
    290                 295                 300

Gly Thr Thr Thr Tyr Ser Ser Thr Ala Gln His Ser Ala Val Ala Ala
305                 310                 315                 320

Glu Pro Pro Ser
```

<210> SEQ ID NO 160
<211> LENGTH: 1176
<212> TYPE: DNA
<213> ORGANISM: Artificial Sequence
<220> FEATURE:
<223> OTHER INFORMATION: E.coli codon optimised H37Rv R3616c polynucleotide

<400> SEQUENCE: 160

```
atgagccgtg cctttattat tgatccgacc attagcgcaa ttgatggtct gtatgatctg     60
ctgggtattg gtattccgaa tcagggtggt attctgtata gcagcctgga atattttgaa    120
```

```
aaagccctgg aagaactggc agcagcattt ccgggtgatg gttggctggg tagcgcagca   180
gataaatatg ccggtaaaaa tcgcaatcat gtgaattttt ttcaggaact ggccgatctg   240
gatcgtcagc tgattagcct gattcatgac caggcaaatg cagttcagac cacccgtgat   300
attctggaag gtgccaaaaa aggtctggaa tttgttcgtc cggtggcagt tgatctgacc   360
tatattccgg ttgttggtca tgcactgagc gcagcatttc aggcaccgtt tgtgccggt    420 gcaatggcag ttgtgggtgg tgctctggca tatctggttg tgaaaaccct gattaatgca   480
acccagctgc tgaaactgct ggcaaaactg cagaactgg ttgcagcagc aattgcagat    540
attatttccg atgtgccga tattattaaa ggcaccctgg gcgaagtttg gaatttatt    600 accaatgccc tgaatggtct gaaagaactg tgggataaac tgaccggttg ggttaccggt   660
ctgtttagcc gtggtggag caatctgaa tcttttttg ccggtgttcc gggtctgacc     720
ggtgcaacca gcggtctgag ccaggtgaca ggtctgtttg gagcagctgg tctgagtgct   780
agtagcggtc tggctcatgc agatagcctg gcaagcagcg catctctgcc tgcactggca   840
ggcattggtg gtggatccgg ttttggtggt ctgccgagcc tggcacaggt tcatgcagca   900
agcacccgtc aggcactgcg tccgcgtgca gatggaccgg ttggagcagc agcagaacag   960
gttggtggtc agagccagct ggttagcgca cagggtagcc agggtatggg tggtccggtg   1020
ggcatgggtg gtatgcatcc gagcagcggt gcaagcaaag gcaccaccac caaaaaatat   1080
agcgaaggag cagctgctgg caccgaagat gcagaacgtg caccggttga agcagatgcc   1140
ggtggaggtc agaaagttct ggttcgcaat gtggtg                             1176
```

<210> SEQ ID NO 161
<211> LENGTH: 344
<212> TYPE: PRT
<213> ORGANISM: Artificial Sequence
<220> FEATURE:
<223> OTHER INFORMATION: H37Rv Rv3616c with deleted residues 136-183

<400> SEQUENCE: 161

```
Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
            20                  25                  30

Tyr Ser Ser Leu Glu Tyr Phe Glu Lys Ala Leu Glu Glu Leu Ala Ala
        35                  40                  45

Ala Phe Pro Gly Asp Gly Trp Leu Gly Ser Ala Ala Asp Lys Tyr Ala
    50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
        115                 120                 125

Leu Ser Ala Ala Phe Gln Ala Asp Val Ala Asp Ile Ile Lys Gly Thr
    130                 135                 140

Leu Gly Glu Val Trp Glu Phe Ile Thr Asn Ala Leu Asn Gly Leu Lys
145                 150                 155                 160

Glu Leu Trp Asp Lys Leu Thr Gly Trp Val Thr Gly Leu Phe Ser Arg
                165                 170                 175
```

```
Gly Trp Ser Asn Leu Glu Ser Phe Phe Ala Gly Val Pro Gly Leu Thr
                180                 185                 190

Gly Ala Thr Ser Gly Leu Ser Gln Val Thr Gly Leu Phe Gly Ala Ala
            195                 200                 205

Gly Leu Ser Ala Ser Ser Gly Leu Ala His Ala Asp Ser Leu Ala Ser
        210                 215                 220

Ser Ala Ser Leu Pro Ala Leu Ala Gly Ile Gly Gly Ser Gly Phe
225                 230                 235                 240

Gly Gly Leu Pro Ser Leu Ala Gln Val His Ala Ala Ser Thr Arg Gln
                245                 250                 255

Ala Leu Arg Pro Arg Ala Asp Gly Pro Val Gly Ala Ala Glu Gln
            260                 265                 270

Val Gly Gly Gln Ser Gln Leu Val Ser Ala Gln Gly Ser Gln Gly Met
        275                 280                 285

Gly Gly Pro Val Gly Met Gly Gly Met His Pro Ser Ser Gly Ala Ser
        290                 295                 300

Lys Gly Thr Thr Thr Lys Lys Tyr Ser Glu Gly Ala Ala Ala Gly Thr
305                 310                 315                 320

Glu Asp Ala Glu Arg Ala Pro Val Glu Ala Asp Ala Gly Gly Gln
                325                 330                 335

Lys Val Leu Val Arg Asn Val Val
            340

<210> SEQ ID NO 162
<211> LENGTH: 381
<212> TYPE: PRT
<213> ORGANISM: Artificial Sequence
<220> FEATURE:
<223> OTHER INFORMATION: H37Rv Rv3616c with deleted residues 150-160

<400> SEQUENCE: 162

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
                20                  25                  30

Tyr Ser Ser

Leu Asn Gly Leu Lys Glu Leu Trp Asp Lys Leu Thr Gly Trp Val Thr
            195                 200                 205

Gly Leu Phe Ser Arg Gly Trp Ser Asn Leu Glu Ser Phe Phe Ala Gly
        210                 215                 220

Val Pro Gly Leu Thr Gly Ala Thr Ser Gly Leu Ser Gln Val Thr Gly
225                 230                 235                 240

Leu Phe Gly Ala Ala Gly Leu Ser Ala Ser Gly Leu Ala His Ala
                245                 250                 255

Asp Ser Leu Ala Ser Ser Ala Ser Leu Pro Ala Leu Ala Gly Ile Gly
                260                 265                 270

Gly Gly Ser Gly Phe Gly Gly Leu Pro Ser Leu Ala Gln Val His Ala
            275                 280                 285

Ala Ser Thr Arg Gln Ala Leu Arg Pro Arg Ala Asp Gly Pro Val Gly
        290                 295                 300

Ala Ala Ala Glu Gln Val Gly Gly Gln Ser Gln Leu Val Ser Ala Gln
305                 310                 315                 320

Gly Ser Gln Gly Met Gly Gly Pro Val Gly Met Gly Gly Met His Pro
                325                 330                 335

Ser Ser Gly Ala Ser Lys Gly Thr Thr Thr Lys Lys Tyr Ser Glu Gly
            340                 345                 350

Ala Ala Ala Gly Thr Glu Asp Ala Glu Arg Ala Pro Val Glu Ala Asp
        355                 360                 365

Ala Gly Gly Gly Gln Lys Val Leu Val Arg Asn Val Val
                370                 375                 380

<210> SEQ ID NO 163
<211> LENGTH: 373
<212> TYPE: PRT
<213> ORGANISM: Artificial Sequence
<220> FEATURE:
<223> OTHER INFORMATION: H37Rv Rv3616c with deleted residues 136-154

<400> SEQUENCE: 163

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
            20                  25                  30

Tyr Ser Ser Leu Glu Tyr Phe Glu Lys Ala Leu Glu Glu Leu Ala Ala
        35                  40                  45

Ala Phe Pro Gly Asp Gly Trp Leu Gly Ser Ala Ala Asp Lys Tyr Ala
    50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
        115                 120                 125

Leu Ser Ala Ala Phe Gln Ala Lys Thr Leu Ile Asn Ala Thr Gln Leu
    130                 135                 140

Leu Lys Leu Leu Ala Lys Leu Ala Glu Leu Val Ala Ala Ala Ile Ala
145                 150                 155                 160

Asp Ile Ile Ser Asp Val Ala Asp Ile Ile Lys Gly Thr Leu Gly Glu
                165                 170                 175

-continued

```
Val Trp Glu Phe Ile Thr Asn Ala Leu Asn Gly Leu Lys Glu Leu Trp
            180                 185                 190

Asp Lys Leu Thr Gly Trp Val Thr Gly Leu Phe Ser Arg Gly Trp Ser
        195                 200                 205

Asn Leu Glu Ser Phe Phe Ala Gly Val Pro Gly Leu Thr Gly Ala Thr
    210                 215                 220

Ser Gly Leu Ser Gln Val Thr Gly Leu Phe Gly Ala Ala Gly Leu Ser
225                 230                 235                 240

Ala Ser Ser Gly Leu Ala His Ala Asp Ser Leu Ala Ser Ser Ala Ser
                245                 250                 255

Leu Pro Ala Leu Ala Gly Ile Gly Gly Ser Gly Phe Gly Gly Leu
            260                 265                 270

Pro Ser Leu Ala Gln Val His Ala Ala Ser Thr Arg Gln Ala Leu Arg
        275                 280                 285

Pro Arg Ala Asp Gly Pro Val Gly Ala Ala Ala Glu Gln Val Gly Gly
    290                 295                 300

Gln Ser Gln Leu Val Ser Ala Gln Gly Ser Gln Gly Met Gly Gly Pro
305                 310                 315                 320

Val Gly Met Gly Gly Met His Pro Ser Ser Gly Ala Ser Lys Gly Thr
                325                 330                 335

Thr Thr Lys Lys Tyr Ser Glu Gly Ala Ala Gly Thr Glu Asp Ala
            340                 345                 350

Glu Arg Ala Pro Val Glu Ala Asp Ala Gly Gly Gln Lys Val Leu
        355                 360                 365

Val Arg Asn Val Val
    370

<210> SEQ ID NO 164
<211> LENGTH: 375
<212> TYPE: PRT
<213> ORGANISM: Artificial Sequence
<220> FEATURE:
<223> OTHER INFORMATION: H37Rv Rv3616c with deleted residues 166-182

<400> SEQUENCE: 164

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
            20                  25                  30

Tyr Ser Ser Leu Glu Tyr Phe Glu Lys Ala Leu Glu Glu Leu Ala Ala
        35                  40                  45

Ala Phe Pro Gly Asp Gly Trp Leu Gly Ser Ala Ala Asp Lys Tyr Ala
    50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
            85                  90                  95

Thr Thr Arg Asp Ile Leu Glu Gly Ala Lys Lys Gly Leu Glu Phe Val
        100                 105                 110

Arg Pro Val Ala Val Asp Leu Thr Tyr Ile Pro Val Val Gly His Ala
    115                 120                 125

Leu Ser Ala Ala Phe Gln Ala Pro Phe Cys Ala Gly Ala Met Ala Val
    130                 135                 140

Val Gly Gly Ala Leu Ala Tyr Leu Val Val Lys Thr Leu Ile Asn Ala
145                 150                 155                 160
```

-continued

```
Thr Gln Leu Leu Lys Ser Asp Val Ala Asp Ile Ile Lys Gly Thr Leu
                165                 170                 175

Gly Glu Val Trp Glu Phe Ile Thr Asn Ala Leu Asn Gly Leu Lys Glu
            180                 185                 190

Leu Trp Asp Lys Leu Thr Gly Trp Val Thr Gly Leu Phe Ser Arg Gly
        195                 200                 205

Trp Ser Asn Leu Glu Ser Phe Phe Ala Gly Val Pro Gly Leu Thr Gly
    210                 215                 220

Ala Thr Ser Gly Leu Ser Gln Val Thr Gly Leu Phe Gly Ala Ala Gly
225                 230                 235                 240

Leu Ser Ala Ser Ser Gly Leu Ala His Ala Asp Ser Leu Ala Ser Ser
                245                 250                 255

Ala Ser Leu Pro Ala Leu Ala Gly Ile Gly Gly Gly Ser Gly Phe Gly
            260                 265                 270

Gly Leu Pro Ser Leu Ala Gln Val His Ala Ala Ser Thr Arg Gln Ala
        275                 280                 285

Leu Arg Pro Arg Ala Asp Gly Pro Val Gly Ala Ala Glu Gln Val
    290                 295                 300

Gly Gly Gln Ser Gln Leu Val Ser Ala Gln Gly Ser Gln Gly Met Gly
305                 310                 315                 320

Gly Pro Val Gly Met Gly Gly Met His Pro Ser Ser Gly Ala Ser Lys
                325                 330                 335

Gly Thr Thr Thr Lys Lys Tyr Ser Glu Gly Ala Ala Ala Gly Thr Glu
            340                 345                 350

Asp Ala Glu Arg Ala Pro Val Glu Ala Asp Ala Gly Gly Gln Lys
        355                 360                 365

Val Leu Val Arg Asn Val Val
    370                 375

<210> SEQ ID NO 165
<211> LENGTH: 387
<212> TYPE: PRT
<213> ORGANISM: Artificial Sequence
<220> FEATURE:
<223> OTHER INFORMATION: H37Rv Rv3616c with deleted residues 135-139

<400> SEQUENCE: 165

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
            20                  25                  30

Tyr Ser Ser Leu Glu Tyr Phe Glu Lys Ala Leu Glu Glu Leu Ala Ala
        35                  40                  45

Ala Phe Pro Gly Asp Gly Trp Leu Gly Ser Ala Ala Asp Lys Tyr Ala
    50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
        115                 120                 125

Leu Ser Ala Ala Phe Gln Gly Ala Met Ala Val Val Gly Gly Ala Leu
    130                 135                 140
```

Ala Tyr Leu Val Val Lys Thr Leu Ile Asn Ala Thr Gln Leu Leu Lys
145                 150                 155                 160

Leu Leu Ala Lys Leu Ala Glu Leu Val Ala Ala Ile Ala Asp Ile
            165                 170                 175

Ile Ser Asp Val Ala Asp Ile Ile Lys Gly Thr Leu Gly Val Trp
        180                 185                 190

Glu Phe Ile Thr Asn Ala Leu Asn Gly Leu Lys Glu Leu Trp Asp Lys
            195                 200                 205

Leu Thr Gly Trp Val Thr Gly Leu Phe Ser Arg Gly Trp Ser Asn Leu
            210                 215                 220

Glu Ser Phe Phe Ala Gly Val Pro Gly Leu Thr Gly Ala Thr Ser Gly
225                 230                 235                 240

Leu Ser Gln Val Thr Gly Leu Phe Gly Ala Ala Gly Leu Ser Ala Ser
                245                 250                 255

Ser Gly Leu Ala His Ala Asp Ser Leu Ala Ser Ser Ala Ser Leu Pro
            260                 265                 270

Ala Leu Ala Gly Ile Gly Gly Ser Gly Phe Gly Gly Leu Pro Ser
            275                 280                 285

Leu Ala Gln Val His Ala Ala Ser Thr Arg Gln Ala Leu Arg Pro Arg
            290                 295                 300

Ala Asp Gly Pro Val Gly Ala Ala Glu Gln Val Gly Gly Gln Ser
305                 310                 315                 320

Gln Leu Val Ser Ala Gln Gly Ser Gln Gly Met Gly Pro Val Gly
                325                 330                 335

Met Gly Gly Met His Pro Ser Gly Ala Ser Lys Gly Thr Thr Thr
                340                 345                 350

Lys Lys Tyr Ser Glu Gly Ala Ala Gly Thr Glu Asp Ala Glu Arg
                355                 360                 365

Ala Pro Val Glu Ala Asp Ala Gly Gly Gly Gln Lys Val Leu Val Arg
            370                 375                 380

Asn Val Val
385

<210> SEQ ID NO 166
<211> LENGTH: 388
<212> TYPE: PRT
<213> ORGANISM: Artificial Sequence
<220> FEATURE:
<223> OTHER INFORMATION: H37Rv Rv3616c with deleted residues 142-145

<400> SEQUENCE: 166

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
            20                  25                  30

Tyr Ser Ser Leu Glu Tyr Phe Glu Lys Ala Leu Glu Glu Leu Ala Ala
            35                  40                  45

Ala Phe Pro Gly Asp Gly Trp Leu Gly Ser Ala Ala Asp Lys Tyr Ala
        50                  55                  60

Gly Lys Asn Arg Asn His Val Asn Phe Phe Gln Glu Leu Ala Asp Leu
65              70                  75                  80

Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
            100                 105                 110

```
Arg Pro Val Ala Val Asp Leu Thr Tyr Ile Pro Val Gly His Ala
            115                 120                 125

Leu Ser Ala Ala Phe Gln Ala Pro Phe Cys Ala Gly Ala Gly Ala
            130                 135                 140

Leu Ala Tyr Leu Val Val Lys Thr Leu Ile Asn Ala Thr Gln Leu Leu
145                 150                 155                 160

Lys Leu Leu Ala Lys Leu Ala Glu Leu Val Ala Ala Ile Ala Asp
            165                 170                 175

Ile Ile Ser Asp Val Ala Asp Ile Ile Lys Gly Thr Leu Gly Glu Val
            180                 185                 190

Trp Glu Phe Ile Thr Asn Ala Leu Asn Gly Leu Lys Glu Leu Trp Asp
            195                 200                 205

Lys Leu Thr Gly Trp Val Thr Gly Leu Phe Ser Arg Gly Trp Ser Asn
210                 215                 220

Leu Glu Ser Phe Phe Ala Gly Val Pro Gly Leu Thr Gly Ala Thr Ser
225                 230                 235                 240

Gly Leu Ser Gln Val Thr Gly Leu Phe Gly Ala Ala Gly Leu Ser Ala
            245                 250                 255

Ser Ser Gly Leu Ala His Ala Asp Ser Leu Ala Ser Ser Ala Ser Leu
            260                 265                 270

Pro Ala Leu Ala Gly Ile Gly Gly Ser Gly Phe Gly Gly Leu Pro
            275                 280                 285

Ser Leu Ala Gln Val His Ala Ala Ser Thr Arg Gln Ala Leu Arg Pro
            290                 295                 300

Arg Ala Asp Gly Pro Val Gly Ala Ala Ala Glu Gln Val Gly Gly Gln
305                 310                 315                 320

Ser Gln Leu Val Ser Ala Gln Gly Ser Gln Gly Met Gly Gly Pro Val
            325                 330                 335

Gly Met Gly Gly Met His Pro Ser Ser Gly Ala Ser Lys Gly Thr Thr
            340                 345                 350

Thr Lys Lys Tyr Ser Glu Gly Ala Ala Ala Gly Thr Glu Asp Ala Glu
            355                 360                 365

Arg Ala Pro Val Glu Ala Asp Ala Gly Gly Gly Gln Lys Val Leu Val
            370                 375                 380

Arg Asn Val Val
385

<210> SEQ ID NO 167
<211> LENGTH: 384
<212> TYPE: PRT
<213> ORGANISM: Artificial Sequence
<220> FEATURE:
<223> OTHER INFORMATION: H37Rv Rv3616c with deleted residues 138-145

<400> SEQUENCE: 167

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
            20                  25                  30

Tyr Ser Ser Leu Glu Tyr Phe Glu Lys Ala Leu Glu Glu Leu Ala Ala
            35                  40                  45

Ala Phe Pro Gly Asp Gly Trp Leu Gly Ser Ala Ala Asp Lys Tyr Ala
            50                  55                  60

Gly Lys Asn Arg Asn His Val Asn Phe Phe Gln Glu Leu Ala Asp Leu
65                  70                  75                  80
```

-continued

Asp Arg Gln Leu Ile Ser Leu Ile His Asp Gln Ala Asn Ala Val Gln
            85                  90                  95

Thr Thr Arg Asp Ile Leu Glu Gly Ala Lys Lys Gly Leu Glu Phe Val
        100                 105                 110

Arg Pro Val Ala Val Asp Leu Thr Tyr Ile Pro Val Val Gly His Ala
        115                 120                 125

Leu Ser Ala Ala Phe Gln Ala Pro Phe Gly Gly Ala Leu Ala Tyr Leu
    130                 135                 140

Val Val Lys Thr Leu Ile Asn Ala Thr Gln Leu Leu Lys Leu Leu Ala
145                 150                 155                 160

Lys Leu Ala Glu Leu Val Ala Ala Ile Ala Asp Ile Ile Ser Asp
                165                 170                 175

Val Ala Asp Ile Ile Lys Gly Thr Leu Gly Glu Val Trp Glu Phe Ile
        180                 185                 190

Thr Asn Ala Leu Asn Gly Leu Lys Glu Leu Trp Asp Lys Leu Thr Gly
        195                 200                 205

Trp Val Thr Gly Leu Phe Ser Arg Gly Trp Ser Asn Leu Glu Ser Phe
    210                 215                 220

Phe Ala Gly Val Pro Gly Leu Thr Gly Ala Thr Ser Gly Leu Ser Gln
225                 230                 235                 240

Val Thr Gly Leu Phe Gly Ala Ala Gly Leu Ser Ala Ser Ser Gly Leu
                245                 250                 255

Ala His Ala Asp Ser Leu Ala Ser Ser Ala Ser Leu Pro Ala Leu Ala
        260                 265                 270

Gly Ile Gly Gly Gly Ser Gly Phe Gly Gly Leu Pro Ser Leu Ala Gln
        275                 280                 285

Val His Ala Ala Ser Thr Arg Gln Ala Leu Arg Pro Arg Ala Asp Gly
    290                 295                 300

Pro Val Gly Ala Ala Ala Glu Gln Val Gly Gly Gln Ser Gln Leu Val
305                 310                 315                 320

Ser Ala Gln Gly Ser Gln Gly Met Gly Gly Pro Val Gly Met Gly Gly
                325                 330                 335

Met His Pro Ser Ser Gly Ala Ser Lys Gly Thr Thr Thr Lys Lys Tyr
        340                 345                 350

Ser Glu Gly Ala Ala Ala Gly Thr Glu Asp Ala Glu Arg Ala Pro Val
    355                 360                 365

Glu Ala Asp Ala Gly Gly Gly Gln Lys Val Leu Val Arg Asn Val Val
        370                 375                 380

<210> SEQ ID NO 168
<211> LENGTH: 384
<212> TYPE: PRT
<213> ORGANISM: Artificial Sequence
<220> FEATURE:
<223> OTHER INFORMATION: H37Rv Rv3616c with deleted residues 145-152

<400> SEQUENCE: 168

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
            20                  25                  30

Tyr Ser Ser Leu Glu Tyr Phe Glu Lys Ala Leu Glu Glu Leu Ala Ala
        35                  40                  45

Ala Phe Pro Gly Asp Gly Trp Leu Gly Ser Ala Ala Asp Lys Tyr Ala
    50                  55                  60

-continued

Gly Lys Asn Arg Asn His Val Asn Phe Phe Gln Glu Leu Ala Asp Leu
 65                  70                  75                  80

Asp Arg Gln Leu Ile Ser Leu Ile His Asp Gln Ala Asn Ala Val Gln
                 85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Gly His Ala
        115                 120                 125

Leu Ser Ala Ala Phe Gln Ala Pro Phe Cys Ala Gly Ala Met Ala Val
        130                 135                 140

Val Val Lys Thr Leu Ile Asn Ala Thr Gln Leu Leu Lys Leu Ala
145                 150                 155                 160

Lys Leu Ala Glu Leu Val Ala Ala Ile Ala Asp Ile Ile Ser Asp
                165                 170                 175

Val Ala Asp Ile Ile Lys Gly Thr Leu Gly Glu Val Trp Glu Phe Ile
            180                 185                 190

Thr Asn Ala Leu Asn Gly Leu Lys Glu Leu Trp Asp Lys Leu Thr Gly
        195                 200                 205

Trp Val Thr Gly Leu Phe Ser Arg Gly Trp Ser Asn Leu Glu Ser Phe
210                 215                 220

Phe Ala Gly Val Pro Gly Leu Thr Gly Ala Thr Ser Gly Leu Ser Gln
225                 230                 235                 240

Val Thr Gly Leu Phe Gly Ala Ala Gly Leu Ser Ala Ser Ser Gly Leu
            245                 250                 255

Ala His Ala Asp Ser Leu Ala Ser Ser Ala Ser Leu Pro Ala Leu Ala
        260                 265                 270

Gly Ile Gly Gly Gly Ser Gly Phe Gly Gly Leu Pro Ser Leu Ala Gln
        275                 280                 285

Val His Ala Ala Ser Thr Arg Gln Ala Leu Arg Pro Arg Ala Asp Gly
        290                 295                 300

Pro Val Gly Ala Ala Ala Glu Gln Val Gly Gly Gln Ser Gln Leu Val
305                 310                 315                 320

Ser Ala Gln Gly Ser Gln Gly Met Gly Gly Pro Val Gly Met Gly Gly
            325                 330                 335

Met His Pro Ser Ser Gly Ala Ser Lys Gly Thr Thr Thr Lys Lys Tyr
        340                 345                 350

Ser Glu Gly Ala Ala Ala Gly Thr Glu Asp Ala Glu Arg Ala Pro Val
        355                 360                 365

Glu Ala Asp Ala Gly Gly Gly Gln Lys Val Leu Val Arg Asn Val Val
        370                 375                 380

<210> SEQ ID NO 169
<211> LENGTH: 386
<212> TYPE: PRT
<213> ORGANISM: Artificial Sequence
<220> FEATURE:
<223> OTHER INFORMATION: H37Rv Rv3616c with deleted residues 149-154

<400> SEQUENCE: 169

Met Ser Arg Ala Phe Ile Ile Asp Pro Thr Ile Ser Ala Ile Asp Gly
  1               5                  10                  15

Leu Tyr Asp Leu Leu Gly Ile Gly Ile Pro Asn Gln Gly Gly Ile Leu
                 20                  25                  30

Tyr Ser Ser Leu Glu Tyr Phe Glu Lys Ala Leu Glu Glu Leu Ala Ala
            35                  40                  45

```
Ala Phe Pro Gly Asp Gly Trp Leu Gly Ser Ala Ala Asp Lys Tyr Ala
 50                  55                  60

Gly Lys Asn Arg Asn His Val Asn Phe Phe Gln Glu Leu Ala Asp Leu
 65                  70                  75                  80

Asp Arg Gln Leu Ile Ser Leu Ile His Asp Gln Ala Asn Ala Val Gln
                 85                  90                  95

Thr Thr Arg Asp Ile Leu Glu Gly Ala Lys Lys Gly Leu Glu Phe Val
                100                 105                 110

Arg Pro Val Ala Val Asp Leu Thr Tyr Ile Pro Val Gly His Ala
                115                 120                 125

Leu Ser Ala Ala Phe Gln Ala Pro Phe Cys Ala Gly Ala Met Ala Val
130                 135                 140

Val Gly Gly Ala Lys Thr Leu Ile Asn Ala Thr Gln Leu Leu Lys Leu
145                 150                 155                 160

Leu Ala Lys Leu Ala Glu Leu Val Ala Ala Ile Ala Asp Ile Ile
                165                 170                 175

Ser Asp Val Ala Asp Ile Ile Lys Gly Thr Leu Gly Glu Val Trp Glu
                180                 185                 190

Phe Ile Thr Asn Ala Leu Asn Gly Leu Lys Glu Leu Trp Asp Lys Leu
                195                 200                 205

Thr Gly Trp Val Thr Gly Leu Phe Ser Arg Gly Trp Ser Asn Leu Glu
                210                 215                 220

Ser Phe Phe Ala Gly Val Pro Gly Leu Thr Gly Ala Thr Ser Gly Leu
225                 230                 235                 240

Ser Gln Val Thr Gly Leu Phe Gly Ala Ala Gly Leu Ser Ala Ser Ser
                245                 250                 255

Gly Leu Ala His Ala Asp Ser Leu Ala Ser Ser Ala Ser Leu Pro Ala
                260                 265                 270

Leu Ala Gly Ile Gly Gly Gly Ser Gly Phe Gly Gly Leu Pro Ser Leu
                275                 280                 285

Ala Gln Val His Ala Ala Ser Thr Arg Gln Ala Leu Arg Pro Arg Ala
                290                 295                 300

Asp Gly Pro Val Gly Ala Ala Ala Glu Gln Val Gly Gly Gln Ser Gln
305                 310                 315                 320

Leu Val Ser Ala Gln Gly Ser Gln Gly Met Gly Gly Pro Val Gly Met
                325                 330                 335

Gly Gly Met His Pro Ser Ser Gly Ala Ser Lys Gly Thr Thr Thr Lys
                340                 345                 350

Lys Tyr Ser Glu Gly Ala Ala Ala Gly Thr Glu Asp Ala Glu Arg Ala
                355                 360                 365

Pro Val Glu Ala Asp Ala Gly Gly Gly Gln Lys Val Leu Val Arg Asn
370                 375                 380

Val Val
385

<210> SEQ ID NO 170
<211> LENGTH: 1032
<212> TYPE: DNA
<213> ORGANISM: Artificial Sequence
<220> FEATURE:
<223> OTHER INFORMATION: H37Rv Rv3616c with deleted codons for residues
      136-183

<400> SEQUENCE: 170
atgagccgtg cctttattat tgatccgacc attagcgcaa ttgatggtct gtatgatctg    60
```

```
ctgggtattg gtattccgaa tcagggtggt attctgtata gcagcctgga atattttg

| agcaaaggca ccaccaccaa aaaatatagc gaaggagcag ctgctggcac cgaagatgca | 1080 |
| gaacgtgcac cggttgaagc agatgccggt ggaggtcaga agttctggt tcgcaatgtg | 1140 |
| gtg | 1143 |

<210> SEQ ID NO 172
<211> LENGTH: 1119
<212> TYPE: DNA
<213> ORGANISM: Artificial Sequence
<220> FEATURE:
<223> OTHER INFORMATION: H37Rv Rv3616c with deleted codons for residues 136-154

<400> SEQUENCE: 172

| atgagccgtg cctttattat tgatccgacc attagcgcaa ttgatggtct gtatgatctg | 60 |
| ctgggtattg gtattccgaa tcagggtggt attctgtata gcagcctgga atattttgaa | 120 |
| aaagccctgg aagaactggc agcagcattt ccgggtgatg gttggctggg tagcgcagca | 180 |
| gataaatatg ccggtaaaaa tcgcaatcat gtgaattttt ttcaggaact ggccgatctg | 240 |
| gatcgtcagc tgattagcct gattcatgac caggcaaatg cagttcagac cacccgtgat | 300 |
| attctggaag gtgccaaaaa aggtctggaa tttgttcgtc cggtggcagt tgatctgacc | 360 |
| tatattccgg ttgttggtca tgcactgagc gcagcatttc aggcaaaaac cctgattaat | 420 |
| gcaacccagc tgctgaaact gctggcaaaa ctggcagaac tggttgcagc agcaattgca | 480 |
| gatattattt ccgatgtggc cgatattatt aaaggcaccc tgggcgaagt tgggaatttt | 540 |
| attaccaatg ccctgaatgg tctgaaagaa ctgtgggata aactgaccgg ttgggttacc | 600 |
| ggtctgttta gccgtggttg gagcaatctg gaatcttttt ttgccggtgt tccgggtctg | 660 |
| accggtgcaa ccagcggtct gagccaggtg acaggtctgt ttggagcagc tggtctgagt | 720 |
| gctagtagcg gtctggctca tgcagatagc ctggcaagca gcgcatctct gcctgcactg | 780 |
| gcaggcattg tggtggatc cggttttggt ggtctgccga gcctggcaca ggttcatgca | 840 |
| gcaagcaccc gtcaggcact gcgtccgcgt gcagatggac cggttggagc agcagcagaa | 900 |
| caggttggtg gtcagagcca gctggttagc gcacagggta gccagggtat gggtggtccg | 960 |
| gtgggcatgg tggtatgca tccgagcagc ggtgcaagca aggcaccac caccaaaaaa | 1020 |
| tatagcgaag gagcagctgc tggcaccgaa gatgcagaac gtgcaccggt tgaagcagat | 1080 |
| gccggtggag gtcagaaagt tctggttcgc aatgtggtg | 1119 |

<210> SEQ ID NO 173
<211> LENGTH: 1125
<212> TYPE: DNA
<213> ORGANISM: Artificial Sequence
<220> FEATURE:
<223> OTHER INFORMATION: H37Rv Rv3616c with deleted codons for residues 166-182

<400> SEQUENCE: 173

| atgagccgtg cctttattat tgatccgacc attagcgcaa ttgatggtct gtatgatctg | 60 |
| ctgggtattg gtattccgaa tcagggtggt attctgtata gcagcctgga atattttgaa | 120 |
| aaagccctgg aagaactggc agcagcattt ccgggtgatg gttggctggg tagcgcagca | 180 |
| gataaatatg ccggtaaaaa tcgcaatcat gtgaattttt ttcaggaact ggccgatctg | 240 |
| gatcgtcagc tgattagcct gattcatgac caggcaaatg cagttcagac cacccgtgat | 300 |
| attctggaag gtgccaaaaa aggtctggaa tttgttcgtc cggtggcagt tgatctgacc | 360 |
| tatattccgg ttgttggtca tgcactgagc gcagcatttc aggcaccgtt tgtgccggt | 420 |

```
gcaatggcag ttgtgggtgg tgctctggca tatctggttg tgaaaaccct gattaatgca      480
acccagctgc tgaaatccga tgtggccgat attattaaag cacccctggg cgaagtttgg      540
gaatttatta ccaatgccct gaatggtctg aaagaactgt gggataaact gaccggttgg      600
gttaccggtc tgtttagccg tggttggagc aatctggaat cttttttttgc cggtgttccg     660 ggtctgaccg gtgcaaccag cggtctgagc caggtgacag gtctgtttgg agcagctggt     720
ctgagtgcta gtagcggtct ggctcatgca gatagcctgg caagcagcgc atctctgcct     780
gcactggcag gcattggtgg tggatccggt tttggtggtc tgccgagcct ggcacaggtt     840
catgcagcaa gcacccgtca ggcactgcgt ccgcgtgcag atggaccggt tggagcagca     900
gcagaacagg ttggtggtca gagccagctg gttagcgcac agggtagcca gggtatgggt     960
ggtccggtgg gcatgggtgg tatgcatccg agcagcggtg caagcaaagg caccaccacc    1020
aaaaaatata gcgaaggagc agctgctggc accgaagatg cagaacgtgc accggttgaa    1080
gcagatgccg gtggaggtca gaaagttctg gttcgcaatg tggtg                    1125

<210> SEQ ID NO 174
<211> LENGTH: 1161
<212> TYPE: DNA
<213> ORGANISM: Artificial Sequence
<220> FEATURE:
<223> OTHER INFORMATION: H37Rv Rv3616c with deleted codons for residues
      135-139

<400> SEQUENCE: 174
atgagccgtg cctttattat tgatccgacc attagcgcaa ttgatggtct gtatgatctg      60
ctgggtattg gtattccgaa tcagggtggt attctgtata gcagcctgga atattttgaa     120
aaagccctgg aagaactggc agcagcattt ccgggtgatg gttggctggg tagcgcagca     180
gataaatatg ccggtaaaaa tcgcaatcat gtgaattttt ttcaggaact ggccgatctg     240
gatcgtcagc tgattagcct gattcatgac caggcaaatg cagttcagac cacccgtgat     300
attctggaag gtgccaaaaa aggtctggaa tttgttcgtc cggtggcagt tgatctgacc     360
tatattccgg ttgttggtca tgcactgagc gcagcatttc agggtgcaat ggcagttgtg     420
ggtggtgctc tggcatatct ggttgtgaaa accctgatta atgcaaccca gctgctgaaa     480
ctgctggcaa aactggcaga actggttgca gcagcaattg cagatattat tccgatgtg      540 gccgatatta ttaaaggcac cctgggcgaa gtttgggaat tattaccaa tgccctgaat      600 ggtctgaaag aactgtggga taaactgacc ggttgggtta ccggtctgtt tagccgtggt     660
tggagcaatc tggaatcttt ttttgccggt gttccgggtc tgaccggtgc aaccagcggt     720
ctgagccagg tgacaggtct gtttggagca gctggtctga gtgctagtag cggtctggct     780
catgcagata gcctggcaag cagcgcatct ctgcctgcac tggcaggcat tggtggtgga    840
tccggttttg gtggtctgcc gagcctggca caggttcatg cagcaagcac ccgtcaggca    900
ctgcgtccgc gtgcagatgg accggttgga gcagcagcag aacaggttgg tggtcagagc    960
cagctggtta gcgcacaggg tagccagggt atgggtggtc cggtgggcat gggtggtatg   1020
catccgagca gcggtgcaag caaaggcacc accaccaaaa aatatagcga aggagcagct   1080
gctggcaccg aagatgcaga acgtgcaccg gttgaagcag atgccggtgg aggtcagaaa   1140
gttctggttc gcaatgtggt g                                             1161

<210> SEQ ID NO 175
<211> LENGTH: 1164
```

<212> TYPE: DNA
<213> ORGANISM: Artificial Sequence
<220> FEATURE:
<223> OTHER INFORMATION: H37Rv Rv3616c with deleted codons for residues
      142-145

<400> SEQUENCE: 175

```
atgagccgtg cctttattat tgatccgacc attagcgcaa ttgatggtct gtatgatctg     60
ctgggtattg gtattccgaa tcagggtggt attctgtata gcagcctgga atattttgaa    120
aaagccctgg aagaactggc agcagcattt ccgggtgatg gttggctggg tagcgcagca    180
gataaatatg ccggtaaaaa tcgcaatcat gtgaattttt ttcaggaact ggccgatctg    240
gatcgtcagc tgattagcct gattcatgac caggcaaatg cagttcagac cacccgtgat    300
attctggaag gtgccaaaaa aggtctggaa tttgttcgtc cggtggcagt tgatctgacc    360
tatattccgg ttgttggtca tgcactgagc gcagcatttc aggcaccgtt ttgtgccggt    420
gcaggtggtg ctctggcata tctggttgtg aaaaccctga ttaatgcaac ccagctgctg    480
aaactgctgg caaaactggc agaactggtt gcagcagcaa ttgcagatat tatttccgat    540
gtggccgata ttattaaagg caccctgggc gaagtttggg aatttattac caatgccctg    600
aatggtctga agaactgtgg gataaactga ccggttgggg ttaccggtct gtttagccgt    660
ggttggagca atctggaatc ttttttttgcc ggtgttccgg tctgaccgg tgcaaccagc    720
ggtctgagcc aggtgacagg tctgtttgga gcagctggtc tgagtgctag tagcggtctg    780
gctcatgcag atagcctggc aagcagcgca tctctgcctg cactggcagg cattggtggt    840
ggatccggtt ttggtggtct gccgagcctg gcacaggttc atgcagcaag caccgtcag    900
gcactgcgtc gcgtgcaga tggaccggtt ggagcagcag cagaacaggt tggtggtcag    960
agccagctgg ttagcgcaca gggtagccag ggtatgggtg tccggtggg catgggtggt   1020
atgcatccga gcagcggtgc aagcaaaggc accaccacca aaaaatatag cgaaggagca   1080
gctgctggca ccgaagatgc agaacgtgca ccggttgaag cagatgccgg tggaggtcag   1140
aaagttctgg ttcgcaatgt ggtg                                          1164
```

<210> SEQ ID NO 176
<211> LENGTH: 1152
<212> TYPE: DNA
<213> ORGANISM: Artificial Sequence
<220> FEATURE:
<223> OTHER INFORMATION: H37Rv Rv3616c with deleted codons for residues
      138-145

<400> SEQUENCE: 176

```
atgagccgtg cctttattat tgatccgacc attagcgcaa ttgatggtct gtatgatctg     60
ctgggtattg gtattccgaa tcagggtggt attctgtata gcagcctgga atattttgaa    120
aaagccctgg aagaactggc agcagcattt ccgggtgatg gttggctggg tagcgcagca    180
gataaatatg ccggtaaaaa tcgcaatcat gtgaattttt ttcaggaact ggccgatctg    240
gatcgtcagc tgattagcct gattcatgac caggcaaatg cagttcagac cacccgtgat    300
attctggaag gtgccaaaaa aggtctggaa tttgttcgtc cggtggcagt tgatctgacc    360
tatattccgg ttgttggtca tgcactgagc gcagcatttc aggcaccgtt tgtggtgct    420
ctggcatatc tggttgtgaa accctgatt aatgcaaccc agctgctgaa actgctggca    480
aaactggcag aactggttgc agcagcaatt gcagatatta tttccgatgt ggccgatatt    540
attaaaggca ccctgggcga agtttgggaa tttattacca atgccctgaa tggtctgaaa    600
```

```
gaactgtggg ataaactgac cggttgggtt accggtctgt ttagccgtgg ttggagcaat        660
ctggaatctt tttttgccgg tgttccgggt ctgaccggtg caaccagcgg tctgagccag        720
gtgacaggtc tgtttggagc agctggtctg agtgctagta gcggtctggc tcatgcagat        780
agcctggcaa gcagcgcatc tctgcctgca ctggcaggca ttggtggtgg atccggtttt        840
ggtggtctgc cgagcctggc acaggttcat gcagcaagca cccgtcaggc actgcgtccg        900
cgtgcagatg gaccggttgg agcagcagca gaacaggttg gtggtcagag ccagctggtt        960
agcgcacagg gtagccaggg tatgggtggt ccggtgggca tgggtggtat gcatccgagc       1020
agcggtgcaa gcaaaggcac caccaccaaa aaatatagcg aaggagcagc tgctggcacc       1080
gaagatgcag aacgtgcacc ggttgaagca gatgccggtg gaggtcagaa agttctggtt       1140
cgcaatgtgg tg                                                           1152
```

<210> SEQ ID NO 177
<211> LENGTH: 1152
<212> TYPE: DNA
<213> ORGANISM: Artificial Sequence
<220> FEATURE:
<223> OTHER INFORMATION: H37Rv Rv3616c with deleted codons for residues
      145-152

<400> SEQUENCE: 177

```
atgagccgtg cctttattat tgatccgacc attagcgcaa ttgatggtct gtatgatctg         60
ctgggtattg gtattccgaa tcagggtggt attctgtata gcagcctgga atattttgaa        120
aaagccctgg aagaactggc agcagcattt ccgggtgatg gttggctggg tagcgcagca        180
gataaatatg ccggtaaaaa tcgcaatcat gtgaattttt ttcaggaact ggccgatctg        240
gatcgtcagc tgattagcct gattcatgac caggcaaatg cagttcagac cacccgtgat        300
attctggaag gtgccaaaaa aggtctggaa tttgttcgtc cggtggcagt tgatctgacc        360
tatattccgg ttgttggtca tgcactgagc gcagcatttc aggcaccgtt ttgtgccggt        420
gcaatggcag ttgttgtgaa accctgatt aatgcaaccc agctgctgaa actgctggca        480
aaactggcag aactggttgc agcagcaatt gcagatatta tttccgatgt ggccgatatt        540
attaaaggca ccctgggcga gtttgggaa tttattacca atgccctgaa tggtctgaaa        600
gaactgtggg ataaactgac cggttgggtt accggtctgt ttagccgtgg ttggagcaat        660
ctggaatctt tttttgccgg tgttccgggt ctgaccggtg caaccagcgg tctgagccag        720
gtgacaggtc tgtttggagc agctggtctg agtgctagta gcggtctggc tcatgcagat        780
agcctggcaa gcagcgcatc tctgcctgca ctggcaggca ttggtggtgg atccggtttt        840
ggtggtctgc cgagcctggc acaggttcat gcagcaagca cccgtcaggc actgcgtccg        900
cgtgcagatg gaccggttgg agcagcagca gaacaggttg gtggtcagag ccagctggtt        960
agcgcacagg gtagccaggg tatgggtggt ccggtgggca tgggtggtat gcatccgagc       1020
agcggtgcaa gcaaaggcac caccaccaaa aaatatagcg aaggagcagc tgctggcacc       1080
gaagatgcag aacgtgcacc ggttgaagca gatgccggtg gaggtcagaa agttctggtt       1140
cgcaatgtgg tg                                                           1152
```

<210> SEQ ID NO 178
<211> LENGTH: 1158
<212> TYPE: DNA
<213> ORGANISM: Artificial Sequence
<220> FEATURE:
<223> OTHER INFORMATION: H37Rv Rv3616c with deleted codons for residues
      149-154

<400> SEQUENCE: 178

```
atgagccgtg cctttattat tgatccgacc attagcgcaa ttgatggtct gtatgatctg     60
ctgggtattg gtattccgaa tcagggtggt attctgtata gcagcctgga atattttgaa    120
aaagccctgg aagaactggc agcagcattt ccgggtgatg gttggctggg tagcgcagca    180
gataaatatg ccggtaaaaa tcgcaatcat gtgaattttt ttcaggaact ggccgatctg    240
gatcgtcagc tgattagcct gattcatgac caggcaaatg cagttcagac cacccgtgat    300
attctggaag gtgccaaaaa aggtctggaa tttgttcgtc cggtggcagt tgatctgacc    360
tatattccgg ttgttggtca tgcactgagc gcagcatttc aggcaccgtt ttgtgccggt    420
gcaatggcag ttgtgggtgg tgctaaaacc ctgattaatg caacccagct gctgaaactg    480
ctggcaaaac tggcagaact ggttgcagca gcaattgcag atattatttc cgatgtggcc    540
gatattatta aaggcaccct gggcgaagtt tgggaattta ttaccaatgc cctgaatggt    600
ctgaaagaac tgtgggataa actgaccggt tgggttaccg gtctgtttag ccgtggttgg    660
agcaatctgg aatcttttttt tgccggtgtt ccgggtctga ccggtgcaac cagcggtctg    720
agccaggtga caggtctgtt tggagcagct ggtctgagtg ctagtagcgg tctggctcat    780
gcagatagcc tggcaagcag cgcatctctg cctgcactgg caggcattgg tggtggatcc    840
ggttttggtg gtctgccgag cctggcacag gttcatgcag caagcacccg tcaggcactg    900
cgtccgcgtg cagatggacc ggttggagca gcagcagaac aggttggtgg tcagagccag    960
ctggttagcg cacagggtag ccagggtatg ggtggtccgg tgggcatggg tggtatgcat   1020
ccgagcagcg gtgcaagcaa aggcaccacc accaaaaaat atagcgaagg agcagctgct   1080
ggcaccgaag atgcagaacg tgcaccggtt gaagcagatg ccggtggagg tcagaaagtt   1140
ctggttcgca atgtggtg                                                  1158
```

<210> SEQ ID NO 179
<211> LENGTH: 391
<212> TYPE: PRT
<213> ORGANISM: Artificial Sequence
<220> FEATURE:
<223> OTHER INFORMATION: Rearrangement around the residues 137-139 from
    M. tuberculosis H37Rv strain, including deletion of Cys138

<400> SEQUENCE: 179

```
Met Ala Gly Ala Met Ala Val Val Gly Gly Ala Leu Ala Tyr Leu Val
 1               5                  10                  15

Val Lys Thr Leu Ile Asn Ala Thr Gln Leu Leu Lys Leu Leu Ala Lys
            20                  25                  30

Leu Ala Glu Leu Val Ala Ala Ala Ile Ala Asp Ile Ile Ser Asp Val
        35                  40                  45

Ala Asp Ile Ile Lys Gly Thr Leu Gly Glu Val Trp Glu Phe Ile Thr
    50                  55                  60

Asn Ala Leu Asn Gly Leu Lys Glu Leu Trp Asp Lys Leu Thr Gly Trp
65                  70                  75                  80

Val Thr Gly Leu Phe Ser Arg Gly Trp Ser Asn Leu Glu Ser Phe Phe
                85                  90                  95

Ala Gly Val Pro Gly Leu Thr Gly Ala Thr Ser Gly Leu Ser Gln Val
            100                 105                 110

Thr Gly Leu Phe Gly Ala Ala Gly Leu Ser Ala Ser Ser Gly Leu Ala
        115                 120                 125

His Ala Asp Ser Leu Ala Ser Ser Ala Ser Leu Pro Ala Leu Ala Gly
```

```
        130                 135                 140
Ile Gly Gly Ser Gly Phe Gly Gly Leu Pro Ser Leu Ala Gln Val
145                 150                 155                 160

His Ala Ala Ser Thr Arg Gln Ala Leu Arg Pro Arg Ala Asp Gly Pro
                165                 170                 175

Val Gly Ala Ala Ala Glu Gln Val Gly Gly Ser Gln Leu Val Ser
                180                 185                 190

Ala Gln Gly Ser Gln Gly Met Gly Gly Pro Val Gly Met Gly Gly Met
                195                 200                 205

His Pro Ser Ser Gly Ala Ser Lys Gly Thr Thr Lys Lys Tyr Ser
    210                 215                 220

Glu Gly Ala Ala Ala Gly Thr Glu Asp Ala Glu Arg Ala Pro Val Glu
225                 230                 235                 240

Ala Asp Ala Gly Gly Gln Lys Val Leu Val Arg Asn Val Val Ser
                245                 250                 255

Arg Ala Phe Ile Ile Asp Pro Thr Ile Ser Ala Ile Asp Gly Leu Tyr
                260                 265                 270

Asp Leu Leu Gly Ile Gly Ile Pro Asn Gln Gly Gly Ile Leu Tyr Ser
    275                 280                 285

Ser Leu Glu Tyr Phe Glu Lys Ala Leu Glu Glu Leu Ala Ala Ala Phe
    290                 295                 300

Pro Gly Asp Gly Trp Leu Gly Ser Ala Ala Asp Lys Tyr Ala Gly Lys
305                 310                 315                 320

Asn Arg Asn His Val Asn Phe Phe Gln Glu Leu Ala Asp Leu Asp Arg
                325                 330                 335

Gln Leu Ile Ser Leu Ile His Asp Gln Ala Asn Ala Val Gln Thr Thr
                340                 345                 350

Arg Asp Ile Leu Glu Gly Ala Lys Lys Gly Leu Glu Phe Val Arg Pro
                355                 360                 365

Val Ala Val Asp Leu Thr Tyr Ile Pro Val Val Gly His Ala Leu Ser
                370                 375                 380

Ala Ala Phe Gln Ala Pro Phe
385                 390

<210> SEQ ID NO 180
<211> LENGTH: 392
<212> TYPE: PRT
<213> ORGANISM: Artificial Sequence
<220> FEATURE:
<223> OTHER INFORMATION: Rearrangement around the residues 152-153 from
      M. tuberculosis H37Rv strain

<400> SEQUENCE: 180

Met Val Val Lys Thr Leu Ile Asn Ala Thr Gln Leu Leu Lys Leu Leu
1               5                   10                  15

Ala Lys Leu Ala Glu Leu Val Ala Ala Ala Ile Ala Asp Ile Ile Ser
                20                  25                  30

Asp Val Ala Asp Ile Ile Lys Gly Thr Leu Gly Glu Val Trp Glu Phe
                35                  40                  45

Ile Thr Asn Ala Leu Asn Gly Leu Lys Glu Leu Trp Asp Lys Leu Thr
                50                  55                  60

Gly Trp Val Thr Gly Leu Phe Ser Arg Gly Trp Ser Asn Leu Glu Ser
65                  70                  75                  80

Phe Phe Ala Gly Val Pro Gly Leu Thr Gly Ala Thr Ser Gly Leu Ser
                85                  90                  95
```

```
Gln Val Thr Gly Leu Phe Gly Ala Ala Gly Leu Ser Ala Ser Ser Gly
            100                 105                 110

Leu Ala His Ala Asp Ser Leu Ala Ser Ser Ala Ser Leu Pro Ala Leu
            115                 120                 125

Ala Gly Ile Gly Gly Gly Ser Gly Phe Gly Gly Leu Pro Ser Leu Ala
            130                 135                 140

Gln Val His Ala Ala Ser Thr Arg Gln Ala Leu Arg Pro Arg Ala Asp
145                 150                 155                 160

Gly Pro Val Gly Ala Ala Glu Gln Val Gly Gly Gln Ser Gln Leu
                165                 170                 175

Val Ser Ala Gln Gly Ser Gln Gly Met Gly Gly Pro Val Gly Met Gly
            180                 185                 190

Gly Met His Pro Ser Ser Gly Ala Ser Lys Gly Thr Thr Thr Lys Lys
            195                 200                 205

Tyr Ser Glu Gly Ala Ala Ala Gly Thr Glu Asp Ala Glu Arg Ala Pro
            210                 215                 220

Val Glu Ala Asp Ala Gly Gly Gly Gln Lys Val Leu Val Arg Asn Val
225                 230                 235                 240

Val Ser Arg Ala Phe Ile Ile Asp Pro Thr Ile Ser Ala Ile Asp Gly
                245                 250                 255

Leu Tyr Asp Leu Leu Gly Ile Gly Ile Pro Asn Gln Gly Gly Ile Leu
            260                 265                 270

Tyr Ser Ser Leu Glu Tyr Phe Glu Lys Ala Leu Glu Glu Leu Ala Ala
            275                 280                 285

Ala Phe Pro Gly Asp Gly Trp Leu Gly Ser Ala Ala Asp Lys Tyr Ala
            290                 295                 300

Gly Lys Asn Arg Asn His Val Asn Phe Phe Gln Glu Leu Ala Asp Leu
305                 310                 315                 320

Asp Arg Gln Leu Ile Ser Leu Ile His Asp Gln Ala Asn Ala Val Gln
                325                 330                 335

Thr Thr Arg Asp Ile Leu Glu Gly Ala Lys Lys Gly Leu Glu Phe Val
            340                 345                 350

Arg Pro Val Ala Val Asp Leu Thr Tyr Ile Pro Val Val Gly His Ala
            355                 360                 365

Leu Ser Ala Ala Phe Gln Ala Pro Phe Cys Ala Gly Ala Met Ala Val
    370                 375                 380

Val Gly Gly Ala Leu Ala Tyr Leu
385                 390
```